United States Patent
Lee et al.

(10) Patent No.: US 9,988,379 B2
(45) Date of Patent: Jun. 5, 2018

(54) GPR40 RECEPTOR AGONIST, METHODS OF PREPARING THE SAME, AND PHARMACEUTICAL COMPOSITIONS CONTAINING THE SAME AS AN ACTIVE AGENT

(71) Applicant: LG CHEM, LTD., Seoul (KR)

(72) Inventors: Sung Bae Lee, Daejeon (KR); Seung Yup Paek, Daejeon (KR); Sook Kyung Yoon, Daejeon (KR); Seung Hyun Yoon, Daejeon (KR); Jeung Soon Choi, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days. days.

(21) Appl. No.: 14/441,591

(22) PCT Filed: Nov. 8, 2013

(86) PCT No.: PCT/KR2013/010135
§ 371 (c)(1),
(2) Date: May 8, 2015

(87) PCT Pub. No.: WO2014/073904
PCT Pub. Date: May 15, 2014

(65) Prior Publication Data
US 2015/0291584 A1 Oct. 15, 2015

(30) Foreign Application Priority Data
Nov. 9, 2012 (KR) .................. 10-2012-0127005

(51) Int. Cl.
| | | |
|---|---|---|
| *C07D 209/08* | (2006.01) |
| *C07D 209/18* | (2006.01) |
| *C07D 209/14* | (2006.01) |
| *C07D 209/12* | (2006.01) |
| *C07D 209/00* | (2006.01) |
| *C07D 231/56* | (2006.01) |
| *C07D 231/54* | (2006.01) |
| *C07D 249/18* | (2006.01) |
| *C07D 471/04* | (2006.01) |
| *A61K 31/405* | (2006.01) |
| *A61K 31/404* | (2006.01) |
| *A61K 31/407* | (2006.01) |
| *A61K 31/416* | (2006.01) |
| *A61K 31/4162* | (2006.01) |
| *A61K 31/4192* | (2006.01) |
| *C07D 409/04* | (2006.01) |
| *C07D 413/14* | (2006.01) |
| *C07D 401/06* | (2006.01) |
| *C07D 235/26* | (2006.01) |
| *C07D 403/06* | (2006.01) |
| *C07D 405/06* | (2006.01) |
| *C07D 405/12* | (2006.01) |
| *C07D 413/12* | (2006.01) |
| *C07D 417/06* | (2006.01) |
| *C07D 261/20* | (2006.01) |
| *C07D 209/30* | (2006.01) |
| *C07D 401/04* | (2006.01) |

(52) U.S. Cl.
CPC ......... *C07D 471/04* (2013.01); *C07D 209/08* (2013.01); *C07D 209/12* (2013.01); *C07D 209/30* (2013.01); *C07D 231/56* (2013.01); *C07D 235/26* (2013.01); *C07D 249/18* (2013.01); *C07D 261/20* (2013.01); *C07D 401/04* (2013.01); *C07D 401/06* (2013.01); *C07D 403/06* (2013.01); *C07D 405/06* (2013.01); *C07D 405/12* (2013.01); *C07D 409/04* (2013.01); *C07D 413/12* (2013.01); *C07D 413/14* (2013.01); *C07D 417/06* (2013.01)

(58) Field of Classification Search
CPC .. C07D 243/02; C07D 235/08; C07D 235/10; C07D 209/08; C07D 209/18; C07D 209/14; C07D 209/12; C07D 209/00; C07D 231/56; C07D 231/54; C07D 249/18; C07D 471/04; A61K 31/405; A61K 31/404; A61K 31/407; A61K 31/416; A61K 31/4162; A61K 31/4192
USPC .... 548/469, 491, 509, 510, 453, 467, 362.5, 548/361.5, 361.1, 360.5, 259, 260, 261; 514/418, 415, 412, 414, 421, 406, 407
See application file for complete search history.

(56) References Cited

U.S. PATENT DOCUMENTS 9,540,362 B2 * 1/2017 Paek .................... C07D 413/04
2009/0111859 A1 4/2009 Brown et al.
(Continued)

FOREIGN PATENT DOCUMENTS

EP 1559422 A1 8/2005
EP 1 630 152 A1 3/2006
(Continued)

OTHER PUBLICATIONS

International Search Report, issued in PCT/KR2013/010135, dated Feb. 28, 2014.
(Continued)

*Primary Examiner* — Matthew P Coughlin
*Assistant Examiner* — Sagar Patel
(74) *Attorney, Agent, or Firm* — Birch, Stewart, Kolasch & Birch, LLP

(57) ABSTRACT

The present invention relates to a novel compound having GPR40 receptor agonist activity that promotes insulin secretion and inhibits blood sugar rise after glucose loading, and is thereby useful for the treatment of diabetes and complications thereof, the preparation method thereof and pharmaceutical composition containing them as an active ingredient.

11 Claims, No Drawings

(56) References Cited

U.S. PATENT DOCUMENTS

2010/0152165 A1 6/2010 Negoro et al.
2011/0313003 A1 12/2011 Shi et al.
2015/0376173 A1* 12/2015 Paek .................... C07D 413/04
                                                     514/210.18

FOREIGN PATENT DOCUMENTS

| EP | 1726580 A1 | 11/2006 | | |
|----|------------|---------|---|---|
| JP | 2010-524932 A | 7/2010 | | |
| WO | WO 99/11255 A1 | 3/1999 | | |
| WO | WO 2004/063155 A1 | 7/2004 | | |
| WO | WO 2004/091604 A1 | 10/2004 | | |
| WO | WO 2005/066136 A1 | 7/2005 | | |
| WO | WO 2005/086661 A2 | 9/2005 | | |
| WO | WO 2005086661 A2 * | 9/2005 | ........... | C07D 227/24 |
| WO | WO 2008/066097 A1 | 6/2008 | | |
| WO | WO 2010/080537 A1 | 7/2010 | | |
| WO | WO 2011/159297 A1 | 12/2011 | | |

OTHER PUBLICATIONS

Chen, C.Y. et al, "A Divergent and Selective Synthesis of Isomeric Benzoxazoles from a Single N—Cl Imine," Organic Letters, 2011, vol. 13, No. 23, pp. 6300-6303.

Hegde, V. et al, "Synthesis of novel molecular probes inspired by harringtonolide," Org. Biomol. Chem., 2011, vol. 9, pp. 4570-4579.

Houze, J.B. et al, "AMG 837: A potent, orally bioavailable GPR40 agonist," Bioorganic & Medical Chemistry Letters, 2012, vol. 22, pp. 1267-1270.

Ohta, Y. et al, "Construction of Nitrogen Heterocycles Bearing an Aminomethyl Group by Copper-Catalyzed Domino Three-Component Coupling-Cyclization," J. Org. Chem., 2009, vol. 74, pp. 7052-7058.

Zhang, H.C. et al, "Synthesis of Trisubstituted Indoles on the Solid Phase via Palladium-Mediated Heteroannulation of Internal Alkynes," Tetrahedron Letters, 1997, vol. 38, No. 14, pp. 2439-2442.

Supplementary European Search Report for European Application No. 13852767, dated Mar. 24, 2016.

* cited by examiner

GPR40 RECEPTOR AGONIST, METHODS OF PREPARING THE SAME, AND PHARMACEUTICAL COMPOSITIONS CONTAINING THE SAME AS AN ACTIVE AGENT

TECHNICAL FIELD

The present invention relates to a novel compound having GPR40 receptor agonist activity that promotes insulin secretion and inhibits blood sugar rise after glucose loading, and is thereby useful for the treatment of diabetes and complications thereof, or pharmaceutically acceptable salts and isomers thereof, and the pharmaceutical compositions containing them.

BACKGROUND ART

Diabetes negatively impacts many people's health and induces various complications. Diabetes is divided into type 1 diabetes and type 2 diabetes. Type 1 diabetes is presented when insulin is not produced due to destruction of pancreatic cells. Type 2 is presented when insulin is not produced for other reasons or the body is not responding to insulin. Type 2 diabetes is found in 90% or more of diabetic patients.

Sulfonylureas (promoting insulin secretion from pancreatic cells), biguanide (suppressing glucose production in the liver), a-glucosidase inhibitor (inhibiting glucose absorption in the intestines), thiazolidine derivatives (TZDs) and the like are currently used for the treatment of diabetes. Incretin-related drugs such as DPPIV inhibitors or Exenatide have recently entered the market.

However, these agents have unwanted side effects such as hypoglycemia, liver failure, gastrointestinal disorders and weight gain, or weak hypoglycemic function or the disadvantage that they must be used as an injection. Therefore, research has been conducted for new therapies based on a new mechanism that is able to avoid the drawbacks and side effects of existing diabetes therapies.

Recently, an insulinotropic mechanism by free fatty acid was revealed more clearly through the study of GPR40 which is a G-protein-coupled receptor. GPR40 receptor is highly expressed in the pancreas, and it has been found that ligands for GPR40 receptor are saturated free fatty acids having 12-16 carbon atoms and unsaturated fatty acids having 18-22 carbon atoms. And it is confirmed that long-chain FFAs activate GPR40 receptor depending on blood glucose concentration, thereby stimulating insulin secretion from the beta cells of the pancreas via experiments that selectively inhibit the expression of GPR40 receptor in the pancreas using siRNA (small interfering RNA) technology and that measure how insulin secretion by blood glucose changes from beta cells of the pancreas in the presence of free fatty acids.

Accordingly, GPR40 agonists have a blood glucose concentration-dependent insulin-secretion stimulating activity, and thus are useful for the treatment and prevention of diabetes and complications thereof.

DISCLOSURE OF INVENTION

Technical Problem

The object of the present invention is to provide novel compounds of Formula (1) as GPR40 receptor agonists.

Another object of the present invention is to provide a method for preparing the compounds of Formula (1).

Still another object of the present invention is to provide a pharmaceutical composition for the prevention and treatment of diabetes and complications of diabetes, which comprises as active components the compounds of Formula (1), and a method for preparing the composition.

A still further object of the present invention is to provide a method for preventing and treating diabetes and complications of diabetes which uses the compounds of Formula (1) as active components.

Solution to Problem

The compound of the present invention is a GPR40 receptor agonist.

The present invention provides a compound of Formula (1), or pharmaceutically acceptable salts or isomers thereof.

[Formula (1)]

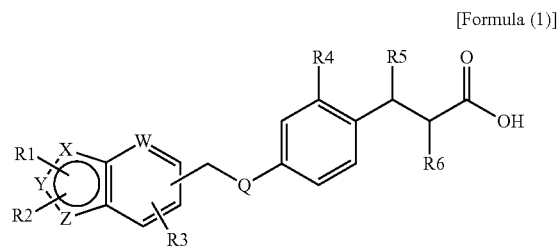

wherein,
X represents C or N,
Y represents C, N, C=O or C-halogen,
Z represents C, N or O,
Q represents O or NH,
W represents C, N, C-alkyl or C-halogen,
R1 represents H, alkyl, heteroalkyl, aryl, heterocycle, aryl-alkyl or heterocycle-alkyl,
R2 represents H, alkyl, heteroalkyl or halogen,
R3 represents H, alkyl or halogen,
R4 represents H, O, alkyl or halogen,
R5 represents H, alkyl, alkoxy, CN, heterocycle or C≡C-Me,
R4 and R5 can be connected together to form 5- or 6-membered ring,
R6 represents H or alkyl, and
R5 and R6 can be connected together to form 3-membered ring.

In the compound of Formula (1) according to the present invention,
the structure of

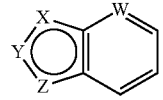

is preferably selected from the following structures:

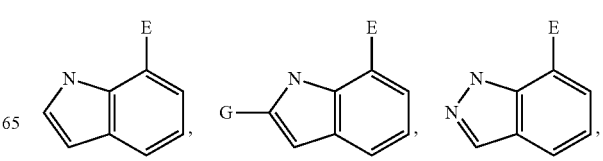

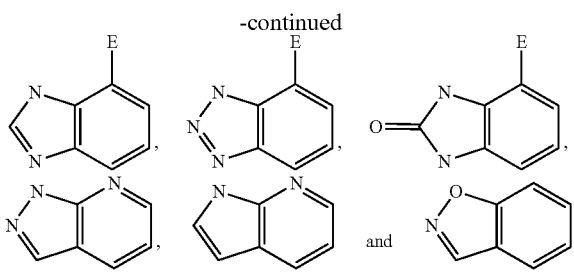

wherein, E represents H, alkyl or halogen, and G represents alkyl, heteroalkyl or halogen.

Upon defining the compounds of Formula (1) herein, concepts defined as follows are used. Unless otherwise indicated, the following definitions are also applicable to the terms being used as part of a larger group, or individually throughout this specification.

The term "alkyl," when used alone or in combination with "heteroalkyl," means a linear, branched or cyclic hydrocarbon radical, preferably a linear or branched saturated hydrocarbon radical having from 1 to 6 carbon atoms; or a cyclic saturated hydrocarbon radical having from 3 to 6 carbon atoms; or a cyclic saturated hydrocarbon radical having from from 3 to 6 carbon atoms bonded to a linear and/or branched saturated hydrocarbon radical having from 1 to 6 carbon atoms. Each carbon atom can be optionally substituted with one or more cyano, hydroxy, $C_{1-6}$ alkoxy, oxo, halogen, or sulfonyl unsubstituted or substituted with alkyl and the like.

The term "alkoxy" means —O-alkyl, and alkyl is as defined above.

The term "heteroalkyl" means an alkyl comprising one or more, preferably one to four heteroatoms selected from N, O and S.

The term "aryl" means an aromatic group including phenyl, naphthyl and the like, and preferably means 6- to 10-membered aromatic groups. Aryl may be optionally substituted with one or more halogen, alkyl, haloalkyl, alkoxy, or sulfonyl unsubstituted or substituted with alkyl and the like.

The term "heterocycle" refers to a saturated, partially saturated or aromatic 3- to 14-membered ring containing 1 to 4 heteroatoms selected from N, O and S, which can optionally fused with benzo or $C_{3-8}$ cycloalkyl. Examples of monocyclic heterocycle include oxetane, tetrahydrofuran, piperidine, morpholine, thiomorpholine, pyrrolidine, imidazolidine, piperazine, thiazole, oxazole, thiophene, furane, pyrrole, imidazole, isoxazole, pyrazole, triazole, thiadiazole, tetrazole, oxadiazole, pyridine, pyridazine, pyrimidine, pyrazine and the like, but is not limited thereto. Examples of bicyclic heterocycle include indole, indazole, azaindole, benzothiophene, benzofuran, benzimidazole, benzoxazole, benzisoxazole, benzothiazole, benzothiadiazole, benzotriazole, quinoline, isoquinoline, purine, furopyridine and the like, but is not limited thereto. Heterocycle may be optionally substituted with alkyl, halogen, heteroalkyl and the like.

The term "halo(gen)" refers to a substituent selected from the group consisting of fluoro, chloro, bromo or iodo.

The terms and abbreviations used herein have their original meanings unless defined otherwise.

In the following, for convenience, unless indicated otherwise, the term "the compounds of Formula (1)" is used to mean all the compounds of Formula (1), including the pharmaceutical salts and isomers thereof.

The compounds according to the present invention can form pharmaceutically acceptable salts thereof. The pharmaceutically acceptable salts comprise acid-addition salts formed by acids containing pharmaceutically acceptable anions and forming nontoxic acid-addition salts—for example, inorganic acids such as hydrochloric acid, sulfuric acid, nitric acid, phosphoric acid, hydrobromic acid, hydroiodic acid and the like, organic carbonic acids such as tartaric acid, formic acid, citric acid, acetic acid, trichloroacetic acid, trifluoroacetic acid, gluconic acid, benzoic acid, lactic acid, fumaric acid, maleic acid or sulfonic acids such as methanesulfonic acid, benzene-sulfonic acid, p-toluenesulfonic acid or naphthalenesulfonic acid, preferably acid-addition salts formed by sulfuric acid, methanesulfonic acid or hydrogen halide acid and the like. The compounds of Formula (1) according to the present invention can be converted into their salts by conventional methods.

Meanwhile, since the compounds according to the present invention can have an asymmetric carbon center, they can exist as R- or S-isomers, racemic mixtures, diastereoisomer mixtures or each diastereoisomer, all of which are within the scope of the present invention. That is, if the asymmetric carbon(s) is included in the structure of Formula (1), as long as the direction is not described separately, it must be understood that all stereoisomers are included.

Representative compounds of Formula 1 according to the present invention include, but are not limited to, the following compounds:

3-{4-[(1-isopropyl-1H-indol-6-ylmethyl)-amino-phenyl}-propanoic acid;
3-{4-[(1-benzyl-1H-indol-6-ylmethyl)-amino]-phenyl}-propanoic acid;
3-{4-[(1-thiophen-3-yl-1H-indol-6-ylmethyl)-amino]-phenyl}-propanoic acid;
3-{4-[(1-phenethyl-1H-indol-6-ylmethyl)-amino]-phenyl}-propanoic acid;
3-{4-[(1-benzyl-3-chloro-1H-indol-6-ylmethyl)-amino]-phenyl}-propanoic acid;
3-{4-[(1-benzyl-2,3-dichloro-1H-indol-6-ylmethyl)-amino]-phenyl}-propanoic acid;
3-{4-[(1-benzyl-7-chloro-1H-indol-6-ylmethyl)-amino]-phenyl}-propanoic acid;
3-{4-[(7-chloro-1-thiophen-3-yl-1H-indol-6-ylmethyl)-amino]-phenyl}-propanoic acid;
3-(4-{[7-chloro-1-(4-fluoro-phenyl)-1H-indol-6-ylmethyl]-amino}-phenyl)-propanoic acid;
3-(4-{[1-(4-fluoro-phenyl)-1H-indol-6-ylmethyl]-amino}-phenyl)-propanoic acid;
3-{4-[(7-chloro-1-cyclohexylmethyl-1H-indol-6-ylmethyl)-amino]-phenyl}-propanoic acid;
[6-(1-benzyl-3-chloro-1H-indol-6-ylmethoxy)-2,3-dihydro-benzofuran-3-yl]-acetic acid;
3-[4-(1-thiophen-3-yl-1H-indol-6-ylmethoxy)-phenyl]-propanoic acid;
3-{4-[1-(4-fluoro-phenyl)-7-methyl-1H-indol-6-ylmethoxy]-phenyl}-propanoic acid;
3-[4-(1-benzyl-7-methyl-1H-indol-6-ylmethoxy)-phenyl]-propanoic acid;
3-[4-(7-methyl-1-thiophen-3-yl-1H-indol-6-ylmethoxy)-phenyl]-propanoic acid;
3-{4-[1-(4-fluoro-2-methyl-phenyl)-1H-indol-6-ylmethoxy]-phenyl}-propanoic acid;
3-[4-(1-benzyl-7-chloro-1H-indol-6-ylmethoxy)-phenyl]-propanoic acid;
3-[4-(1-cyclohexylmethyl-1H-indol-6-ylmethoxy)-phenyl]-propanoic acid;
3-[4-(3-benzyl-1-methyl-1H-indol-5-ylmethoxy)-phenyl]-propanoic acid;

3-[4-(1-methyl-3-o-tolyl-1H-indol-5-ylmethoxy)-phenyl]-propanoic acid;
3-{4-[3-chloro-1-(4-fluoro-2-methyl-phenyl)-1H-indol-6-ylmethoxy]-phenyl}-propanoic acid;
3-{4-[5-fluoro-1-(4-fluoro-2-methyl-phenyl)-1H-indol-6-ylmethoxy]-phenyl}-propanoic acid;
{6-[1-(4-fluoro-2-methyl-phenyl)-1H-indol-6-ylmethoxy]-2,3-dihydro-benzofuran-3-yl}-acetic acid;
(S)-3-[4-(1-benzyl-7-methyl-1H-indol-6-ylmethoxy)-phenyl]-hex-4-ynoic acid;
(S)-3-{4-[1-(4-fluoro-2-methyl-phenyl)-1H-indol-6-ylmethoxy]-phenyl}-hex-4-ynoic acid;
(S)-3-{4-[1-(4-methanesulfonyl-benzyl)-7-methyl-1H-indol-6-ylmethoxy]-phenyl}-hex-4-ynoic acid;
(S)-3-{4-[1-(4-methoxy-benzyl)-7-methyl-1H-indol-6-ylmethoxy]-phenyl}-hex-4-ynoic acid;
(S)-3-{4-[7-methyl-1-(4-trifluoromethyl-benzyl)-1H-indol-6-ylmethoxy]-phenyl}-hex-4-ynoic acid;
(S)-3-{4-[1-(3-methoxymethyl-benzyl)-7-methyl-1H-indol-6-ylmethoxy]-phenyl}-hex-4-ynoic acid;
(S)-3-[4-(1-benzyl-1H-indol-4-ylmethoxy)-phenyl]-hex-4-ynoic acid;
(S)-3-{4-[1-(4-fluoro-2-methyl-phenyl)-1H-indol-4-ylmethoxy]-phenyl}-hex-4-ynoic acid;
(S)-3-{4-[1-(2,6-difluoro-benzyl)-7-methyl-1H-indol-6-ylmethoxy]-phenyl}-hex-4-ynoic acid;
(S)-3-{4-[1-benzyl-2-(2-methoxy-ethyl)-7-methyl-1H-indol-6-ylmethoxy]-phenyl}-hex-4-ynoic acid;
(S)-3-{4-[1-(3-methanesulfonylmethyl-benzyl)-7-methyl-1H-indol-6-ylmethoxy]-phenyl}-hex-4-ynoic acid;
(S)-3-{4-[7-methyl-1-(2-methyl-benzyl)-1H-indol-6-ylmethoxy]-phenyl}-hex-4-ynoic acid;
(S)-3-{4-[1-(2-fluoro-benzyl)-7-methyl-1H-indol-6-ylmethoxy]-phenyl}-hex-4-ynoic acid;
(S)-3-{4-[1-(2-chloro-benzyl)-7-methyl-1H-indol-6-ylmethoxy]-phenyl}-hex-4-ynoic acid;
(S)-3-{4-[1-(2,6-dimethyl-benzyl)-7-methyl-1H-indol-6-ylmethoxy]-phenyl}-hex-4-ynoic acid;
(S)-3-[4-(1-benzyl-7-chloro-1H-indol-6-ylmethoxy)-phenyl]-hex-4-ynoic acid;
(S)-3-[4-(1-benzyl-5-fluoro-1H-indol-6-ylmethoxy)-phenyl]-hex-4-ynoic acid;
(S)-3-{4-[1-(3-fluoro-benzyl)-7-methyl-1H-indol-6-ylmethoxy]-phenyl}-hex-4-ynoic acid;
(S)-3-{4-[7-methyl-1-(3-trifluoromethyl-benzyl)-1H-indol-6-ylmethoxy]-phenyl}-hex-4-ynoic acid;
(S)-3-{4-[7-methyl-1-(5-methyl-pyrazin-2-ylmethyl)-1H-indol-6-ylmethoxy]-phenyl}-hex-4-ynoic acid;
(S)-3-{4-[1-(4-methanesulfonylmethyl-benzyl)-7-methyl-1H-indol-6-ylmethoxy]-phenyl}-hex-4-ynoic acid;
(S)-3-{4-[1-(6-chloro-pyridin-3-ylmethyl)-7-methyl-1H-indol-6-ylmethoxy]-phenyl}-hex-4-ynoic acid;
(S)-3-[4-(2-benzyl-2H-indazol-4-ylmethoxy)-phenyl]-hex-4-ynoic acid;
(S)-3-[4-(1-benzyl-1H-indazol-4-ylmethoxy)-phenyl]-hex-4-ynoic acid;
(S)-3-[4-(1-benzyl-5-fluoro-7-methyl-1H-indol-6-ylmethoxy)-phenyl]-hex-4-ynoic acid;
(S)-3-{4-[1-(4-fluoro-benzyl)-7-methyl-1H-indol-6-ylmethoxy]-phenyl}-hex-4-ynoic acid;
(S)-3-{4-[1-(3,4-difluoro-benzyl)-7-methyl-1H-indol-6-ylmethoxy]-phenyl}-hex-4-ynoic acid;
(S)-3-{4-[1-(3,5-difluoro-benzyl)-7-methyl-1H-indol-6-ylmethoxy]-phenyl}-hex-4-ynoic acid;
(S)-3-{4-[1-(2,4-difluoro-benzyl)-7-methyl-1H-indol-6-ylmethoxy]-phenyl}-hex-4-ynoic acid;
3-[4-(1-benzyl-1H-indol-4-ylmethoxy)-2-fluoro-phenyl]-propanoic acid;
3-[4-(1-benzyl-7-methyl-1H-indol-6-ylmethoxy)-2-fluoro-phenyl]-propanoic acid;
(S)-3-[4-(7-methyl-1-thiazol-4-ylmethyl-1H-indol-6-ylmethoxy]-phenyl}-hex-4-ynoic acid;
(S)-3-{4-[7-methyl-1-(2-methyl-thiazol-4-ylmethyl)-1H-indol-6-ylmethoxy]-phenyl}-hex-4-ynoic acid;
(S)-3-[4-(2-benzyl-2H-indazol-6-ylmethoxy)-phenyl]-hex-4-ynoic acid;
(S)-3-[4-(1-benzyl-1H-indazol-6-ylmethoxy)-phenyl]-hex-4-ynoic acid;
(S)-3-[4-(7-methyl-1-pyrazin-2-ylmethyl-1H-indol-6-ylmethoxy)-phenyl]-hex-4-ynoic acid;
(S)-3-[4-(7-methyl-1-pyrimidin-4-ylmethyl-1H-indol-6-ylmethoxy)-phenyl]-hex-4-ynoic acid;
(S)-3-[4-(1-benzyl-3-fluoro-7-methyl-1H-indol-6-ylmethoxy)-phenyl]-hex-4-ynoic acid;
(S)-3-{4-[7-methyl-1-(1-methyl-1H-pyrazol-4-ylmethyl)-1H-indol-6-ylmethoxy)-phenyl]-hex-4-ynoic acid;
(S)-3-[4-(7-methyl-1-pyrimidin-2-ylmethyl-1H-indol-6-ylmethoxy)-phenyl]-hex-4-ynoic acid;
3-[4-(1-benzyl-1H-indazol-6-ylmethoxy)-phenyl]-3-(4,5-dihydro-isoxazol-3-yl)-propanoic acid;
(S)-3-{4-[1-(4-fluoro-benzyl)-1H-indazol-6-ylmethoxy]-phenyl}-hex-4-ynoic acid;
(S)-3-{4-[2-(4-fluoro-benzyl)-2H-indazol-6-ylmethoxy]-phenyl}-hex-4-ynoic acid;
(S)-3-[4-(1-pyrimidin-2-ylmethyl-1H-indazol-6-ylmethoxy)-phenyl}-hex-4-ynoic acid;
(S)-3-[4-(2-pyrimidin-2-ylmethyl-2H-indazol-6-ylmethoxy]-phenyl}-hex-4-ynoic acid;
(S)-3-[4-(1-pyrazin-2-ylmethyl-1H-indazol-6-ylmethoxy]-phenyl}-hex-4-ynoic acid;
(S)-3-{4-[1-(4-fluoro-benzyl)-1H-indazol-4-ylmethoxy]-phenyl}-hex-4-ynoic acid;
(S)-3-{4-[2-(4-fluoro-benzyl)-2H-indazol-4-ylmethoxy]-phenyl}-hex-4-ynoic acid;
(S)-3-{4-[1-(5-methyl-pyrazin-2-ylmethyl)-1H-indazol-6-ylmethoxy]-phenyl}-hex-4-ynoic acid;
(S)-3-{4-[2-(5-methyl-pyrazin-2-ylmethyl)-2H-indazol-6-ylmethoxy]-phenyl}-hex-4-ynoic acid;
(S)-3-[4-(1-pyrimidin-4-ylmethyl-1H-indazol-6-ylmethoxy)-phenyl]-hex-4-ynoic acid;
(S)-3-[4-(2-pyrimidin-4-ylmethyl-2H-indazol-6-ylmethoxy]-phenyl}-hex-4-ynoic acid;
(S)-3-{4-[1-(5-methyl-pyrazin-2-ylmethyl)-1H-indazol-4-ylmethoxy]-phenyl}-hex-4-ynoic acid;
(S)-3-{4-[2-(5-methyl-pyrazin-2-ylmethyl)-2H-indazol-4-ylmethoxy]-phenyl}-hex-4-ynoic acid;
(S)-3-[4-(1-pyridin-3-ylmethyl-1H-indazol-6-ylmethoxy)-phenyl]-hex-4-ynoic acid;
(S)-3-[4-(2-pyridin-3-ylmethyl-2H-indazol-6-ylmethoxy)-phenyl]-hex-4-ynoic acid;
(S)-3-{4-[7-methyl-1-(6-methyl-pyridin-3-ylmethyl)-1H-indol-6-ylmethoxy]-phenyl}-hex-4-ynoic acid;
(S)-3-{4-[1-(1-methyl-1H-pyrazol-4-ylmethyl)-1H-indazol-6-ylmethoxy]-phenyl}-hex-4-ynoic acid;
(S)-3-[4-(1-benzyl-7-methyl-1H-indol-6-ylmethoxy)-phenyl]-3-isoxazol-3-yl-propanoic acid;
(S)-3-{4-[1-(4-fluoro-benzyl)-7-methyl-1H-indol-6-ylmethoxy]-phenyl}-3-isoxazol-3-yl-propanoic acid;
(S)-3-[4-(1-benzyl-1H-indazol-6-ylmethoxy)-phenyl]-3-isoxazol-3-yl-propanoic acid;
(S)-3-{4-[1-(4-fluoro-benzyl)-1H-indazol-6-ylmethoxy]-phenyl}-3-isoxazol-3-yl-propanoic acid;

(S)-3-[4-(1-isobutyl-1H-indazol-6-ylmethoxy)-phenyl]-3-isoxazol-3-yl-propanoic acid;
(S)-3-[4-(2-isobutyl-2H-indazol-6-ylmethoxy)-phenyl]-3-isoxazol-3-yl-propanoic acid;
(S)-3-isoxazol-3-yl-3-[4-(7-methyl-1-pyrazin-2-ylmethyl-1H-indol-6-ylmethoxy)-phenyl]-propanoic acid;
(S)-3-[4-(1-benzyl-1H-pyrrolo[2,3-b]pyridin-6-ylmethoxy)-phenyl]-hex-4-ynoic acid;
(S)-3-[4-(1-benzyl-1H-pyrrolo[2,3-b]pyridin-6-ylmethoxy)-phenyl]-3-isoxazol-3-yl-propanoic acid;
(S)-3-isoxazol-3-yl-3-{4-[7-methyl-1-(5-methyl-pyrazin-2-ylmethyl)-1H-indol-6-ylmethoxy]-phenyl}-propanoic acid;
(S)-3-{4-[1-(6-methyl-pyridin-3-ylmethyl)-1H-indazol-6-ylmethoxy]-phenyl}-hex-4-ynoic acid
(S)-3-[4-(1-benzyl-1H-indazol-4-ylmethoxy)-phenyl]-3-isoxazol-3-yl-propanoic acid;
(S)-3-{4-[1-(4-fluoro-benzyl)-1H-pyrrolo[2,3-b]pyridin-6-ylmethoxy]-phenyl}-3-isoxazol-3-yl-propanoic acid;
(S)-3-[4-(1-isopropyl-1H-indazol-6-ylmethoxy)-phenyl]-3-isoxazol-3-yl-propanoic acid;
(S)-3-[4-(1-cyclopropylmethyl-1H-indazol-6-ylmethoxy)-phenyl]-3-isoxazol-3-yl-propanoic acid;
(S)-3-[4-(1-isobutyl-1H-pyrrolo[2,3-b]pyridin-6-ylmethoxy)-phenyl]-3-isoxazol-3-yl-propanoic acid;
(S)-3-[4-(2-isopropyl-2H-indazol-6-ylmethoxy)-phenyl]-3-isoxazol-3-yl-propanoic acid;
[6-(1-isopropyl-1H-indazol-6-ylmethoxy)-2,3-dihydro-benzofuran-3-yl]-acetic acid;
(S)-3-isoxazol-3-yl-3-[4-(1-methyl-1H-indazol-6-ylmethoxy)-phenyl]-propanoic acid;
(S)-3-[4-(1H-indazol-6-ylmethoxy)-phenyl]-3-isoxazol-3-yl-propanoic acid;
(S)-3-[4-(1-cyclopentylmethyl-1H-indazol-6-ylmethoxy)-phenyl]-3-isoxazol-3-yl-propanoic acid;
(S)-3-isoxazol-3-yl-3-[4-(1-pyrazin-2-ylmethyl-1H-pyrrolo[2,3-b]pyridin-6-ylmethoxy)-phenyl]-propanoic acid;
[6-(1-benzyl-1H-indazol-6-ylmethoxy)-2,3-dihydro-benzofuran-3-yl]-acetic acid;
3-[4-(1-benzyl-1H-indazol-6-ylmethoxy)-2-fluoro-phenyl]-propanoic acid;
3-[4-(1-cyclopentylmethyl-1H-indazol-6-ylmethoxy)-2-fluoro-phenyl]-propanoic acid;
[6-(1-cyclopentylmethyl-1H-indazol-6-ylmethoxy)-2,3-dihydro-benzofuran-3-yl]-acetic acid;
[5-(1-benzyl-1H-indazol-6-ylmethoxy)-indan-1-yl]-acetic acid;
[6-(1-benzyl-1H-indazol-6-ylmethoxy)-1,2,3,4-tetrahydro-naphthalen-1-yl]-acetic acid;
(S)-3-[4-(1-benzyl-1H-indazol-5-ylmethoxy)-phenyl]-hex-4-ynoic acid;
(S)-3-[4-(2-benzyl-2H-indazol-5-ylmethoxy)-phenyl]-hex-4-ynoic acid;
[6-(2-benzyl-2H-indazol-6-ylmethoxy)-2,3-dihydro-benzofuran-3-yl]-acetic acid;
(S)-3-[4-(1-isobutyl-1H-indazol-6-ylmethoxy)-phenyl]-hex-4-ynoic acid;
(S)-3-[4-(1-isobutyl-1H-pyrrolo[2,3-b]pyridin-6-ylmethoxy)-phenyl]-hex-4-ynoic acid;
(S)-3-[4-(1-isopropyl-1H-indazol-5-ylmethoxy)-phenyl]-hex-4-ynoic acid;
3-[4-(1-benzyl-1H-indazol-6-ylmethoxy)-phenyl]-butyric acid;
[5-(1-benzyl-1H-indazol-5-ylmethoxy)-indan-1-yl]-acetic acid;
[6-(1-benzyl-1H-indazol-5-ylmethoxy)-1,2,3,4-tetrahydro-naphthalen-1-yl]-acetic acid;
[7-(1-benzyl-1H-indazol-5-ylmethoxy)-chroman-4-yl]-acetic acid;
[6-(1-benzyl-1H-pyrrolo[2,3-b]pyridin-6-ylmethoxy)-2,3-dihydro-benzofuran-3-yl]-acetic acid;
(S)-3-[4-(1-benzyl-5-fluoro-1H-indazol-6-ylmethoxy)-phenyl]-hex-4-ynoic acid;
(S)-3-[4-(1-benzyl-1H-indol-5-ylmethoxy)-phenyl]-hex-4-ynoic acid;
(S)-3-[4-(1-benzyl-1H-benzotriazol-5-ylmethoxy)-phenyl]-hex-4-ynoic acid;
(S)-3-[4-(1-benzyl-1H-benzoimidazol-5-ylmethoxy)-phenyl]-hex-4-ynoic acid;
(S)-3-[4-(1-benzyl-7-methyl-1H-indazol-5-ylmethoxy)-phenyl]-hex-4-ynoic acid;
(S)-3-[4-(2-benzyl-7-methyl-2H-indazol-5-ylmethoxy)-phenyl]-hex-4-ynoic acid;
[6-(1-benzyl-7-methyl-1H-indazol-5-ylmethoxy)-2,3-dihydro-benzofuran-3-yl]-acetic acid;
[6-(1-benzyl-7-methyl-1H-indazol-5-ylmethoxy)-chroman-4-yl]-acetic acid;
(S)-3-[4-(1-isobutyl-7-methyl-1H-indazol-5-ylmethoxy)-phenyl]-hex-4-ynoic acid;
[7-(1-isobutyl-7-methyl-1H-indazol-5-ylmethoxy)-chroman-4-yl]-acetic acid;
(S)-3-[4-(1-isobutyl-1H-indazol-5-ylmethoxy)-phenyl]-hex-4-ynoic acid;
[7-(1-isobutyl-1H-indazol-5-ylmethoxy)-chroman-4-yl]-acetic acid;
(S)-3-[4-(1-phenethyl-1H-indazol-5-ylmethoxy)-phenyl]-hex-4-ynoic acid;
[7-(1-phenethyl-1H-indazol-5-ylmethoxy)-chroman-4-yl]-acetic acid;
(S)-3-{4-[1-(3-methyl-butyl)-1H-indazol-5-ylmethoxy]-phenyl}-hex-4-ynoic acid;
7-[1-(3-methyl-butyl)-1H-indazol-5-ylmethoxy]-chroman-4-yl}-acetic acid;
(S)-3-[4-(1-cyclohexylmethyl-1H-indazol-5-ylmethoxy)-phenyl]-hex-4-ynoic acid;
[7-(1-cyclohexylmethyl-1H-indazol-5-ylmethoxy)-chroman-4-yl]-acetic acid;
(S)-3-[4-(2-isobutyl-7-methyl-2H-indazol-5-ylmethoxy)-phenyl]-hex-4-ynoic acid;
(S)-3-[4-(1-pyridine-2-ylmethyl-1H-indazol-5-ylmethoxy)-phenyl]-hex-4-ynoic acid;
[7-(1-pyridine-2-ylmethyl-1H-indazol-5-ylmethoxy)-chroman-4-yl]-acetic acid;
(S)-3-[4-(1-benzyl-1H-pyrrolo[2,3-b]pyridin-5-ylmethoxy)-phenyl]-hex-4-ynoic acid;
(S)-3-[4-(1-isobutyl-1H-pyrrolo[2,3-b]pyridin-5-ylmethoxy)-phenyl]-hex-4-ynoic acid;
[7-(1-benzyl-7-methyl-1H-indol-6-ylmethoxy)-chroman-4-yl]-acetic acid;
[7-(2-benzyl-7-methyl-2H-indazol-5-ylmethoxy)-chroman-4-yl]-acetic acid;
(S)-3-[4-(1-pyridin-3-ylmethyl-1H-indazol-5-ylmethoxy)-phenyl]-hex-4-ynoic acid;
[7-(1-pyridin-3-ylmethyl-1H-indazol-5-ylmethoxy)-chroman-4-yl]-acetic acid;
7-[1-(2-ethoxy-ethyl)-1H-indazol-5-ylmethoxy]-chroman-4-yl}-acetic acid;
(S)-3-[4-(5-fluoro-1-isobutyl-1H-indazol-6-ylmethoxy)-phenyl]-hex-4-ynoic acid;
(S)-3-{4-[1-(tetrahydrofuran-2-ylmethyl)-1H-indazol-5-ylmethoxy]-phenyl}-hex-4-ynoic acid;
(S)-3-{4-[1-(3-methanesulfonyl-propyl)-1H-indazol-5-ylmethoxy]-phenyl}-hex-4-ynoic acid;

(S)-3-{4-[1-(tetrahydrofuran-3-ylmethyl)-1H-indazol-5-yl-methoxy]-phenyl}-hex-4-ynoic acid;
(S)-3-{4-[2-(tetrahydrofuran-3-ylmethyl)-2H-indazol-5-yl-methoxy]-phenyl}-hex-4-ynoic acid;
3-[4-(1-benzyl-1H-indazol-5-ylmethoxy)-phenyl]-3-methoxy-propanoic acid;
(S)-3-[4-(1-isobutyl-1H-pyrazolo[3,4-b]pyridin-5-yl-methoxy)-phenyl]-hex-4-ynoic acid;
(S)-3-{4-[1-(2-ethoxy-ethyl)-1H-indazol-5-ylmethoxy]-phenyl}-hex-4-ynoic acid;
3-[4-(1-benzyl-1H-indazol-5-ylmethoxy)-phenyl]-butyric acid;
3-[4-(1-benzyl-1H-indazol-5-ylmethoxy)-phenyl]-pentanoic acid;
(S)-3-{4-[2-(2-ethoxy-ethyl)-2H-indazol-5-ylmethoxy]-phenyl}-hex-4-ynoic acid;
(S)-3-[4-(1-benzyl-3-methyl-2-oxo-2,3-dihydro-1H-benzoimidazol-5-ylmethoxy)-phenyl]-hex-4-ynoic acid;
3-[4-(1-benzyl-1H-indazol-5-ylmethoxy)-phenyl]-3-cyanopropanoic acid;
(S)-3-[4-(1-cyclopentylmethyl-1H-indazol-5-ylmethoxy)-phenyl]-hex-4-ynoic acid;
(S)-3-[4-(1-cyclopentyl-1H-indazol-5-ylmethoxy)-phenyl]-hex-4-ynoic acid;
(S)-3-[4-(1-cyclopropylmethyl-1H-indazol-5-ylmethoxy)-phenyl]-hex-4-ynoic acid;
(S)-3-[4-(3-isobutyl-3H-benzotriazol-5-ylmethoxy)-phenyl]-hex-4-ynoic acid;
2-[4-(1-benzyl-1H-indazol-6-ylmethoxy)-phenyl]-cyclopropanecarboxylic acid;
(S)-3-[4-(1-isobutyl-7-methyl-1H-indazol-5-ylmethoxy)-phenyl]-hex-4-ynoic acid;
(S)-3-[4-(1-cyclopentylmethyl-7-methyl-1H-indazol-5-ylmethoxy)-phenyl]-hex-4-ynoic acid;
(S)-3-[4-(1-isobutyl-3-methyl-1H-indazol-5-ylmethoxy)-phenyl]-hex-4-ynoic acid;
(S)-3-[4-(1-cyclopentyl-7-methyl-1H-indazol-5-ylmethoxy)-phenyl]-hex-4-ynoic acid;
(S)-3-[4-(1-cyclopentyl-1H-indazol-6-ylmethoxy)-phenyl]-hex-4-ynoic acid;
(S)-3-[4-(1-cyclopentylmethyl-1H-indazol-6-ylmethoxy)-phenyl]-hex-4-ynoic acid;
(S)-3-{4-[1-(2-methanesulfonyl-ethyl)-1H-indazol-5-yl-methoxy]-phenyl}-hex-4-ynoic acid;
(S)-3-{4-[1-(2-methoxy-ethyl)-1H-indazol-5-ylmethoxy]-phenyl}-hex-4-ynoic acid;
(S)-3-{4-[1-(3-methoxy-propyl)-1H-indazol-5-ylmethoxy]-phenyl}-hex-4-ynoic acid;
(S)-3-{4-[1-(3-methyl-oxetan-3-ylmethyl)-1H-indazol-6-yl-methoxy]-phenyl}-hex-4-ynoic acid;
(S)-3-[4-(1-isobutyl-3-methyl-1H-indazol-6-ylmethoxy)-phenyl]-hex-4-ynoic acid;
(S)-3-[4-(2-isobutyl-3-methyl-2H-indazol-6-ylmethoxy)-phenyl]-hex-4-ynoic acid;
(S)-3-[4-(1-isopropyl-1H-indazol-6-ylmethoxy)-phenyl]-hex-4-ynoic acid;
(S)-3-[4-(3-isobutyl-benzo[d]isoxazol-5-ylmethoxy)-phenyl]-hex-4-ynoic acid;
(S)-3-{4-[1-(2,2-dimethyl-propyl)-1H-indazol-6-yl-methoxy]-phenyl}-hex-4-ynoic acid;
(S)-3-[4-(1-isobutyl-6-methyl-1H-indazol-5-ylmethoxy)-phenyl]-hex-4-ynoic acid;
(S)-3-[4-(1-isobutyl-1H-indazol-4-ylmethoxy)-phenyl]-hex-4-ynoic acid;
(S)-3-[4-(1-isopropyl-3-methyl-1H-indazol-6-ylmethoxy)-phenyl]-hex-4-ynoic acid;
(S)-3-[4-(3-isobutyl-1-methyl-1H-indazol-5-ylmethoxy)-phenyl]-hex-4-ynoic acid;
(S)-3-[4-(1-isopropyl-3-methyl-1H-indazol-5-ylmethoxy)-phenyl]-hex-4-ynoic acid;
(S)-3-[4-(1-isobutyl-3-methoxymethyl-1H-indazol-6-yl-methoxy)-phenyl]-hex-4-ynoic acid;
(S)-3-[4-(3-fluoro-1-isobutyl-1H-indazol-4-ylmethoxy)-phenyl]-hex-4-ynoic acid;
(S)-3-[4-(1-isopropyl-1H-indazol-4-ylmethoxy)-phenyl]-hex-4-ynoic acid;
(S)-3-[4-(3-ethoxymethyl-1-isobutyl-1H-indazol-6-yl-methoxy)-phenyl]-hex-4-ynoic acid;
(S)-3-[4-(3-chloro-1-isobutyl-1H-indazol-4-ylmethoxy)-phenyl]-hex-4-ynoic acid;
(S)-3-[4-(1-isobutyl-3-isopropoxymethyl-1H-indazol-6-yl-methoxy)-phenyl]-hex-4-ynoic acid;
(S)-3-[4-(3-fluoro-1-isopropyl-1H-indazol-4-ylmethoxy)-phenyl]-hex-4-ynoic acid;
(S)-3-[4-(3-bromo-1-methyl-1H-indazol-7-ylmethoxy)-phenyl]-hex-4-ynoic acid;
(S)-3-[4-(1-isobutyl-3-methoxymethyl-7-methyl-1H-indazol-6-ylmethoxy)-phenyl]-hex-4-ynoic acid;
(S)-3-[4-(1-butyl-1H-indazol-4-ylmethoxy)-phenyl]-hex-4-ynoic acid;
(S)-3-[4-(1-butyl-3-fluoro-1H-indazol-4-ylmethoxy)-phenyl]-hex-4-ynoic acid;
(S)-3-[4-(1-cyclopropylmethyl-1H-indazol-4-ylmethoxy)-phenyl]-hex-4-ynoic acid;
(S)-3-[4-(1-cyclopropylmethyl-3-fluoro-1H-indazol-4-yl-methoxy)-phenyl]-hex-4-ynoic acid;
(S)-3-[4-(3-chloro-1-methyl-1H-indazol-7-ylmethoxy)-methyl]-hex-4-ynoic acid;
(S)-3-[4-(1-isopropyl-3-pyrazol-1-ylmethyl-1H-indazol-6-ylmethoxy)-phenyl]-hex-4-ynoic acid;
(S)-3-[4-(3-fluoro-1-methyl-1H-indazol-7-ylmethoxy)-phenyl]-hex-4-ynoic acid;
(S)-3-[4-(1-isobutyl-1H-pyrrolo[2,3-b]pyridin-4-yl-methoxy)-phenyl]-hex-4-ynoic acid;
(S)-3-[4-(1-butyl-3-methyl-1H-indazol-4-ylmethoxy)-phenyl]-hex-4-ynoic acid;
(S)-3-[4-(3-butyl-1-methyl-1H-indazol-7-ylmethoxy)-phenyl]-hex-4-ynoic acid;
(S)-3-[4-(3-isobutyl-1-methyl-1H-indazol-7-ylmethoxy)-phenyl]-hex-4-ynoic acid;
(S)-3-[4-(1-isobutyl-7-methyl-1H-indazol-4-ylmethoxy)-phenyl]-hex-4-ynoic acid;
(S)-3-[4-(3-isopropyl-1-methyl-1H-indazol-7-ylmethoxy)-phenyl]-hex-4-ynoic acid;
(S)-3-[4-(1-methyl-3-propyl-1H-indazol-7-ylmethoxy)-phenyl]-hex-4-ynoic acid;
(S)-3-[4-(1-isobutyl-7-methyl-1H-indazol-6-ylmethoxy)-phenyl]-hex-4-ynoic acid;
(S)-3-[4-(1-isobutyl-3,7-dimethyl-1H-indazol-6-yl-methoxy)-phenyl]-hex-4-ynoic acid;
(S)-3-[4-(3-fluoro-1-isobutyl-7-methyl-1H-indazol-4-yl-methoxy)-phenyl]-hex-4-ynoic acid;
(S)-3-[4-(1-ethyl-3-fluoro-7-methyl-1H-indazol-6-yl-methoxy)-phenyl]-hex-4-ynoic acid;
(S)-3-[4-(1-isobutyl-7-methyl-3-morpholin-4-ylmethyl-1H-indazol-6-ylmethoxy)-phenyl]-hex-4-ynoic acid;
(S)-3-[4-(7-chloro-1-isobutyl-3-morpholin-4-ylmethyl-1H-indazol-6-ylmethoxy)-phenyl]-hex-4-ynoic acid;
(S)-3-[4-(1-isobutyl-7-methyl-3-pyrrolidin-1-ylmethyl-1H-indazol-6-ylmethoxy)-phenyl]-hex-4-ynoic acid;
(S)-3-[4-(1-isobutyl-7-methyl-3-piperidin-1-ylmethyl-1H-indazol-6-ylmethoxy)-phen yl]-hex-4-ynoic acid;

(S)-3-[4-(1-isobutyl-3-morpholin-4-ylmethyl-1H-indazol-6-ylmethoxy)-phenyl]-hex-4-ynoic acid;

(S)-3-[4-(1-isopropyl-7-methyl-1H-indazol-6-ylmethoxy)-phenyl]-hex-4-ynoic acid;

(S)-3-[4-(7-methyl-1-propyl-1H-indazol-6-ylmethoxy)-phenyl]-hex-4-ynoic acid;

(S)-3-[4-(3-fluoromethyl-1-isobutyl-7-methyl-1H-indazol-6-ylmethoxy)-phenyl]-hex-4-ynoic acid;

(S)-3-[4-(1-isopropyl-7-methyl-1H-indazol-4-ylmethoxy)-phenyl]-hex-4-ynoic acid;

(S)-3-[4-(1-isopropyl-1H-pyrrolo[2,3-b]pyridin-4-ylmethoxy)-phenyl]-hex-4-ynoic acid;

(S)-3-[4-(3-fluoro-1-isobutyl-1H-pyrrolo[2,3-b]pyridin-4-ylmethoxy)-phenyl]-hex-4-ynoic acid;

(S)-3-[4-(7-methyl-1-pyridin-3-ylmethyl-1H-indazol-6-ylmethoxy)-phenyl]-hex-4-ynoic acid;

(S)-3-{4-[3-(3,3-difluoro-piperidin-1-ylmethyl)-1-isobutyl-7-methyl-1H-indazol-6-yl methoxy]-phenyl}-hex-4-ynoic acid;

(S)-3-[4-(1-isobutyl-7-methyl-3-pyrazol-1-ylmethyl-1H-indazol-6-ylmethoxy)-phenyl]-hex-4-ynoic acid;

(S)-3-{4-[3-((S)-3-fluoro-pyrrolidin-1-ylmethyl)-1-isobutyl-7-methyl-1H-indazol-6-ylmethoxy]-phenyl}-hex-4-ynoic acid;

(S)-3-{4-[3-(3,3-difluoro-pyrrolidin-1-ylmethyl)-1-isobutyl-7-methyl-1H-indazol-6-ylmethoxy]-phenyl}-hex-4-ynoic acid;

(S)-3-{4-[3-(3,3-difluoro-pyrrolidin-1-ylmethyl)-1-isobutyl-1H-pyrrolo[2,3-b]pyridin-6-ylmethoxy]-phenyl}-hex-4-ynoic acid; and (S)-3-{4-[3-(3,3-difluoro-piperidin-1-ylmethyl)-1-isobutyl-1H-pyrrolo[2,3-b]pyridin-6-ylmethoxy]-phenyl}-hex-4-ynoic acid.

The present invention also provides a process for preparing a compound of Formula (1). Hereinafter, the method for preparing the compounds of Formula (1) is explained based on exemplary reaction schemes in order to illustrate the present invention. However, a person skilled in the art could prepare the compounds of Formula (1) by various methods based on the structure of Formula (1), and such methods should be interpreted as being within the scope of the present invention. That is, the compounds of Formula (1) may be prepared by the methods described herein or by combining various methods disclosed in the prior art, which should be interpreted as being within the scope of the present invention. In the following reaction schemes, unless indicated differently, all substituents are as previously defined above.

The compound of Formula (1) according to the present invention may be obtained via hydrolysis of ester groups using compound (2) as shown in Reaction Scheme 1. Compound (2) may be obtained via a coupling reaction of compound (3) and compound (4) or a coupling reaction of compound (5) and compound (6).

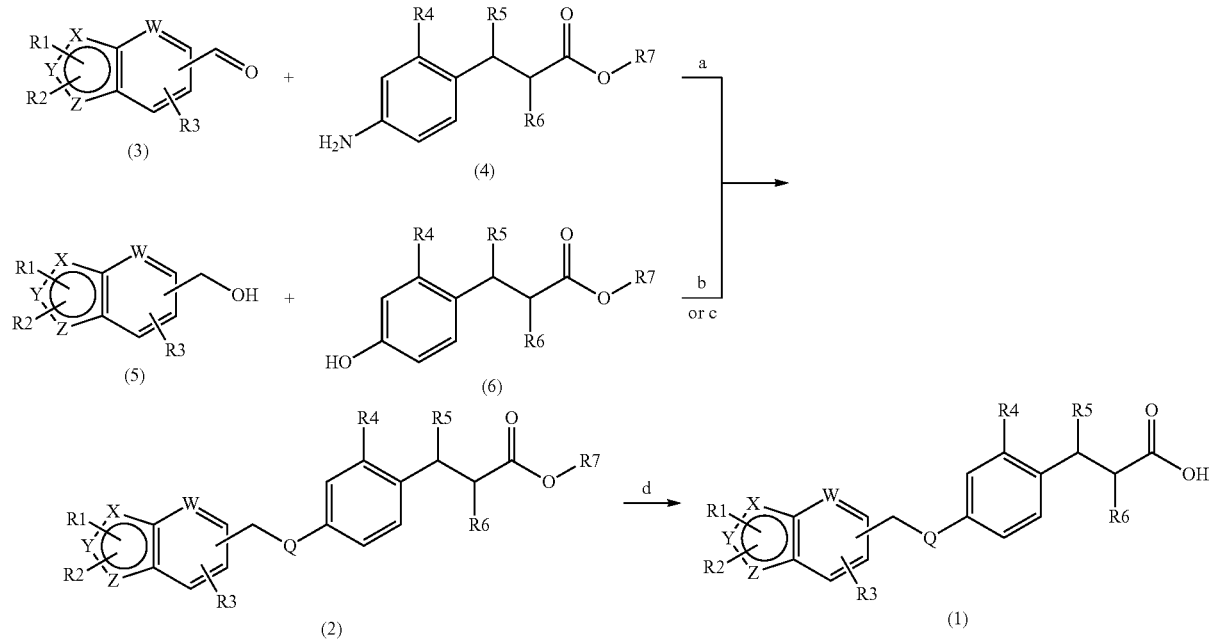

[Reaction Scheme 1]

In the above Reaction Scheme 1, a is a reducing agent such as sodium triacetoxyborohydride{NaBH(OAc)₃} and the like, b is a binding agent such as 1,1'-(azodicarbonyl)dipiperidine (ADD) and the like and a phosphine such as tributylphosphin (Bu₃P) and the like, c is a reagent providing a leaving group such as methanesulfonylchloride and the like; and a base such as metal carbonate (for example, potassium carbonate) and the like, d is a base such as metal hydroxide (for example, sodium hydroxide) and the like, R1~R6 are the same as defined in Formula (1), and R7 is H, or alkyl such as methyl or ethyl and the like.

Compounds of Formula (1) may be obtained by reacting compound (2) in a solvent under heating or at room temperature in the presence of a base. The base is preferably aqueous solution of sodium hydroxide or lithium hydroxide and the like. The solvent is preferably tetrahydrofuran, alcohols such as methanol, or mixtures thereof.

Compound (2) may be obtained via a reductive alkylation between the aldehyde group of compound (3) and amine group of compound (4) in a solvent using a reducing agent. The available reducing agent is sodium borohydride, sodium cyanoborohydride, sodium triacetoxyborohydride and the like. The solvent is preferably dichloroethane or chloroform.

Compound (2) can also be obtained via a coupling reaction between compound (5) and compound (6) under Mitsunobu condition. Mitsunobu condition is widely known in the art, there are numerous methods and reagents. Among them, binding reaction is included between the alcohol compound (5) and the phenol compound (6) using a phosphine such as tributylphosphin, triphenylphosphine and the like, and 1,1'-(azodicarbonyl)dipiperidine (ADD) or diethyl azodicarboxylate (DEAD) as a binding agent. The solvent is preferably toluene, tetrahydrofuran and the like. Alternatively, it can be obtained by binding the phenol compound (6) with compound (5) wherein the alcohol group is changed to a leaving group with the appropriate brominating agents, chlorinating agents or methanesulfonylation agents.

Compound (3) can be prepared by the method described in Reaction Scheme 2, and compound (4) is commercially available.

[Reaction Scheme 2]

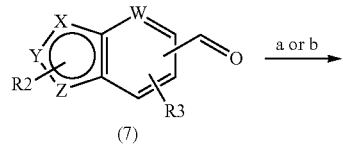

In the above Reaction Scheme 2,
a is an alkylation agent such as R1-OSO$_2$CH$_3$, R1-halogen and the like, and a base such as sodium hydride,
b is an arylating agent such as R1-halogen and the like, cyclohexane 1,2-diamine, potassium phosphate tribasic and copper iodide, and
R1~R3 are the same as defined in Formula (1).

Specifically, compound (3) may be obtained by the alkylation or arylation of compound (7). Compound (7) is a compound commercially available. Alkylation condition is well known in the art, and it is possible to obtain by reacting compound (7) with an alkylating agent having a leaving group such as a halogen or methanesulfonate in the presence of a base such as sodium hydride or potassium carbonate in a solvent. The solvent is preferably tetrahydrofuran, dimethylformamide or a mixture thereof. Arylation condition is well known in the art and comprises a reaction between compound (7) and aryl halide in the presence of cyclohexane 1,2-diamine, potassium phosphate tribasic and copper iodide. The solvent is preferably tetrahydrofuran or dioxane.

Compound (5) can be prepared by the method described in the following Reaction Schemes 3 and 4, and compound (6) may be prepared by known methods.

[Reaction Scheme 3]

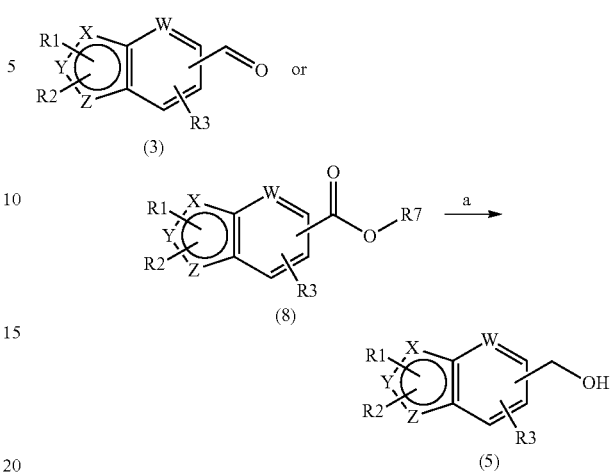

In the above Reaction Scheme 3,
a is a reducing agent such as sodium borohydride (NaBH$_4$), lithium borohydride (LiBH$_4$) or lithium aluminum hydride (LiAlH$_4$),
R1~R3 are the same as defined in Formula (1), and
R7 is H or alkyl such as methyl or ethyl and the like.

Specifically, compound (5) may be obtained by reduction of the aldehyde group of compound (3) or the ester group of compound (8) using a reducing agent. Sodium borohydride (NaBH$_4$), lithium borohydride (LiBH$_4$) or lithium aluminum hydride (LiAlH$_4$) and the like may be used as the reducing agent. Preferably, tetrahydrofuran may be used as the solvent. Compound (8) may be selected from compounds which can be prepared by the method described in the following Reaction Schemes 5 to 14.

[Reaction Scheme 4]

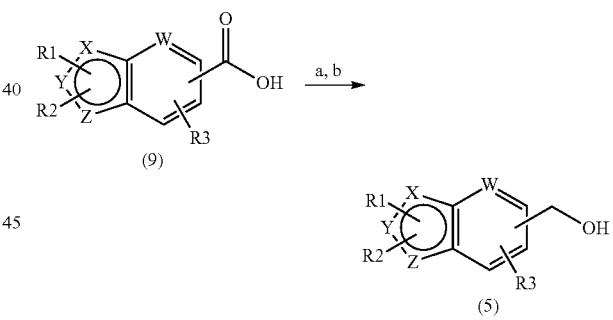

In the above Reaction Scheme 4,
a is alkylchloroformate,
b is a reducing agent such as sodium borohydride (NaBH$_4$) or lithium borohydride (LiBH$_4$), and
R1~R3 are the same as defined in Formula (1).

Specifically, compound (5) can be obtained by reacting the acid group of compound (9) with alkyl chloroformate in the presence of a base to prepare the anhydride group and then reducing it to alcohol groups using a reducing agent. The base is preferably triethylamine or N-methylmorpholine. The reducing agent is preferably sodium borohydride (NaBH$_4$) or lithium borohydride (LiBH$_4$). The solvent is preferably tetrahydrofuran. Compound (9) can be purchased or can be selected from compounds which can be prepared by the method described in the following Reaction Schemes 5 to 14.

Compounds (8) and (9) can be selected from compounds which can be prepared by the method described in the following Reaction Schemes 5 to 14.

[Reaction Scheme 5]

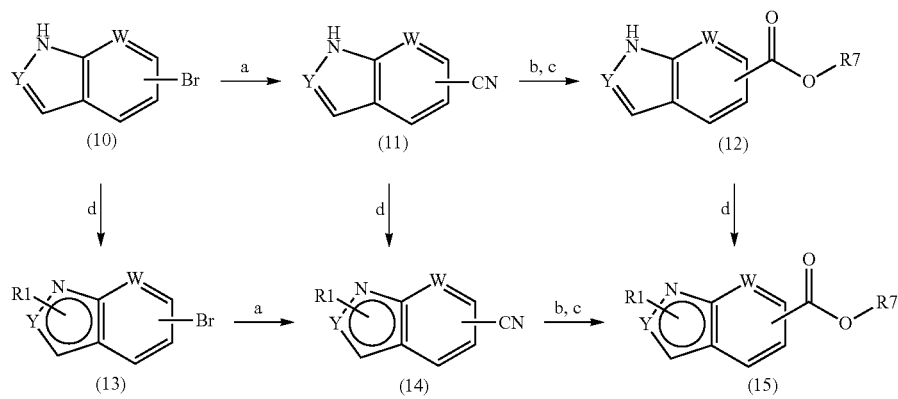

In the above Reaction Scheme 5, a is a cyanide such as zinc cyanide (ZnCN$_2$), and a palladium catalyst such as palladium tetrakistriphenylphosphine {Pd(PPh$_3$)$_4$}, b is a basic aqueous solution, such as sodium hydroxide, c is diazomethane (CH$_2$N$_2$), d is R1-OSO$_2$CH$_3$ or R1-halogen, and a base such as sodium hydride, R1 is the same as defined in Formula (1), and R7 is H or alkyl such as methyl or ethyl.

Compound (10) is typically available for purchase.

Compound (11) can be obtained by reacting the bromide group of compound (10) with cyanide under a palladium catalyst. Palladium tetrakistriphenylphosphine {Pd(PPh$_3$)$_4$} is the most commonly used palladium catalyst, and the solvent is preferably dimethylformamide or N-methylpyrrolidone.

Compound (12) can be obtained by changing the carbonitrile group of compound (11) to acid group using an acidic or basic aqueous solution and then esterifying it with methanol or ethanol under acid catalyst such as anhydrous hydrochloric acid or anhydrous sulfuric acid. It can be also obtained via the methyl esterfication reaction of the acid group and diazomethane in the solvent of tetrahydrofuran or dichloromethane.

The acidic solution used in the condition for making acid group is preferably an aqueous solution of sulfuric or hydrochloric acid, and as the basic aqueous solution, sodium hydroxide or lithium hydroxide aqueous solution is generally used.

Compound (13) may be prepared using compound (10) by the alkylating or arylating method used to prepare the compound (3).

Compound (14) can be prepared using compound (13) under the same condition that is used for preparing compound (11).

Compound (15) can be prepared using compound (12) by the alkylating or arylating method used to prepare the compound (3) or using compound (14) by the method by which compound (12) is prepared.

[Reaction Scheme 6]

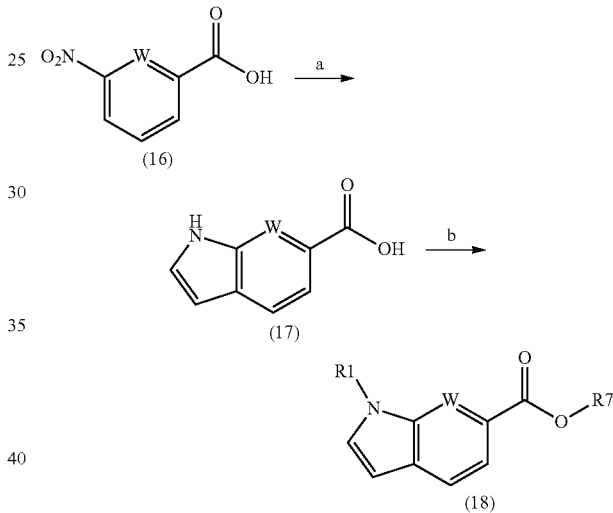

In the above Reaction Scheme 6, a is vinyl magnesium bromide (CH$_2$=CHMgBr), b is diazomethane(CH$_2$N$_2$), R1 is the same as defined in Formula (1), and R7 is H or alkyl such as methyl or ethyl.

Compound (16) is typically available for purchase.

Compound (17) can be prepared by reacting the nitrobenzene compound (16) and vinyl magnesium bromide with the method described in WO 2008/0221091.

Compound (18) may be made via an esterification reaction of compound (17). The esterification reaction may be carried out using ethanol or methanol under the condition of the anhydrous sulfuric acid or hydrochloric acid. Alternatively, it can be performed using diazomethane in tetrahydrofuran or dichloromethane.

[Reaction Scheme 7]

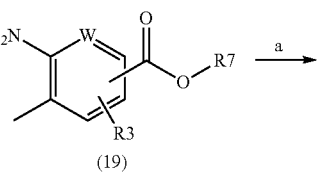

17

-continued

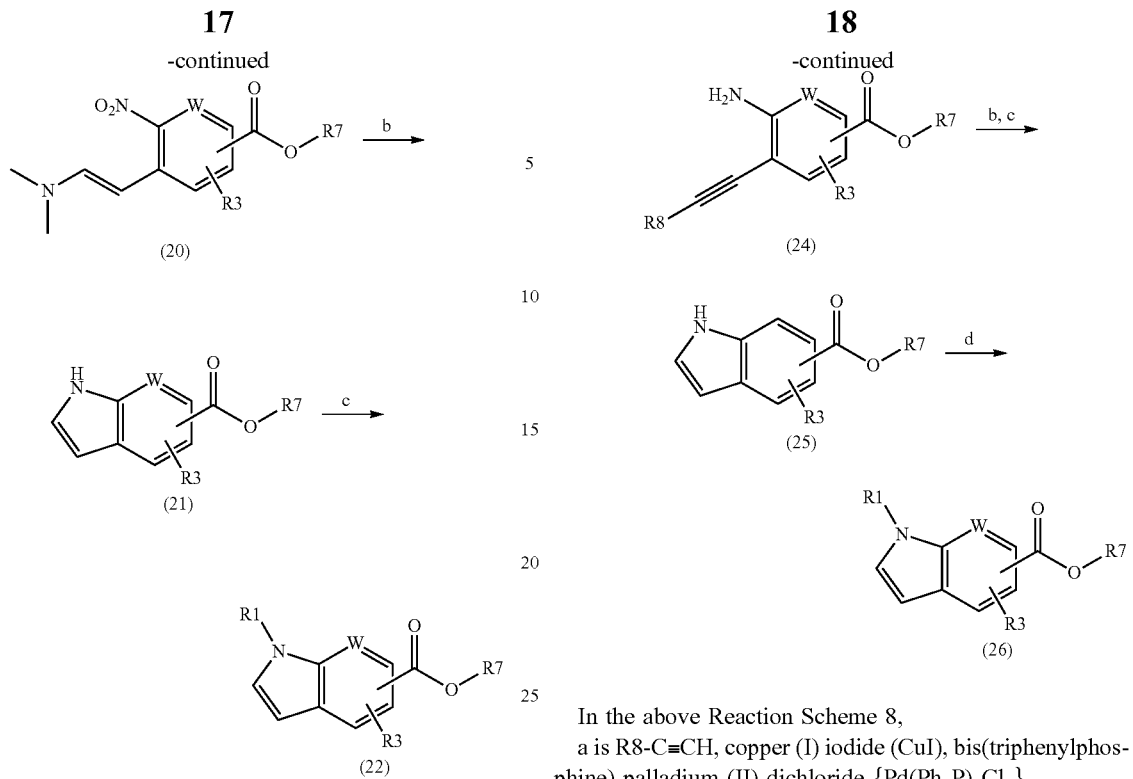

In the above Reaction Scheme 7, a is N,N-dimethylformamide dimethyl acetal, b is palladium/carbon (Pd/C) and hydrogen, c is R1-OSO$_2$CH$_3$ or R1-halogen and a base such as sodium hydride, R3 is the same as defined in Formula (1), and R7 is H or alkyl such as methyl or ethyl.

Compound (19) is commercially available or can be prepared by the method described in WO 2010/089127.

The compound (20) can be prepared by reacting the methyl group of compound (19) with N,N-dimethylformamide dimethyl acetal according to the method described in WO 2010/054138.

Compound (21) may be prepared by reacting compound (20) with hydrogen gas under Pd/C catalyst. The suitable solvent is ethyl acetate, ethanol, etc.

Compound (22) may be prepared by alkylation or arylation of compound (21) according to the method used for compound (3).

[Reaction Scheme 8]

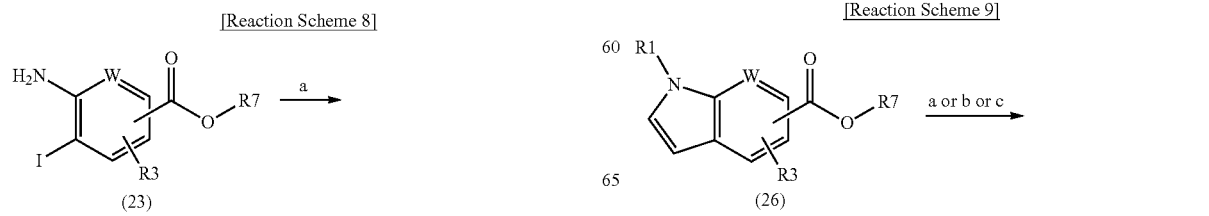

18

-continued

In the above Reaction Scheme 8, a is R8-C≡CH, copper (I) iodide (CuI), bis(triphenylphosphine) palladium (II) dichloride {Pd(Ph$_3$P)$_2$Cl$_2$}, b is acetylchloride, c is tetrabutylammonium fluoride, d is R1-OSO$_2$CH$_3$ or R1-halogen and sodium hydride, R3 is the same as defined in Formula (1), R7 is H or alkyl such as methyl or ethyl, and R8 is trimethylsilyl {(CH$_3$)$_3$Si}, alkyl or heteroalkyl.

Compound (23) can be purchased or can be prepared by the method described in Tetrahedron Letters, 38 (14), 2439, 1997.

Compound (24) can be made according to the method described in Journal of Organic Chemistry, 4 (18), 7052, 2009 by reacting R8-C≡CH with compound (23) in the presence of copper (I) iodide (CuI), bis(triphenylphosphine) palladium (II) dichloride {Pd(Ph$_3$P)$_2$Cl$_2$} and a base. The base is preferably triethylamine or diethylamine, and as the solvent N,N-dimethylformamide or tetrahydrofuran can be used.

Compound (25) can be prepared by reacting compound (24) with tetrabutylammonium fluoride according to the method described in Example 58 of WO 2010/123975.

Compound (26) may be prepared by alkylation or arylation of compound (25) according to the method used for compound (3).

[Reaction Scheme 9]

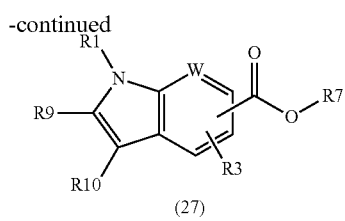

In the above Reaction Scheme 9, a is a halogenating agent such as N-fluoro-2,4,6-trimethyl pyridinium triplate or chlorine ($Cl_2$), b is R1-Br, and a metal acid catalyst such as zinc bromide ($ZnBr_2$), c is a halogenating agent such as N-bromosuccinimide; R10-boronic acid and palladium tetrakistriphenylphosphine $\{Pd(Ph_3)_4\}$, R1 and R3 are the same as defined in Formula (1), R7 is H or alkyl such as methyl or ethyl, R9 is H or halogen, and R10 is halogen, alkyl, aryl or aryl-alkyl.

Compound (26) can be prepared under the condition described in Reaction Scheme 8.

Compound (27) can be synthesized by carrying out one reaction under any of a to c reaction conditions.

The halogenation (the reaction condition of a) of compound (26) can be carried out using a fluorinating reagent (for example, N-fluoro-2,4,6-trimethyl pyridinium triplate), chlorine or brominating reagent (for example, N-bromosuccinimide, bromine).

The alkylation (the reaction condition of b) of compound (26) can be carried out by reacting with an alkyl-halogen compound (for example, benzyl bromide) in the presence of a metal acid catalyst such as zinc bromide ($ZnBr_2$).

The arylation (the reaction condition of c) of compound (26) can be carried out by brominating the indole compound and then reacting with R10-boronic acid and a base (for example, palladium phosphate tribasic) under a palladium tetrakistriphenylphosphine $\{Pd(Ph_3)_4\}$ catalyst.

In the above Reaction Scheme 10, a is acetic anhydride($Ac_2O$), isoamyl nitrite and potassium acetate (KOAc)

b is a cyanide such as zinc cyanide ($ZnCN_2$), and a palladium catalyst such as palladium tetrakistriphenylphosphine $\{Pd(PPh_3)_4\}$, c is a base such as sodium hydroxide, d is diazomethane ($CH_2N_2$), e is palladium/carbon (Pd/C) and hydrogen, R3 is the same as defined in Formula (1), R7 is H or alkyl such as methyl or ethyl, and R11 is alkyl or aryl-alkyl.

Compound (28) is commercially available, or can be prepared by a known method.

Compound (29) can be prepared using the indazole synthesis method well known in the art. The indazole synthesis conditions include the condition that the 1-amino-2-alkylphenyl compound (28) is reacted with acetic anhydride ($Ac_2O$) in the presence of potassium acetate (KOAc), and then it is reacted with isoamyl nitrite.

Compound (30) may be obtained by reacting the bromide group of compound (29) with cyanide under a palladium catalyst. As a palladium catalyst, palladium tetrakistriphenylphosphine $\{Pd(PPh_3)_4\}$ is commonly used, and the solvent is preferably dimethylformamide or N-methylpyrrolidone.

Compound (31) is commercially available or can be prepared by the method as described in US 2010/0040554.

Compound (32) can be prepared by reduction of the compound (31) with hydrogen gas under Pd/C catalyst.

The compound (33) is commercially available, or can be prepared by changing the carbonitrile of compound (30) to the acid group using an acidic or basic aqueous solution and then esterifying it with alcohol under acid catalyst or diazomethane. It can also be made using the compound (32) under the conditions by which to prepare compound (29) or by the method described in WO 2008/001883.

[Reaction Scheme 10]

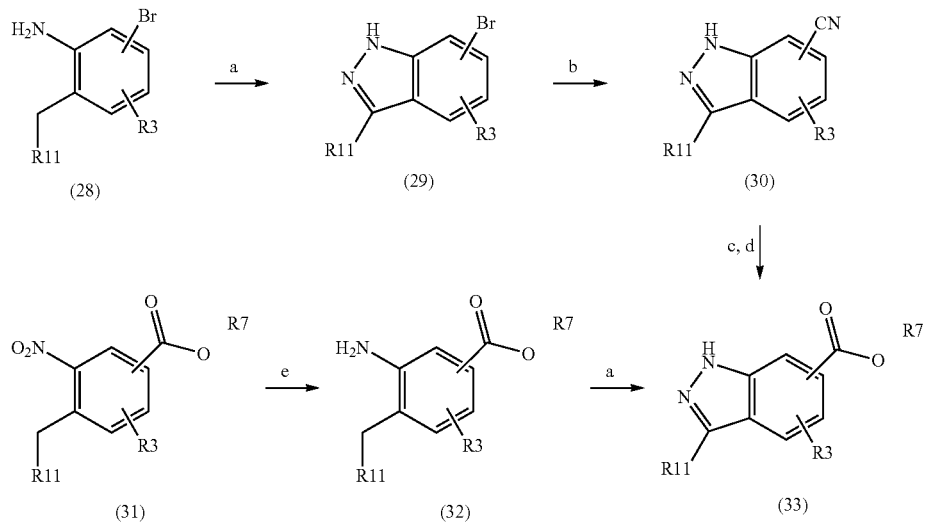

[Reaction Scheme 11]

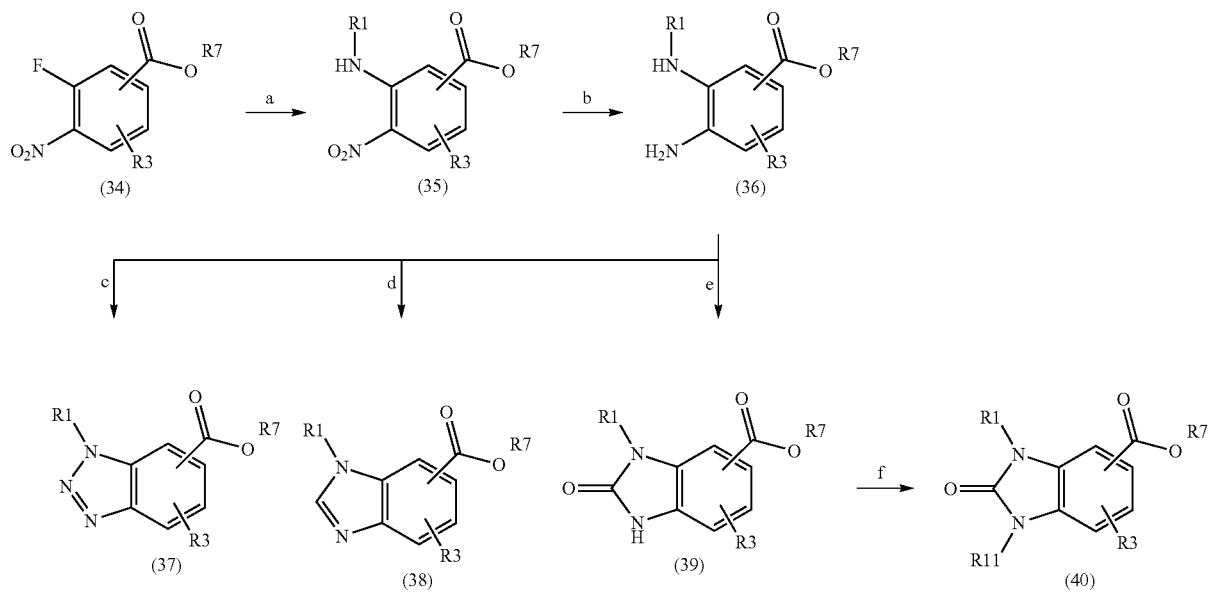

In the above Reaction Scheme 11, a is R1-amine, b is palladium/carbon (Pd/C) and hydrogen, c is sodium nitride (NaNO$_2$) and an acidic aqueous solution such as hydrochloric acid, d is triethylorthoformate and an acidic aqueous solution such as p-toluenesulfonic acid, e is triphosgene, f is R11-halogen, and a base such as sodium hydride, R1 and R3 are the same as defined in Formula (1), R7 is H or alkyl such as methyl or ethyl, and R11 is alkyl or aryl-alkyl.

Compound (34) is commercially available or can be prepared by a known method.

Compound (35) can be prepared by reacting compound (34) with amine according to the method described in WO 2007/095340.

Compound (36) can be prepared by reduction of compound (35) with hydrogen gas under Pd/C catalyst.

Compound (37) can be prepared by reacting compound (36) with sodium nitride (NaNO$_2$) under an acidic condition (for example, hydrochloric acid), according to the method described in WO 2010/027500.

Compound (38) can be prepared by reacting compound (36) with triethylorthoformate under an acidic condition (for example, p-toluenesulfonic acid), according to the method described in WO 2009/129335.

Compound (39) can be prepared by reacting compound (36) with triphosgene according to the method described in US 2008/0249101.

Compound (40) can be prepared by reacting compound (39) with an alkylating agent (for example, methyl iodide) in the presence of a base (for example, sodium hydride).

[Reaction Scheme 12]

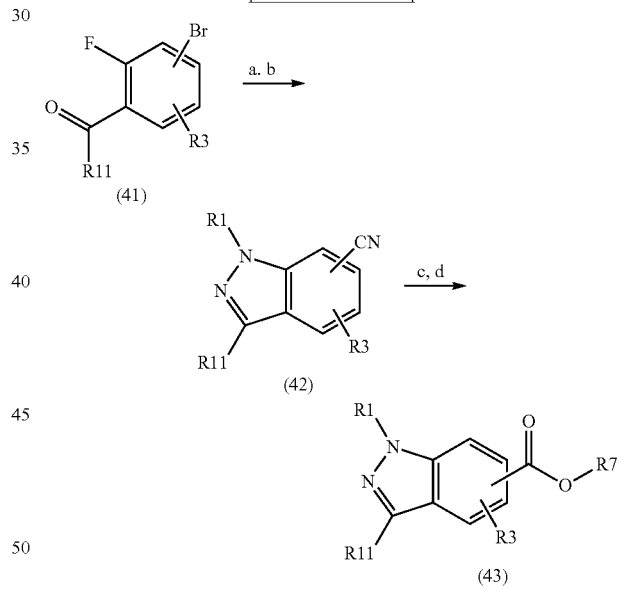

In the above Reaction Scheme 12, a is R1-hydrazine, b is zinc cyanide (ZnCN$_2$) and palladium tetrakistriphenylphosphine {Pd(PPh$_3$)$_4$}, c is a basic aqueous solution such as sodium hydroxide, d is diazomethane (CH$_2$N$_2$), R1 and R3 are the same as defined in Formula (1), R7 is H or alkyl such as methyl or ethyl, and R11 is alkyl or aryl-alkyl.

Compound (41) is commercially available or can be prepared by the method described in US 2008/153813.

Compound (42) can be prepared by reacting compound (41) with R1-hydrazine and then reacting with zinc cyanide (ZnCN$_2$) under palladium tetrakistriphenylphosphine {Pd (PPh$_3$)$_4$}, or it can be prepared by reacting R1-hydrazine after reacting zinc cyanide (ZnCN$_2$).

Compound (43) can be prepared by changing the carbonitrile group of compound (42) to the acid group using an acidic or basic aqueous solution, and then esterifying it with alcohol under acid catalyst or diazomethane.

[Reaction Scheme 13]

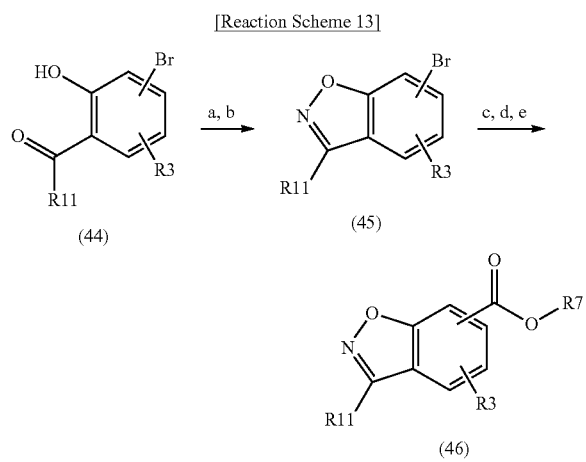

In the above Reaction Scheme 13, a is ammonia, b is N-chlorosuccinimide (NCS) and potassium carbonate, c is zinc cyanide (ZnCN$_2$) and palladium tetrakistriphenylphosphine {Pd(PPh$_3$)$_4$}, d is sodium hydroxide, e is diazomethane (CH$_2$N$_2$), R3 is the same as defined in Formula (1), R7 is H or alkyl such as methyl or ethyl, and R11 is alkyl or aryl-alkyl.

Compound (44) is commercially available or can be prepared by the method described in WO 95/04739.

Compound (45) can be prepared by reacting compound (44) with ammonia and then N-chlorosuccinimide (NCS) according to the method described in Organic Letter, 12(23), 6300, 2011.

Compound (46) can be prepared using compound (45) according to the method by which compound (12) was prepared.

The compounds of Formula (1) can be separated or purified from the reaction products by conventional methods such as recrystallization, ionospheresis, silica gel column chromatography or ion-exchange chromatography.

As described above, the compounds according to the present invention, starting materials or intermediates for the preparation thereof can be prepared by a variety of methods, which should be interpreted as being within the scope of the present invention in connection with the preparation of the compounds of Formula (1).

The compounds of Formula (1), the pharmaceutically acceptable salts and isomers thereof are useful for the treatment and prevention for the diseases associated with GPR40 receptor. The compound of Formula (1) according to the present invention has GPR40 receptor modulating activity and is especially useful as a GPR40 receptor agonist. The compound of formula (1) according to the present invention has an excellent GPR40 receptor modulating activity in mammals, particularly in humans, and thus is useful as a therapeutic agent for the treatment or prevention of GPR40 receptor-related diseases which can be treated by controlling the efficacy of the GPR40 receptor. Specifically, the compound according to the present invention is useful as insulin secretion regulating agents, preferably insulin secretagogues, hypoglycemic agents and pancreatic beta-cell protective agents. Particularly, the compound of the present invention shows blood glucose concentration-dependent insulin secretion stimulating activity based on GPR40 receptor agonist activity, and thus it is useful as an insulin secretagogue that does not cause side effects such as hypoglycemia—namely, as a therapeutic agent for the treatment or prevention of diabetes, high blood sugar, glucose tolerance, and impaired fasting blood glucose. It is also effective in the treatment or prevention of diabetes complications such as hyperlipidemia, hypertension, retinopathy, renal failure and obesity. The diabetes complications treatable by the compound of the present invention include, but are not limited to, hyperlipidemia, hypertension, retinopathy, renal failure, obesity, etc. The relevance between the said diseases and the modulation of GPR40 receptor has already been known in the art and disclosed in detail in documents such as WO 2004/041266, WO 2004/106276, WO 2005/063729 and WO 2008/001931.

The present invention also provides a pharmaceutical composition as a GPR40 agonist comprising an effective amount of the compound of Formula (1), pharmaceutically acceptable salts or isomers thereof and a pharmaceutically acceptable carrier. The pharmaceutical composition comprising the compound of Formula (1) can be used for the treatment or prevention of diseases or conditions which can be treated by modulation of the GPR40 receptor such as diabetes, high blood sugar, glucose tolerance, impaired fasting blood glucose, diabetes complications, hyperlipidemia, hypertension, retinopathy, renal failure, obesity, etc., and is particularly useful for the treatment or prevention of type 2 diabetes.

In addition, the present invention provides a method for preparing the composition for preventing or treating diabetes and/or complications of diabetes which comprises the step of mixing the compound of Formula (1), a pharmaceutically acceptable salt or isomer thereof as an active component and a pharmaceutically acceptable carrier.

According to the present invention, the "pharmaceutical composition" can include other chemical components such as carriers, diluents, etc., in addition to the active component of the present invention. Accordingly, the pharmaceutical composition can include pharmaceutically acceptable carriers, diluents, excipients or combinations thereof as necessary. The pharmaceutical composition facilitates the administration of compounds into the body. Various methods for administering the compounds include, but are not limited to, oral, injection, aerosol, parenteral and local administration.

Herein, the term "carriers" means compounds that facilitate the addition of compounds into the cell or tissue. For example, dimethylsulfoxide is a conventional carrier facilitating the administration of various organic compounds into the living cell or tissue.

Herein, the term "diluents" means compounds that not only stabilize a biologically active form but are also diluted in solvent dissolving the compounds. Dissolved salts in buffer are used as diluents in this field. A conventionally used buffer is a phosphate buffer saline that copies salt form in bodily fluid. Since buffer solution can control the pH of the solution at low concentration, buffer diluents hardly modify the biological activity of compounds.

Herein, the term "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula (1), a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compounds of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or stabilizing agents. In addition, the formulation may be, for example, dry powder form which is dissolved in sterilized pyrogen-free water before use. The compounds of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compounds according to the present invention and the composition comprising them can be administered in combination with other drugs—for example, other antidiabetics, as required.

The dose of the compounds of Formula (1) is determined by a physician's prescription considering the patient's body weight, age and disease condition. A typical dose for adults is in the range of about 1 to 500 mg per day according to the frequency and intensity of administration. A typical daily dose of intramuscular or intravenous administration for adults is in the range of about 1 to 300 mg per day which can be administered in divided unit dosage. Some patients need a higher daily dose.

Herein, the term "treatment" is used to mean deterring, delaying or ameliorating the progress of diseases in a subject exhibiting symptoms of diseases. The term "prevention" is used to mean deterring, delaying or ameliorating the sign of diseases in a subject at risk of exhibiting symptoms of diseases, even if he or she does not exhibit the symptoms.

MODE FOR THE INVENTION

The present invention is explained in more detail by the following Examples. However, the scope of the present invention is not limited by them. When preparing the compounds of the present invention, it is possible to appropriately change the reaction sequence. That is, it is possible to run first optional processes or insert optional processes to change substituents, and use any reagents other than exemplified reagents as needed. Compounds obtained in each process can be separated or purified by conventional methods such as recrystallization, distillation or silica gel column. Furthermore, the compound obtained in each process can be used in the next step without further purification or separation.

Reagents and starting materials can be obtained readily commercially. Others can be produced by synthetic methods described in the following Examples, including known synthetic methods for structurally similar compounds. Unless otherwise noted, compounds used as starting materials are known ones or those which can be prepared by known synthetic methods or similar methods from known compounds. Hereinafter, M means molar concentration, N means normal concentration and "room temperature" means 1 to 40° C.

Preparation Example 1

Synthesis of 1-isopropyl-1H-indole-6-carbaldehyde

1-H-indole-6-carbaldehyde (320 mg, 2.2 mmol) was dissolved in dimethylformamide (2 ml), and isopropyl iodide (0.33 ml, 3.3 mmol) and sodium hydride (104 mg, 2.6 mmol) were slowly added thereto at 0° C., and then the mixture was stirred for 8 hours at 50° C. 1N hydrochloric acid solution was added thereto, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (300 mg, 73%).

NMR:$^1$H-NMR(400 HMz, CDCl$_3$); δ 10.11 (s, 1H), 7.96 (s, 1H), 7.71 (d 1H), 7.62 (dd, 1H), 7.45 (d, 1H), 6.59 (d, 1H), 4.73-4.84 (m, 1H), 1.57 (d, 6H)

Preparation Example 2

Synthesis of 1-benzyl-1H-indole-6-carbaldehyde

1-H-indole-6-carbaldehyde (320 mg, 2.2 mmol) and benzyl bromide (0.36 ml, 3.3 mmol) were reacted according to the method of Preparation Example 1 to obtain the title compound (400 mg, 77%).

NMR:$^1$H-NMR(400 HMz, CDCl$_3$); δ 10.06 (s, 1H), 7.86 (s, 1H), 7.73 (d 1H), 7.64 (dd, 1H), 7.35 (d, 1H), 7.28-7.33 (m, 3H), 7.12 (dd, 2H), 6.62 (d, 1H), 5.41 (s, 2H)

Preparation Example 3

Synthesis of 1-benzyl-3-chloro-1H-indole-6-carbaldehyde

1-Benzyl-1H-indole-6-carbaldehyde (835 mg, 3.5 mmol) obtained from Preparation Example 2 was dissolved in tetrahydrofuran (30 ml). N-chlorosuccinimide (NCS, 474 mg, 3.5 mmol) was added dropwise thereto, and then the mixture was stirred for 2 hours at 70° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (800 mg, 76%).

NMR:$^1$H-NMR(400 HMz, CDCl$_3$); δ 10.29 (s, 1H), 7.92 (s, 1H), 7.79 (m, 2H), 7.37 (m, 4H), 7.20 (d, 2H), 5.41 (s, 2H)

Preparation Example 4

Synthesis of 1-benzyl-2,3-dichloro-1H-indole-6-carbaldehyde

1-Benzyl-3-chloro-1H-indole-6-carbaldehyde (100 mg, 0.43 mmol) obtained from Preparation Example 3 was dissolved in dichloromethane (25 ml). N-chlorosuccinimide (NCS, 132 mg, 1.0 mmol) was added dropwise thereto, and then the mixture was stirred for 4 hours at room temperature. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (40 mg, 30%).

NMR:$^1$H-NMR(400 HMz, CDCl$_3$); δ 10.06 (s, 1H), 7.86 (s, 1H), 7.76 (m, 2H), 7.34 (m, 3H), 7.14 (m, 1H), 5.53 (s, 2H)

Preparation Example 5

Synthesis of 1-phenethyl-1H-indole-6-carbaldehyde

1-H-Indole-6-carbaldehyde (300 mg, 2.1 mmol) and (2-bromo-ethyl)-benzene (0.34 ml, 2.48 mmol) were reacted according to the method of Preparation Example 1 to obtain the title compound (80 mg, 15%).

NMR:$^1$H-NMR(400 HMz, CDCl$_3$); δ 10.08 (s, 1H), 7.88 (s, 1H), 7.74 (m, 1H), 7.66 (m, 1H), 7.35 (m, 3H), 7.14 (d, 1H), 7.08 (m, 3H), 6.54 (m, 1H), 4.50 (t, 2H), 3.18 (t, 2H)

Preparation Example 6-1

Synthesis of 1-thiophen-3-yl-1H-indole-6-carboxylic acid methyl ester 1H-indole-6-carboxylic acid methyl ester (560 mg, 3.2 mmol) was dissolved in xylene (30 ml). 3-Bromothiophene (1.0 g, 6.4 mmol), copper (I) iodide (122 mg, 0.64 mmol), potassium carbonate (890 mg, 6.4 mmol) and cyclohexane 1,2-diamine (0.08 ml, 0.64 mmol) were added dropwise thereto, and then the mixture was stirred for 8 hours at 120° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (526 mg, 64%).

Preparation Example 6-2

Synthesis of (1-thiophen-3-yl-1H-indol-6-yl)-methanol

The compound (500 mg, 1.9 mmol) obtained from Preparation Example 6-1 was dissolved in tetrahydrofuran (20 ml), and 2M solution of lithium borohydride in tetrahydrofuran (2.4 ml, 4.8 mmol) was added dropwise thereto. The mixture was stirred for 8 hours at 80° C., 1N hydrochloric acid solution was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (400 mg, 90%).

NMR:$^1$H-NMR(400 HMz, CDCl$_3$); δ 7.65 (d, 1H), 7.58 (s, 1H), 7.46 (dd, 1H), 7.29-7.32 (m, 3H), 7.17 (dd, 1H), 6.64 (dd, 1H), 4.79 (d, 2H), 1.61 (br s, 1H)

Preparation Example 6-3

Synthesis of 1-thiophen-3-yl-1H-indole-6-carbaldehyde

The compound (100 mg, 0.44 mmol) obtained from Preparation Example 6-2 was dissolved in dichloromethane (10 ml), and pyridinium chlorochromate (PCC, 188 mg, 0.87 mmol) was added thereto. The mixture was stirred for 1 hour at 0° C. and then excess ethyl acetate was added thereto. The mixture was filtered with Celite. Water was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (86 mg, 69%).

NMR:$^1$H-NMR(400 HMz, CDCl$_3$); δ 10.05 (s, 1H), 8.06 (s, 1H), 7.77 (d, 1H), 7.70 (dd, 1H), 7.51-7.53 (m, 2H), 7.37 (dd, 1H), 7.31 (dd, 1H), 6.73 (d, 1H)

Preparation Example 7-1

Synthesis of 7-chloro-1H-indole-6-carboxylic acid

2-Chloro-3-nitro-benzoic acid (3.0 g, 14.9 mmol) was dissolved in tetrahydrofuran (150 ml), and 1M vinyl magnesium bromide solution in tetrahydrofuran (60 ml, 60 mmol) was added dropwise thereto at −45° C. The mixture was stirred while heating to 0° C. After completion of the reaction, a saturated solution of ammonium chloride and then 1N hydrochloric acid solution were added. The mixture was extracted with ethyl acetate, and the extract was washed with saturated aqueous sodium chloride solution, dried over anhydrous magnesium sulfate and filtered. Filtrate was distilled under reduced pressure and separated by column chromatography to obtain the title compound (800 mg, 28%).

Preparation Example 7-2

Synthesis of 7-chloro-1H-indole-6-carboxylic acid methyl ester

The compound (750 mg, 3.8 mmol) obtained from Preparation Example 7-1 was dissolved in tetrahydrofuran (150 ml), and 0.25M solution of diazomethane in diethyl ether (18.4 ml, 4.6 mmol) was slowly added thereto. The mixture was stirred at room temperature for 30 minutes and distilled under reduced pressure to obtain the title compound (800 mg, 99%).

Preparation Example 7-3

Synthesis of 1-benzyl-7-chloro-1H-indole-6-carboxylic acid methyl ester

The compound (300 mg, 1.43 mmol) obtained from Preparation Example 7-2 was dissolved in dimethylformamide (10 ml), and bromomethylbenzene (0.19 ml, 1.7 mmol)

and sodium hydride (69 mg, 1.7 mmol) were slowly added dropwise thereto at 0° C. The mixture was stirred at room temperature for 8 hours, 1N hydrochloric acid solution was added thereto, and the mixture was extracted with ethyl acetate. Extract was washed with saturated aqueous sodium chloride solution, dried over anhydrous magnesium sulfate and filtered. Filtrate was distilled under reduced pressure and separated by column chromatography to obtain the title compound (380 mg, 89%).

NMR:$^1$H-NMR(400 HMz, CDCl$_3$); δ 7.52 (s, 2H), 7.21-7.28 (m, 3H), 7.19 (d, 1H), 6.97 (d, 2H), 6.56 (d, 1H), 5.80 (s, 2H), 3.89 (s, 3H)

Preparation Example 7-4

Synthesis of (1-benzyl-7-chloro-1H-indol-6-yl)-methanol

The compound (380 mg, 1.3 mmol) obtained from Preparation Example 7-3 was dissolved in tetrahydrofuran (25 ml) and 2M solution of lithium borohydride in tetrahydrofuran (1.9 ml, 3.9 mmol) was added dropwise thereto. The mixture was stirred at 80° C. for 8 hours, 1N hydrochloric acid solution was added and the mixture was extracted with ethyl acetate. Extract was washed with saturated aqueous sodium chloride solution, dried over anhydrous magnesium sulfate and filtered. Filtrate was distilled under reduced pressure and separated by column chromatography to obtain the title compound (250 mg, 73%).

NMR:$^1$H-NMR(400 HMz, CDCl$_3$); δ 7.53 (d, 1H), 7.21-7.30 (m, 3H), 7.19 (d, 1H), 7.11 (d, 1H), 7.00 (d, 2H), 6.55 (d, 1H), 5.79 (s, 2H), 4.85 (d, 2H), 1.84 (br t, 1H)

Preparation Example 7-5

Synthesis of 1-benzyl-7-chloro-1H-indole-6-carbaldehyde

The compound (100 mg, 0.44 mmol) obtained from Preparation Example 7-4 was dissolved in dichloromethane (20 ml), and pyridinium chlorochromate (PCC, 159 mg, 0.74 mmol) was added thereto. The mixture was stirred for 1 hour at 0° C., excess ethyl acetate was added and the mixture was filtered with Celite. Water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (100 mg, 100%).

Preparation Example 8-1

Synthesis of 7-chloro-1-thiophen-3-yl-1H-indole-6-carboxylic acid methyl ester

In the method described in Preparation Example 6-1, 7-chloro-1H-indole-6-carboxylic acid methyl ester (300 mg, 1.43 mmol) rather than 1H-indole-6-carboxylic acid methyl ester was used to obtain the title compound (33 mg, 7.5%).

NMR:$^1$H-NMR(400 HMz, CDCl$_3$); δ 7.60 (d, 1H), 7.32 (m, 2H), 7.27 (d, 1H), 7.14 (dd, 1H), 6.68 (d, 1H), 3.92 (s, 3H)

Preparation Example 8-2

Synthesis of 7-chloro-1-thiophen-3-yl-1H-indole-6-carbaldehyde

In the methods described in Preparation Examples 7-4 and 7-5, the compound (33 mg, 0.11 mmol) obtained from Preparation Example 8-1 rather than the compound obtained from Preparation Example 7-3 was used to obtain the title compound (17 mg, 59%).

Preparation Example 9-1

Synthesis of 7-chloro-1-(4-fluoro-phenyl)-1H-indole-6-carboxylic acid methyl ester According to the method described in Preparation Example 6-1, 7-chloro-1H-indole-6-carboxylic acid methyl ester (100 mg, 0.48 mmol) and 1-fluoro-4-iodo-benzene were used to obtain the title compound (15 mg, 10%).

NMR:$^1$H-NMR(400 HMz, CDCl$_3$); δ 7.63 (d, 2H), 7.34 (m. 2H), 7.24 (d, 1H), 7.15 (m, 2H), 6.65 (d, 1H), 3.90 (s, 3H)

Preparation Example 9-2

Synthesis of 7-chloro-1-(4-fluoro-phenyl)-1H-indole-6-carbaldehyde

In the methods described in Preparation Examples 7-4 and 7-5, the compound (15 mg, 0.05 mmol) obtained from Preparation Example 9-1 was used rather than the compound obtained from Preparation Example 7-3 to obtain the title compound (10 mg, 74%).

Preparation Example 10-1

Synthesis of 7-chloro-1-cyclohexylmethyl-1H-indole-6-carboxylic acid methyl ester According to the method described in Preparation Example 7-3, the compound (100 mg, 0.51 mmol) obtained from Preparation Example 7-2 and bromomethyl cyclohexane (181 mg, 1.02 mmol) were used to obtain the title compound (57 mg, 36%).

NMR:$^1$H-NMR(400 HMz, CDCl$_3$); δ 7.49 (s, 1H), 7.12 (d, 1H), 6.46 (s, 1H), 4.34 (d, 2H), 3.94 (s, 2H), 1.87-1.97 (m, 1H), 1.68-1.70 (m, 3H), 1.55 (s, 3H), 1.15-1.19 (m, 3H), 0.96-1.01 (m, 2H)

Preparation Example 10-2

Synthesis of 7-chloro-1-cyclohexylmethyl-1H-indole-6-carbaldehyde

In the methods described in Preparation Examples 7-4 and 7-5, the compound (57 mg, 0.19 mmol) obtained from Preparation Example 10-1 rather than the compound obtained from Preparation Example 7-3 was used to obtain the title compound (32 mg, 64%).

Preparation Example 11-1

Synthesis of 1-(4-fluoro-2-methyl-phenyl)-1H-indole-6-carboxylic acid methyl ester 1H-indole-6-carboxylic acid methyl ester (200 mg, 1.14 mmol) was dissolved in dioxane (2 ml). 1-Bromo-4-fluoro- 2-methyl-benzene (0.3 ml, 2.28 mmol), copper (I) iodide (22 mg, 0.11 mmol), potassium phosphate tribasic (K$_3$PO$_4$, 509 mg, 2.40 mmol), dodecane (0.2 ml, 0.11 mmol) and cyclohexane 1,2-diamine (0.03 ml, 0.23 mmol) were added dropwise thereto, and then the mixture was stirred for 8 hours at 110° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (150 mg, 46%).

Preparation Example 11-2

Synthesis of [1-(4-fluoro-2-methyl-phenyl)-1H-indol-6-yl]-methanol

The compound (150 mg, 0.53 mmol) obtained from Preparation Example 11-1 was dissolved in tetrahydrofuran (10 ml), and lithium aluminium hydride (200 mg, 5.27 mmol) was added dropwise thereto. The mixture was stirred for 2 hours at room temperature, and then water (1 ml), 6N sodium hydroxide (2 ml) and water (3 ml) were added sequentially. Ethyl acetate was added thereto. The mixture was filtered with Celite, distilled under reduced pressure and separated by column chromatography to obtain the title compound (135 mg, 100%).
NMR:$^1$H-NMR(400 HMz, CDCl$_3$); δ 7.66 (d, 1H), 7.27 (m, 1H), 7.16 (m, 1H), 7.12 (d, 1H), 7.08 (m, 1H), 7.01 (m, 2H), 6.65 (d, 1H), 4.74 (d, 2H), 2.03 (s, 3H)

Preparation Example 12-1

Synthesis of 3-chloro-1-(4-fluoro-2-methyl-phenyl)-1H-indole-6-carboxylic acid methyl ester The compound (70 mg, 0.25 mmol) obtained from Preparation Example 11-1 was dissolved in tetrahydrofuran (10 ml), and N-chloro-succinimide (NCS, 40 mg, 0.30 mmol) was added dropwise thereto. The mixture was stirred for 4 hours at 60° C. Water was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (70 mg, 89%).
NMR:$^1$H-NMR(400 HMz, CDCl$_3$); δ 7.91 (dd, 1H), 7.72 (d, 1H), 7.70 (dd, 1H), 7.21-7.24 (m, 2H), 7.02-7.13 (m, 2H), 3.89 (s, 3H), 2.03 (s, 3H)

Preparation Example 12-2

Synthesis of [3-chloro-1-(4-fluoro-2-methyl-phenyl)-1H-indol-6-yl]-methanol

The compound (70 mg, 0.22 mmol) obtained from Preparation Example 12-1 was dissolved in tetrahydrofuran (10 ml), and lithium aluminium hydride (200 mg, 5.27 mmol) was added dropwise thereto. The mixture was stirred for 2 hours at room temperature, and water (1 ml), 6N sodium hydroxide (2 ml) and water (3 ml) were added sequentially. Ethyl acetate was added, and the mixture was filtered with Celite. Filtrate was distilled under reduced pressure and separated by column chromatography to obtain the title compound (50 mg, 89%).

NMR:$^1$H-NMR(400 HMz, CDCl$_3$); δ 7.68 (d, 1H), 7.23-7.26 (m, 2H), 7.13-7.06 (m, 2H), 7.04-6.99 (m, 2H), 4.75 (s, 2H), 2.04 (s, 3H)

Preparation Example 13-1

Synthesis of 2-fluoro-4-methyl-5-nitro-benzoic acid

2-Fluoro-4-methyl-benzoic acid (2.0 g, 13 mmol) was dissolved in 12N sulfuric acid solution (40 ml). A mixture of 12N sulfuric acid solution (15.6 mmol) and nitric acid solution (19.5 mmol) was added dropwise thereto at 0° C. After stirring for 1 hour at 0° C., an excess of ice water was added. The resulting solid was filtered and dried to obtain the title compound (2.3 g, 88%).

Preparation Example 13-2

Synthesis of 2-fluoro-4-methyl-5-nitro-benzoic acid methyl ester

The compound (2.3 g, 11.5 mmol) obtained from Preparation Example 13-1 was dissolved in tetrahydrofuran (30 ml), and 0.25M solution of diazomethane in diethyl ether (50 ml, 12.5 mmol) was added dropwise thereto. After stirring for 30 minutes at 0° C., the mixture was distilled under reduced pressure to obtain the title compound (2.4 g, 98%).
NMR:$^1$H-NMR(400 HMz, CDCl$_3$); δ 8.63 (d, 1H), 7.12 (d, 1H), 7.09 (d, 1H), 3.95 (s, 3H), 2.66 (s, 3H)

Preparation Example 13-3

Synthesis of 4-((E)-2-dimethylamine-vinyl)-2-fluoro-5-nitro-benzoic acid methyl ester The compound (2.4 g, 11.2 mmol) obtained from Preparation Example 13-2 was dissolved in dimethylformamide (10 ml). N, N-dimethylformamide dimethyl acetal (1.8 ml, 13.4 mmol) was added thereto, and the mixture was stirred for 1 hour at 100° C. Excess water was added, and then resulting solids were filtered and dried to obtain the title compound (2.0 g, 67%).
NMR:$^1$H-NMR(400 HMz, CDCl$_3$); δ 8.54 (d, 1H), 7.15 (d, 1H), 7.09 (d, 1H), 5.97 (dd, 1H), 3.90 (s, 3H), 3.01 (s, 6H)

Preparation Example 13-4

Synthesis of 5-fluoro-1H-indole-6-carboxylic acid methyl ester

The compound (2.0 g, 7.5 mmol) obtained from Preparation Example 13-3 was dissolved in ethyl acetate (100 ml). 5% Palladium/carbon (100 mg) was added, and the mixture was stirred for 2 hours under hydrogen gas. After completion of the reaction, the mixture was filtered with Celite, distilled under reduced pressure and separated by column chromatography to obtain the title compound (1.3 g, 90%).
NMR:$^1$H-NMR(400 HMz, CDCl$_3$); δ 8.68 (br s, 1H), 8.04 (d, 1H), 7.40 (dd, 1H), 7.34 (d, 1H), 6.54 (dd, 1H), 3.95 (s, 3H)

Preparation Example 13-5

Synthesis of [5-fluoro-1-(4-fluoro-2-methyl-phenyl)-1H-indol-6-yl]-methanol

In the methods described in Preparation Examples 11-1 and 11-2, the compound (200 mg, 1.14 mmol) obtained from Preparation Example 13-4 was used rather than 1H-indole-6-carboxylic acid methyl ester to obtain the title compound (74 mg, 23%).

Preparation Example 14-1

Synthesis of 1-cyclohexylmethyl-1H-indole-6-carboxylic acid methyl ester 1H-indole-6-carboxylic acid methyl ester (300 mg, 1.71 mmol) was dissolved in dimethyl formamide (7 ml). Bromomethyl cyclohexane (0.5 ml, 3.42 mmol) and sodium hydride (150 mg, 3.42 mmol) were added dropwise thereto at 0° C., and then the mixture was stirred for 8 hours at room temperature. 1N hydrochloric acid solution was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (150 mg, 32%).
NMR:$^1$H-NMR(400 HMz, CDCl$_3$); δ 7.29-7.39 (m, 2H), 7.19 (d, 1H), 7.13 (m, 1H), 7.00-7.09 (m, 2H), 6.66 (m, 1H), 4.83 (s, 2H), 2.06 (s, 3H)

Preparation Example 14-2

Synthesis of (1-cyclohexylmethyl-1H-indol-6-yl)-methanol

The compound (150 mg, 0.55 mmol) obtained from Preparation Example 14-1 was dissolved in tetrahydrofuran (10 ml), and lithium aluminium hydride (200 mg, 5.27 mmol) was added dropwise thereto. The mixture was stirred for 2 hours at room temperature, and then water (1 ml), 6N sodium hydroxide (1 ml) and water (3 ml) were added sequentially. Ethyl acetate was added and the mixture was filtered with Celite. Filtrate was distilled under reduced pressure and separated by column chromatography to obtain the title compound (130 mg, 97%).

Preparation Example 15-1

Synthesis of 7-methyl-1H-indole-6-carboxylic acid methyl ester

In the methods described in Preparation Examples 7-1 and 7-2, 2-methyl-3-nitro-benzoic acid (5.0 g, 27.6 mmol) was used rather than 2-chloro-3-nitro-benzoic acid to obtain the title compound (1.4 g, 27%).
NMR:$^1$H-NMR(400 HMz, CDCl$_3$); δ 8.39 (br s, 1H), 7.74 (d, 1H), 7.49 (d, 1H), 7.35 (dd, 1H), 6.58 (dd, 1H), 3.91 (s, 3H), 2.79 (s, 3H)

Preparation Example 15-2

Synthesis of 1-(4-fluoro-phenyl)-7-methyl-1H-indole-6-carboxylic acid methyl ester 7-Methyl-1H-indole-6-carboxylic acid methyl ester (100 mg, 0.53 mmol) obtained from Preparation Example 15-1 was dissolved in dioxane (1 ml). 1-Fluoro-4-iodo-benzene (0.12 ml, 1.06 mmol), copper (I) iodide (10 mg, 0.05 mmol), potassium phosphate tribasic (K$_3$PO$_4$, 236 mg, 1.11 mmol), dodecane (0.1 ml, 0.05 mmol) and cyclohexane 1,2-diamine (0.01 ml, 0.11 mmol) were added dropwise thereto and then the mixture was stirred for 18 hours at 110° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (100 mg, 67%).
NMR:$^1$H-NMR(400 HMz, CDCl$_3$); δ 7.71 (d, 1H), 7.57 (d, 1H), 7.36-7.41 (m, 2H), 7.18-7.25 (m, 3H), 6.67 (d, 1H), 3.93 (s, 3H), 2.22 (s, 3H)

Preparation Example 15-3

Synthesis of [1-(4-fluoro-phenyl)-7-methyl-1H-indol-6-yl]-methanol 1-(4-Fluoro-phenyl)-7-methyl-1H-indole-6-carboxylic acid methyl ester (100 mg, 0.35 mmol) obtained from Preparation Example 15-2 was dissolved in tetrahydrofuran (7 ml), and lithium aluminium hydride (67 mg, 1.76 mmol) was added dropwise thereto. The mixture was stirred for 2 hours at room temperature and then water (1 ml), 6N sodium hydroxide (1 ml) and water (3 ml) were added sequentially. Ethyl acetate was added thereto, and the mixture was filtered with Celite. Filtrate was distilled under reduced pressure and separated by column chromatography to obtain the title compound (90 mg, 100%).

Preparation Example 16

Synthesis of (7-methyl-1-thiophen-3-yl-1H-indol-6-yl)-methanol

In the methods described in Preparation Examples 15-2 and 15-3, 3-bromothiophene was used rather than 1-fluoro-4-iodo-benzene to obtain the title compound (30 mg, 23%).

Preparation Example 17-1

Synthesis of 1-benzyl-7-methyl-1H-indole-6-carboxylic acid methyl ester

7-Methyl-1H-indole-6-carboxylic acid methyl ester (100 mg, 0.53 mmol) obtained from Preparation Example 15-1 was dissolved in dimethylformamide (5 ml). Benzyl bromide (0.13 ml, 1.06 mmol) and sodium hydride (46 mg, 1.06 mmol) were added dropwise thereto and then the mixture was stirred for 8 hours at room temperature. 1N hydrochloric acid solution was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (100 mg, 68%).
NMR:$^1$H-NMR(400 HMz, CDCl$_3$)); δ 7.61 (d, 1H), 7.48 (d, 1H), 7.21-7.31 (m, 3H), 7.17 (d, 1H), 6.90 (d, 2H), 6.56 (d, 1H), 5.63 (s, 2H), 3.86 (s, 3H), 2.73 (s, 3H)

Preparation Example 17-2

Synthesis of (1-benzyl-7-methyl-1H-indol-6-yl)-methanol

1-Benzyl-7-methyl-1H-indole-6-carboxylic acid methyl ester (100 mg, 0.36 mmol) obtained from Preparation Example 17-1 was dissolved in tetrahydrofuran (7 ml), and lithium aluminium hydride (100 mg, 2.63 mmol) was added dropwise thereto. The mixture was stirred for 2 hours at room temperature and then water (1 ml), 6N sodium hydroxide (2 ml) and water (3 ml) were added sequentially. Ethyl acetate was added thereto, and the mixture was filtered with Celite. Filtrate was distilled under reduced pressure and separated by column chromatography to obtain the title compound (92 mg, 100%).
NMR:$^1$H-NMR(500 HMz, CDCl$_3$); δ 7.53 (d, 1H), 7.31 (m, 3H), 7.11 (m, 2H), 6.96 (d, 2H), 6.59 (d, 1H), 5.60 (s, 1H), 4.73 (d, 2H), 2.55 (s, 3H), 1.89 (t, 1H)

Preparation Example 18-1

Synthesis of 1-(2-fluoro-benzyl)-7-methyl-1H-indole-6-carboxylic acid methyl ester In the method described in Preparation Example 17-1, 1-bromomethyl-2-fluoro-benzene was used rather than benzyl bromide to obtain the title compound (279 mg, 94%).
NMR:$^1$H-NMR(400 HMz, CDCl$_3$); δ 7.55 (d, 1H), 7.40 (d, 1H), 7.22-7.30 (m 1H), 7.20 (d, 1H), 7.04-7.10 (m, 1H), 6.91-6.97 (m, 1H), 6.55 (d, 1H), 6.33 (dd, 1H), 5.68 (s, 2H), 3.85 (s, 3H), 2.71 (s, 3H)

Preparation Example 18-2

Synthesis of [1-(2-fluoro-benzyl)-7-methyl-1H-indol-6-yl]-methanol

According to the method described in Preparation Example 17-2, the compound (279 mg, 1.04 mmol) obtained from Preparation Example 18-1 was used to obtain the title compound (161 mg, 34%).

Preparation Example 19-1

Synthesis of 1-(3-fluoro-benzyl)-7-methyl-1H-indole-6-carboxylic acid methyl ester In the method described in Preparation Example 17-1, 3-fluorobenzyl bromide (270 mg, 1.45 mmol) was used rather than benzyl bromide to obtain the title compound (202 mg, 94%).
NMR:$^1$H-NMR(400 HMz, CDCl$_3$); δ 7.54 (d, 1H), 7.48 (d, 1H), 7.23 (dd, 1H), 7.15 (d, 1H), 6.86-6.94 (m, 1H), 6.66 (d, 1H), 6.56 (d, 1H), 6.52 (s, 1H), 5.59 (s, 2H), 3.86 (s, 3H), 2.71 (s, 3H)

Preparation Example 19-2

Synthesis of [1-(3-fluoro-benzyl)-7-methyl-1H-indol-6-yl]-methanol

According to the method described in Preparation Example 17-2, the compound (202 mg, 0.682 mmol) obtained from Preparation Example 19-1 was used to obtain the title compound (201 mg, 100%).

Preparation Example 20-1

Synthesis of 1-(4-fluoro-benzyl)-7-methyl-1H-indole-6-carboxylic acid methyl ester In the method described in Preparation Example 17-1, 4-fluorobenzyl chloride (189 mg, 1.31 mmol) was used rather than benzyl bromide to obtain the title compound (152 mg, 78%).
NMR:$^1$H-NMR(400 HMz, CDCl$_3$); δ 7.55 (d, 1H), 7.47 (d, 1H), 7.14 (d, 1H), 6.92-6.97 (m, 2H), 6.81-6.86 (m, 2H), 6.55 (d, 1H), 5.56 (s, 2H), 3.86 (s, 3H), 2.71 (s, 3H)

Preparation Example 20-2

Synthesis of [1-(4-fluoro-benzyl)-7-methyl-1H-indol-6-yl]-methanol

According to the method described in Preparation Example 17-2, the compound (153 mg, 0.51 mmol) obtained from Preparation Example 20-1 was used to obtain the title compound (124 mg, 90%).

Preparation Example 21-1

Synthesis of 1-(3,4-difluoro-benzyl)-7-methyl-1H-indole-6-carboxylic acid methyl ester In the method described in Preparation Example 17-1, 3,4-difluorobenzyl bromide (275 mg, 1.33 mmol) was used rather than benzyl bromide to obtain the title compound (203 mg, 97%).
NMR:$^1$H-NMR(400 HMz, CDCl$_3$); δ 7.58 (d, 1H), 7.48 (d, 1H), 7.14 (d, 1H), 7.01-7.09 (m, 2H), 6.63-6.68 (m, 1H), 6.57 (d, 1H), 5.53 (s, 2H), 3.86 (s, 3H), 2.70 (s, 3H)

Preparation Example 21-2

Synthesis of [1-(3,4-difluoro-benzyl)-7-methyl-1H-indol-6-yl]-methanol

According to the method described in Preparation Example 17-2, the compound (203 mg, 0.64 mmol) obtained from Preparation Example 21-1 was used to obtain the title compound (162 mg, 57%).

Preparation Example 22

Synthesis of [1-(2,6-difluoro-benzyl)-7-methyl-1H-indol-6-yl]-methanol

In the methods described in Preparation Examples 17-1 and 17-2, 2,6-difluorobenzyl bromide was used rather than benzyl bromide to obtain the title compound (200 mg, 100%).

Preparation Example 23

Synthesis of [1-(3,5-difluoro-benzyl)-7-methyl-1H-indol-6-yl]-methanol

In the methods described in Preparation Examples 17-1 and 17-2, 3,5-difluorobenzyl bromide (0.2 g, 0.99 mmol) was used rather than benzyl bromide to obtain the title compound (0.13 g, 91%).

Preparation Example 24

Synthesis of [1-(2,4-difluoro-benzyl)-7-methyl-1H-indol-6-yl]-methanol

In the methods described in Preparation Examples 17-1 and 17-2, 2,4-difluorobenzyl bromide (0.22 g, 1.05 mmol) was used rather than benzyl bromide to obtain the title compound (0.14 g, 94%).

Preparation Example 25-1

Synthesis of 1-(2-chloro-benzyl)-7-methyl-1H-indole-6-carboxylic acid methyl ester In the method described in Preparation Example 17-1, 2-chlorobenzyl bromide (437 mg, 2.13 mmol) was used rather than benzyl bromide to obtain the title compound (302 mg, 91%).
NMR:$^1$H-NMR(400 HMz, CDCl$_3$); δ 7.56 (d, 1H), 7.48 (d, 1H), 7.20 (d, 1H), 7.17 (dd, 1H), 7.12 (d, 1H), 7.10 (dd, 1H), 6.51 (d, 1H), 6.27 (d, 1H), 5.67 (s, 2H), 5.66 (s, 3H), 3.84 (s, 3H), 2.63 (s, 3H)

Preparation Example 25-2

Synthesis of [1-(2-chloro-benzyl)-7-methyl-1H-indol-6-yl]-methanol

According to the method described in Preparation Example 17-2, the compound (302 mg, 0.96 mmol) obtained from Preparation Example 25-1 was used to obtain the title compound (275 mg, 100%).

Preparation Example 26-1

Synthesis of 7-methyl-1-(2-methyl-benzyl)-1H-indole-6-carboxylic acid methyl ester In the method described in Preparation Example 17-1, 2-methylbenzyl bromide (393 mg, 2.13 mmol) was used rather than benzyl bromide to obtain the title compound (278 mg, 89%).
NMR:$^1$H-NMR(400 HMz, CDCl$_3$); δ 7.54 (d, 1H), 7.47 (d, 1H), 7.09-7.20 (m, 2H), 7.04 (d, 1H), 6.98 (dd, 1H), 6.53 (d, 1H), 6.29 (d, 1H), 5.53 (s, 2H), 3.83 (s, 3H), 2.64 (s, 3H), 2.29 (s, 3H)

Preparation Example 26-2

Synthesis of [7-methyl-1-(2-methyl-benzyl)-1H-indol-6-yl]-methanol

According to the method described in Preparation Example 17-2, the compound (186 mg, 0.63 mmol) obtained from Preparation Example 26-1 was used to obtain the title compound (125 mg, 100%).

Preparation Example 27-1

Synthesis of 7-methyl-1-(3-trifluoromethyl-benzyl)-1H-indole-6-carboxylic acid methyl ester In the method described in Preparation Example 17-1, 3-trifluoromethyl-benzyl (359 mg, 1.50 mmol) was used rather than benzyl bromide to obtain the title compound (239 mg, 92%).
NMR:$^1$H-NMR(400 HMz, CDCl$_3$); δ 7.69 (d, 1H), 7.56 (d, 1H), 7.51 (d, 1H), 7.33 (dd, 2H), 7.12 (d, 1H), 6.89 (d, 1H), 6.31 (d, 1H), 5.79 (s, 2H), 3.84 (s, 3H), 2.59 (s, 3H)

Preparation Example 27-2

Synthesis of [7-methyl-1-(3-trifluoromethyl-benzyl)-1H-indol-6-yl]-methanol

According to the method described in Preparation Example 17-2, the compound (239 mg, 0.69 mmol) obtained from Preparation Example 27-1 was used to obtain the title compound (203 mg, 100%).

Preparation Example 28

Synthesis of [7-methyl-1-(4-trifluoromethyl-benzyl)-1H-indol-6-yl]-methanol

In the methods described in Preparation Examples 17-1 and 17-2, 4-trifluoromethylbenzyl bromide was used rather than benzyl bromide to obtain the title compound (488 mg, 100%).

Preparation Example 29-1

Synthesis of 1-(2,6-dimethyl-benzyl)-7-methyl-1H-indole-6-carboxylic acid methyl ester In the method described in Preparation Example 17-1, 2,6-dimethylbenzyl bromide (210 mg, 1.06 mmol) was used rather than benzyl bromide to obtain the title compound (213 mg, 91%).
NMR:$^1$H-NMR(400 HMz, CDCl$_3$); δ 7.62 (d, 1H), 7.50 (d, 1H), 7.20 (dd, 1H), 7.11 (d, 2H), 6.62 (d, 1H), 6.32 (d, 1H), 5.67 (s, 2H), 3.92 (s, 3H), 3.14 (s, 3H), 2.24 (s, 6H)

Preparation Example 29-2

Synthesis of [1-(2,6-dimethyl-benzyl)-7-methyl-1H-indol-6-yl]-methanol

According to the method described in Preparation Example 17-2, the compound (189 mg, 0.61 mmol) obtained from Preparation Example 29-1 was used to obtain the title compound (181 mg, 99%).

Preparation Example 30

Synthesis of [1-(4-methoxy-benzyl)-7-methyl-1H-indol-6-yl]-methanol

In the methods described in Preparation Examples 17-1 and 17-2, 4-methoxybenzyl bromide was used rather than benzyl bromide to obtain the title compound.

Preparation Example 31-1

Synthesis of 1-[3-(t-butyl-dimethyl-silanyl oxymethyl)-benzyl]-7-methyl-1H-indole-6-carboxylic acid methyl ester In the method described in Preparation Example 17-1, t-butyl-(3-chloromethyl-benzyloxy)-dimethyl-silane (1.0 g, 3.7 mmol) was used rather than benzyl bromide to obtain the title compound (800 mg, 51%).
NMR:$^1$H-NMR(400 HMz, CDCl$_3$); δ 7.55 (d, 2H), 7.48 (d, 1H), 7.23 (d, 21H), 7.18 (s, 1H), 7.17 (d, 1H), 6.87 (s, 1H), 6.78 (d, 1H), 6.55 (d, 1H), 5.62 (s, 2H), 4.64 (s, 2H), 3.85 (s, 3H), 2.70 (s, 3H), 1.56 (s, 2H), 0.86 (s, 9H), 0.01 (s, 6H)

Preparation Example 31-2

Synthesis of 1-(3-hydroxymethyl-benzyl)-7-methyl-1H-indol-6-yl-carboxylic acid methyl The compound (800 mg, 1.9 mmol) obtained from Preparation Example 31-1 was dissolved in tetrahydrofuran (20 ml). A solution of tetrabutylammonium fluoride in tetrahydrofuran (1.7 ml, 1.0M) was added thereto, and then the mixture was stirred for 2 hours at room temperature. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (350 mg, 67%).

NMR:$^1$H-NMR(400 HMz, CDCl$_3$); 7.56 (d, 1H), 7.50 (d, 1H), 7.26 (m, 2H), 7.18 (d, 1H), 6.95 (s, 1H), 6.80 (s, 1H), 6.57 (d, 1H), 5.64 (s, 2H), 4.62 (d, 2H), 3.86 (s, 3H), 2.73 (s, 3H),

Preparation Example 31-3

Synthesis of 1-(3-methoxymethyl-benzyl)-7-methyl-1H-indol-6-yl-carboxylic acid methyl ester The compound (178 mg, 0.58 mmol) obtained from Preparation Example 31-2 was dissolved in tetrahydrofuran (10 ml), and methyl iodide (0.11 ml, 1.7 mmol) and sodium hydride (69 mg, 2.9 mmol) were added dropwise at 0° C. The mixture was stirred for 8 hours at room temperature. 1N hydrochloric acid solution was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (141 mg, 75%).

NMR:$^1$H-NMR(400 HMz, CDCl$_3$); δ 7.59 (d, 1H), 7.49 (d, 1H), 7.19-7.25 (m, 2H), 7.15 (d, 1H), 6.96 (s, 1H), 6.76 (d, 1H), 6.55 (d, 1H), 5.66 (s, 2H), 4.37 (s, 2H), 3.85 (s, 3H), 3.34 (s, 3H), 2.72 (s, 3H)

Preparation Example 31-4

Synthesis of [1-(3-methoxymethyl-benzyl)-7-methyl-1H-indol-6-yl]-methanol

According to the method described in Preparation Example 17-2, the compound (99.6 mg, 0.31 mmol) obtained from Preparation Example 31-3 was used to obtain the title compound (90.3 mg, 98%).

Preparation Example 32

Synthesis of [1-(4-methanesulfonyl-benzyl)-7-methyl-1H-indol-6-yl]-methanol

In the methods described in Preparation Examples 17-1 and 17-2, 1-bromomethyl-4-methanesulfonyl-benzene was used rather than benzyl bromide to obtain the title compound (368 mg, 100%).

NMR:$^1$H-NMR(400 HMz, CDCl$_3$); δ 7.91 (t, 2H), 7.58 (d, 2H), 7.42 (d, 1H), 7.10 (d, 2H), 6.51 (d, 1H), 4.62 (d, 2H), 4.51 (d, 2H), 2.51 (s, 3H), 2.38 (s, 3H)

Preparation Example 33-1

Synthesis of 1-(3-methanesulfonylmethyl-benzyl)-7-methyl-1H-indole-6-carboxylic acid methyl ester In the method described in Preparation Example 17-1, methanesulfonic acid 3-methanesulfonylmethyl-benzyl ester was used rather than benzyl bromide to obtain the title compound (150 mg, 51%)).

NMR:$^1$H-NMR(400 HMz, CDCl$_3$); δ 7.54 (d, 1H), 7.49 (d, 1H), 7.28-7.36 (m, 2H), 7.20 (d, 1H), 6.94 (d, 1H), 6.78 (s, 1H), 6.59 (d, 1H), 5.66 (s, 2H), 4.12 (s, 2H), 3.86 (s, 3H), 2.68 (s, 3H), 2.56 (s, 3H)

Preparation Example 33-2

Synthesis of [1-(3-methanesulfonylmethyl-benzyl)-7-methyl-1H-indol-6-yl]-methanol According to the method described in Preparation Example 17-2, the compound (150 mg, 0.40 mmol) obtained from Preparation Example 33-1 was used to obtain the title compound (130 mg, 94%).

Preparation Example 34

Synthesis of 1-(4-methanesulfonylmethyl-benzyl)-7-methyl-1H-indole-6-carboxylic acid methyl ester In the method described in Preparation Example 17-1, methanesulfonic acid 4-methanesulfonylmethyl-benzyl ester was used rather than benzyl bromide to obtain the title compound (250 mg, 85%).

NMR:$^1$H-NMR(400 HMz, CDCl$_3$); δ 7.56 (d, 1H), 7.49 (d, 1H), 7.32 (dd, 2H), 7.17 (d, 1H), 6.93 (d, 2H), 6.58 (d, 1H), 5.66 (s, 2H), 4.20 (s, 2H), 3.87 (s, 3H), 2.74 (s, 3H), 2.70 (s, 3H)

Preparation Example 35

Synthesis of [1-(4-methanesulfonylmethyl-benzyl)-7-methyl-1H-indol-6-yl]-methanol According to the method described in Preparation Example 17-2, the compound (250 mg, 0.67 mmol) obtained from Preparation Example 34 was used to obtain the title compound (230 mg, 100%).

Preparation Example 36-1

Synthesis of 7-methyl-1-(6-methyl-pyridin-3-ylmethyl)-1H-indole-6-carboxylic acid methyl ester In the method described in Preparation Example 17-1, methanesulfonic acid 6-methyl-pyridin-3-ylmethyl ester (1.20 g, 5.96 mmol) was used rather than benzyl bromide to obtain the title compound (0.38 g, 41%).

NMR:$^1$H-NMR(400 HMz, CDCl$_3$); δ 8.22 (s, 1H), 7.55 (d, 1H), 7.47 (d, 1H), 7.10 (d, 1H), 7.00 (d, 1H), 6.93 (dd, 1H), 6.56 (d, 1H), 5.58 (s, 2H), 3.86 (s, 3H), 2.73 (s, 3H), 2.50 (s, 3H)

Preparation Example 36-2

Synthesis of [7-methyl-1-(6-methyl-pyridin-3-ylmethyl)-1H-indol-6-yl]-methanol

According to the method described in Preparation Example 17-2, the compound obtained from Preparation Example 36-1 was used to obtain the title compound (137 mg, 100%).

Preparation Example 37-1

Synthesis of 1-(6-chloro-pyridin-3-ylmethyl)-7-methyl-1H-indole-6-carboxylic acid methyl ester In the method described in Preparation Example 17-1, 5-bromomethyl-2-chloro-pyridine (223 mg, 1.38 mmol) was used rather than benzyl bromide to obtain the title compound (178 mg, 82%).
NMR:$^1$H-NMR(400 HMz, CDCl$_3$); δ 8.16 (d, 1H), 7.61 (d, 1H), 7.50 (d, 1H), 7.21 (d, 1H), 7.18 (d, 1H), 7.03 (dd, 1H), 6.62 (d, 1H), 5.63 (s, 2H), 3.91 (s, 3H), 2.74 (s, 3H)

Preparation Example 37-2

Synthesis of [1-(6-chloro-pyridin-3-ylmethyl)-7-methyl-1H-indol-6-yl]-methanol

According to the method described in Preparation Example 17-2, the compound obtained from Preparation Example 37-1 was used to obtain the title compound (148 mg, 89%).

Preparation Example 38-1

Synthesis of 7-methyl-1-pyrazin-2-ylmethyl-1H-indole-6-carboxylic acid methyl ester In the method described in Preparation Example 17-1, methanesulfonic acid pyrazin-2-yl methyl ester (132 mg, 0.70 mmol) was used rather than benzyl bromide to obtain the title compound (59 mg, 41%).
NMR:$^1$H-NMR(400 HMz, CDCl$_3$); δ 8.54 (d, 1H), 8.47 (d, 1H), 7.90 (s, 1H), 7.57 (d, 1H), 7.49 (d, 1H), 7.24 (d, 1H), 6.62 (d, 1H), 5.76 (s, 2H), 3.87 (s, 3H), 2.72 (s, 3H)

Preparation Example 38-2

Synthesis of (7-methyl-1-pyrazin-2-ylmethyl-1H-indol-6-yl)-methanol

According to the method described in Preparation Example 17-2, the compound obtained from Preparation Example 38-1 was used to obtain the title compound (39.8 mg, 75%).

Preparation Example 39

Synthesis of (7-methyl-1-pyrimidin-4-ylmethyl-1H-indol-6-yl)-methanol

In the methods described in Preparation Examples 17-1 and 17-2, 4-bromomethyl-pyrimidine (0.74 g, 4.26 mmol) was used rather than benzyl bromide to obtain the title compound (0.05 g, 5%).
NMR:$^1$H-NMR(400 HMz, CDCl$_3$); δ 9.18 (s, 1H), 8.55 (d, 1H), 7.50 (d, 1H), 7.13 (d, 1H), 7.06 (d, 1H), 6.59 (d, 1H), 6.44 (d, 1H), 5.65 (s, 2H), 4.75 (d, 2H), 3.87 (t, 1H), 2.46 (s, 3H)

Preparation Example 40

Synthesis of (7-methyl-1-pyrimidin-2-ylmethyl-1H-indol-6-yl)-methanol

In the methods described in Preparation Examples 17-1 and 17-2, 2-bromomethyl-pyrimidine (0.39 g, 2.22 mmol) was used rather than benzyl bromide to obtain the title compound (0.09 g, 18%).
NMR:$^1$H-NMR(400 HMz, CDCl$_3$); δ 8.62 (d, 2H), 7.38 (d, 1H), 7.17 (d, 1H), 7.12 (t, 1H), 7.02 (d, 1H), 6.53 (d, 1H), 5.73 (s, 2H), 4.71 (s, 2H), 2.57 (s, 3H)

Preparation Example 41

Synthesis of 7-methyl-1-(5-methyl-pyrazin-2-ylmethyl)-1H-indole-6-carboxylic acid methyl ester In the method described in Preparation Example 17-1, methanesulfonic acid 5-methyl-pyrazin-2-yl methyl ester (144 mg, 0.71 mmol) was used rather than benzyl bromide to obtain the title compound (96 mg, 91%).
NMR:$^1$H-NMR(400 HMz, CDCl$_3$); δ 7.76 (s, 1H), 7.58 (d, 1H), 7.47 (d, 1H), 7.22 (d, 1H), 6.59 (d, 1H), 5.71 (s, 2H), 3.86 (s, 3H), 2.73 (s, 3H), 2.46 (s, 3H)

Preparation Example 42

Synthesis of [7-methyl-1-(5-methyl-pyrazin-2-ylmethyl)-1H-indol-6-yl]-methanol

According to the method described in Preparation Example 17-2, the compound (96 mg, 0.33 mmol) obtained from Preparation Example 41 was used to obtain the title compound (87 mg, 100%).

Preparation Example 43-1

Synthesis of 7-methyl-1-thiazol-4-ylmethyl-1H-indole-6-carboxylic acid methyl ester In the method described in Preparation Example 17-1, 4-chloromethyl-thiazole (144 mg, 0.85 mmol) was used rather than benzyl bromide to obtain the title compound (159 mg, 86%).
NMR:$^1$H-NMR(400 HMz, CDCl$_3$); δ 8.79 (d, 1H), 7.55 (d, 1H), 7.47 (d, 1H), 7.22 (d, 1H), 6.56 (d, 1H), 6.34 (s, 1H), 5.77 (s, 2H), 3.87 (s, 3H), 2.75 (s, 3H)

Preparation Example 43-2

Synthesis of (7-methyl-1-thiazol-4-ylmethyl-1H-indol-6-yl)-methanol

According to the method described in Preparation Example 17-2, the compound (108 mg, 0.38 mmol) obtained from Preparation Example 43-1 was used to obtain the title compound (93 mg, 95%).

Preparation Example 44-1

Synthesis of 7-methyl-1-(2-methyl-thiazol-4-ylmethyl)-1H-indole-6-carboxylic acid methyl ester In the method described in Preparation Example 17-1, 4-chloromethyl-2-methyl-thiazole (152 mg, 0.83 mmol) was used rather than benzyl bromide to obtain the title compound (118 mg, 62%).
NMR:$^1$H-NMR(400 HMz, CDCl$_3$); δ 7.54 (d, 1H), 7.46 (d, 1H), 7.20 (s, 1H), 6.54 (d, 1H), 6.23 (s, 1H), 5.62 (s, 2H), 3.87 (s, 3H), 2.76 (s, 3H), 2.70 (s, 3H)

Preparation Example 44-2

Synthesis of [7-methyl-1-(2-methyl-thiazol-4-ylmethyl)-1H-indol-6-yl]-methanol

According to the method described in Preparation Example 17-2, the compound (118 mg, 0.39 mmol) obtained from Preparation Example 44-1 was used to obtain the title compound (91 mg, 85%).

Preparation Example 45

Synthesis of [7-methyl-1-(1-methyl-1H-pyrazol-4-ylmethyl)-1H-indol-6-yl]-methanol The compound obtained by using 4-bromomethyl-pyrazol-1-carboxylic acid—t butyl ester (0.75 g, 2.89 mmol) rather than benzyl bromide in the method described in Preparation Example 17-1 was dissolved in methylene chloride (4 ml). 4M hydrochloride solution was added thereto and the mixture was stirred for 1 hour. The mixture was distilled under reduced pressure to remove the solvent. The residue was dissolved in dimethylformamide (6 ml), and sodium hydride (0.09 g, 2.04 mmol) and methyl iodide (0.33 g, 2.36 mmol) were added thereto. The mixture was stirred for 2 hours. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the ester compound. The title compound (0.06 g, 9%) was obtained by using the ester compound according to the method described in Preparation Example 17-2.
NMR:$^1$H-NMR(400 HMz, CDCl$_3$); δ 7.44 (d, 1H), 7.25 (s, 1H), 7.07 (d, 2H), 6.91 (s, 1H), 6.48 (d, 1H), 5.44 (s, 2H), 4.77 (s, 2H), 3.75 (s, 3H), 2.68 (s, 3H)

Preparation Example 46

Synthesis of (1-benzyl-7-chloro-1H-indol-6-yl)-methanol

In the methods described in Preparation Examples 17-1 and 17-2, 7-chloro-1H-indole-6-carboxylic acid methyl ester (300 mg, 1.43 mmol) was used rather than 7-methyl-1H-indole-6-carboxylic acid methyl ester to obtain the title compound (250 mg, 64%).
NMR:$^1$H-NMR(400 HMz, CDCl$_3$); δ 7.53 (d, 1H), 7.21-7.30 (m, 3H), 7.19 (d, 1H), 7.11 (d, 1H), 7.00 (d, 2H), 6.55 (d, 1H), 5.79 (s, 2H), 4.85 (d, 2H), 1.84 (br t, 1H)

Preparation Example 47-1

Synthesis of 1-benzyl-5-fluoro-1H-indole-6-carboxylic acid methyl ester

According to the method described in Preparation Example 17-1, the compound (321 mg, 1.66 mmol) obtained from Preparation Example 13-4 and benzyl bromide (569 mg, 3.33 mmol) were used to obtain the title compound (391 mg, 83%).
NMR:$^1$H-NMR(400 HMz, CDCl$_3$); δ 7.92 (d, 1H), 7.23-7.30 (m, 5H), 7.08 (d, 2H), 6.50 (d, 1H), 5.31 (s, 2H), 3.90 (s, 3H)

Preparation Example 47-2

Synthesis of (1-benzyl-5-fluoro-1H-indol-6-yl)-methanol

According to the method described in Preparation Example 17-2, the compound (391 mg, 1.38 mmol) obtained from Preparation Example 47-1 was used to obtain the title compound (352 mg, 100%).

Preparation Example 48-1

Synthesis of 3-amino-6-fluoro-4-iodo-2-methyl-benzoic acid methyl ester

3-Amino-6-fluoro-2-methyl-benzoic acid methyl ester (2.6 g, 14.2 mmol) was dissolved in acetic acid (20 ml). N-iodo-succinimide (NIS, 2.53 g, 14.2 mmol) was added dropwise thereto, and the mixture was stirred for 4 hours at room temperature. The mixture was distilled under reduced pressure. Water was added thereto, and then extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (4.06 g, 93%).
NMR:$^1$H-NMR(400 HMz, CDCl$_3$); δ 7.31 (d, 1H), 3.97 (br s, 2H), 3.92 (s, 3H), 2.21 (s, 3H)

Preparation Example 48-2

Synthesis of 3-amino-6-fluoro-2-methyl-4-trimethylsilanyl ethinyl-benzoic acid methyl ester The compound (2.0 g, 6.47 mmol) obtained from Preparation Example 48-1 was dissolved in tetrahydrofuran (50 ml). Trimethylsilylacetylene (0.95 ml, 9.7 mmol), copper (I) iodide (25 mg, 0.13 mmol), bis(triphenylphosphine) palladium (II) dichloride (Pd(Ph$_3$P)$_2$Cl$_2$, 91 mg, 0.13 mmol) and triethylamine (2.7 ml, 19.4 mmol) were added dropwise thereto, and then the mixture was stirred for 8 hours at 110° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (1.79 mg, 98%).

NMR:¹H-NMR(400 HMz, CDCl₃); δ 6.94 (d, 1H), 4.13 (br s, 2H), 3.92 (s, 3H), 2.13 (s, 3H), 0.27 (s, 9H)

Preparation Example 48-3

Synthesis of
5-fluoro-7-methyl-1H-indole-6-carboxylic acid
methyl ester

The compound (1.54 g, 5.51 mmol) obtained from Preparation Example 48-2 was dissolved in pyridine (40 ml). Acetylchloride (3.9 ml, 55.1 mmol) was slowly added dropwise at −15° C., and the mixture was stirred while slowly raising the reaction temperature up to 0° C. The mixture was distilled under reduced pressure and 1N hydrochloric acid solution was added thereto. The mixture was extracted with ethyl acetate, washed with saturated aqueous sodium chloride solution, dried over anhydrous magnesium sulfate and filtered. Filtrate was distilled under reduced pressure to obtain a compound. To the obtained compound, tetrahydrofuran (50 ml) and 2 N solution of tetrabutylammonium fluoride in tetrahydrofuran (5.5 ml, 11.0 mml) were added. The mixture was stirred for 8 hours at 80° C. and water was added. The mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (810 mg, 71%).

NMR:¹H-NMR(400 HMz, CDCl₃); δ 8.23 (br s, 1H), 7.32 (m, 1H), 7.18 (d, 1H), 6.52 (m, 1H), 3.95 (s, 3H), 2.55 (s, 3H)

Preparation Example 48-4

Synthesis of (1-benzyl-5-fluoro-7-methyl-1H-indol-6-yl)-methanol

In the methods described in Preparation Examples 17-1 and 17-2, the compound (200 mg, 1.04 mmol) obtained from Preparation Example 48-3 was used rather than 7-methyl-1H-indole-6-carboxylic acid methyl ester to obtain the title compound (251 mg, 96%).

NMR:¹H-NMR(400 HMz, CDCl₃); δ 7.29 (m, 3H), 7.18 (d, 1H), 7.12 (d, 1H), 6.87 (d, 1H), 6.49 (d, 1H), 5.59 (s, 2H), 4.82 (m, 2H), 2.57 (s, 3H)

Preparation Example 49-1

Synthesis of
1-benzyl-3-fluoro-7-methyl-1H-indole-6-carboxylic
acid methyl ester The compound (258 mg, 0.92 mmol) obtained from Preparation Example 17-1 and N-fluoro-2,4,6-trimethylpyridinium triflate (321 mg, 1.11 mmol) were used to obtain the title compound (30 mg, 11%).

NMR:¹H-NMR(400 HMz, CDCl₃); δ 7.59 (d, 1H), 7.54 (d, 1H), 7.30-7.36 (m, 3H), 7.00 (d, 1H), 6.97 (d, 1H), 6.95 (d, 1H), 3.92 (s, 2H), 3.92 (s, 3H), 2.77 (s, 3H)

Preparation Example 49-2

Synthesis of (1-benzyl-3-fluoro-7-methyl-1H-indol-6-yl)-methanol

According to the method described in Preparation Example 17-2, the compound (30 mg, 0.10 mmol) obtained from Preparation Example 49-1 was used to obtain the title compound (27 mg, 100%).

Preparation Example 50-1

Synthesis of 1-methyl-1H-indole-5-carboxylic acid
methyl ester 1H-indole-6-carboxylic acid methyl ester (1.0 g, 5.71 mmol) was dissolved in dimethylformamide (10 ml), and methyl iodide (0.53 ml, 8.56 mmol) and sodium hydride (374 mg, 8.56 mmol) were added dropwise thereto at 0° C. The mixture was stirred for 8 hours at room temperature. 1N hydrochloric acid solution was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (600 mg, 56%).

Preparation Example 50-2

Synthesis of
3-benzyl-1-methyl-1H-indole-5-carboxylic acid
methyl ester

The compound (200 mg, 1.06 mmol) obtained from the Preparation Example 50-1 was dissolved in dioxane (7 ml). Benzyl bromide (0.25 ml, 2.11 mmol) and zinc bromide (ZnBr₂, 140 mg, 0.53 mmol) were added thereto, and the mixture was stirred for 3 hours at 60° C. Water was added thereto, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the mixture of the title compound and 2,3-dibenzyl-1-methyl-1H-indole-5-carboxylic acid methyl ester.

Preparation Example 50-3

Synthesis of
(3-benzyl-1-methyl-1H-indol-5-yl)-methanol

According to the method described in Preparation Example 17-2, the compound obtained from Preparation Example 50-2 was used to obtain a mixture of the title compound and (2,3-dibenzyl-1-methyl-1H-indol-5-yl)-methanol.

Preparation Example 51-1

Synthesis of
3-bromo-1-methyl-1H-indole-5-carboxylic acid
methyl ester

1-Methyl-1H-indole-5-carboxylic acid methyl ester (200 mg, 1.06 mmol) obtained from Preparation Example 50-1 was dissolved in dimethylformamide (5 ml). N-bromosuccinimide (NBS, 208 mg, 1.17 mmol) was added dropwise thereto, and then the mixture was stirred for 2 hours at 0° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (250 mg, 88%).

Preparation Example 51-2

Synthesis of 1-methyl-3-o-tolyl-1H-indole-5-carboxylic acid methyl ester

The compound obtained from Preparation Example 51-1 was dissolved in dimethylformamide (5 ml). 2-Methylphenylboronic acid (102 mg, 0.75 mmol), potassium phosphate tribasic ($K_3PO_4$, 509 mg, 2.40 mmol) and palladium tetrakistriphenylphosphine ($Pd(PPh_3)_4$, 86 mg, 0.07 mmol) were added dropwise thereto, and then the mixture was stirred for 8 hours at 100° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (85 mg, 81%).
NMR:$^1$H-NMR(400 HMz, $CDCl_3$); δ 8.24 (d, 1H), 7.97 (dd, 1H), 7.33-7.39 (m, 2H), 7.29-7.31 (m, 1H), 7.26-7.28 (m, 3H), 3.89 (s, 3H), 3.88 (s, 3H), 2.31 (s, 3H)

Preparation Example 51-3

Synthesis of (1-methyl-3-o-tolyl-1H-indol-5-yl)-methanol

According to the method described in Preparation Example 17-2, the compound (85 mg, 0.30 mmol) obtained from Preparation Example 51-2 was used to obtain the title compound (59 mg, 78%).
NMR:$^1$H-NMR(500 HMz, $CDCl_3$); δ 7.49 (s, 1H), 7.24-7.42 (m, 6H), 7.06 (s, 1H), 4.74 (s, 2H), 3.85 (s, 3H), 2.33 (s, 3H)

Preparation Example 52-1

Synthesis of 2-[2-(tetrahydro-pyran-2-yloxy)-ethyl]-1H-indole-6-carboxylic acid methyl ester In the methods described in Preparation Examples 48-1 to 48-3, 3-amino-4-iodo-benzoic acid methyl ester (500 mg, 1.8 mmol) rather than 3-amino-6-fluoro-4-iodo-2-methyl-benzoic acid methyl ester and 2-buty-3-yloxy-tetrahydropyrane rather than trimethylsilylacetylene were used to obtain the title compound (200 mg, 37%).

Preparation Example 52-2

Synthesis of 1-benzyl-2-[2-(tetrahydro-pyran-2-yloxy)-ethyl]-1H-indole-6-carboxylic acid methyl ester According to the method described in Preparation Example 17-1, the compound (200 mg, 0.66 mmol) obtained from Preparation Example 52-1 was used to obtain the title compound (240 mg, 92%).
NMR:$^1$H-NMR(400 HMz, $CDCl_3$); δ 8.01 (s, 1H), 7.78 (dd, 1H), 7.58 (d, 1H), 7.21-7.24 (m, 3H), 6.93 (d, 2H), 6.46 (s, 1H), 5.46 (s, 2H), 4.57 (t, 1H), 3.89 (s, 3H), 4.02-4.08 (m, 1H), 3.71 (t, 2H), 3.67-3.76 (m, 2H), 3.44-3.47 (m, 1H), 3.00 (t, 2H), 1.78-1.80 (m, 1H), 1.66-1.71 (m, 1H), 1.51-1.56 (m, 4H)

Preparation Example 52-3

Synthesis of 1-benzyl-2-(2-hydroxy-ethyl)-1H-indole-6-carboxylic acid methyl ester The compound (240 mg, 0.61 mmol) obtained from Preparation Example 52-2 was dissolved in ethanol (5 ml) and p-toluenesulfonic acid (23 mg, 0.12 mmol) was added thereto. The mixture was stirred for 3 hours at room temperature and excess triethylamine was added. The mixture was distilled under reduced pressure and the residue was isolated by column chromatography to obtain the title compound (160 mg, 85%).

Preparation Example 52-4

Synthesis of 1-benzyl-2-(2-methoxy-ethyl)-1H-indole-6-carboxylic acid methyl ester In the method described in Preparation Example 17-1, the compound (160 mg, 0.52 mmol) prepared from Preparation Example 52-3 and methyl iodide rather than benzyl bromide were used to obtain the title compound (160 mg, 94%).

Preparation Example 52-5

Synthesis of [1-benzyl-2-(2-methoxy-ethyl)-1H-indol-6-yl]-methanol

According to the method described in Preparation Example 17-2, the compound (160 mg, 0.49 mmol) obtained from Preparation Example 52-4 was used to obtain the title compound (130 mg, 90%).

Preparation Example 53-1

Synthesis of 1H-pyrrolo[2,3-b]pyridine-6-carboxylic acid 1H-pyrrolo[2,3-b]pyridine-6-carbonitrile (120 mg, 0.84 mmol) was dissolved in ethanol (10 ml). 6N Sodium hydroxide (1.4 ml, 8.4 mmol) was added, and the mixture was stirred for 18 hours at 90° C. The mixture was distilled under reduced pressure, and then 1N hydrochloric acid solution was added. The resulting solution was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (100 mg, 74%).
NMR:$^1$H-NMR(400 HMz, DMS)-$d_6$); δ 12.08 (brs, 1H), 8.11 (d, 1H), 7.83 (d, 1H), 7.70 (d, 1H), 6.58 (d, 1H)

Preparation Example 53-2

Synthesis of 1H-pyrrolo[2,3-b]pyridine-6-carboxylic acid methyl ester

According to the method described in Preparation Example 7-2, the compound (100 mg, 0.62 mmol) obtained from Preparation Example 53-1 was used to obtain the title compound (90 mg, 82%).

NMR:¹H-NMR(400 HMz, CDCl₃); δ 8.06 (dd, 1H), 8.00 (d, 1H), 7.73 (dd, 1H), 6.60 (dd, 1H), 4.06 (s, 3H)

Preparation Example 53-3

Synthesis of 1-(4-fluoro-benzyl)-1H-pyrazolo[2,3-b]pyridine-6-carboxylic acid methyl ester According to the method described in Preparation Example 17-1, the compound (90 mg, 0.51 mmol) obtained from Preparation Example 53-2 and 4-fluorobenzyl bromide were used to obtain the title compound (100 mg, 69%).

NMR:¹H-NMR(400 HMz, CDCl₃); δ 8.01 (d, 1H), 7.98 (d, 1H), 7.23-7.29 (m, 2H), 6.98-7.02 (m, 3H), 6.54 (d, 1H), 5.55 (s, 2H), 4.02 (s, 3H)

Preparation Example 53-4

Synthesis of [1-(4-fluoro-benzyl)-1H-pyrrolo[2,3-b]pyridin-6-yl]-methanol

According to the method described in Preparation Example 17-2, the compound (100 mg, 0.35 mmol) obtained from Preparation Example 53-3 was used to obtain the title compound (70 mg, 77%).

Preparation Example 54-1

Synthesis of 1-benzyl-1H-pyrrolo[2,3-b]pyridine-6-carbonitrile

According to the method described in Preparation Example 17-1, 1H-pyrrolo[2,3-b]pyridine-6-carbonitrile (150 mg, 1.18 mmol) and benzyl bromide were used to obtain the title compound (270 mg, 97%).

NMR:¹H-NMR(400 HMz, CDCl₃); δ7.98 (d, 1H), 7.46 (d, 1H), 7.40 (d, 1H), 7.21-7.35 (m, 5H), 6.56 (d, 1H), 5.50 (s, 2H)

Preparation Example 54-2

Synthesis of (1-benzyl-1H-pyrrolo[2,3-b]pyridin-6-yl)-methanol

The compound (270 mg, 1.15 mmol) obtained from Preparation Example 54-1 was dissolved in ethanol (50 ml). 6N Sodium hydroxide (2.0 ml, 11.57 mmol) was added, and the mixture was stirred for 18 hours at 90° C. The mixture was distilled under reduced pressure, and then 1N hydrochloric acid solution was added. The resulting solution was extracted with ethyl acetate. The extract was washed with saturated aqueous sodium chloride solution, dried over anhydrous magnesium sulfate and filtered. Filtrate was distilled under reduced pressure to obtain 1-benzyl-1H-pyrrolo[2,3-b]pyridine-6-carboxylic acid.

1-Benzyl-1H-pyrrolo[2,3-b]pyridine-6-carboxylic acid was dissolved in methylenechloride (20 ml) and 0.25M solution of diazomethane in diethyl ether (5.0 ml, 1.38 mmol) was slowly added dropwise. The mixture was stirred for 30 minutes at room temperature, and then distilled under reduced pressure to obtain 1-benzyl-1H-pyrrolo[2,3-b]pyridine-6-carboxylic acid methyl ester (310 mg, 100%).

According to the method described in Preparation Example 17-2, 1-benzyl-1H-pyrrolo[2,3-b]pyridine-6-carboxylic acid methyl ester (310 mg, 1.15 mmol) was used to obtain the title compound (275 mg, 99%).

NMR:¹H-NMR(400 HMz, CDCl₃); δ 7.90 (d, 1H), 7.12-7.37 (m, 6H), 6.98 (d, 1H), 6.48 (d, 1H), 5.50 (s, 2H), 4.85 (d, 2H), 3.92 (t, 1H)

Preparation Example 55

Synthesis of 1-benzyl-1H-indazole-6-carboxylic acid methyl ester and 2-benzyl-1H-indazole-6-carboxylic acid methyl ester 1H-indazole-6-carboxylic acid methyl ester (300 mg, 1.7 mmol) was dissolved in dimethylformamide (7 ml), and sodium hydride (82 mg, 1.87 mmol) and benzyl bromide (0.22 ml, 1.87 mmol) were slowly added dropwise at 0° C. The mixture was stirred for 8 hours at room temperature. 1N hydrochloric acid solution was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography. The first compound that passed through the column chromatography was 1-benzyl-1H-indazole-6-carboxylic acid methyl ester (209 mg, 46%), and the second one was 2-benzyl-1H-indazole-6-carboxylic acid methyl ester (160 mg, 35%).

NMR:¹H-NMR(400 HMz, CDCl₃); δ 8.15 (s, 1H), 8.10 (s, 1H), 7.82 (q, 2H), 7.33 (m, 3H), 7.20 (d, 2H), 5.65 (s, 2H), 3.94 (s, 3H)

NMR:¹H-NMR(400 HMz, CDCl₃); δ 8.53 (s, 1H), 7.91 (s, 1H), 7.72 (d 1H), 7.64 (d, 1H), 7.37 (m, 3H), 7.29 (d, 2H), 5.63 (s, 2H), 3.95 (s, 3H)

Preparation Example 56

Synthesis of (1-benzyl-1H-indazol-6-yl)-methanol

According to the method described in Preparation Example 17-2, 1-benzyl-1H-indazole-6-carboxylic acid methyl ester (209 mg, 0.78 mmol) obtained from Preparation Example 55 was used to obtain the title compound (187 mg, 100%).

NMR:¹H-NMR(500 HMz, CDCl₃); δ 8.02 (s, 1H), 7.72 (d, 1H), 7.37 (s, 1H), 7.27 (m, 3H), 7.18 (d, 2H), 7.13 (d, 1H), 5.59 (s, 2H), 4.80 (d, 2H), 1.80 (t, 1H)

Preparation Example 57

Synthesis of (2-benzyl-2H-indazol-6-yl)-methanol

According to the method described in Preparation Example 17-2, 2-benzyl-1H-indazole-6-carboxylic acid methyl ester (160 mg, 0.6 mmol) obtained from Preparation Example 55 was used to obtain the title compound (143 mg, 100%).

NMR:¹H-NMR(400 HMz, CDCl₃); δ 8.02 (s, 1H), 7.64 (s, 1H), 7.59 (d, 1H), 7.28-7.36 (m, 5H), 7.08 (d, 1H), 5.27 (s, 2H), 4.72 (s, 2H), 2.39 (br s, 1H)

Preparation Example 58

Synthesis of [1-(4-fluoro-benzyl)-1H-indazol-6-yl]-methanol

In the methods described in Preparation Examples 55 and 56, 4-fluorobenzylchloride (1.81 g, 12.50 mmol) was used rather than benzyl bromide to obtain the title compound (870 mg, 30%).

NMR:¹H-NMR(400 HMz, CDCl₃); δ 8.02 (s, 1H), 7.72 (d, 1H), 7.38 (s, 1H), 7.12~7.18 (m, 3H), 6.97 (t, 2H), 5.55 (s, 2H), 4.82 (d, 2H), 1.90 (t, 1H)

Preparation Example 59

Synthesis of [2-(4-fluoro-benzyl)-2H-indazol-6-yl]-methanol

In the methods described in Preparation Examples 55 and 57, 4-fluorobenzylchloride (1.81 g, 12.50 mmol) was used rather than benzyl bromide to obtain the title compound (580 mg, 20%).
NMR:¹H-NMR(400 HMz, CDCl₃); δ 7.87 (s, 1H), 7.67 (s, 1H), 7.61 (d, 1H), 7.25 (t, 2H), 7.12 (d, 1H), 7.10 (t, 2H), 5.56 (s, 2H), 4.78 (d, 2H), 1.75 (t, 1H)

Preparation Example 60-1

Synthesis of 1-pyrimidin-2-ylmethyl-1H-indazole-carboxylic acid methyl ester and 2-pyrimidin-2-ylmethyl-1H-indazole-carboxylic acid methyl ester In the method described in Preparation Example 55, 1H-indazole-6-carboxylic acid methyl ester (402 mg, 2.3 mmol), and 2-bromomethyl-pyrimidine rather than benzyl bromide were used to obtain 1-pyrimidin-2-ylmethyl-1H-indazole-carboxylic acid methyl ester (272 mg, 44%) which was the first compound that passed through column chromatography and 2-pyrimidin-2-ylmethyl-1H-indazole-carboxylic acid methyl ester (110 mg, 18%) which was the second one.

Preparation Example 60-2

Synthesis of (1-pyrimidin-2-ylmethyl-1H-indazol-6-yl)-methanol

1-Pyrimidin-2-ylmethyl-1H-indazole-carboxylic acid methyl ester (1.27 g, 4.75 mmol) obtained from Preparation Example 60-1 was dissolved in the mixture of tetrahydrofuran (10 ml) and methanol (3 mL). 2N sodium hydroxide solution (3 ml) was added dropwise, and then the mixture was stirred for 2 hours. The mixture was acidified with 1N hydrochloric acid solution, and then extracted with ethyl acetate. The extract was dried over anhydrous magnesium sulfate, and then distilled under reduced pressure. The residue was dissolved in tetrahydrofuran (15 ml). N-methyl morpholine (0.50 g, 4.95 mmol) and isobutylchloroformate (0.62 g, 4.54 mmol) were added dropwise at 0° C. The mixture was filtered to remove insoluble solids. To the filtrate, sodium borohydride (0.31 g, 8.26 mmol) was added and the mixture was stirred for 3 hours. The reaction was terminated with an aqueous solution of ammonium chloride, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (0.61 g, 62%).
NMR:¹H-NMR(400 HMz, CDCl₃); δ 8.51 (d, 2H), 7.97 (s, 1H), 7.61 (d, 1H), 7.36 (s, 1H), 7.04 (d, 1H), 7.02 (d, 1H), 5.68 (s, 2H), 4.69 (s, 2H), 3.83 (br s, 1H)

Preparation Example 61

Synthesis of (2-pyrimidin-2-ylmethyl-2H-indazol-6-yl)-methanol

According to the method described in Preparation Example 60-2, 2-pyrimidin-2-ylmethyl-1H-indazole-carboxylic acid methyl ester obtained from Preparation Example 60-1 was used to the title compound (131 mg, 24%)
NMR:¹H-NMR(400 HMz, CDCl₃); δ 8.67 (d, 2H), 8.08 (s, 1H), 7.63 (d, 1H), 7.55 (s, 1H), 7.19 (dd, 1H), 7.08 (dd, 1H), 5.81 (s, 2H), 4.70 (d, 2H), 2.61 (br t, 1H)

Preparation Example 62

Synthesis of (1-pyrazin-2-ylmethyl-1H-indazol-6-yl)-methanol

In the methods described in Preparation Examples 55 and 56, 2-bromomethylpyrazine (1.40 g, 8.09 mmol) was used rather than benzyl bromide to obtain the title compound (0.40 g, 23%).
NMR:¹H-NMR(400 HMz, CDCl₃); δ 8.54 (d, 1H), 8.48 (d, 1H), 8.27 (s, 1H), 8.07 (s, 1H), 7.75 (d, 1H), 7.47 (s, 1H), 7.17 (d, 1H), 5.76 (s, 2H), 4.84 (d, 2H), 1.82 (t, 1H)

Preparation Example 63

Synthesis of [1-(5-methyl-pyrazin-2-ylmethyl)-1H-indazol-6-yl]-methanol

In the methods described in Preparation Examples 55 and 56, methanesulfonic acid 5-methyl-pyrazin-2-ylmethyl ester (2.4 g, 12.08 mmol) was used rather than benzyl bromide to obtain the title compound (760 mg, 28%).
NMR:¹H-NMR(400 HMz, CDCl₃); δ 8.39 (s, 1H), 8.19 (s, 1H), 8.05 (s, 1H), 7.73 (d, 1H), 7.47 (s, 1H), 7.16 (d, 1H), 5.76 (s, 2H), 4.85 (d, 2H), 2.52 (s, 3H), 1.92 (t, 1H)

Preparation Example 64

Synthesis of [2-(5-methyl-pyrazin-2-ylmethyl)-2H-indazol-6-yl]-methanol

In the methods described in Preparation Examples 55 and 57, methanesulfonic acid 5-methyl-pyrazin-2-ylmethyl ester (2.4 g, 12.08 mmol) was used rather than benzyl bromide to obtain the title compound (0.78 g, 19%).
NMR:¹H-NMR(400 HMz, CDCl₃); δ 8.43 (d, 2H), 8.08 (s, 1H), 7.66 (d, 2H), 7.13 (d, 1H), 5.69 (s, 2H), 4.77 (d, 2H), 2.55 (s, 3H), 1.84 (t, 1H)

Preparation Example 65

Synthesis of (1-pyrimidin-4-ylmethyl-1H-indazol-6-yl)-methanol

In the methods described in Preparation Examples 55 and 56, 4-chloromethyl-pyrimidine (0.66 g, 5.12 mmol) was used rather than benzyl bromide to obtain the title compound (0.13 g, 22%).
NMR:¹H-NMR(400 HMz, CDCl₃); δ 9.11 (s, 1H), 8.50 (d, 1H), 8.07 (s, 1H), 7.74 (d, 1H), 7.37 (s, 1H), 7.15 (d, 1H), 6.69 (d, 1H), 5.65 (s, 2H), 4.80 (s, 2H), 2.87 (brs, 1H)

Preparation Example 66

Synthesis of (2-pyrimidin-4-ylmethyl-2H-indazol-6-yl)-methanol

In the methods described in Preparation Examples 55 and 57, 4-chloromethyl-pyrimidine (0.66 g, 5.12 mmol) was used rather than benzyl bromide to obtain the title compound (0.03 g, 5%).
NMR:$^1$H-NMR(400 HMz, CDCl$_3$); δ 9.18 (s, 1H), 8.64 (d, 1H), 8.07 (s, 1H), 7.64 (d, 1H), 7.16 (d, 1H), 6.90 (d, 1H), 5.69 (s, 2H), 4.78 (s, 2H), 2.09 (brs, 1H)

Preparation Example 67

Synthesis of (1-pyridin-3-ylmethyl-1H-indazol-6-yl)-methanol

In the methods described in Preparation Examples 55 and 56, 3-bromomethyl-pyridine was used rather than benzyl bromide to obtain the title compound (406 mg, 60%).

Preparation Example 68

Synthesis of (2-pyridin-3-ylmethyl-2H-indazol-6-yl)-methanol

In the methods described in Preparation Examples 55 and 57, 3-bromomethyl-pyridine was used rather than benzyl bromide to obtain the title compound (237 mg, 35%).

Preparation Example 69

Synthesis of [1-(1-methyl-1H-pyrazol-4-ylmethyl)-1H-indazol-6-yl]-methanol

In the method described in Preparation Example 45, 1H-indazole-6-carboxylic acid methyl ester (0.56 g, 3.19 mmol) was used rather than 7-methyl-1H-indole-6-carboxylic acid methyl ester to obtain the title compound (0.16 g, 20%).
NMR:$^1$H-NMR(400 HMz, CDCl$_3$); δ 7.94 (s, 1H), 7.66 (d, 1H), 7.43 (s, 1H), 7.37 (s, 1H), 7.22 (s, 1H), 7.10 (d, 1H), 5.37 (s, 2H), 4.80 (s, 1H), 3.72 (s, 3H), 3.24 (brs, 1H)

Preparation Example 70

Synthesis of (1H-indazol-6-yl)-methanol

According to the method described in Preparation Example 17-2, 1H-indazole-6-carboxylic acid methyl ester (0.18 g, 0.99 mmol) was used to obtain the title compound (0.15 g, 100%).
NMR:$^1$H-NMR(400 HMz, MeOD); δ 8.05 (s, 1H), 7.72 (d, 1H), 7.55 (s, 1H), 7.14 (d, 1H), 4.75 (s, 2H),

Preparation Example 71

Synthesis of (1-methyl-1H-indazol-6-yl)-methanol

In the methods described in Preparation Examples 55 and 56, methyl iodide (0.93 g, 6.52 mmol) was used rather than benzyl bromide to obtain the title compound (0.15 g, 28%).
NMR:$^1$H-NMR(400 HMz, CDCl$_3$); δ 7.91 (s, 1H), 7.62 (d, 1H), 7.27 (s, 1H), 7.09 (d, 1H), 4.81 (s, 2H), 3.92 (s, 3H), 3.59 (brs, 1H)

Preparation Example 72

Synthesis of (1-isopropyl-1H-indazol-6-yl)-methanol

In the methods described in Preparation Examples 55 and 56, 2-bromo-propane (1.42 g, 11.55 mmol) was used rather than benzyl bromide to obtain the title compound (0.19 g, 17%).
NMR:$^1$H-NMR(400 HMz, CDCl$_3$); δ 7.87 (s, 1H), 7.65 (d, 1H), 7.47 (s, 1H), 7.08 (d, 1H), 4.87 (s, 2H), 4.75 (m, 1H), 3.39 (brs, 1H), 1.53 (d, 6H)

Preparation Example 73

Synthesis of (2-isopropyl-2H-indazol-6-yl)-methanol

In the methods described in Preparation Examples 55 and 57, 2-bromo-propane (1.42 g, 11.55 mmol) was used rather than benzyl bromide to obtain the title compound (0.14 g, 12%).
NMR:$^1$H-NMR(400 HMz, CDCl$_3$); δ 7.82 (s, 1H), 7.56 (d, 2H), 7.07 (d, 1H), 4.74 (m, 1H), 4.68 (s, 2H), 4.00 (br s, 1H), 1.59 (d, 6H)

Preparation Example 74

Synthesis of (1-cyclopropylmethyl-1H-indazol-6-yl)-methanol

In the methods described in Preparation Examples 55 and 56, bromomethyl cyclopropane (1.46 g, 10.84 mmol) was used rather than benzyl bromide to obtain the title compound (0.16 g, 15%).
NMR:$^1$H-NMR(400 HMz, CDCl$_3$); δ 7.90 (s, 1H), 7.63 (d, 1H), 7.42 (s, 1H), 7.09 (d, 1H), 4.82 (s, 2H), 4.16 (d, 2H), 3.50 (br s, 1H), 1.25 (m, 1H), 0.53 (m, 2H), 0.38 (m, 2H)

Preparation Example 75-1

Synthesis of (1-isobutyl-1H-indazol-6-yl)-methanol

In the methods described in Preparation Examples 55 and 56, 1-chloro-2-methyl-propane (1.16 g, 12.5 mmol) was used rather than benzyl bromide to obtain the title compound (0.70 g, 29%).
NMR:$^1$H-NMR(400 HMz, CDCl$_3$); δ 7.81 (s, 1H), 7.60 (m, 2H), 7.09 (d, 1H), 4.71 (d, 2H), 4.11 (d, 2H), 2.38 (m, 1H), 1.86 (t, 1H), 0.91 (d, 6H)

Preparation Example 75-2

Synthesis of (2-isobutyl-1H-indazol-6-yl)-methanol

In the methods described in Preparation Examples 55 and 57, 1-chloro-2-methyl-propane (1.16 g, 12.5 mmol) was used rather than benzyl bromide to obtain the title compound (0.69 g, 29%).
NMR:$^1$H-NMR(400 HMz, CDCl$_3$); δ 7.82 (s, 1H), 7.60 (d, 2H), 7.09 (d, 1H), 4.71 (s, 2H), 4.13 (d, 2H), 3.30 (br s, 1H), 2.39 (m, 1H), 0.90 (d, 6H)

Preparation Example 76

Synthesis of
(1-cyclopentyl-1H-indazol-6-yl)-methanol

In the methods described in Preparation Examples 55 and 56, cyclopentyl bromide (1.69 g, 11.36 mmol) was used rather than benzyl bromide to obtain the title compound (481 mg, 88%).
NMR:$^1$H-NMR(400 HMz, CDCl$_3$); δ 7.97 (s, 1H), 7.70 (d, 1H), 7.49 (s, 1H), 7.11 (d, 1H), 5.01 (m, 1H), 4.86 (d, 2H), 2.16-2.21 (m, 4H), 1.98 (m, 2H), 1.73-1.77 (m, 2H)

Preparation Example 77

Synthesis of
(1-cyclopentylmethyl-1H-indazol-6-yl)-methanol

In the methods described in Preparation Examples 55 and 56, cyclopentyl methyl methanesulfonate (4.05 g, 22.7 mmol) was used rather than benzyl bromide to obtain the title compound (1.13 g, 67%).
NMR:$^1$H-NMR(400 HMz, CDCl$_3$); δ 7.89 (s, 1H), 7.64 (d, 1H), 7.42 (s, 1H), 7.11 (d, 1H), 4.82 (s, 2H), 4.19 (d, 2H), 3.58 (br s, 1H), 2.53 (m, 1H), 1.60 (m, 4H), 1.50 (m, 2H), 1.30 (m, 2H)

Preparation Example 78

Synthesis of [1-(2,2-dimethyl-propyl)-1H-indazol-6-yl]-methanol

In the methods described in Preparation Examples 55 and 56, neopentyl iodide (844 mg, 4.26 mmol) was used rather than benzyl bromide to obtain the title compound (270 mg, 56%).
NMR:$^1$H-NMR(400 HMz, CDCl$_3$); δ 7.98 (s, 1H), 7.69 (d, 1H), 7.43 (s, 1H), 7.11 (d, 1H), 4.85 (d, 2H), 4.16 (s, 2H), 1.76 (t, 1H), 1.03 (s, 9H)

Preparation Example 79-1

Synthesis of [1-(2-methanesulfonyl-ethyl)-1H-indazol-5-yl]-methanol

According to the methods described in Preparation Examples 55 and 56, 1H-indazole-5-carboxylic acid methyl ester (0.88 g, 5.0 mmol) and methanesulfonic acid 2-methanesulfonyl-ethyl ester (2.02 g, 10.0 mmol) were used to obtain the title compound (0.20 g, 16%).
NMR:$^1$H-NMR(500 HMz, CDCl$_3$); δ 8.05 (s, 1H), 7.72 (s, 1H), 7.56-7.46 (m, 2H), 4.86 (t, 2H), 4.80 (d, 2H), 3.71 (t, 2H), 2.45 (s, 3H), 1.70 (t, 1H)

Preparation Example 79-2

Synthesis of [1-(3-methanesulfonyl-propyl)-1H-indazol-5-yl]-methanol

According to the methods described in Preparation Examples 55 and 56, 1H-indazole-5-carboxylic acid methyl ester (1.0 g, 5.15 mmol) and methanesulfonic acid 3-methanesulfonyl-propyl ester (1.4 g, 10.3 mmol) were used to obtain the title compound (0.49 g, 36%).
NMR:$^1$H-NMR(400 HMz, CDCl$_3$); δ 8.02 (s, 1H), 7.69 (s, 1H), 7.38-7.47 (m, 2H), 4.83 (s, 2H), 4.57 (t, 2H), 2.93 (t, 2H), 2.85 (s, 3H), 2.49 (pent, 2H)

Preparation Example 80

Synthesis of [1-(2-methoxy-ethyl)-1H-indazol-5-yl]-methanol

According to the methods described in Preparation Examples 55 and 56, 1H-indazole-5-carboxylic acid methyl ester (0.88 g, 5.0 mmol) and 1-bromo-2-methoxy-ethane (0.7 ml, 7.5 mmol) were used to obtain the title compound (0.56 g, 54%).
NMR:$^1$H-NMR(400 HMz, CDCl$_3$); δ 7.99 (s, 1H), 7.69 (s, 1H), 7.52-7.37 (m, 2H), 4.79 (d, 2H), 4.55 (t, 2H), 3.83 (t, 2H), 3.29 (s, 3H), 1.67 (t, 1H)

Preparation Example 81

Synthesis of [1-(3-methoxy-propyl)-1H-indazol-5-yl]-methanol

According to the methods described in Preparation Examples 55 and 56, 1H-indazole-5-carboxylic acid methyl ester (0.88 g, 5.0 mmol) and methanesulfonic acid 3-methoxy-propyl ester (1.26 g, 7.5 mmol) were used to obtain the title compound (0.60 g, 54%).
NMR:$^1$H-NMR(400 HMz, CDCl$_3$); δ 7.98 (s, 1H), 7.70 (s, 1H), 7.48-7.37 (m, 2H), 4.79 (d, 2H), 4.49 (t, 2H), 3.29 (s, 3H), 3.27 (t, 2H), 2.25-2.12 (m, 2H), 1.71 (t, 1H)

Preparation Example 82

Synthesis of [1-(3-methyl-oxetan-3-ylmethyl)-1H-indazol-6-yl]-methanol

In the methods described in Preparation Examples 55 and 56, 3-methyl-3-oxetane methanesulfonate (768 mg, 4.26 mmol) was used rather than benzyl bromide to obtain the title compound (297 mg, 89%).
NMR:$^1$H-NMR(400 HMz, CDCl$_3$); δ 8.01 (s, 1H), 7.67 (d, 1H), 7.37 (s, 1H), 7.10 (d, 1H), 4.82 (s, 2H), 4.77 (d, 2H), 4.49 (s, 2H), 4.40 (d, 2H), 2.74 (br s, 1H), 1.23 (s, 3H)

Preparation Example 83-1

Synthesis of 5-amino-2-fluoro-4-methyl-benzoic acid methyl ester

The compound (2.4 g, 11.3 mmol) obtained from Preparation Example 13-2 was dissolved in methanol (100 ml). 10% Palladium/carbon (100 mg) was added thereto, and the mixture was stirred under hydrogen gas for 8 hours. After completion of the reaction, the mixture was filtered with Celite. Filtrate was distilled under reduced pressure and separated by column chromatography to obtain the title compound (2.0 g, 97%).
NMR:$^1$H-NMR(500 HMz, CDCl$_3$); δ 7.19 (d, 1H), 6.84 (d, 1H), 3.89 (s, 3H), 3.54 (br s, 2H), 2.18 (s, 3H)

Preparation Example 83-2

Synthesis of
1-acetyl-5-fluoro-1H-indazole-6-carboxylic acid methyl ester

The compound (1.83 g, 10 mmol) obtained from Preparation Example 83-1 was dissolved in chloroform (50 ml), and the solution was cooled to 0° C. Acetic anhydride (2.36 ml, 25 mmol) was added thereto, and the solution was stirred for 1 hour at room temperature. Potassium acetate (0.29 g, 3 mmol) and isopentylnitrite (2.69 ml, 20 mmol) were added thereto, and the mixture was heated to 70° C. and stirred for 16 hours. The mixture was cooled to room temperature, diluted with dichloromethane, washed with saturated solution of sodium hydrogen carbonate, dried over anhydrous magnesium sulfate and filtered. Filtrate was distilled under reduced pressure and separated by column chromatography to obtain the title compound (0.77 g, 33%).

NMR:$^1$H-NMR(500 HMz, CDCl$_3$); δ 9.00 (d, 1H), 8.14 (s, 1H), 7.46 (d, 1H), 3.98 (s, 3H), 2.80 (s, 3H)

Preparation Example 83-3

Synthesis of 5-fluoro-1H-indazole-6-carboxylic acid methyl ester

The compound (664 mg, 2.81 mmol) obtained from Preparation Example 83-2 was dissolved in a mixture of tetrahydrofuran (8 ml) and methanol (4 ml). 1M Sodium hydroxide aqueous solution 3.4 ml was added, and the reaction solution was stirred for 10 minutes. The solution was cooled to 0° C., acidified with 1N hydrochloric acid aqueous solution and extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (484 mg, 89%).

NMR:$^1$H-NMR(500 HMz, CDCl$_3$); δ 10.30 (br s, 1H), 8.14 (d, 1H), 8.10 (s, 1H), 7.48 (d, 1H), 3.98 (s, 3H)

Preparation Example 84

Synthesis of (1-benzyl-5-fluoro-1H-indazol-6-yl)-methanol

According to the methods described in Preparation Examples 55 and 56, the compound (388 mg, 2.0 mmol) obtained from Preparation Example 83-3 was used to obtain the title compound (233 mg, 45%).

NMR:$^1$H-NMR(400 HMz, CDCl$_3$); δ 7.99 (s, 1H), 7.43-7.13 (m, 7H), 5.59 (s, 2H), 4.84 (d, 2H), 1.89 (t, 1H)

Preparation Example 85

Synthesis of (5-fluoro-1-isobutyl-1H-indazol-6-yl)-methanol

In the methods described in Preparation Examples 55 and 56, the compound (243 mg, 1.3 mmol) prepared from Preparation Example 83-3 and isobutylchloride rather than benzyl bromide were used to obtain the title compound (78 mg, 73%).

NMR:$^1$H-NMR(400 HMz, CDCl$_3$); δ 7.99 (s, 1H), 7.48 (d, 1H), 7.32 (d, 1H), 4.88 (s, 2H), 3.95 (d, 2H), 3.28 (s, 1H), 2.25-2.36 (m, 1H), 0.89 (d, 6H)

Preparation Example 86-1

Synthesis of 4-ethyl-3-nitro-benzoic acid

4-Ethyl-benzoic acid (15 g, 100 mmol) was dissolved in concentrated sulfuric acid (80 ml), and the solution was stirred for 2 hours while adding dropwise nitric acid (40 ml) at 0° C. The reaction solution was added to ice water and resulting solids were filtered and dried to obtain the title compound (20 g, 100%).

NMR:$^1$H-NMR(400 HMz, CDCl$_3$); δ 8.62 (s, 1H), 8.25 (d, 1H), 7.53 (d, 1H), 3.01 (m, 2H), 1.39 (q, 3H)

Preparation Example 86-2

Synthesis of 4-ethyl-3-nitro-benzoic acid methyl ester

The compound obtained form Preparation Example 86-1 was dissolved in methanol (200 ml) to which hydrochloric acid had been added, and the solution was stirred for 20 hours under reflux. The solution was cooled to room temperature, distilled under reduced pressure to remove methanol and separated by column chromatography to obtain the title compound (12.30 g, 59%)

NMR:$^1$H-NMR(500 HMz, CDCl$_3$); δ 8.49 (s, 1H), 8.16 (d, 1H), 7.45 (d, 1H), 3.93 (s, 3H), 2.95 (q, 2H), 1.31 (t, 3H)

Preparation Example 86-3

Synthesis of 3-amino-4-ethyl-benzoic acid methyl ester

The compound obtained from Preparation Example 86-2 was dissolved in methanol (100 ml), and the solution was allowed to react using palladium (1.25 g) and hydrogen and filtered using Celite pad. Filtrate was separated by column chromatography to obtain the title compound (9.75 g, 93%).

NMR:$^1$H-NMR(500 HMz, CDCl$_3$); δ 7.34 (d, 1H), 7.25 (s, 1H), 7.12 (d, 1H), 3.87 (s, 3H), 3.71 (brs, 2H), 2.56 (q, 2H), 1.27 (t, 3H)

Preparation Example 86-4

Synthesis of 3-methyl-1H-indazole-6-carboxylic acid methyl ester

The compound obtained from Preparation Example 86-3 was dissolved in chloroform (50 ml), and potassium acetate (6.4 g, 65.28 mmol) was added thereto. The mixture was cooled to 0° C. Acetic anhydride (16.7 g, 163.2 mmol) was added dropwise, and the reaction solution was diluted with chloroform (100 ml). After adding dropwise isoamylnitrite (12.8 g, 108.8 mmol), the solution was stirred for 18 hours under reflux. The solution was cooled to room temperature, distilled under reduced pressure to remove the solvent. The residue was dissolved in dichloromethane and washed with brine, dried over anhydrous magnesium sulfate and filtered. Filtrate was distilled under reduced pressure and the residue was dissolved in tetrahydrofuran (100 ml). 6N sodium hydroxide (20 ml) was added thereto, and the solution was stirred for 2 hours and then extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (5.90 g, 48%).

NMR:$^1$H-NMR(500 HMz, CDCl$_3$); δ 8.18 (s, 1H), 7.82 (d, 1H), 7.70 (d, 1H), 3.96 (s, 3H), 2.61 (s, 3H)

Preparation Example 87

Synthesis of (1-isobutyl-3-methyl-1H-indazol-6-yl)-methanol

According to the methods described in Preparation Examples 55 and 56, the compounds (0.50 g, 2.63 mmol)

obtained from Preparation Example 86-4 and 1-chloro-2-methyl-propane (0.48 g, 5.26 mmol) were used to obtain the title compound (0.40 g, 60%).

NMR:$^1$H-NMR(400 HMz, CDCl$_3$); δ 7.58 (d, 1H), 7.33 (s, 1H), 7.06 (d, 1H), 4.82 (s, 2H), 4.03 (d, 2H), 3.07 (brs, 1H), 2.53 (s, 3H), 2.33 (m, 1H), 0.88 (d, 6H)

Preparation Example 88

Synthesis of (2-isobutyl-3-methyl-2H-indazol-6-yl)-methanol

In the methods described in Preparation Examples 55 and 57, the compound (0.50 g, 2.63 mmol) prepared from Preparation Example 86-4 and 1-chloro-2-methyl-propane (0.48 g, 5.26 mmol) rather than benzyl bromide were used to obtain the title compound (0.11 g, 18%).

NMR:$^1$H-NMR(400 HMz, CDCl$_3$); δ 7.52 (d, 2H), 7.04 (d, 1H), 4.65 (s, 2H), 4.10 (d, 2H), 3.44 (brs, 1H), 2.56 (s, 3H), 2.42 (m, 1H), 0.92 (d, 6H)

Preparation Example 89-1

Synthesis of 1-(5-bromo-2-hydroxy-phenyl)-3-methyl-butan-1-one

1-Bromo-4-methoxy-benzene (5.0 g, 26.7 mmol) was dissolved in dichloromethane (100 ml), and aluminium chloride (5.3 g, 40.0 mmol) was added thereto at 0° C. The mixture was stirred for 5 minutes, and then isovaleryl chloride (4.9 ml, 40.0 mmol) was added dropwise. The mixture was stirred for 8 hours at room temperature and 2N hydrochloride solution was added. The mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (3.0 g, 44%).

Preparation Example 89-2

Synthesis of 5-bromo-3-isobutyl-benzo[d]isoxazole 7N solution of ammonia in methanol (10 ml) was added to the compound (2.0 g, 7.8 mmol) obtained from Preparation Example 89-1, and the solution was stirred for 3 hours at room temperature. Resulting solids were filtered, washed with diethyl ether and dried. The obtained yellow compound (1.6 g, 6.2 mmol) was dissolved in tetrahydrofuran (20 ml). N-chlorosuccinimide (NCS, 1.3 g, 9.7 mmol) and potassium carbonate (1.7 g, 12.3 mmol) were added, and the mixture was stirred for 8 hours at room temperature. Water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (1.2 g, 60%).

Preparation Example 89-3

Synthesis of 3-isobutyl-benzo[d]isoxazole-5-carbonitrile

5-Bromo-3-isobutyl-benzo[d]isoxazole (1.2 g, 4.7 mmol) obtained from Preparation Example 89-2 was dissolved in dimethylformamide (30 ml). Zinc cyanide (ZnCN$_2$, 0.73 g, 6.2 mmol) and palladium tetrakistriphenylphosphine (Pd (PPh$_3$)$_4$, 0.55 g, 0.4 mmol) were added dropwise thereto, and the mixture was stirred for 8 hours at 100° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (56 mg, 6%).

NMR:$^1$H-NMR(400 HMz, CDCl$_3$): δ 8.04 (s, 1H), 7.80 (dd, 1H), 7.67 (d, 1H), 2.89 (d, 2H), 2.16-2.34 (m, 1H), 1.04 (d, 6H)

Preparation Example 89-4

Synthesis of (3-isobutyl-benzo[d]isoxazol-5-yl)-methanol

According to the method described in Preparation Example 54-2, the compound (56 mg, 0.28 mmol) prepared from Preparation Example 89-3 was used to obtain the title compound (40 mg, 69%).

NMR:$^1$H-NMR(500 HMz, CDCl$_3$); δ 7.64 (s, 1H), 7.51 (s, 2H), 4.80 (s, 2H), 2.82 (d, 2H), 2.22 (m, 1H), 1.00 (d, 6H)

Preparation Example 90

Synthesis of (1-benzyl-1H-indol-5-yl)-methanol

In the methods described in Preparation Examples 17-1 and 17-2, 1H-indole-5-carboxylic acid methyl ester (350 mg, 2.0 mmol) was used rather than 7-methyl-1H-indole-6-carboxylic acid methyl ester to obtain the title compound (444 mg, 93%).

NMR:$^1$H-NMR(400 HMz, CDCl$_3$); δ 7.64 (s, 1H), 7.07-7.33 (m, 8H), 6.55 (d, 1H), 5.33 (s, 2H), 4.76 (d, 2H), 1.51 (t, 1H)

Preparation Example 91

Synthesis of (1-benzyl-1H-indazol-5-yl)-methanol

According to the methods described in Preparation Examples 55 and 56, 1H-indazole-5-carbaldehyde (970 mg, 4.11 mmol) was used to obtain the title compound (755 mg, 77%).

NMR:$^1$H-NMR(400 HMz, CDCl$_3$); δ 8.03 (s, 1H), 7.72 (s, 1H), 7.23-7.39 (m, 5H), 7.18 (d, 2H), 5.60 (s, 2H), 4.78 (d, 2H), 1.64 (t, 1H)

Preparation Example 92

Synthesis of (2-benzyl-2H-indazol-5-yl)-methanol

According to the methods described in Preparation Examples 55 and 57, 1H-indazole-5-carbaldehyde (548 mg, 2.32 mmol) was used to obtain the title compound (322 mg, 58%).

NMR:$^1$H-NMR(400 HMz, CDCl$_3$); δ 7.84 (s, 1H), 7.70 (d, 1H), 7.57 (s, 1H), 7.25-7.37 (m, 6H), 5.56 (s, 2H), 4.74 (d, 2H), 2.17 (br s, 1H)

Preparation Example 93

Synthesis of (1-phenethyl-1H-indazol-5-yl)-methanol

According to the methods described in Preparation Examples 55 and 56, 1H-indazole-5-carboxylic acid methyl ester and (2-bromo-ethyl)-benzene were used to obtain the title compound (630 mg, 44%).
NMR:$^1$H-NMR(400 HMz, CDCl$_3$); δ 7.99 (s, 1H), 7.68 (s, 1H), 7.32 (m, 1H), 7.11-7.24 (m, 4H), 7.11 (m, 2H), 4.76 (d, 2H), 4.59 (t, 3H), 3.22 (t, 2H)

Preparation Example 94

Synthesis of (1-pyridin-2-ylmethyl-1H-indazol-5-yl)-methanol

According to the methods described in Preparation Examples 55 and 56, 1H-indazole-5-carboxylic acid methyl ester (1 g, 5.68 mmol) and 2-bromomethyl-pyridine hydrobromide (4.31 g, 17.04 mmol) were used to obtain the title compound (222 mg, 84%).
NMR:$^1$H-NMR(400 HMz, CDCl$_3$); δ 8.47 (dd, 1H), 7.96 (s, 1H), 7.66 (s, 1H), 7.44-7.48 (m, 1H), 7.28-7.34 (m, 2H), 7.08-7.12 (m, 1H), 6.74 (d, 1H), 5.62 (s, 2H), 4.73 (s, 2H), 4.13 (br s, 1H)

Preparation Example 95

Synthesis of (1-pyridin-3-ylmethyl-1H-indazol-5-yl)-methanol

According to the methods described in Preparation Examples 55 and 56, 1H-indazole-5-carboxylic acid methyl ester (0.88 g, 5.0 mmol) and 3-bromomethyl-pyridine (1.52 g, 6.0 mmol) were used to obtain the title compound (0.42 g, 35%).
NMR:$^1$H-NMR(400 HMz, CDCl$_3$); δ 8.56 (d, 1H), 8.51 (dd, 1H), 8.04 (s, 1H), 7.73 (s, 1H), 7.48-7.32 (m, 3H), 7.20 (dd, 1H), 5.61 (s, 2H), 4.79 (s, 2H), 1.83 (br s, 1H)

Preparation Example 96

Synthesis of (1-isopropyl-1H-indazol-5-yl)-methanol

According to the methods described in Preparation Examples 55 and 56, 1H-indazole-5-carboxylic acid methyl ester (1.5 g, 8.51 mmol) and isopropyl iodide (2.17 g, 12.77 mmol) were used to obtain the title compound (866 mg, 99%).
NMR:$^1$H-NMR(400 HMz, CDCl$_3$); δ 7.98 (s, 1H), 7.70 (s, 1H), 7.42 (dd, 2H), 4.83-4.86 (m, 1H), 4.78 (d, 2H), 1.70 (br t, 1H), 1.59 (d, 6H)

Preparation Example 97

Synthesis of (1-isobutyl-1H-indazol-5-yl)-methanol

According to the methods described in Preparation Examples 55 and 56, 1H-indazole-5-carboxylic acid methyl ester and 1-iodo-2-methyl-propane were used to obtain the title compound (600 mg, 52%).
NMR:$^1$H-NMR(400 HMz, CDCl$_3$); δ 7.97 (s, 1H), 7.70 (s, 1H), 7.40 (dd, 2H), 4.78 (d, 2H), 4.16 (d, 2H), 2.34 (m, 1H), 0.91 (d, 6H)

Preparation Example 98

Synthesis of [1-(3-methyl-butyl)-1H-indazol-5-yl]-methanol

According to the methods described in Preparation Examples 55 and 56, 1H-indazole-5-carboxylic acid methyl ester (0.88 g, 5.0 mmol) and 1-bromo-3-methyl-butane (1.8 ml, 15.0 mmol) were used to obtain the title compound (0.49 g, 45%).
NMR:$^1$H-NMR(400 HMz, CDCl$_3$); δ 7.97 (s, 1H), 7.70 (s, 1H), 7.41 (d, 2H), 4.78 (d, 2H), 4.40 (t, 2H), 1.82 (q, 2H), 1.66 (t, 1H), 1.58 (m, 1H), 0.97 (d, 6H)

Preparation Example 99

Synthesis of (1-cyclopropylmethyl-1H-indazol-5-yl)-methanol

According to the methods described in Preparation Examples 55 and 56, 1H-indazole-5-carboxylic acid methyl ester and bromomethyl-cyclopropane (0.84 g, 6.24 mmol) were used to obtain the title compound (0.59 g, 51%).
NMR:$^1$H-NMR(500 HMz, CDCl$_3$); δ 7.94 (s, 1H), 7.67 (s, 1H), 7.40 (m, 2H), 4.76 (s, 2H), 4.25 (d, 2H), 2.26 (brs, 1H), 1.55 (m, 1H), 1.31 (m, 1H), 0.56 (m, 2H), 0.38 (m, 2H)

Preparation Example 100

Synthesis of (1-cyclopentyl-1H-indazol-5-yl)-methanol

According to the methods described in Preparation Examples 55 and 56, 1H-indazole-5-carboxylic acid methyl ester (1 g, 5.68 mmol) and cyclopentyl bromide (1.22 ml, 11.36 mmol) were used to obtain the title compound (212 mg, 42%).
NMR:$^1$H-NMR(400 HMz, CDCl$_3$); δ 7.82 (s, 1H), 7.59 (s, 1H), 7.28-7.41 (m, 2H), 4.83-4.91 (m, 1H), 4.67 (s, 2H), 4.45 (br s, 1H), 2.06-2.10 (m, 4H), 1.87-1.93 (m, 2H), 1.63-1.69 (m, 2H)

Preparation Example 101

Synthesis of (1-cyclopentylmethyl-1H-indazol-5-yl)-methanol

According to the methods described in Preparation Examples 55 and 56, 1H-indazole-5-carboxylic acid methyl ester (1 g, 5.68 mmol) and cyclopentyl methane sulfonate (2.02 g, 11.36 mmol) were used to obtain the title compound (549 mg, 53%).
NMR:$^1$H-NMR(400 HMz, CDCl$_3$); δ 7.92 (s, 1H), 7.67 (s, 1H), 7.16-7.36 (m, 2H), 4.73 (d, 2H), 4.22 (d, 2H), 3.45 (t, 1H), 2.44-2.54 (m, 1H), 1.45-1.63 (m, 6H), 1.26-1.29 (m, 2H)

Preparation Example 102

Synthesis of (1-cyclohexylmethyl-1H-indazol-5-yl)-methanol

According to the methods described in Preparation Examples 55 and 56, 1H-indazole-5-carboxylic acid methyl ester (0.88 g, 5.0 mmol) and bromomethyl cyclohexane (2.1 ml, 15.0 mmol) were used to obtain the title compound (0.53 g, 44%).
NMR:$^1$H-NMR(400 HMz, CDCl$_3$); δ 7.97 (s, 1H), 7.70 (s, 1H), 7.41 (d, 2H), 4.79 (d, 2H), 4.20 (d, 2H), 2.00 (m, 1H), 1.77-1.53 (m, 5H), 1.28-0.96 (m, 5H)

Preparation Example 103

Synthesis of [1-(tetrahydrofuran-2-ylmethyl)-1H-indazol-5-yl]-methanol

According to the methods described in Preparation Examples 55 and 56, 1H-indazole-5-carboxylic acid methyl ester (1 g, 5.68 mmol) and methanesulfonic acid tetrahydrofuran-2-ylmethyl ester (2.52 g, 11.36 mmol) were used to obtain the title compound (533 mg, 40%).
NMR:$^1$H-NMR(400 HMz, CDCl$_3$); δ 7.90 (s, 1H), 7.59 (s, 1H), 7.38 (d, 1H), 7.32 (d, 1H), 4.67 (d, 2H), 4.94-4.52 (m, 1H), 4.34 (d, 2H), 4.23-4.26 (m, 1H), 3.61-3.67 (m, 3H), 1.58-1.70 (m, 3H)

Preparation Example 104

Synthesis of [1-(tetrahydro-furan-3-ylmethyl)-1H-indazol-5-yl]-methanol

According to the methods described in Preparation Examples 55 and 56, 1H-indazole-5-carboxylic acid methyl ester and methanesulfonic acid tetrahydrofuran-3yl methyl ester (1.12 g, 6.24 mmol) were used to obtain the title compound (0.87 g, 60%).
NMR:$^1$H-NMR(400 HMz, CDCl$_3$); δ 7.97 (s, 1H), 7.70 (s, 1H), 7.42 (m, 2H), 4.78 (s, 2H), 4.33 (d, 2H), 3.95 (m, 1H), 3.74 (m, 2H), 3.64 (m, 1H), 2.97 (m, 1H), 2.03 (m, 1H), 1.72 (m, 1H)

Preparation Example 105

Synthesis of [2-(tetrahydrofuran-3-ylmethyl)-2H-indazol-5-yl]-methanol

According to the methods described in Preparation Examples 55 and 57, 1H-indazole-5-carboxylic acid methyl ester and methanesulfonic acid tetrahydrofuran-3ylmethyl ester (1.12 g, 6.24 mmol) were used to obtain the title compound (0.38 g, 26%).
NMR:$^1$H-NMR(400 HMz, CDCl$_3$); δ 7.85 (s, 1H), 7.64 (d, 1H), 7.59 (s, 1H), 7.31 (s, 1H), 4.73 (s, 2H), 4.34 (d, 2H), 3.94 (m, 1H), 3.77 (m, 2H), 3.59 (m, 1H), 3.01 (m, 1H), 2.07 (m, 1H), 1.70 (m, 1H)

Preparation Example 106

Synthesis of [1-(2-ethoxy-ethyl)-1H-indazol-5-yl]-methanol

According to the methods described in Preparation Examples 55 and 56, 1H-indazole-5-carboxylic acid methyl ester and 1-chloro-2-ethoxy-ethane were used to obtain the title compound (670 mg, 54%).
NMR:$^1$H-NMR(400 HMz, CDCl$_3$); δ 7.98 (s, 1H), 7.69 (s, 1H), 7.49 (d, 1H), 7.42 (d, 1H), 4.79 (s, 2H), 4.55 (t, 2H), 3.86 (t, 2H), 3.42 (q, 2H), 1.09 (t, 3H)

Preparation Example 107

Synthesis of [2-(2-ethoxy-ethyl)-2H-indazol-5-yl]-methanol

According to the methods described in Preparation Examples 55 and 57, 1H-indazole-5-carboxylic acid methyl ester and 1-chloro-2-ethoxy-ethane were used to obtain the title compound (280 mg, 22%)

NMR:$^1$H-NMR(400 HMz, CDCl$_3$); δ 8.02 (s, 1H), 7.71 (d, 1H), 7.63 (s, 1H), 7.31 (m, 1H), 4.75 (s, 2H), 4.57 (t, 2H), 3.91 (t, 2H), 3.46 (q, 2H), 1.14 (t, 3H)

Preparation Example 108-1

Synthesis of 4-fluoro-3-formyl-benzonitrile

According to the method described in Preparation Example 89-3, 5-bromo-2-fluoro-benzaldehyde (10.15 g, 50 mmol) was used to obtain the title compound (4.54 g, 61%).
NMR:$^1$H-NMR(400 HMz, CDCl$_3$); δ 10.35 (s, 1H), 8.22 (dd, 1H), 7.91 (m, 1H), 7.35 (t, 1H)

Preparation Example 108-2

Synthesis of 4-fluoro-3-formyl-benzonitrile

The compound (4.54 g, 30.44 mmol) obtained from Preparation Example 108-1 was dissolved in tetrahydrofuran (100 ml), and 2M solution of isobutyl magnesium bromide in diethyl ether (15.98 ml, 31.96 mmol) was added dropwise thereto at 0° C. The mixture was heated to room temperature, stirred for 1 hour and then cooled to 0° C. Reaction was terminated with a saturated aqueous solution of ammonium chloride. Water was added thereto, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (1.67 g, 26%).
NMR:$^1$H-NMR(500 HMz, CDCl$_3$); δ 7.85 (dd, 1H), 7.55 (m, 1H), 7.11 (t, 1H), 5.09 (m, 1H), 2.02 (d, 1H), 1.78 (m, 1H), 1.67 (m, 1H), 1.49 (m, 1H), 0.98 (d, 3H), 0.96 (d, 3H)

Preparation Example 108-3

Synthesis of 4-fluoro-3-(3-methyl-butyryl)-benzonitrile

According to the method described in Preparation Example 7-5, the compound (1.67 g, 8.04 mmol) obtained from Preparation Example 108-2 was used to obtain the title compound (1.56 g, 95%).
NMR:$^1$H-NMR(400 HMz, CDCl$_3$); δ 8.16 (dd, 1H), 7.79 (m, 1H), 7.27 (m, 1H), 2.85 (dd, 2H), 2.27 (m, 1H), 0.99 (d, 6H)

Preparation Example 108-4

Synthesis of 3-isobutyl-1-methyl-1H-indazole-5-carbonitrile

The compound (513 mg, 2.5 mmol) obtained from Preparation Example 108-3 was dissolved in tetrahydrofuran (100 ml), and methylhydrazine sulfate (378 mg, 2.63 mmol) and 6M aqueous solution of sodium hydroxide (0.88 ml, 5.25 mmol) were added dropwise thereto. The mixture was stirred for 16 hours, water was added thereto, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (473 mg, 89%).

NMR:¹H-NMR(400 HMz, CDCl$_3$); δ 8.05 (s, 1H), 7.55 (d, 1H), 7.40 (d, 1H), 4.05 (s, 3H), 2.83 (d, 2H), 2.13 (m, 1H), 0.98 (d, 6H)

Preparation Example 108-5

Synthesis of (3-isobutyl-1-methyl-1H-indazol-5-yl)-methanol

According to the method described in Preparation Example 54-2, the compound (473 mg, 2.22 mmol) obtained from Preparation Example 108-4 was used to obtain the title compound (475 mg, 98%).
NMR:¹H-NMR(400 HMz, CDCl$_3$); δ 7.64 (s, 1H), 7.42-7.30 (m, 2H), 4.79 (d, 2H), 4.01 (s, 3H), 2.82 (d, 2H), 2.15 (m, 1H), 1.65 (t, 1H), 0.98 (d, 6H)

Preparation Example 109-1

Synthesis of 3,5-dimethyl-4-nitro-benzoic acid methyl ester

According to the method described in Preparation Example 86-2, 3,5-dimethyl-4-nitro-benzoic acid (5.3 g, 27.15 mmol) was used to obtain the title compound (5.80 g, 100%).
NMR:¹H-NMR(400 HMz, CDCl$_3$); δ 7.82 (s, 2H), 3.94 (s, 3H), 2.35 (s, 6H)

Preparation Example 109-2

Synthesis of 4-amino-3,5-dimethyl-benzoic acid methyl ester

According to the method described in Preparation Example 86-3, the compound (5.80 g, 27.15 mmol) obtained from Preparation Example 109-1 was used to obtain the title compound (4.40 g, 90%).
NMR:¹H-NMR(400 HMz, CDCl$_3$); δ 7.66 (s, 2H), 3.98 (brs, 2H), 3.85 (s, 3H), 2.19 (s, 6H)

Preparation Example 109-3

Synthesis of 7-methyl-1H-indazole-5-carboxylic acid methyl ester

According to the method described in Preparation Example 86-4, the compound (4.40 g, 24.55 mmol) obtained from Preparation Example 109-2 was used to obtain the title compound (3.80 g, 82%).
NMR:¹H-NMR(500 HMz, CDCl$_3$); δ 10.40 (brs, 1H), 8.39 (s, 1H), 8.18 (s, 1H), 7.86 (s, 1H), 3.94 (s, 3H), 2.59 (s, 3H)

Preparation Example 110

Synthesis of (1-benzyl-7-methyl-1H-indazol-5-yl)-methanol

According to the methods described in Preparation Examples 55 and 56, 7-methyl-1H-indazole-5-carboxylic acid methyl ester (500 mg, 2.63 mmol) was used to obtain the title compound (111 mg, 17%).
NMR:¹H-NMR(400 HMz, CDCl$_3$); δ 8.17 (s, 1H), 7.47 (s, 1H), 7.15-7.23 (m, 3H), 7.03 (s, 1H), 6.91 (dd, 2H), 5.75 (s, 2H), 4.65 (br t, 2H), 3.21 (br s, 1H), 2.52 (s, 3H)

Preparation Example 111

Synthesis of (2-benzyl-7-methyl-2H-indazol-5-yl)-methanol

According to the methods described in Preparation Examples 55 and 57, 7-methyl-1H-indazole-5-carboxylic acid methyl ester (500 mg, 2.63 mmol) was used to obtain the title compound (395 mg, 60%).
NMR:¹H-NMR(400 HMz, CDCl$_3$); δ 7.73 (s, 1H), 7.24-7.28 (m, 4H), 7.16-7.20 (m, 2H), 6.99 (s, 1H), 5.54 (s, 2H), 4.62 (br t, 2H), 3.33 (br s, 1H), 2.62 (s, 3H)

Preparation Example 112

Synthesis of (1-isobutyl-7-methyl-1H-indazol-5-yl)-methanol

According to the methods described in Preparation Examples 55 and 56, 7-methyl-1H-indazole-5-carboxylic acid methyl ester (1 g, 5.26 mmol) and isobutyl chloride (1.46 ml, 15.78 mmol) were used to obtain the title compound (282 mg, 25%).
NMR:¹H-NMR(400 HMz, CDCl$_3$); δ 7.87 (s, 1H), 7.43 (s, 1H), 7.13 (s, 1H), 4.84 (s, 2H), 4.27 (d, 2H), 3.90 (br s, 1H), 2.62 (s, 3H), 2.10-2.22 (m, 1H), 0.86 (d, 6H)

Preparation Example 113

Synthesis of (2-isobutyl-7-methyl-2H-indazol-5-yl)-methanol

According to the methods described in Preparation Examples 55 and 57, 7-methyl-1H-indazole-5-carboxylic acid methyl ester (1 g, 5.26 mmol) and isobutyl chloride (1.46 ml, 15.78 mmol) were used to obtain the title compound (478 mg, 42%).
NMR:¹H-NMR(400 HMz, CDCl$_3$); δ 7.77 (s, 1H), 7.34 (s, 1H), 7.03 (s, 1H), 4.64 (br t, 3H), 4.04 (d, 2H), 2.81 (s, 3H), 2.21-2.29 (m, 1H), 0.82 (d, 6H)

Preparation Example 114

Synthesis of (1-isopropyl-7-methyl-1H-indazol-5-yl)-methanol

According to the methods described in Preparation Examples 55 and 56, 7-methyl-1H-indazole-5-carboxylic acid methyl ester (1 g, 5.26 mmol) and isobutyl iodide (1.58 ml, 15.78 mmol) were used to obtain the title compound (357 mg, 33%).
NMR:¹H-NMR(400 HMz, CDCl$_3$); δ 7.98 (s, 1H), 7.52 (s, 1H), 7.13 (s, 1H), 5.16-5.22 (m, 1H), 4.73 (d, 2H), 2.74 (s, 3H), 1.59 (d, 6H)

Preparation Example 115

Synthesis of (1-cyclopentyl-7-methyl-1H-indazol-5-yl)-methanol

According to the methods described in Preparation Examples 55 and 56, 7-methyl-1H-indazole-5-carboxylic acid methyl ester (1 g, 5.26 mmol) and cyclopentyl bromide (1.69 ml, 15.78 mmol) were used to obtain the title compound (146 mg, 12%).
NMR:¹H-NMR(400 HMz, CDCl$_3$); δ 7.99 (s, 1H), 7.48 (s, 1H), 7.17 (s, 1H), 5.18-5.39 (m, 1H), 4.71 (s, 2H), 2.91

(br s, 1H), 2.75 (s, 3H), 2.21-2.25 (m, 2H), 2.09-2.15 (m, 2H), 1.96-2.03 (m, 2H), 1.73-1.78 (m, 2H)

Preparation Example 116

Synthesis of (1-cyclopentylmethyl-7-methyl-1H-indazol-5-yl)-methanol

According to the methods described in Preparation Examples 55 and 56, 7-methyl-1H-indazole-5-carboxylic acid methyl ester (1 g, 5.26 mmol) and cyclopentyl methylmethanesulfonate (1.88 g, 10.52 mmol) were used to obtain the title compound (406 mg, 45%).

NMR: $^1$H-NMR(400 HMz, CDCl$_3$); δ 7.93 (s, 1H), 7.52 (s, 1H), 7.13 (s, 1H), 4.74 (d, 2H), 4.50 (d, 2H), 2.73 (s, 3H), 2.42-2.48 (m, 1H), 1.53-1.67 (m, 6H), 1.34-1.37 (m, 2H)

Preparation Example 117-1

Synthesis of (5-bromo-2-fluoro-phenyl)-methanol

5-Bromo-2-fluoro-benzaldehyde (5.0 g, 24.36 mmol) was dissolved in tetrahydrofuran (100 ml), and 3M solution of methylmagnesium bromide in tetrahydrofuran (10.26 ml, 30.78 mmol) was slowly added dropwise thereto at 0° C. for 3 minutes. 30 minutes later, the mixture was added to a saturated solution of sodium hydrogen carbonate and extracted with ethyl acetate. The organic layer was dried over anhydrous magnesium sulfate and filtered. Filtrate was distilled under reduced pressure and separated by column chromatography to obtain the title compound (3.3 g, 61%).

Preparation Example 117-2

Synthesis of 5-(bromo-2-fluoro-phenyl)-ethanone

The compound (3.3 g, 15.07 mmol) obtained from Preparation Example 117-1 was dissolved in dichloromethane (20 ml), and pyridinium chlorochromate (3.9 g, 18.08 mmol) was added thereto. The mixture was stirred for 16 hours at room temperature and then filtered with Celite. Filtrate was distilled under reduced pressure and separated by column chromatography to obtain the title compound (2.3 g, 70%).

NMR: $^1$H-NMR(400 HMz, CDCl$_3$); δ 7.98 (m, 1H), 7.61 (m, 1H), 7.02 (m, 1H), 2.63 (d, 3H)

Preparation Example 117-3

Synthesis of 5-bromo-3-methyl-1H-indazole

The compound (2.3 g, 1060 mmol) obtained from Preparation Example 117-2 was dissolved in ethylene glycol (10 ml), and hydrazine (2.57 ml, 53.00 mmol) was added thereto. The reactant was stirred under reflux at 160° C. for 16 hours in a pressure tube. The reactant was diluted with ethyl acetate, washed with water, distilled under reduced pressure and separated by column chromatography to obtain the title compound (1.5 g, 67%).

NMR: $^1$H-NMR(400 HMz, CDCl$_3$); δ 9.77 (br s, 1H), 7.83 (m, 1H), 7.44 (m, 1H), 7.31 (m, 1H), 2.56 (s, 3H)

Preparation Example 117-4

Synthesis of 5-bromo-1-isobutyl-3-methyl-1H-indazole and 5-bromo-2-isobutyl-3-methyl-2H-indazole The compound (1.5 g, 7.11 mmol) obtained from Preparation Example 117-3 was dissolved in dimethylformamide (20 ml), and sodium hydride (340 mg, 8.53 mmol) and isobutyl iodide (2.45 ml, 21.32 mmol) were slowly added dropwise thereto at 0° C. The mixture was stirred for 8 hours at room temperature. 1N hydrochloric acid solution was added and the mixture was extracted with ethyl acetate. The extract was washed with saturated aqueous sodium chloride solution, dried over anhydrous magnesium sulfate and filtered. Filtrate was distilled under reduced pressure and separated by column chromatography. The first compound that passed through the column chromatography was 5-bromo-1-isobutyl-3-methyl-1H-indazole (1.16 g, 61%), and the second one was 5-bromo-2-isobutyl-3-methyl-2H-indazole (0.39 g, 21%).

NMR: $^1$H-NMR(400 HMz, CDCl$_3$); δ 7.78 (m, 1H), 7.39 (m, 1H), 7.20 (m, 1H), 4.05 (d, 2H), 2.53 (s, 3H), 2.27 (m, 1H), 0.90 (d, 6H)

NMR: $^1$H-NMR(400 HMz, CDCl$_3$); δ 7.71 (m, 1H), 7.50 (m, 1H), 7.28 (m, 1H), 4.11 (d, 2H), 2.56 (s, 3H), 2.38 (m, 1H), 0.94 (d, 6H)

Preparation Example 117-5

Synthesis of 1-isobutyl-3-methyl-1H-indazole-5-carbonitrile

5-Bromo-1-isobutyl-3-methyl-1H-indazole (1.16 g, 4.34 mmol) obtained from Preparation Example 117-4 was dissolved in dimethylformamide (30 ml). Zinc cyanide (0.66 g, 5.64 mmol) and palladium tetrakistriphenylphosphine (0.50 g, 0.43 mmol) were added thereto, and then the mixture was stirred for 8 hours at 100° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (580 mg, 63%).

NMR: $^1$H-NMR(400 HMz, CDCl$_3$); δ 8.04 (m, 1H), 7.52 (m, 1H), 7.38 (m, 1H), 4.10 (d, 2H), 2.59 (s, 3H), 2.29 (m, 1H), 0.91 (d, 6H)

Preparation Example 117-6

Synthesis of 1-isobutyl-3-methyl-1H-indazole-5-carboxylic acid methyl ester

The compound (580 mg, 2.72 mmol) obtained from Preparation Example 117-5 was dissolved in ethanol (50 ml), and 6N sodium hydroxide (2.27 ml, 13.60 mmol) was added thereto. The mixture was stirred for 18 hours at 90° C. and then distilled under reduced pressure. 1N hydrochloric acid solution was added thereto, and the residue was extracted with ethyl acetate. The extract was washed with saturated aqueous sodium chloride solution, dried over anhydrous magnesium sulfate and filtered. Filtrate was distilled under reduced pressure, and 1-isobutyl-3-methyl-1H-indazole-5-carboxylic acid was obtained.

The obtained 1-isobutyl-3-methyl-1H-indazole-5-carboxylic acid was dissolved in methylenechloride (20 ml), and 0.25M solution of diazomethane in diethyl ether (13.05 ml, 3.25 mmol) was slowly added dropwise thereto. The mixture was stirred for 30 minutes at room temperature and distilled under reduced pressure to obtain the title compound (670 mg, 100%).

NMR:$^1$H-NMR(400 HMz, CDCl$_3$); δ 8.43 (m, 1H), 8.01 (m, 1H), 7.31 (m, 1H), 4.09 (d, 2H), 3.95 (s, 3H), 2.30 (m, 1H), 0.92 (d, 6H)

Preparation Example 118

Synthesis of (1-isobutyl-3-methyl-1H-indazol-5-yl)-methanol

The compound (670 mg, 2.72 mmol) obtained from Preparation Example 117-6 was dissolved in tetrahydrofuran (20 ml), and lithium aluminium hydride (114 mg, 2.99 mmol) was added dropwise thereto. The mixture was stirred for 2 hours at room temperature, and water (1 ml), 6N sodium hydroxide (1 ml) and water (3 ml) were added sequentially. Ethyl acetate was added and the mixture was filtered with Celite. Filtrate was distilled under reduced pressure and separated by column chromatography to obtain the title compound (590 mg, 99%).
NMR:$^1$H-NMR(400 HMz, CDCl$_3$); δ 7.61 (s, 1H), 7.36 (d, 1H), 7.34 (d, 1H), 4.80 (d, 1H), 4.10 (d, 2H), 2.57 (s, 3H), 2.32 (m, 1H), 0.91 (d, 6H)

Preparation Example 119-1

Synthesis of N-(4-bromo-2,5-dimethyl-phenyl)-acetamide

N-(2,5-dimethyl-phenyl)-acetamide (5.0 g, 30.6 mmol) was dissolved in a mixture of dichloromethane (250 ml) and methanol (100 ml), and benzyl-trimethyl-ammonium dibromochloride (11.6 g, 33.7 mmol) was added dropwise thereto. The mixture was stirred for 2 hours at room temperature, and then distilled under reduced pressure. Water was added and the residue was extracted with ethyl acetate. The extract was washed with saturated aqueous sodium chloride solution, dried over anhydrous magnesium sulfate and filtered. Filtrate was distilled under reduced pressure to obtain N-(4-bromo-2,5-dimethyl-phenyl)-acetamide (7.0 g, 94%).
NMR:$^1$H-NMR(500 HMz, DMSO-d$_6$); δ 9.28 (brs, 1H), 7.36 (s, 1H), 7.34 (s, 1H), 2.21 (s, 3H), 2.10 (s, 3H), 2.00 (s, 3H)

Preparation Example 119-2

Synthesis of 5-bromo-6-methyl-1H-indazole

According to the method described in Preparation Example 86-4, the compound (7.0 g, 28.9 mmol) obtained from Preparation Example 119-1 was used to obtain the title compound (4.1 g, 67%).
NMR:$^1$H-NMR(400 HMz, CDCl$_3$); δ 9.97 (br s, 1H), 7.97 (s, 1H), 7.96 (s, 1H), 7.39 (s, 1H), 2.53 (s, 3H)

Preparation Example 119-3

Synthesis of 5-bromo-1-isobutyl-6-methyl-1H-indazole

According to the method described in Preparation Example 55, the compound (2.11 g, 10 mmol) obtained from Preparation Example 119-2 and 1-bromo-2-methyl-propane (2.3 ml, 20 mmol) were used to obtain the title compound (1.45 g, 54%).
NMR:$^1$H-NMR(400 HMz, CDCl$_3$); δ 7.91 (s, 1H), 7.88 (s, 1H), 7.26 (s, 1H), 4.12 (d, 2H), 2.54 (s, 3H), 2.33 (m, 1H), 0.92 (d, 6H)

Preparation Example 119-4

Synthesis of 1-isobutyl-6-methyl-1H-indazole-5-carbonitrile

According to the method described in Preparation Example 89-3, the compound (1.45 g, 5.42 mmol) obtained from Preparation Example 119-3 was used to obtain the title compound (0.81 g, 70%).
NMR:$^1$H-NMR(400 HMz, CDCl$_3$); δ 8.07 (s, 1H), 8.03 (s, 1H), 7.28 (s, 1H), 4.15 (d, 2H), 2.67 (s, 3H), 2.34 (m, 1H), 0.93 (d, 6H)

Preparation Example 120

Synthesis of (1-isobutyl-6-methyl-1H-indazol-5-yl)-methanol

According to the method described in Preparation Example 54-2, the compound (0.81 g, 3.8 mmol) obtained from Preparation Example 119-4 was used to obtain the title compound (0.54 g, 65%).
NMR:$^1$H-NMR(400 HMz, CDCl$_3$); δ 7.92 (s, 1H), 7.67 (s, 1H), 7.20 (s, 1H), 4.79 (d, 2H), 4.14 (d, 2H), 2.53 (s, 3H), 2.34 (m, 1H), 1.53 (t, 1H), 0.92 (d, 6H)

Preparation Example 121

Synthesis of 1H-pyrrolo[2,3-b]pyridine-5-carbonitrile

5-Bromo-1H-pyrrolo[2,3-b]-pyridine (2.0 g, 10.1 mmol) was dissolved in dimethylformamide (50 ml). Zinc cyanide (ZnCN$_2$, 2.4 g, 20.2 mmol) and palladium tetrakistriphenylphosphine ((Pd(PPh$_3$)$_4$, 1.3 g, 1.0 mmol) were added dropwise thereto, and then the mixture was stirred for 3 hours at 100° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure to obtain the title compound.

Preparation Example 122

Synthesis of 1H-pyrrolo[2,3-b]pyridine-5-carboxylic acid methyl ester

The compound obtained from Preparation Example 121 was dissolved in ethanol (100 ml), and 6N sodium hydroxide (17 ml, 102 mmol) was added thereto. The mixture was stirred for 3 days at 100° C. and then distilled under reduced pressure. 1 N hydrochloride solution was added and the residue was extracted with ethyl acetate. The extract was washed with saturated aqueous sodium chloride solution, dried over anhydrous magnesium sulfate and filtered. Filtrate was distilled under reduced pressure and the residue was dissolved in tetrahydrofuran (400 ml). 0.25M solution of dia zomethane in diethyl ether (30 ml, 7.5 mmol) was slowly added dropwise. The mixture was stirred for 30 minutes at 0° C. and then distilled under reduced pressure to obtain the title compound (1.2 g, 67%).

Preparation Example 123

Synthesis of (1-benzyl-1H-pyrrolo[2,3-b]pyridin-5-yl)-methanol

According to the methods described in Preparation Examples 17-1 and 17-2, 1H-pyrrolo[2,3-b]pyridine-5-carboxylic acid methyl ester (0.25 g, 1.42 mmol) and benzyl bromide (0.27 g, 1.56 mmol) were used to obtain the title compound (0.13 g, 37%).

NMR:$^1$H-NMR(400 HMz, CDCl$_3$); δ 8.35 (s, 1H), 7.95 (s, 1H), 7.19-7.31 (m, 6H), 6.48 (d, 1H), 5.50 (s, 2H), 4.80 (s, 2H), 1.82 (brs, 1H)

Preparation Example 124

Synthesis of (1-isobutyl-1H-pyrrolo[2,3-b]pyridin-5-yl)-methanol

According to the methods described in Preparation Examples 55 and 56, 1H-pyrrolo[2,3-b]pyridine-5-carboxylic acid methyl ester (0.25 g, 1.42 mmol) and 1-chloro-2-methyl-propane (0.39 g, 4.26 mmol) were used to obtain the title compound (0.1 g, 33%).

NMR:$^1$H-NMR(400 HMz, CDCl$_3$); δ 8.32 (s, 1H), 7.94 (s, 1H), 7.22 (d, 1H), 6.45 (d, 1H), 4.79 (s, 2H), 4.08 (m, 2H), 2.26 (m, 1H), 0.92 (d, 6H)

Preparation Example 125-1

Synthesis of 4-benzylamine-3-nitro-benzoic acid methyl ester

4-Fluoro-3-nitro-benzoic acid (2.0 g, 10.8 mmol) was dissolved in ethanol (100 ml), and benzyl amine (1.3 ml, 11.9 mmol) was added thereto. The mixture was stirred at 100° C. for 3 hours and then distilled under reduced pressure.

The obtained compound was dissolved in tetrahydrofuran (100 ml) and 0.25M solution of diazomethane in diethyl ether (48 ml, 11.9 mmol) was slowly added dropwise thereto. The mixture was stirred at room temperature for 30 minutes and then distilled under reduced pressure to obtain the title compound (1.8 g, 58%).

Preparation Example 125-2

Synthesis of 3-amino-4-benzylamine-benzoic acid methyl ester

The compound (1.8 g, 6.3 mmol) obtained from Preparation Example 125-1 was dissolved in a mixed solution of ethyl acetate and methanol (2/1, 100 ml), and 10% palladium/carbon (200 mg) was added. The mixture was stirred for 1 hour under hydrogen gas. After completion of the reaction, the mixture was filtered with Celite, and the filtrate was distilled under reduced pressure and separated by column chromatography to obtain the title compound (1.6 g, 99%).

NMR:$^1$H-NMR(400 HMz, CDCl$_3$); δ 7.55 (dd, 1H), 7.42 (d, 1H), 7.35 (m, 4), 7.28 (m, 1H), 6.62 (d, 1H), 4.39 (d, 2H), 4.31 (brs, 1H), 3.80 (s, 3H), 3.27 (brs, 2H)

Preparation Example 125-3

Synthesis of 1-benzyl-1H-benzotriazole-5-carboxylic acid methyl ester

3-Amino-4-benzylamine-benzoic acid methyl ester (500 mg, 2.0 mmol) obtained from Preparation Example 125-2 was dissolved in methanol (40 ml). 1N Hydrochloric acid solution (30 ml) was added, and then sodium nitrite (NaNO$_2$, 148 mg) was added thereto. The mixture was stirred for 1 hour at room temperature. After completion of the reaction, the mixture was distilled under reduced pressure. A saturated sodium bicarbonate solution was added thereto, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (320 mg, 60%).

NMR:$^1$H-NMR(400 HMz, CDCl$_3$); δ 8.84 (s, 1H), 8.14 (dd, 1H), 7.40 (m, 4H), 7.31 (m, 2H), 5.91 (s, 2H), 4.00 (s, 3H)

Preparation Example 125-4

Synthesis of (1-benzyl-1H-benzotriazol-5-yl)-methanol

According to the method described in Preparation Example 17-2, the compound (470 mg, 1.76 mmol) obtained from Preparation Example 125-3 was used to obtain the title compound (394 mg, 94%).

NMR:$^1$H-NMR(400 HMz, DMSO-d$_6$); δ 7.92 (s, 1H), 7.76 (d, 1H), 7.47 (d, 1H), 7.29-7.36 (m, 5H), 5.96 (s, 2H), 5.32 (t, 1H), 4.62 (d, 2H)

Preparation Example 126-1

Synthesis of 1-benzyl-1H-benzimidazole-5-carboxylic acid methyl ester

3-Amino-4-benzylamine-benzoic acid methyl ester (500 mg, 2.0 mmol) obtained from Preparation Example 125-2 was dissolved in toluene (50 ml), and triethylorthoformate (0.65 ml, 4.0 mmol) and p-toluenesulfonic acid (50 mg) were added thereto. The mixture was stirred at 120° C. for 2 hours and then distilled under reduced pressure. Water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (250 mg, 47%).

NMR:$^1$H-NMR(400 HMz, CDCl$_3$); 8.55 (s, 1H), 8.09 (s, 1H), 8.00 (d, 1H), 7.78 (d, 1H), 7.36 (m, 3H), 7.18 (m, 2H), 5.40 (s, 2H), 3.94 (s, 3H)

Preparation Example 126-2

Synthesis of (1-benzyl-1H-benzimidazole-5-yl)-methanol

According to the method described in Preparation Example 17-2, the compound (480 mg, 1.80 mmol) obtained from Preparation Example 126-1 was used to obtain the title compound (333 mg, 78%).

NMR:$^1$H-NMR(400 HMz, DMSO-d$_6$); δ 8.37 (s, 1H), 7.58 (s, 1H), 7.43 (d, 1H), 7.27-7.35 (m, 5H), 7.16 (d, 1H), 5.48 (s, 2H), 5.10 (t, 1H), 4.56 (d, 2H)

Preparation Example 127-1

Synthesis of 1-benzyl-2-oxo-2,3-dihydro-1H-benzimidazole-5-carboxylic acid methyl ester 3-Amino-4-benzylamine-benzoic acid methyl ester (2.38 g, 8.8 mmol) obtained from Preparation Example 125-2 was dissolved in toluene (50 ml) and triphosgene (2.87 g, 9.7 mmol) was added thereto. The mixture was stirred at 120° C. for 2 hours and then distilled under reduced pressure. Water was added thereto and the residue was extracted with ethyl acetate. The extract was washed with saturated aqueous sodium chloride solution, dried over anhydrous magnesium sulfate and filtered. Filtrate was distilled under reduced pressure and separated by column chromatography. The separated compound was dissolved in dimethylformamide (10 ml), and potassium carbonate (1.4 g, 10.4 mmol) and methyl iodide (1.5 g, 104 mmol) were slowly added dropwise thereto. The mixture was stirred for 2 hours and then distilled under reduced pressure. Water was added thereto and the residue was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (2.30 g, 90%).

NMR:$^1$H-NMR(500 HMz, CDCl$_3$); δ 7.78 (d, 1H), 7.67 (s, 1H), 7.31 (m, 4H), 7.26 (m, 1H), 6.89 (d, 1H), 5.09 (s, 2H), 3.50 (s, 3H)

Preparation Example 127-2

Synthesis of 1-benzyl-5-hydroxymethyl-3-methyl-1, 3-dihydro-benzimidazol-2-one

According to the method described in Preparation Example 17-2, the compound (0.68 g, 2.30 mmol) obtained from Preparation Example 127-1 was used to obtain the title compound (0.54 g, 88%).

NMR:$^1$H-NMR(400 HMz, CDCl$_3$); δ 7.31 (m, 5H), 7.04 (s, 1H), 6.99 (d, 1H), 6.83 (d, 1H), 5.07 (s, 2H), 4.70 (d, 2H), 3.45 (s, 3H), 1.76 (t, 1H)

Preparation Example 128-1

Synthesis of 3-isobutyl-3H-benzotriazole-5-carboxylic acid methyl ester

According to the methods described in Preparation Examples 125-1 to 125-3, 3-fluoro-4-nitro-benzoic acid rather than 4-fluoro-3-nitro-benzoic acid and isobutylamine rather than benzylamine were used to obtain the title compound (1.18 g, 32%).

Preparation Example 128-2

Synthesis of (3-isobutyl-3H-benzotriazol-yl)-methanol

According to the method described in Preparation Example 17-2, the compound obtained from Preparation Example 128-1 was used to obtain the title compound (950 mg, 79%).

NMR:$^1$H-NMR(400 HMz, CDCl$_3$); δ 8.01 (d, 1H), 7.56 (s, 1H), 7.31 (m, 1H), 4.90 (d, 2H), 4.43 (d, 2H), 2.41 (m, 1H), 2.01 (t, 1H), 0.97 (d, 6H)

Preparation Example 129-1

Synthesis of 5-bromo-2-fluoro-pyridine-3-carbaldehyde

Diisopropylamine (2.6 ml, 25 mmol) was dissolved in tetrahydrofuran (100 ml), 2.5M solution of butyllithium in tetrahydrofuran (10 ml, 25 mmol) was slowly added dropwise at 0° C. and then the mixture was stirred for 1 minute. A solution of 5-bromo-fluoro-2-pyridine (4.0 g, 22.7 mmol) in tetrahydrofuran (20 ml) was slowly added dropwise at −78° C. and stirred for 30 minutes. Ethylformate (2.8 ml, 34 mmol) was added dropwise and then the mixture was stirred for 10 minutes at −78° C. After completion of the reaction, 1N hydrochloric acid solution was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (4.1 g, 88%).

Preparation Example 129-2

Synthesis of 5-bromo-1H-pyrazolo[3,4-b]pyridine

5-Bromo-2-fluoro-pyridine-3-carbaldehyde (4.1 g, 20 mmol) obtained from Preparation Example 129-1 was dissolved in ethanol (50 ml). After adding hydrazine hydrate (5.0 ml, 100 mmol), the mixture was stirred for 8 hours at 100° C. and then distilled under reduced pressure. Water was added thereto and the residue was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (1.8 g, 40%).

NMR:$^1$H-NMR(400 HMz, CDCl$_3$); δ 11.29 (br s, 1H), 8.63 (s, 1H), 8.26 (s, 1H), 8.07 (s, 1H)

Preparation Example 129-3

Synthesis of 1H-pyrazolo[3,4-b]pyridine-5-carboxylic acid methyl ester

According to the methods described in Preparation Examples 117-4 to 117-6, the compound (2.0 g, 10.10 mmol) obtained from Preparation Example 129-2 was used to obtain the title compound (1.38 g, 59%).

Preparation Example 130

Synthesis of (1-isobutyl-1H-pyrazol[3,4-b]pyridin-5-yl)-methanol

According to the method described in Preparation Example 17-2, the compound (1.38 g, 5.93 mmol) obtained from Preparation Example 129-3 was used to obtain the title compound (950 mg, 79%).

NMR:$^1$H-NMR(400 HMz, CDCl$_3$); δ 8.55 (m, 1H), 8.07 (m, 1H), 8.00 (s, 1H), 4.84 (d, 2H), 4.33 (d, 2H), 2.41 (m, 1H), 1.83 (t, 1H), 0.92 (d, 6H)

Preparation Example 131-1

Synthesis of 1-benzyl-1H-indole-4-carboxylic acid methyl ester

In the method described in Preparation Example 17-1, 1H-indole-4-carboxylic acid methyl ester (370 mg, 2.1 mmol) was used rather than 7-methyl-1H-indole-6-carboxylic acid methyl ester to obtain the title compound (560 mg, 100%).

NMR:¹H-NMR(400 HMz, CDCl₃); δ 7.91 (d, 1H), 7.47 (d, 1H), 7.25-7.32 (m, 4H), 7.16-7.23 (m, 2H), 7.07 (d, 2H), 5.16 (s, 2H), 3.97 (s, 3H)

Preparation Example 131-2

Synthesis of (1-benzyl-1H-indol-4-yl)-methanol

According to the method described in Preparation Example 17-2, the compound (560 mg, 2.11 mmol) obtained from Preparation Example 131-1 was used to obtain the title compound (500 mg, 99%).

Preparation Example 132-1

Synthesis of [1-(4-fluoro-2-methyl-phenyl)-1H-indol-4-yl]-carboxylic acid methyl ester In the method described in Preparation Example 11-1, 1H-indole-4-carboxylic acid methyl ester (300 mg, 1.7 mmol) was used rather than 1H-indole-6-carboxylic acid methyl ester to obtain the title compound (280 mg, 55%).

NMR:¹H-NMR(400 HMz, CDCl₃); δ 7.96 (d, 1H), 7.17-7.31 (m, 5H), 7.11 (m, 1H), 7.03 (m, 1H), 4.02 (s, 3H), 2.00 (s, 3H)

Preparation Example 132-2

Synthesis of [1-(4-fluoro-2-methyl-phenyl)-1H-indol-4-yl]-methanol

According to the method described in Preparation Example 11-2, the compound (280 mg, 0.94 mmol) obtained from Preparation Example 132-1 was used to obtain the title compound (150 mg, 63%).

Preparation Example 133-1

Synthesis of 1-benzyl-1H-indazole-4-carboxylic acid methyl ester

According to the method described in Preparation Example 55, 1H-indazole-4-carboxylic acid methyl ester (200 mg, 1.13 mmol) and benzyl bromide (0.15 ml, 1.24 mmol) were used to obtain the title compound (160 mg, 53%).

NMR:¹H-NMR(400 HMz, CDCl₃); δ 8.54 (s, 1H), 7.91 (d, 1H), 7.55 (d, 1H), 7.38 (dd, 1H), 7.24-7.29 (m, 3H), 7.17 (dd, 2H), 5.65 (s, 2H), 4.01 (s, 3H)

Preparation Example 133-2

Synthesis of (1-benzyl-1H-indazol-4-yl)-methanol

According to the method described in Preparation Example 56, the compound (160 mg, 0.60 mmol) obtained from Preparation Example 133-1 was used to obtain the title compound (140 mg, 100%).

Preparation Example 134-1

Synthesis of 2-benzyl-2H-indazole-4-carboxylic acid methyl ester

According to the method described in Preparation Example 55, 1H-indazole-4-carboxylic acid methyl ester (200 mg, 1.13 mmol) and benzyl bromide (0.15 ml, 1.24 mmol) were used to obtain the title compound (100 mg, 33%).

NMR:¹H-NMR(400 HMz, CDCl₃); δ 8.44 (s, 1H), 7.95 (d, 1H), 7.90 (d, 1H), 7.30-7.37 (m, 6H), 5.63 (s, 2H), 3.95 (s, 3H)

Preparation Example 134-2

Synthesis of (2-benzyl-2H-indazol-4-yl)-methanol

According to the method described in Preparation Example 57, the compound (100 mg, 0.38 mmol) obtained from Preparation Example 134-1 was used to obtain the title compound (90 mg, 100%).

Preparation Example 135-1

Synthesis of 1-(4-fluoro-benzyl)-1H-indazole-4-carboxylic acid methyl ester

According to the method described in Preparation Example 55, 1H-indazole-4-carboxylic acid methyl ester (300 mg, 1.70 mmol) and 4-fluorobenzyl bromide (0.22 ml, 1.84 mmol) were used to obtain the title compound (200 mg, 41%).

NMR:¹H-NMR(400 HMz, CDCl₃); δ 8.59 (s, 1H), 7.97 (dd, 1H), 7.59 (d, 1H), 7.44 (dd, 1H), 7.19-7.23 (m, 2H), 7.01-7.05 (m, 2H), 5.66 (s, 2H), 4.07 (s, 3H)

Preparation Example 135-2

Synthesis of [1-(4-fluoro-benzyl)-1H-indazol-4-yl]-methanol

According to the method described in Preparation Example 56, the compound (200 mg, 0.70 mmol) obtained from Preparation Example 135-1 was used to obtain the title compound (190 mg, 100%).

Preparation Example 136-1

Synthesis of 2-(4-fluoro-benzyl)-2H-indazole-4-carboxylic acid methyl ester

According to the method described in Preparation Example 55, 1H-indazole-4-carboxylic acid methyl ester (300 mg, 1.70 mmol) and 4-fluorobenzyl bromide (0.22 ml, 1.84 mmol) were used to obtain the title compound (160 mg, 33%).

NMR:¹H-NMR(400 HMz, CDCl₃); δ 8.44 (s, 1H), 7.95 (dd, 1H), 7.91 (dd, 1H), 7.29-7.37 (m, 3H), 7.02-7.07 (m, 2H), 5.60 (s, 2H), 3.96 (s, 3H)

Preparation Example 136-2

Synthesis of [2-(4-fluoro-benzyl)-2H-indazol-4-yl]-methanol

According to the method described in Preparation Example 57, the compound (160 mg, 0.56 mmol) obtained from Preparation Example 136-1 was used to obtain the title compound (150 mg, 100%).

Preparation Example 137-1

Synthesis of 1-(5-methyl-pyrazin-2-ylmethyl)-1H-indazole-4-carboxylic acid methyl ester According to the method described in Preparation Example 55, 1H-indazole-4-carboxylic acid methyl ester (798 mg, 4.53 mmol) and methanesulfonic acid 5-methyl-pyrazin-2-ylmethyl ester (1.0 g, 4.99 mmol) were used to obtain the title compound (580 mg, 45%).
NMR:$^1$H-NMR(400 HMz, CDCl$_3$); δ 8.56 (s, 1H), 8.39 (s, 1H), 8.27 (s, 1H), 7.94 (d, 1H), 7.70 (d, 1H), 7.44 (dd, 1H), 5.75 (s, 2H), 4.02 (s, 3H), 2.52 (s, 3H)

Preparation Example 137-2

Synthesis of [1-(5-methyl-pyrazin-2-ylmethyl)-1H-indazol-4-yl]-methanol

According to the method described in Preparation Example 56, the compound (580 mg, 2.05 mmol) obtained from Preparation Example 137-1 was used to obtain the title compound (522 mg, 100%).

Preparation Example 138-1

Synthesis of 2-(5-methyl-pyrazin-2-ylmethyl)-2H-indazole-4-carboxylic acid methyl ester According to the method described in Preparation Example 55, 1H-indazole-4-carboxylic acid methyl ester (798 mg, 4.53 mmol) and methanesulfonic acid 5-methyl-pyrazin-2-ylmethyl ester (1.0 g, 4.99 mmol) were used to obtain the title compound (250 mg, 20%).
NMR:$^1$H-NMR(400 HMz, CDCl$_3$); δ 8.60 (s, 1H), 8.45 (s, 1H), 8.42 (d, 1H), 7.93 (s, 1H), 7.91 (d, 1H), 7.34 (dd, 1H), 5.74 (s, 2H), 3.97 (s, 3H), 2.55 (s, 3H)

Preparation Example 138-2

Synthesis of [2-(5-methyl-pyrazin-2-ylmethyl)-2H-indazol-4-yl]-methanol

According to the method described in Preparation Example 57, the compound (250 mg, 0.89 mmol) obtained from Preparation Example 138-1 was used to obtain the title compound (225 mg, 100%).
NMR:$^1$H-NMR(400 HMz, CDCl$_3$); δ 8.42 (d, 1H), 8.26 (s, 1H), 7.63 (d, 1H), 7.24 (m, 2H), 7.01 (d, 1H), 5.70 (s, 2H), 4.93 (br s, 2H), 2.56 (s, 4H)

Preparation Example 139

Synthesis of 1-(4-fluoro-phenyl)-1H-indole-6-carbaldehyde

According to the methods described in Preparation Examples 6-1 to 6-3, 1H-indole-carboxylic acid methyl ester and 1-fluoro-4-iodo-benzene were used to obtain the title compound.

Preparation Example 140

Synthesis of (1-benzyl-3-chloro-1H-indol-6-yl)-methanol

1-Benzyl-3-chloro-1H-indole-6-carbaldehyde (177 mg, 0.66 mmol) obtained from Preparation Example 3 was dissolved in a mixed solution of tetrahydrofuran and methanol (1/1, 20 ml), and sodium borohydride (37 mg, 1.0 mmol) was added thereto at 0° C. The mixture was stirred for 30 minutes, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (120 mg, 67%).

Preparation Example 141

Synthesis of (1-pyrazin-2-ylmethyl-1H-pyrrolo[2,3-b]pyridin-6-yl)-methanol

According to the methods described in Preparation Examples 54-1 and 54-2, 1H-pyrrolo[2,3-b]pyridine-6-carbonitrile (170 mg, 0.96 mmol) and 2-bromomethyl-pyrazine (332 mg, 1.92 mmol) were used to obtain the title compound (140 mg, 60%).

Preparation Example 142-1

Synthesis of 1-isobutyl-1H-pyrrolo[2,3-b]pyridine-6-carbonitrile

According to the method described in Preparation Example 17-1, 1H-pyrrolo[2,3-b]pyridine-6-carbonitrile (300 mg, 2.1 mmol) and 1-chloro-2-methyl-propane (0.86 ml, 8.8 mmol) were used to obtain the title compound (370 mg, 89%).
NMR:$^1$H-NMR(400 HMz, CDCl$_3$); δ 7.96 (d, 1H), 7.44 (d, 1H), 7.42 (d, 1H), 6.54 (d, 1H), 4.11 (d, 2H), 2.17-2.31 (m, 1H), 0.92 (d, 6H)

Preparation Example 142-2

Synthesis of (1-isobutyl-1H-pyrrolo[2,3-b]pyridin-6-yl)-methanol

According to the method described in Preparation Example 54-2, the compound (370 mg, 1.86 mmol) obtained from Preparation Example 142-1 was used to obtain the title compound (360 mg, 88%).

Preparation Example 143

Synthesis of (1-isopropyl-3-methyl-1H-indazol-6-yl)-methanol

According to the methods described in Preparation Examples 55 and 56, 3-methyl-1H-indazole-6-carboxylic acid methyl ester (0.50 g, 2.63 mmol) and 2-bromo-propane (0.49 g, 3.95 mmol) were used to obtain the title compound (0.25 g, 49%).
NMR:$^1$H-NMR(400 HMz, CDCl$_3$); δ 7.62 (d, 1H), 7.40 (s, 1H), 7.08 (d, 1H), 4.84 (s, 2H), 4.80 (m, 1H), 2.57 (s, 3H), 1.82 (brs, 1H), 1.57 (d, 6H)

Preparation Example 144

Synthesis of (1-isopropyl-7-methyl-1H-indazol-5-yl)-methanol

According to the methods described in Preparation Examples 55 and 56, 7-methyl-1H-indazole-5-carboxylic acid methyl ester (1 g, 5.26 mmol) and isobutyl iodide (1.58 ml, 15.78 mmol) were used to obtain the title compound (357 mg, 100%).

NMR:$^1$H-NMR(400 HMz, CDCl$_3$); δ 7.98 (s, 1H), 7.52 (s, 1H), 7.13 (s, 1H), 5.16-5.22 (m, 1H), 4.73 (d, 2H), 2.74 (s, 3H), 1.59 (d, 6H)

Preparation Example 145

Synthesis of (1-isobutyl-1H-indazol-4-yl)-methanol

According to the methods described in Preparation Examples 55 and 56, 1H-indazole-4-carboxylic acid methyl ester (500 mg, 2.84 mmol) and isobutyl chloride (0.6 ml, 5.68 mmol) were used to obtain the title compound (257 mg, 44%).

NMR:$^1$H-NMR(400 HMz, CDCl$_3$); δ 8.13 (s, 1H), 7.35 (d, 1H), 7.33 (d, 1H), 7.12 (dd, 1H), 5.03 (d, 2H), 4.19 (d, 2H), 2.30-2.40 (m, 1H), 1.84 (br t, 1H), 0.93 (d, 6H)

Preparation Example 146

Synthesis of 1-(6-methyl-pyridin-3-ylmethyl)-1H-indazole-6-carboxylic acid methyl ester According to the method described in Preparation Example 55, 1H-indazole-6-carboxylic acid methyl ester and methanesulfonic acid 6-methyl-pyridin-3-ylmethyl ester were used to obtain the title compound (324 mg, 26%).

NMR:$^1$H-NMR(400 HMz, CDCl$_3$); δ 8.52 (s, 1H), 8.15 (s, 1H), 8.13 (s, 1H), 7.87 (dd, 1H), 7.77 (dd, 1H), 7.42 (dd, 1H), 6.96 (d, 1H), 5.61 (s, 2H), 3.95 (s, 3H), 2.51 (s, 3H)

Preparation Example 147

Synthesis of [1-(6-methyl-pyridin-3-ylmethyl)-1H-indazol-6-yl]-methanol

According to the method described in Preparation Example 56, the compound (324 mg, 1.15 mmol) obtained from Preparation Example 146 was used to obtain the title compound (72.2 mg, 24%).

Preparation Example 148

Synthesis of (1-isopropyl-3-methyl-1H-indazol-5-yl)-methanol

In the method described in Preparation Example 118, 1-isopropyl-3-methyl-1H-indazole-5-carboxylic acid methyl ester (680 mg, 2.93 mmol) was used rather than 1-isobutyl-3-methyl-1H-indazole-5-carboxylic acid methyl ester to obtain the title compound (540 mg, 90%).

NMR:$^1$H-NMR(400 HMz, CDCl$_3$); δ 7.63 (s, 1H), 7.37 (m, 2H), 4.78 (m, 3H), 2.57 (s, 3H), 1.56 (d, 6H)

Preparation Example 149

Synthesis of 3-(2-fluoro-4-hydroxy-phenyl)-propanoic acid ethylester

The title compound was prepared according to the method described in WO 2012/011125.

NMR:$^1$H-NMR(400 HMz, CDCl$_3$); δ 7.02 (m, 1H), 6.51 (m, 2H), 5.38 (s, 1H), 4.13 (q, 2H), 2.89 (t, 2H), 2.59 (t, 2H), 1.25 (t, 3H)

Preparation Example 150

Synthesis of 3-(4-hydroxy-phenyl)-butyric acidethylester

The title compound was prepared according to the method described in Bioorganic & Medicinal Chemistry Letters, 22(2012), 1267-1270.

NMR:$^1$H-NMR(400 HMz, CDCl$_3$); δ 7.08 (m, 2H), 6.71 (m, 2H), 4.84 (s, 1H), 4.08 (q, 2H), 3.22 (m, 1H), 2.52 (q, 2H), 1.27 (d, 3H), 1.20 (t, 3H)

Preparation Example 151

Synthesis of 3-(4-hydroxy-phenyl)-pentanoic acid ethylester

The title compound was prepared according to the method described in Bioorganic & Medicinal Chemistry Letters, 22(2012), 1267-1270.

NMR:$^1$H-NMR(400 HMz, CDCl$_3$); δ 7.04 (d, 2H), 6.74 (d, 2H), 4.70 (m, 1H), 4.03 (q, 2H), 2.94 (m, 1H), 2.46-2.66 (m, 2H), 1.47-1.73 (m, 2H), 1.14 (t, 3H), 0.78 (t, 3H)

Preparation Example 152

Synthesis of 2-(4-hydroxy-phenyl)-cyclopropane carboxylic acid methyl ester (E)-3-(4-benzyloxy-phenyl)-acrylic acid benzylester (3.5 g, 8.7 mmol) was dissolved in tetrahydrofuran (100 ml), palladium(II) acetate (100 mg, 0.45 mmol) was added at 0° C. and then 0.25M solution of diazomethane in diethyl ether (150 ml, 37.5 mmol) was slowly added dropwise. The mixture was stirred for 3 hours at 0° C., acetic acid (0.1 ml) was added thereto and the mixture was stirred further for 10 minutes. Water was added and the mixture was extracted with ethyl acetate. The extract was washed with saturated aqueous sodium chloride solution, dried over anhydrous magnesium sulfate and filtered. Filtrate was distilled under reduced pressure to obtain 2-(4-benzyloxy-phenyl)-cyclopropanecarboxylic acid benzyl ester.

The obtained 2-(4-benzyloxy-phenyl)-cyclopropanecarboxylic acid benzyl ester was dissolved in dichloromethane (40 ml) and trifluoroacetic acid (20 ml) was added thereto. The mixture was stirred at room temperature for 8 hours and then distilled under reduced pressure. The residue was dissolved in tetrahydrofuran (100 ml) and 0.25M solution of diazomethane in diethyl ether (50 ml, 12.5 mmol) was added thereto. The mixture was stirred at 0° C. for 30 minutes and then distilled under reduced pressure and separated by column chromatography to obtain the title compound (0.72 g, 43%).

NMR:$^1$H-NMR(400 HMz, CDCl$_3$); δ 6.98 (dd, 2H), 6.74 (dd, 2H), 3.72 (s, 3H), 2.46-2.51 (m, 1H), 1.80-1.84 (m, 1H), 1.52-1.58 (m, 1H), 1.22-1.29 (m, 1H)

Preparation Example 153-1

Synthesis of 3-[4-(t-butyl-dimethyl-silanyloxy)-phenyl]-3-hydroxy-propanoic acid ethylester 4-(t-Butyl-dimethyl-silanyloxy)-benzaldehyde (2.0 g, 8.5 mmol) was dissolved in tetrahydrofuran (100 ml), and zinc (1.1 g, 16.8 mmol) and copper (I) iodide (80 mg, 0.4 mmol) were added thereto. At 80° C., ethylbromo acetate (1.4 ml, 12.8 mmol) was slowly added dropwise for 1 hour thereto.

After completion of the reaction, a saturated aqueous solution of ammonium chloride was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (1.5 g, 54%).

NMR:$^1$H-NMR(400 HMz, CDCl$_3$); δ 7.03 (d, 2H), 6.62 (d, 2H), 4.88 (m, 1H), 4.00 (q, 2H), 2.99 (d, 1H), 2.55 (m, 2H), 1.07 (t, 3H), 0.79 (s, 9H), 0.01 (s, 6H)

Preparation Example 153-2

Synthesis of 3-[4-(t-butyl-dimethyl-silanyloxy)-phenyl]-3-methoxy-propanoic acid ethyl ester The compound (700 mg, 2.2 mmol) obtained from Preparation Example 153-1 was dissolved in toluene (30 ml). Methyl iodide (1.3 ml, 22.0 mmol) and silver oxide (1.2 g, 5.2 mmol) were added and the mixture was stirred under reflux for 8 hours. The mixture was filtered with Celite. Filtrate was distilled under reduced pressure and separated by column chromatography to obtain the title compound (470 mg, 63%).

Preparation Example 153-3

Synthesis of 3-(4-hydroxy-phenyl)-3-methoxy-propanoic acid ethyl ester

The compound (470 mg, 1.4 mmol) obtained from Preparation Example 153-2 was dissolved in tetrahydrofuran (30 ml), tetrabutylammonium fluoride (786 mg, 2.8 mmol) was added thereto and the mixture was stirred for 1 hour. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (260 mg, 83%).

NMR:$^1$H-NMR(400 HMz, CDCl$_3$); δ 7.05 (d, 2H), 6.71 (d, 2H), 4.45-4.52 (m, 1H), 3.95-4.18 (m, 2H), 3.08 (s, 3H), 2.72-2.81 (m, 1H), 2.45-2.59 (m, 1H), 1.10 (t, 3H)

Preparation Example 154

Synthesis of 3-cyano-3-(4-hydroxy-phenyl)-propanoic acid ethyl ester

The title compound was obtained according to the method described in WO 2005/086661.

NMR:$^1$H-NMR(400 HMz, CDCl$_3$); δ 7.21 (d, 2H), 6.83 (d, 2H), 4.07-4.25 (m, 3H), 2.95-3.01 (m, 1H), 2.78-2.84 (m, 1H), 1.23 (t, 3H)

Preparation Example 155

Synthesis of (S)-3-(4-hydroxy-phenyl)-hex-4-ynoic acid methyl ester

The title compound was obtained according to the methods described in WO 2009/054479 and WO 2005/086661.

NMR:$^1$H-NMR(400 HMz, CDCl$_3$); δ 7.22 (d, 2H), 6.77 (d, 2H), 5.11 (s, 1H), 4.04 (m, 1H), 3.67 (s, 3H), 2.70 (m, 2H), 1.82 (s, 3H)

Preparation Example 156

Synthesis of 3-(4,5-dihydro-isoxazol-3-yl)-3-(4-hydroxy-phenyl)-propanoic acid methyl ester The title compound was obtained according to the methods described in the Example 6 of U.S. Pat. No. 8,003,648 B2 (Synthetic methods 6-1 to 6-10).

NMR:$^1$H-NMR(400 HMz, CDCl$_3$); δ 7.06 (d, 2H), 6.79 (d, 2H), 5.86 (s, 1H), 4.23 (m, 2H), 4.07 (t, 1H), 3.78 (m, 1H), 3.63 (s, 3H), 3.23 (dd, 1H), 2.83 (m, 2H)

Preparation Example 157

Synthesis of (S)-3-(4-hydroxy-phenyl)-3-isoxazol-3-yl-propanoic acid methyl ester The title compound was obtained according to the method described in the Example 6 of U.S. Pat. No. 8,003,648 B2 (Synthetic method 6-8).

NMR:$^1$H-NMR(400 HMz, CDCl$_3$); δ 8.27 (s, 1H), 7.08 (d, 2H), 6.76 (d, 2H), 6.08 (s, 1H), 6.00 (s, 1H), 4.56 (t, 1H), 3.63 (s, 3H), 3.32 (dd, 1H), 2.98 (dd, 1H)

Preparation Example 158

Synthesis of (6-hydroxy-2,3-dihydro-benzofuran-3-yl)-acetic acid methyl ester

The title compound was obtained according to the methods described in WO 2012/011125.

NMR:$^1$H-NMR(400 HMz, CDCl$_3$); δ 6.97 (d, 1H), 6.32-6.64 (m, 2H), 5.07 (br s, 1H), 4.75 (t, 1H), 4.15-4.28 (m, 1H), 3.75-3.81 (m, 1H), 3.72 (s, 3H), 2.72-2.77 (m, 1H), 2.53-2.59 (m, 1H)

Preparation Example 159

Synthesis of (5-hydroxy-indan-1-yl)-acetic acid methyl ester

The title compound was obtained according to the methods described in Organic & Biomolecular Chemistry 2011, 9, 4570.

NMR:$^1$H-NMR(400 HMz, CDCl$_3$); δ 7.03 (d, 1H), 6.69 (s, 1H), 6.62 (m, 1H), 4.62 (s, 1H), 4.17 (q, 2H), 3.51 (m, 1H), 2.76-2.92 (m, 2H), 2.70 (dd, 1H), 2.33-2.43 (m, 2H), 1.74 (m, 1H), 1.27 (t, 3H)

Preparation Example 160

Synthesis of (7-hydroxy-chroman-4-yl)-acetic acid methyl ester

The title compound was obtained according to the methods described in Organic & Biomolecular Chemistry 2011, 9, 4570.

NMR:$^1$H-NMR(500 HMz, CDCl$_3$); δ 6.97 (d, 1H), 6.37 (m, 1H), 6.29 (m, 1H), 4.82 (s, 1H), 4.14-4.17 (m, 4H), 3.27 (m, 1H), 2.72 (dd, 1H), 2.46 (dd, 1H), 2.11 (m, 1H), 1.08 (m, 1H), 1.26 (t, 3H)

Preparation Example 161

Synthesis of (6-hydroxy-1,2,3,4-tetrahydro-naphthalen-1-yl)-acetic acid methyl ester The title compound was obtained according to the methods described in Organic & Biomolecular Chemistry 2011, 9, 4570.
NMR:$^1$H-NMR(400 HMz, CDCl$_3$); δ 7.04 (d, 1H), 6.92 (m, 1H), 6.54 (m, 1H), 4.58 (s, 1H), 4.16 (q, 2H), 3.27 (m, 1H), 2.63-2.73 (m, 3H), 2.47 (dd, 1H), 1.66-1.89 (m, 4H), 1.26 (t, 3H)

Preparation Example 162-1

Synthesis of 3-methyl-indazole-1,6-dicarboxylic acid 1-t-butyl ester-6-methyl ester The compound (3.8 g, 20 mmol) obtained from Preparation Example 86-4 was dissolved in acetonitrile (40 ml). 4-(Dimethylamino) pyridine (0.49 g, 4 mmol) and triethylamine (3.07 ml, 22 mmol) were added thereto. Di-t-butyl dicarbonate (5.24 g, 24 mmol) in acetonitrile (20 ml) was added dropwise and then the mixture was stirred for 16 hours. After completion of the reaction, water was added thereto and the mixture was extracted with ethyl acetate. The extract was washed with 1N hydrochloric acid aqueous solution and saturated aqueous sodium chloride solution, dried over anhydrous magnesium sulfate and filtered. Filtrate was distilled under reduced pressure and separated by column chromatography to obtain the title compound (4.48 g, 77%).
NMR:$^1$H-NMR(500 HMz, CDCl$_3$); δ 8.82 (s, 1H), 7.98 (d, 1H), 7.69 (d 1H), 3.97 (s, 3H), 2.62 (s, 3H), 1.74 (s, 9H)

Preparation Example 162-2

Synthesis of 3-bromomethyl-indazole-1,6-dicarboxylic acid 1-t-butyl ester 6-methyl ester The compound (2.9 g, 10 mmol) obtained from Preparation Example 162-1 was dissolved in dichloroethane (50 ml). N-Bromosuccinimide (NBS, 1.96 g, 11 mmol) and 2,2'-azobis(2-methylpropionitrile) (0.33 g, 2 mmol) were added dropwise thereto. The mixture was stirred under reflux for 16 hours, cooled to room temperature, distilled under reduced pressure to remove the solvent and separated by column chromatography to obtain the title compound (2.13 g, 58%).
NMR:$^1$H-NMR(400 HMz, CDCl$_3$); δ 8.86 (s, 1H), 8.05 (d, 1H), 7.92 (d 1H), 4.80 (s, 2H), 3.99 (s, 3H), 1.75 (s, 9H)

Preparation Example 162-3

Synthesis of 3-methoxymethyl-1H-indazole-6-carboxylic acid methyl ester

The compound (1.11 g, 3 mmol) obtained from Preparation Example 162-2 was dissolved in methanol (30 ml) and triethylamine (0.42 ml, 3 mmol) was added dropwise thereto. The mixture was stirred under reflux for 16 hours, cooled to room temperature, distilled under reduced pressure to remove the solvent. Water was added thereto and the residue was extracted with dichloromethane. The extract was dried over anhydrous magnesium sulfate and filtered. Filtrate was distilled under reduced pressure. Dichloromethane and hexane were used to produce solids, and the solids were filtered, washed with hexane and dried to obtain the title compound (0.5 g, 76%).
NMR:$^1$H-NMR(500 HMz, CDCl$_3$); δ 11.0 (br s, 1H), 8.23 (s, 1H), 7.88 (d, 1H), 7.83 (d 1H), 4.89 (s, 2H), 3.96 (s, 3H), 3.45 (s, 3H)

Preparation Example 162-4

Synthesis of (1-isobutyl-3-methoxymethyl-1H-indazol-6-yl)-methanol

According to the methods described in Preparation Examples 55 and 56, the compound (164 mg, 0.745 mmol) obtained from Preparation Example 162-3 and isobutyliodide (0.13 ml, 1.118 mmol) were used to obtain the title compound (90 mg, 49%).
NMR:$^1$H-NMR(500 HMz, CDCl$_3$); δ 7.78 (d, 1H), 7.40 (s, 1H), 7.11 (d, 1H), 4.85 (d, 2H), 4.81 (s, 2H), 4.14 (d, 2H), 3.40 (s, 3H), 2.35 (m, 1H), 1.74 (t, 1H), 0.92 (d, 6H)

Preparation Example 163-1

Synthesis of 1-isobutyl-1H-indazole-carboxylic acid methyl ester

According to the method described in Preparation Example 55, 1H-indazole-4-carboxylic acid methyl ester (250 mg, 1.42 mmol) and isobutyl iodide (0.33 ml, 2.84 mmol) were used to obtain the title compound (57 mg, 57%).
NMR:$^1$H-NMR(500 HMz, CDCl$_3$); δ 8.48 (s, 1H), 7.91 (d, 1H), 7.61 (d, 1H), 7.42 (dd, 1H), 4.21 (d, 2H), 4.01 (s, 3H), 2.32-2.36 (m, 1H), 0.91 (d, 6H)

Preparation Example 163-2

Synthesis of 3-fluoro-1-isobutyl-1H-indazole-4-carboxylic acid methyl ester

1-Isobutyl-1H-indazole-4-carboxylic acid methyl ester (188 mg, 0.81 mmol) was dissolved in acetonitrile (8 ml). Selectfluor (429 mg, 1.21 mmol) and acetic acid (1.5 ml) were added thereto and then the mixture was stirred for 1 hour at 100° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (98.3 mg, 48%).
NMR:$^1$H-NMR(500 HMz, CDCl$_3$); δ 7.75 (d, 1H), 7.44 (d, 1H), 7.36 (dd, 1H), 3.99 (d, 2H), 3.93 (s, 3H), 2.23 (m, 1H), 0.84 (d, 6H)

Preparation Example 163-3

Synthesis of (3-fluoro-1-isobutyl-1H-indazol-4-yl)-methanol

The compound (98.3 mg, 0.39 mmol) obtained from Preparation Example 163-2 was dissolved in tetrahydrofuran (5 ml) and lithium aluminium hydride (16.4 mg, 0.43 mmol) was added dropwise thereto. The mixture was stirred for 30 minutes at room temperature, water (1 ml), 6N sodium hydroxide (1 ml) and water (3 ml) were added sequentially. Ethyl acetate was added and the mixture was filtered with Celite. Filtrate was distilled under reduced pressure to obtain the title compound (64.7 mg, 75%).

NMR:$^1$H-NMR(500 HMz, CDCl$_3$); δ 7.34 (dd, 1H), 7.24 (d, 1H), 7.14 (d, 1H), 5.02 (d, 2H), 3.99 (d, 2H), 2.27-2.30 (m, 1H), 1.92 (t, 1H), 0.91 (d, 6H)

Preparation Example 164-1

Synthesis of 1-isopropyl-1H-indazole-4-carboxylic acid methyl ester

According to the method described in Preparation Example 55, 1H-indazole-4-carboxylic acid methyl ester (176 mg, 1.0 mmol) and isopropyl iodide (0.15 ml, 1.5 mmol) were used to obtain the title compound (116 mg, 53%).

NMR:$^1$H-NMR(500 HMz, CDCl$_3$); δ 8.47 (s, 1H), 7.95 (d, 1H), 7.90 (d, 1H), 7.33 (m, 1H), 4.84 (m, 1H), 3.98 (s, 3H), 1.68 (d, 6H)

Preparation Example 164-2

Synthesis of (1-isopropyl-1H-indazol-4-yl)-methanol

According to the method described in Preparation Example 56, the compound (116 mg, 0.531 mmol) obtained from Preparation Example 164-1 was used to obtain the title compound (96 mg, 95%).

NMR:$^1$H-NMR(500 HMz, CDCl$_3$); δ 8.14 (s, 1H), 7.41-7.31 (m, 2H), 7.12 (d, 1H), 5.02 (d, 2H), 4.86 (m, 1H), 1.76 (t, 1H), 1.59 (d, 6H)

Preparation Example 165-1

Synthesis of 3-ethoxymethyl-1H-indazole-6-carboxylic acid methyl ester

According to the method described in Preparation Example 162-3, the compound (1.11 g, 3.0 mmol) obtained from Preparation Example 162-2 and ethanol (30 ml) were used to obtain the title compound (0.25 g, 36%).

NMR:$^1$H-NMR(500 HMz, CDCl$_3$); δ 10.13 (br s, 1H), 8.21 (s, 1H), 7.93-7.83 (m, 2H), 4.91 (s, 2H), 3.96 (s, 3H), 3.61 (q, 2H), 1.25 (t, 3H)

Preparation Example 165-2

Synthesis of (3-ethoxymethyl-1-isobutyl-1H-indazol-6-yl)-methanol

According to the methods described in Preparation Examples 55 and 56, the compound (125 mg, 0.533 mmol) obtained from Preparation Example 165-1 and isobutyl iodide (0.1 ml, 0.800 mmol) were used to obtain the title compound (92 mg, 65%).

NMR:$^1$H-NMR(500 HMz, CDCl$_3$); δ 7.81 (d, 1H), 7.38 (s, 1H), 7.11 (d, 1H), 4.86 (s, 2H), 4.85 (d, 2H), 4.13 (d, 2H), 3.56 (q, 2H), 2.34 (m, 1H), 1.74 (t, 1H), 1.22 (t, 3H), 0.92 (d, 6H)

Preparation Example 166-1

Synthesis of 3-chloro-1-isobutyl-1H-indazole-4-carboxylic acid methyl ester

1-Isobutyl-1H-indazole-4-carboxylic acid methyl ester (98 mg, 0.42 mmol) was dissolved in acetonitrile (5 ml). N-chlorosuccinimide (NCS, 62 mg, 0.46 mmol) was added thereto and then the mixture was stirred for 1 hour at 80° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure to obtain the title compound (112 mg, 100%).

NMR:$^1$H-NMR(500 HMz, CDCl$_3$); δ 7.64 (d, 1H), 7.54 (d, 1H), 7.43 (dd, 1H), 4.13 (d, 2H), 4.01 (s, 3H), 2.33 (m, 1H), 0.92 (d, 6H)

Preparation Example 166-2

Synthesis of (3-chloro-1-isobutyl-1H-indazol-4-yl)-methanol

According to the method described in Preparation Example 118, 3-chloro-1-isobutyl-1H-indazole-4-carboxylic acid methyl ester (112 mg, 0.42 mmol) was used to obtain the title compound (100 mg, 100%).

NMR:$^1$H-NMR(500 HMz, CDCl$_3$); δ 7.34 (dd, 1H), 7.31 (d, 1H), 7.19 (d, 1H), 5.17 (d, 2H), 4.10 (d, 2H), 2.32 (m, 1H), 2.00 (t, 1H), 0.92 (d, 6H)

Preparation Example 167-1

Synthesis of 3-isopropoxymethyl-1H-indazole-6-carboxylic acid methyl ester

According to the method described in Preparation Example 162-3, the compound (369 mg, 1.0 mmol) obtained from Preparation Example 162-2 and isopropanol (30 ml) were used to obtain the title compound (136 mg, 55%).

NMR:$^1$H-NMR(500 HMz, CDCl$_3$); δ 10.06 (br s, 1H), 8.20 (s, 1H), 7.92 (d, 1H), 7.84 (d, 1H), 4.90 (s, 2H), 3.96 (s, 3H), 3.76 (m, 1H), 1.24 (d, 6H)

Preparation Example 167-2

Synthesis of (1-isobutyl-3-isopropoxymethyl-1H-indazol-6-yl)-methanol

According to the methods described in Preparation Examples 55 and 56, the compound (136 mg, 0.548 mmol) obtained from Preparation Example 167-1 and isobutyl iodide (0.1 ml, 0.822 mmol) were used to obtain the title compound (85 mg, 56%).

NMR:$^1$H-NMR(500 HMz, CDCl$_3$); δ 7.81 (d, 1H), 7.37 (s, 1H), 7.10 (d, 1H), 4.86 (s, 2H), 4.84 (d, 2H), 4.12 (d, 2H), 3.72 (m, 1H), 2.33 (m, 1H), 1.74 (t, 1H), 1.21 (d, 6H), 0.92 (d, 6H)

Preparation Example 168-1

Synthesis of 3-fluoro-1-isopropyl-1H-indazole-4-carboxylic acid methyl ester

According to the method described in Preparation Example 163-2, the compound (146 mg, 0.669 mmol)

obtained from Preparation Example 164-1 was used to obtain the title compound (103 mg, 65%).
NMR:$^1$H-NMR(500 HMz, CDCl$_3$); δ 7.83 (d, 1H), 7.55 (d, 1H), 7.42 (m, 1H), 4.75 (m, 1H), 3.99 (s, 3H), 1.54 (d, 6H)

Preparation Example 168-2

Synthesis of (3-fluoro-1-isopropyl-1H-indazol-4-yl)-methanol

According to the method described in Preparation Example 56, the compound (103 mg, 0.436 mmol) obtained from Preparation Example 168-1 was used to obtain the title compound (75 mg, 82%).
NMR:$^1$H-NMR(500 HMz, CDCl$_3$); δ 7.36 (m, 1H), 7.27 (m, 1H), 7.14 (d, 1H), 5.02 (d, 2H), 4.71 (m, 1H), 1.94 (m, 1H), 1.51 (d, 6H)

Preparation Example 169-1

Synthesis of 1H-indazole-7-carboxylic acid methyl ester

2-Amino-3-methyl-benzoic acid methyl ester (4.5 g, 27 mmol) was dissolved in chloroform (100 ml) and the solution was cooled to 0° C. Acetic anhydride (7.7 ml, 81 mmol) and potassium acetate (3.2 g, 32 mmol) were added thereto and the mixture was stirred for 12 hours at 50° C. Isopentyl nitrite (7.3 ml, 54 mmol) was added thereto and the mixture was heated to 70° C. and stirred for 12 hours. The mixture was cooled to room temperature, diluted with dichloromethane, washed with saturated solution of sodium hydrogen carbonate, dried over anhydrous magnesium sulfate and filtered. The filtrate was distilled under reduced pressure and the residue was dissolved in tetrahydrofuran (50 ml). 6M aqueous solution of sodium hydroxide (4.8 ml) was added and the solution was stirred for 1 hour. After acidifying with 1N hydrochloric acid aqueous solution, the mixture was extracted with ethyl acetate. The extract was dried over anhydrous magnesium sulfate and filtered. The filtrate was distilled under reduced pressure and separated by column chromatography to obtain the title compound (4.6 g, 96%).
NMR:$^1$H-NMR(500 HMz, CDCl$_3$); δ 11.3 (br s, 1H), 8.15 (s, 1H), 8.08 (d, 1H), 7.99 (d, 1H), 7.23 (t, 1H), 4.03 (s, 3H)

Preparation Example 169-2

Synthesis of 3-bromo-1H-indazole-7-carboxylic acid methyl ester 1H-indazole-7-carboxylic acid methyl ester (2.0 g, 11 mmol) obtained from Preparation Example 169-1 was dissolved in acetonitrile (50 ml). N-bromosuccinimide (NBS, 2.0 g, 11 mmol) was added dropwise and then the mixture was stirred for 2 hours at 100° C. The mixture was distilled under reduced pressure and the residue was separated by column chromatography to obtain the title compound (720 mg, 25%).
NMR:$^1$H-NMR(500 HMz, CDCl$_3$); δ 11.2 (br s, 1H), 8.13 (d, 1H), 7.88 (d, 1H), 7.30 (t, 1H), 4.03 (s, 3H)

Preparation Example 169-3

Synthesis of 3-bromo-1-methyl-1H-indazole-7-carboxylic acid methyl ester

According to the method described in Preparation Example 55, 3-bromo-1H-indazole-7-carboxylic acid methyl ester (720 mg, 2.82 mmol) obtained from Preparation Example 169-2 and methyl iodide (0.26 ml, 4.23 mmol) were used to obtain the title compound (500 mg, 66%).
NMR:$^1$H-NMR(500 HMz, CDCl$_3$); δ 8.01 (d, 1H), 7.78 (d, 1H), 7.22 (t, 1H), 4.24 (s, 3H), 3.98 (s, 3H)

Preparation Example 169-4

Synthesis of (3-bromo-1-methyl-1H-cyclo)-methanol

According to the method described in Preparation Example 56, the compound (425 mg, 1.579 mmol) obtained from Preparation Example 169-3 was used to obtain the title compound (375 mg, 98%).
NMR:$^1$H-NMR(400 HMz, CDCl$_3$); δ 7.59 (d, 1H), 7.33 (d, 1H), 7.14 (t, 1H), 5.02 (d, 2H), 4.36 (s, 3H), 1.78 (t, 1H)

Preparation Example 170-1

Synthesis of 3-formyl-7-methyl-1H-indazole-6-carboxylic acid methyl ester

7-Methyl-1H-indole-6-carboxylic acid methyl ester (2.0 g, 10.6 mmol) obtained from Preparation Example 15-1 was dissolved in a mixed solution of water (50 ml) and tetrahydrofuran (100 ml). To the mixture, sodium nitrite (3.6 g, 52.8 mmol) was added and then 1N hydrochloric acid aqueous solution (63 ml) was slowly added dropwise at 0° C. After stirring for 12 hours, the mixture was extracted with ethyl acetate. The extract was dried over anhydrous magnesium sulfate and filtered. The filtrate was distilled under reduced pressure to obtain the title compound (750 mg, 32%).
NMR:$^1$H-NMR(500 HMz, DMSO-d$_6$); δ 10.18 (s, 1H), 7.99 (d, 1H), 7.73 (d, 1H), 3.83 (s, 3H), 2.78 (s, 3H)

Preparation Example 170-2

Synthesis of 3-formyl-1-isobutyl-7-methyl-1H-indazole-6-carboxylic acid methyl ester According to the method described in Preparation Example 55, the compound (400 mg, 1.83 mmol) obtained from Preparation Example 170-1 and isobutyl iodide (0.32 ml, 2.75 mmol) were used to obtain the title compound (310 mg, 60%).
NMR:$^1$H-NMR(400 HMz, CDCl$_3$); δ 7.64 (d, 1H), 7.49 (d, 1H), 5.00 (d, 2H), 4.36 (d, 2H), 3.93 (s, 3H), 2.80 (s, 3H), 2.18 (m, 1H), 1.81 (br s, 1H). 0.94 (d, 6H)

Preparation Example 170-3

Synthesis of 3-hydroxymethyl-1-isobutyl-7-methyl-1H-indazole-carboxylic acid methyl ester The compound (300 mg, 1.09 mmol) obtained from Preparation Example 170-2 was dissolved in tetrahydrofuran (10 ml), sodium borohydride (62 mg, 1.64 mmol) was added thereto at 0° C., and then the mixture was stirred at room temperature for 30 minutes. The reaction was terminated with an aqueous solution of ammonium chloride and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (230 mg, 76%).

NMR:$^1$H-NMR(400 HMz, CDCl$_3$); δ 7.64 (d, 1H), 7.49 (d, 1H), 5.00 (d, 2H), 4.36 (d, 2H), 3.93 (s, 3H), 2.80 (s, 3H), 2.18 (m, 1H), 1.81 (br s, 1H), 0.94 (d, 6H)

Preparation Example 170-4

Synthesis of 1-isobutyl-3-methoxymethyl-7-methyl-1H-indazole-6-carboxylic acid methyl ester According to the method described in Preparation Example 55, the compound (220 mg, 0.83 mmol) obtained from Preparation Example 170-3 and methyl iodide (0.1 ml, 15.9 mmol) were used to obtain the title compound (237 mg, 98%).

NMR:$^1$H-NMR(500 HMz, CDCl$_3$); δ 7.59 (d, 1H), 7.47 (d, 1H), 4.79 (s, 2H), 4.27 (d, 2H), 3.91 (s, 3H), 3.32 (s, 3H), 2.91 (s, 3H), 2.50 (m, 1H), 0.94 (d, 6H)

Preparation Example 170-5

Synthesis of (1-isobutyl-3-methoxymethyl-7-methyl-1H-indazol-6-yl)-methanol

According to the method described in Preparation Example 56, the compound (230 mg, 0.79 mmol) obtained from Preparation Example 170-4 was used to obtain the title compound (100 mg, 48%).

NMR:$^1$H-NMR(500 HMz, CDCl$_3$); δ 7.64 (d, 1H), 7.16 (d, 1H), 4.85 (d, 2H), 4.79 (s, 2H), 4.41 (d, 2H 3.37 (s, 3H), 2.71 (s, 3H), 2.21 (m, 1H), 0.91 (d, 6H)

Preparation Example 171-1

Synthesis of 1-butyl-1H-indazole-4-carboxylic acid methyl ester

According to the method described in Preparation Example 55, 1H-indazole-4-carboxylic acid methyl ester (800 mg, 4.54 mmol) and butyl iodide (1.04 ml, 9.08 mmol) were used to obtain the title compound (379 mg, 36%)

NMR:$^1$H-NMR(400 HMz, CDCl$_3$); δ 8.48 (s, 1H), 7.92 (d, 1H), 7.63 (d, 1H), 7.43 (dd, 1H), 4.43 (t, 2H), 4.02 (s, 3H), 1.88-1.96 (m, 2H), 1.29-1.36 (m, 2H), 0.94 (t, 3H)

Preparation Example 171-2

Synthesis of (1-butyl-1H-indazol-4-yl)-methanol

According to the method described in Preparation Example 56, the compound (72 mg, 0.31 mmol) obtained from Preparation Example 171-1 was used to obtain the title compound (56 mg, 88%).

NMR:$^1$H-NMR(400 HMz, CDCl$_3$); δ 8.13 (s, 1H), 7.35 (d, 2H), 7.12 (dd, 1H), 5.04 (d, 2H), 4.40 (t, 2H), 1.87-1.95 (m, 2H), 1.77 (t, 1H), 1.29-1.39 (m, 2H), 0.96 (t, 3H)

Preparation Example 172

Synthesis of (1-butyl-3-fluoro-1H-indazol-4-yl)-methane

According to the methods described in Preparation Examples 163-2 and 163-3, the compound (306.5 mg, 1.32 mmol) obtained from Preparation Example 171-1 and Selectfluor (701 mg, 1.98 mmol) were used to obtain the title compound (73.6 mg, 25%).

NMR:$^1$H-NMR(400 HMz, CDCl$_3$); δ 7.38 (dd, 1H), 7.23 (d, 1H), 7.15 (d, 1H), 5.03 (d, 2H), 4.21 (t, 2H), 1.93 (t, 1H), 1.82-1.90 (m, 2H), 1.30-1.35 (m, 2H), 0.93 (t, 3H)

Preparation Example 173-1

Synthesis of 1-cyclopropylmethyl-1H-indazole-4-carboxylic acid methyl ester

According to the method described in Preparation Example 55, 1H-indazole-4-carboxylic acid methyl ester (800 mg, 4.54 mmol) and chloromethyl cyclopropane (0.84 ml, 9.08 mmol) were used to obtain the title compound (353 mg, 34%).

NMR:$^1$H-NMR(400 HMz, CDCl$_3$); δ 8.49 (s, 1H), 7.92 (d, 1H), 7.65 (d, 1H), 7.44 (dd, 1H), 4.32 (d, 2H), 4.02 (s, 3H), 1.33 (m, 1H), 0.57-0.62 (m, 2H), 0.40-0.44 (m, 2H)

Preparation Example 173-2

Synthesis of (1-cyclopropylmethyl-1H-indazol-4-yl)-methanol

According to the method described in Preparation Example 56, the compound (77 mg, 0.33 mmol) obtained from Preparation Example 173-1 was used to obtain the title compound (65.2 mg, 98%).

NMR:$^1$H-NMR(400 HMz, CDCl$_3$); δ 8.14 (s, 1H), 7.35 (dd, 2H), 7.14 (d, 1H), 5.04 (s, 2H), 4.29 (d, 2H), 1.35 (m, 1H), 0.56-0.61 (m, 2H), 0.40-0.44 (m, 2H)

Preparation Example 174

Synthesis of (1-cyclopropylmethyl-3-fluoro-1H-indazol-4-yl)-methanol

According to the methods described in Preparation Examples 163-2 and 163-3, the compound (276 mg, 1.2 mmol) obtained from Preparation Example 173-1 and Selectfluor (638 mg, 1.8 mmol) were used to obtain the title compound (89.4 mg, 34%)

NMR:$^1$H-NMR(400 HMz, CDCl$_3$); δ 7.38 (dd, 1H), 7.25 (d, 1H), 7.16 (d, 1H), 5.04 (d, 2H), 4.10 (d, 2H), 1.69 (br s, 1H), 1.29 (m, 1H), 0.56-0.60 (m, 2H), 0.37-0.41 (m, 2H)

Preparation Example 175-1

Synthesis of 3-chloro-1H-indazole-7-carboxylic acid methyl ester

According to the method described in Preparation Example 12-1, 1H-indazole-7-carboxylic acid methyl ester (176 mg, 1.0 mmol) was used to obtain the title compound (126 mg, 60%).

NMR:$^1$H-NMR(400 HMz, CDCl$_3$); δ 11.03 (br s, 1H), 8.17 (d, 1H), 7.99 (d, 1H), 7.35 (t, 1H), 4.08 (s, 3H)

Preparation Example 175-2

Synthesis of (3-chloro-1-methyl-1H-indazol-7-yl)-methanol

According to the methods described in Preparation Examples 55 and 56, the compound (126 mg, 0.598 mmol)

obtained from Preparation Example 175-1 and iodomethane (0.056 ml, 0.897 mmol) were used to obtain the title compound (66 mg, 56%).

NMR:$^1$H-NMR(400 HMz, CDCl$_3$); δ 7.65 (d, 1H), 7.32 (d, 1H), 7.13 (m, 1H), 5.01 (d, 2H), 4.33 (s, 3H), 1.78 (t, 1H)

Preparation Example 176-1

Synthesis of 1-isopropyl-3-pyrazol-1-ylmethyl-1H-indazole-6-carboxylic acid methyl ester According to the method described in Preparation Example 55, 3-methyl-1H-indazole-6-carboxylic acid methyl ester and isopropylbromide were reacted to obtain a compound of 1-isopropyl-3-methyl-1H-indazole-6-carboxylic acid methyl ester. The compound (1.0 g, 4.31 mmol) was dissolved in dichloroethane (30 ml). N-bromosuccinimide (0.84 g, 4.74 mmol) and 2,2'-azobis(2-methylpropionitrile) (0.14 g, 0.86 mmol) were added thereto. The mixture was stirred for 2 hours under reflux and cooled to room temperature. After removing solvent under reduced pressure, a compound of 3-bromomethyl-1-isopropyl-1H-indazole-6-carboxylic acid methyl ester was obtained by column chromatography. The compound (0.85 g, 2.73 mmol) was dissolved in acetone (30 ml). Pyrazole (0.18 g, 2.73 mmol) and cesium carbonate (1.06 g, 3.28 mmol) were added and the mixture was stirred for 2 hours at 50° C. After completion of the reaction, water was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (0.37 g, 29%).

NMR:$^1$H-NMR(500 HMz, CDCl$_3$); δ 8.16 (s, 1H), 7.72 (d, 1H), 7.54 (s, 1H), 7.49 (d, 1H), 7.44 (s, 1H), 6.25 (d, 1H), 5.70 (s, 2H), 4.91 (m, 1H), 3.94 (s, 3H), 1.61 (d, 6H)

Preparation Example 176-2

Synthesis of (1-isopropyl-3-pyrazol-1-ylmethyl-1H-indazol-6-yl)methanol

According to the method described in Preparation Example 56, 1-isopropyl-3-pyrazol-1-ylmethyl-1H-indazole-6-carboxylic acid methyl ester (0.37 g, 1.24 mmol) obtained from Preparation Example 176-1 was used to obtain the title compound (0.30 g, 90%).

NMR:$^1$H-NMR(500 HMz, CDCl$_3$); δ 7.54 (s, 1H), 7.43 (s, 1H), 7.42 (m, 2H), 7.03 (d, 1H), 5.68 (s, 2H), 4.89 (m, 1H), 4.83 (d, 2H), 1.59 (d, 6H)

Preparation Example 177-1

Synthesis of 1-methyl-1H-indazole-7-carboxylic acid methyl ester

According to the method described in Preparation Example 55, 1H-indazole-7-carboxylic acid methyl ester (400 mg, 2.27 mmol) and methyl iodide (0.28 ml, 4.54 mmol) were used to obtain the title compound (165 mg, 38%).

NMR:$^1$H-NMR(500 HMz, CDCl$_3$); δ 8.05 (s, 1H), 7.94 (d, 1H), 7.90 (d, 1H), 7.15 (dd, 1H), 4.26 (s, 3H), 3.98 (s, 3H)

Preparation Example 177-2

Synthesis of (3-fluoro-1-methyl-1H-cyclo)-methanol

According to the methods described in Preparation Examples 163-2 and 163-3, the compound (114.4 mg, 0.6 mmol) obtained from Preparation Example 177-1 and Selectfluor (320 mg, 0.9 mmol) were used to obtain the title compound (40 mg, 37%).

NMR:$^1$H-NMR(500 HMz, CDCl$_3$); δ 7.62 (d, 1H), 7.29 (d, 1H), 7.08 (dd, 1H), 4.98 (d, 2H), 4.21 (s, 3H), 1.74 (t, 1H)

Preparation Example 178-1

Synthesis of 1H-pyrrolo[2,3-b]pyridine-4-carbonitrile

4-Chloro-1H-pyrrolo[2,3-b]-pyridine (1.0 g, 6.55 mmol) was dissolved in dimethylformamide (20 ml). Zinc cyanide (ZnCN$_2$, 0.77 g, 6.55 mmol) and [1,1'-bis(diphenylphosphino)ferrocene]dichloro palladium (II) {PdCl$_2$(dppf), 1.3 g, 1.0 mmol} were added dropwise thereto and then the mixture was stirred for 3 hours at 100° C. After completion of the reaction, water was added thereto and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (0.85 g, 91%).

NMR:$^1$H-NMR(400 HMz, CDCl$_3$); δ 10.17 (br s, 1H), 8.43 (d, 1H), 7.58 (d, 1H), 7.39 (m, 1H), 6.76 (d, 1H)

Preparation Example 178-2

Synthesis of 1H-pyrrolo[2,3-b]pyridine-4-carboxylic acid methyl ester

According to the method described in Preparation Example 122, 1H-pyrrolo[2,3-b]pyridine-4-carbonitrile (0.85 g, 5.94 mmol) obtained from Preparation Example 178-1 was used to obtain the title compound (0.73 g, 70%).

NMR:$^1$H-NMR(400 HMz, CDCl$_3$); δ 10.34 (br s, 1H), 8.44 (d, 1H), 7.74 (d, 1H), 7.52 (d, 1H), 7.07 (d, 1H), 4.03 (s, 3H)

Preparation Example 178-3

Synthesis of (1-isobutyl-1H-pyrrolo[2,3-b]pyridin-4-yl)-methanol

According to the methods described in Preparation Examples 55 and 56, 1H-pyrrolo[2,3-b]pyridine-4-carboxylic acid methyl ester (0.20 g, 1.14 mmol) obtained from Preparation Example 178-2 and isobutyl iodide (0.31 g, 1.70 mmol) were used to obtain the title compound (0.19 g, 72%).

NMR:$^1$H-NMR(400 HMz, CDCl$_3$); δ 8.29 (d, 1H), 7.19 (d, 1H), 7.11 (d, 1H), 6.52 (d, 1H), 5.01 (s, 2H), 4.08 (d, 2H), 2.50 (br s, 1H), 2.29 (m, 1H), 0.92 (d, 6H)

Preparation Example 179-1

Synthesis of 3-formyl-1H-indazole-4-carboxylic acid methyl ester 1H-indole-4-carboxylic acid methyl ester (2.17 g, 12.39 mmol) was dissolved in a mixed solution of water (120 ml) and tetrahydrofuran (60 ml) and sodium nitrite (4.48 g, 61.95 mmol) was added thereto. 1N hydrochloric acid aqueous solution (74 ml) was slowly added dropwise at 0° C. and the mixture was stirred for 12 hours at room temperature. The mixture was extracted with ethyl acetate and the extract was dried over anhydrous magnesium sulfate and filtered. The filtrate was distilled under reduced pressure to obtain the title compound (2.31 g, 91%).

NMR:$^1$H-NMR(400 HMz, CDCl$_3$); δ 10.69 (s, 1H), 7.95 (dd, 2H), 7.54 (dd, 1H), 4.03 (s, 3H)

Preparation Example 179-2

Synthesis of 3-methyl-1H-indazole-4-carboxylic acid methyl ester

The compound (1 g, 4.9 mmol) obtained from Preparation Example 179-1, p-toluenesulfonic acid (121.1 mg, 0.64 mmol), p-toluenesulfonyl hydrazide (1.19 g, 6.37 mmol) and sulfolane (11.2 ml) were dissolved in dimethylformamide (11 ml) and the mixture was stirred for 1 hour at 100° C. The mixture was cooled to room temperature and sodium cyanoborohydride (1.84 g, 29.4 mmol) was added. The mixture was stirred for 30 minutes and then further stirred for 3 hours at 100° C. After completion of the reaction, the mixture was cooled to room temperature, water was added thereto and then the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (897 mg, 96%).

NMR:$^1$H-NMR(500 HMz, CDCl$_3$); δ 10.2 (br s, 1H), 7.74 (d, 1H), 7.61 (d, 1H), 7.38 (dd, 1H), 3.98 (s, 3H), 2.73 (s, 3H)

Preparation Example 179-3

Synthesis of (1-butyl-3-methyl-1H-indazol-4-yl)-methanol

According to the methods described in Preparation Examples 55 and 56, the compound (200 mg, 1.05 mmol) obtained from Preparation Example 179-2 and butyl iodide (0.24 ml, 2.1 mmol) were used to obtain the title compound (31 mg, 14%).

NMR:$^1$H-NMR(400 HMz, CDCl$_3$); δ 7.28 (dd, 2H), 7.07 (dd, 1H), 5.02 (s, 2H), 4.26 (t, 2H), 2.70 (s, 3H), 1.76-1.88 (m, 2H), 1.65 (t, 1H), 1.23-1.37 (m, 2H), 0.92 (t, 3H)

Preparation Example 180-1

Synthesis of 2-fluoro-3-(1-hydroxy-pentyl)-benzonitrile

N,N-diisopropylamine (1.47 ml, 10.5 mmol) was dissolved in tetrahydrofuran (10 ml). At −30° C., 2.5M solution of butyl lithium in hexane (4.2 ml, 10.5 mmol) was slowly added dropwise, and the mixture was stirred for 30 minutes. 2-Fluorobenzonitrile (1.06 ml, 10 mmol) in tetrahydrofuran (20 ml) was cooled to −78° C., the prepared LDA solution was slowly added dropwise thereto, and the mixture was stirred for 2 hours. After adding pentanal (1.26 ml, 12 mmol) dropwise thereto, the mixture was heated slowly to 0° C. and stirred for 1 hour. After completion of the reaction, a saturated aqueous solution of ammonium chloride was added, and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (0.58 g, 28%).

NMR:$^1$H-NMR(500 HMz, CDCl$_3$); δ 7.77 (m, 1H), 7.53 (m, 1H), 7.27 (t 1H), 5.06 (m, 1H), 1.92 (d, 1H), 1.81-1.70 (m, 2H), 1.45-1.27 (m, 4H), 0.90 (t, 3H)

Preparation Example 180-2

Synthesis of 2-fluoro-3-pentanoyl-benzonitrile

According to the method described in Preparation Example 6-3, the compound (0.58 g, 2.799 mmol) obtained from Preparation Example 180-1 was used to obtain the title compound (0.5 g, 86%).

NMR:$^1$H-NMR(500 HMz, CDCl$_3$); δ 8.09 (m, 1H), 7.79 (m, 1H), 7.36 (t, 1H), 2.98 (m, 2H), 1.74~1.67 (m, 2H), 1.45~1.35 (m, 2H), 0.94 (t, 3H)

Preparation Example 180-3

Synthesis of 3-butyl-1-methyl-1H-indazole-7-carbonitrile

The compound (496 mg, 2.417 mmol) obtained from Preparation Example 180-2 was dissolved in dimethyl sulfoxide (15 ml). Methylhydrazine sulfate (383 mg, 2.659 mmol) and potassium carbonate (1.0 g, 7.251 mmol) were added thereto and the mixture was stirred for 16 hours at 100° C. The mixture was cooled to room temperature and water was added. The mixture was extracted with ethyl acetate. The extract was washed with saturated aqueous sodium chloride solution, dried over anhydrous magnesium sulfate and filtered. The filtrate was distilled under reduced pressure and separated by column chromatography to obtain the title compound (355 mg, 69%).

NMR:$^1$H-NMR(500 HMz, CDCl$_3$); δ 7.90 (d, 1H), 7.71 (d, 1H), 7.14 (t, 1H), 4.31 (s, 3H), 2.95 (t, 2H), 1.80~1.72 (m, 2H), 1.47~1.37 (m, 2H), 0.95 (t, 3H)

Preparation Example 180-4

Synthesis of 3-butyl-1-methyl-1H-indazole-7-carboxylic acid methyl ester

According to the method described in Preparation Example 122, the compound (355 mg, 1.664 mmol) obtained from Preparation Example 180-3 was used to obtain the title compound (381 mg, 93%).

NMR:$^1$H-NMR(500 HMz, CDCl$_3$); δ 7.91 (d, 1H), 7.84 (d, 1H), 7.11 (t, 1H), 4.18 (s, 3H), 3.97 (s, 3H), 2.95 (t, 2H), 1.81~1.72 (m, 2H), 1.47~1.38 (m, 2H), 0.95 (t, 3H)

Preparation Example 180-5

Synthesis of (3-butyl-1-methyl-1H-cyclo)-methanol

According to the method described in Preparation Example 56, the compound (381 mg, 0.547 mmol) obtained from Preparation Example 180-4 was used to obtain the title compound (332 mg, 98%).

NMR:$^1$H-NMR(500 HMz, CDCl$_3$); δ 7.65 (d, 1H), 7.24 (d, 1H), 7.03 (t, 1H), 5.01 (d, 2H), 4.31 (s, 3H), 2.94 (t, 2H), 1.82~1.72 (m, 2H), 1.70 (t, 1H), 1.48~1.38 (m, 2H), 0.95 (t, 3H)

Preparation Example 181-1

Synthesis of 2-fluoro-3-(1-hydroxy-3-methyl-butyl)-benzonitrile

According to the method described in Preparation Example 180-1, 2-fluorobenzonitrile (1.06 ml, 10 mmol) and 3-methylbutanal (1.29 ml, 12 mmol) were used to obtain the title compound (0.51 g, 25%).
NMR:$^1$H-NMR(500 HMz, CDCl$_3$); δ 7.78 (m, 1H), 7.53 (m, 1H), 7.27 (t 1H), 5.14 (m, 1H), 1.87 (d, 1H), 1.82-1.66 (m,2H), 1.51 (m, 1H), 0.99 (d, 3H), 0.97 (d, 3H)

Preparation Example 181-2

Synthesis of 2-fluoro-3-(3-methyl-butyryl)-benzonitrile

According to the method described in Preparation Example 6-3, the compound (0.51 g, 2.461 mmol) obtained from Preparation Example 181-1 was used to obtain the title compound (0.47 g, 94%).
NMR:$^1$H-NMR(500 HMz, CDCl$_3$); δ 8.07 (m, 1H), 7.79 (m, 1H), 7.36 (t, 1H), 2.86 (dd, 2H), 2.26 (m, 1H), 0.99 (d, 6H)

Preparation Example 181-3

Synthesis of 3-isobutyl-1-methyl-1H-indazole-7-carbonitrile

According to the method described in Preparation Example 180-3, the compound (0.474 mg, 2.31 mmol) obtained from Preparation Example 181-2 was used to obtain the title compound (378 mg, 77%).
NMR:$^1$H-NMR(500 HMz, CDCl$_3$); δ 7.89 (d, 1H), 7.70 (d, 1H), 7.14 (t, 1H), 4.32 (s, 3H), 2.82 (d, 2H), 2.12 (m, 1H), 0.97 (d, 6H)

Preparation Example 181-4

Synthesis of 3-isobutyl-1-methyl-1H-indazole-7-carboxylic acid methyl ester

According to the method described in Preparation Example 122, the compound (378 mg, 1.772 mmol) obtained from Preparation Example 181-3 was used to obtain the title compound (393 mg, 90%).
NMR:$^1$H-NMR(500 HMz, CDCl$_3$); δ 7.91 (d, 1H), 7.83 (d, 1H), 7.11 (t, 1H), 4.19 (s, 3H), 3.98 (s, 3H), 2.82 (d, 2H), 2.12 (m, 1H), 0.97 (d, 6H)

Preparation Example 181-5

Synthesis of (3-isobutyl-1-methyl-1H-cyclo)-methanol

According to the method described in Preparation Example 56, the compound (393 mg, 1.596 mmol) obtained from Preparation Example 181-4 was used to obtain the title compound (339 mg, 97%).
NMR:$^1$H-NMR(500 HMz, CDCl$_3$); δ 7.63 (d, 1H), 7.24 (d, 1H), 7.03 (t, 1H), 5.01 (d, 2H), 4.32 (s, 3H), 2.80 (d, 2H), 2.13 (m, 1H), 1.72 (t, 1H), 0.97 (d, 6H)

Preparation Example 182-1

Synthesis of 4-bromo-7-methyl-1H-indazole

According to the method described in Preparation Example 86-4, 3-bromo-2,6-dimethylaniline (53.2 g, 265 mmol) was used to obtain the title compound (21 g, 37%).
NMR:$^1$H-NMR(500 HMz, CDCl$_3$); δ 10.83 (br s, 1H), 8.10 (s, 1H), 7.25 (d, 1H), 7.02 (d, 1H), 2.57 (s, 3H)

Preparation Example 182-2

Synthesis of 7-methyl-1H-indazole-4-carboxylic acid methyl ester

According to the methods described in Preparation Examples 178-1 and 178-2, 4-bromo-7-methyl-1H-indazole (10.0 g, 47.38 mmol) obtained from Preparation Example 182-1 was used to obtain the title compound (4.86 g, 55%).
NMR:$^1$H-NMR(400 HMz, CDCl$_3$); δ 10.98 (br s, 1H), 8.60 (s, 1H), 7.88 (d, 1H), 7.25 (d, 1H), 4.01 (s, 3H), 2.64 (s, 3H)

Preparation Example 182-3

Synthesis of (1-isobutyl-7-methyl-1H-indazol-4-yl)-methanol

According to the methods described in Preparation Examples 55 and 56, 7-methyl-1H-indazole-4-carboxylic acid methyl ester (1.9 g, 9.99 mmol) obtained from Preparation Example 182-2 and isobutyl iodide (3.68 g, 19.98 mmol) were used to obtain the title compound (0.70 g, 32%).
NMR:$^1$H-NMR(400 HMz, CDCl$_3$); δ 8.10 (s, 1H), 7.70 (d, 1H), 6.92 (d, 1H), 4.98 (d, 2H), 4.40 (d, 2H), 2.71 (s, 3H), 2.29 (m, 1H), 1.78 (m, 1H), 0.95 (d, 6H)

Preparation Example 183-1

Synthesis of 2-fluoro-3-(1-hydroxy-2-methyl-propyl)-benzonitrile

According to the method described in Preparation Example 180-1, 2-fluorobenzonitrile (1.06 ml, 10 mmol) and 2-methylpropanal (1.1 ml, 12 mmol) were used to obtain the title compound (0.47 g, 24%).
NMR:$^1$H-NMR(500 HMz, CDCl$_3$); δ 7.75 (m, 1H), 7.54 (m, 1H), 7.27 (t 1H), 4.82 (m, 1H), 1.98 (m, 1H), 1.90 (d, 1H), 0.97 (d, 3H), 0.89 (d, 3H)

Preparation Example 183-2

Synthesis of 2-fluoro-3-isobutyryl-benzonitrile

According to the method described in Preparation Example 6-3, the compound (0.47 g, 2.417 mmol) obtained from Preparation Example 183-1 was used to obtain the title compound (0.43 g, 93%).
NMR:$^1$H-NMR(500 HMz, CDCl$_3$); δ 8.02 (m, 1H), 7.79 (m, 1H), 7.37 (t, 1H), 3.36 (m, 1H), 1.21 (d, 6H)

Preparation Example 183-3

Synthesis of 3-isopropyl-1-methyl-1H-indazole-7-carbonitrile

According to the method described in Preparation Example 180-3, the compound (429 mg, 2.244 mmol)

obtained from Preparation Example 183-2 was used to obtain the title compound (324 mg, 72%).
NMR:$^1$H-NMR(500 HMz, CDCl$_3$); δ 7.96 (d, 1H), 7.70 (d, 1H), 7.14 (t, 1H), 4.32 (s, 3H), 3.39 (m, 1H), 1.43 (d, 6H)

Preparation Example 183-4

Synthesis of
3-isopropyl-1-methyl-1H-indazole-7-carboxylic acid methyl ester

According to the method described in Preparation Example 122, the compound (324 mg, 1.626 mmol) obtained from Preparation Example 183-3 was used to obtain the title compound (344 mg, 91%).
NMR:$^1$H-NMR(500 HMz, CDCl$_3$); δ 7.92-7.87 (m, 2H), 7.10 (t, 1H), 4.17 (s, 3H), 3.97 (s, 3H), 3.39 (m, 1H), 1.44 (d, 6H)

Preparation Example 183-5

Synthesis of
(3-isopropyl-1-methyl-1H-cyclo)-methanol

According to the method described in Preparation Example 56, the compound (344 mg, 1.481 mmol) obtained from Preparation Example 183-4 was used to obtain the title compound (300 mg, 99%).
NMR:$^1$H-NMR(500 HMz, CDCl$_3$); δ 7.71 (d, 1H), 7.24 (d, 1H), 7.03 (t, 1H), 5.00 (d, 2H), 4.31 (s, 3H), 3.38 (m, 1H), 1.69 (t, 1H), 1.44 (d, 6H)

Preparation Example 184-1

Synthesis of
2-fluoro-3-(1-hydroxy-2-butyl)-benzonitrile

According to the method described in Preparation Example 180-1, 2-fluorobenzonitrile (1.06 ml, 10 mmol) and butyladehyde (1.06 ml, 12 mmol) were used to obtain the title compound (0.63 g, 33%).
NMR:$^1$H-NMR(500 HMz, CDCl$_3$); δ 7.78 (m, 1H), 7.53 (m, 1H), 7.26 (t 1H), 5.08 (m, 1H), 1.91 (br s, 1H), 1.81-1.30 (m, 4H), 0.95 (t, 3H)

Preparation Example 184-2

Synthesis of 3-butyryl-2-fluoro-benzonitrile

According to the method described in Preparation Example 6-3, the compound (0.63 g, 3.26 mmol) obtained from Preparation Example 184-1 was used to obtain the title compound (0.53 g, 85%).
NMR:$^1$H-NMR(500 HMz, CDCl$_3$); δ 8.10 (m, 1H), 7.79 (m, 1H), 7.36 (t, 1H), 3.00-2.94 (m, 2H), 1.80-1.70 (m, 2H), 1.00 (t, 3H)

Preparation Example 184-3

Synthesis of
1-methyl-3-propyl-1H-indazole-7-carbonitrile

According to the method described in Preparation Example 180-3, the compound (327 mg, 1.71 mmol) obtained from Preparation Example 184-2 was used to obtain the title compound (233 mg, 68%).

NMR:$^1$H-NMR(500 HMz, CDCl$_3$); δ 7.90 (d, 1H), 7.71 (d, 1H), 7.14 (t, 1H), 4.31 (s, 3H), 2.92 (t, 2H), 1.86-1.76 (m, 2H), 1.00 (t, 3H)

Preparation Example 184-4

Synthesis of
1-methyl-3-propyl-1H-indazole-7-carboxylic acid methyl ester

According to the method described in Preparation Example 122, the compound (233 mg, 1.169 mmol) obtained from Preparation Example 184-3 was used to obtain the title compound (211 mg, 78%).
NMR:$^1$H-NMR(500 HMz, CDCl$_3$); δ 7.91 (d, 1H), 7.84 (d, 1H), 7.11 (t, 1H), 4.18 (s, 3H), 3.97 (s, 3H), 2.92 (t, 2H), 1.86-1.77 (m, 2H), 1.00 (t, 3H)

Preparation Example 184-5

Synthesis of
(1-methyl-3-propyl-1H-cyclo)-methanol

According to the method described in Preparation Example 56, the compound (211 mg, 0.908 mmol) obtained from Preparation Example 184-4 was used to obtain the title compound (185 mg, 100%).
NMR:$^1$H-NMR(500 HMz, CDCl$_3$); δ 7.64 (d, 1H), 7.24 (d, 1H), 7.03 (t, 1H), 5.01 (d, 2H), 4.31 (s, 3H), 2.91 (t, 2H), 1.86-1.77 (m, 2H), 1.73 (t, 1H), 1.00 (t, 3H)

Preparation Example 185-1

Synthesis of 6-bromo-7-methyl-1H-indazole

According to the method described in Preparation Example 86-4, 3-bromo-2,6-dimethylaniline (53.2 g, 265 mmol) was used to obtain the title compound (11.3 g, 20%).
NMR:$^1$H-NMR(500 HMz, CDCl$_3$); δ 10.62 (br s, 1H), 8.05 (s, 1H), 7.45 (d, 1H), 7.33 (d, 1H), 2.61 (s, 3H)

Preparation Example 185-2

Synthesis of 7-methyl-1H-indazole-6-carboxylic acid methyl ester

According to the methods described in Preparation Examples 178-1 and 178-2, 6-bromo-7-methyl-1H-indazole (6.2 g, 29.38 mmol) obtained from Preparation Example 185-1 was used to obtain the title compound (3.14 g, 56%).
NMR:$^1$H-NMR(400 HMz, CDCl$_3$); δ 8.10 (s, 1H), 7.72 (d, 1H), 7.62 (d, 1H), 3.94 (s, 3H), 2.82 (s, 3H)

Preparation Example 185-3

Synthesis of
(1-isobutyl-7-methyl-1H-indazol-6-yl)-methanol

According to the methods described in Preparation Examples 55 and 56, 7-methyl-1H-indazole-6-carboxylic acid methyl ester (1.0 g, 5.26 mmol) obtained from Preparation Example 185-2 and isobutyl iodide (1.94 g, 10.52 mmol) were used to obtain the title compound (0.27 g, 21%).
NMR:$^1$H-NMR(400 HMz, CDCl$_3$); δ 7.93 (s, 1H), 7.54 (d, 1H), 7.14 (d, 1H), 4.84 (d, 2H), 4.43 (d, 2H), 2.72 (s, 3H), 2.25 (m, 1H), 1.85 (m, 1H), 0.92 (d, 6H)

Preparation Example 186-1

Synthesis of 3,7-dimethyl-1H-indazole-6-carboxylic acid methyl ester

According to the method described in Preparation Example 179-2, the compound (1.44 g, 6.6 mmol) obtained from Preparation Example 170-1 was used to obtain the title compound (317 mg, 24%).
NMR:$^1$H-NMR(500 HMz, CDCl$_3$); δ 9.84 (br s, 1H), 7.68 (d, 1H), 7.52 (d, 1H), 3.93 (s, 3H), 2.82 (s, 3H), 2.59 (s, 3H)

Preparation Example 186-2

Synthesis of (1-isobutyl-3,7-dimethyl-1H-indazol-6-yl)-methanol

According to the methods described in Preparation Examples 55 and 56, the compound (164 mg, 0.8 mmol) obtained from Preparation Example 186-1 and isobutyl iodide (0.18 ml, 1.6 mmol) were used to obtain the title compound (70 mg, 38%).
NMR:$^1$H-NMR(500 HMz, CDCl$_3$); δ 7.45 (d, 1H), 7.11 (d, 1H), 4.83 (d, 2H), 4.34 (d, 2H), 2.70 (s, 3H), 2.52 (s, 3H), 2.16-2.24 (m, 1H), 0.90 (d, 6H)

Preparation Example 187-1

Synthesis of 3-fluoro-1-isobutyl-7-methyl-1H-indazole-4-carboxylic acid methyl ester According to the methods described in Preparation Examples 163-1 and 163-2, 7-methyl-1H-indazole-4-carboxylic acid methyl ester (0.36 g, 1.89 mmol) obtained from Preparation Example 182-2 was used to obtain the title compound (0.17 g, 34%).
NMR:$^1$H-NMR(400 HMz, CDCl$_3$); δ 7.70 (d, 1H), 7.16 (d, 1H), 4.24 (d, 2H), 3.97 (s, 3H), 2.71 (s, 3H), 2.22 (m, 1H), 0.93 (d, 6H)

Preparation Example 187-2

Synthesis of (3-fluoro-1-isobutyl-7-methyl-1H-indazol-4-yl)-methanol

According to the method described in Preparation Example 17-2, 3-fluoro-1-isobutyl-7-methyl-1H-indazole-4-carboxylic acid methyl ester (0.17 g, 0.64 mmol) obtained from Preparation Example 187-1 was used to obtain the title compound (0.09 g, 59%).
NMR:$^1$H-NMR(400 HMz, CDCl$_3$); δ 7.08 (d, 1H), 7.02 (d, 1H), 4.96 (s, 2H), 4.19 (d, 2H), 2.64 (s, 3H), 2.22 (m, 1H), 0.93 (d, 6H)

Preparation Example 188-1

Synthesis of 3-fluoro-7-methyl-1H-indazole-6-carboxylic acid methyl ester

According to the method described in Preparation Example 163-2, 7-methyl-1H-indazole-6-carboxylic acid methyl ester (1.1 g, 5.78 mmol) obtained from Preparation Example 185-2 was used to obtain the title compound (0.08 g, 7%).
NMR:$^1$H-NMR(500 HMz, CDCl$_3$); δ 9.28 (br s, 1H), 7.72 (d, 1H), 7.56 (d, 1H), 3.95 (s, 3H), 2.75 (s, 3H)

Preparation Example 188-2

Synthesis of (1-ethyl-3-fluoro-7-methyl-1H-indazol-6-yl)-methanol

According to the methods described in Preparation Examples 55 and 56, 3-fluoro-7-methyl-1H-indazole-6-carboxylic acid methyl ester (0.08 g, 0.39 mmol) obtained from Preparation Example 188-1 and ethylbromide (0.08 g, 0.79 mmol) were used to obtain the title compound (0.08 g, 98%).
NMR:$^1$H-NMR(400 HMz, CDCl$_3$); δ 7.44 (d, 1H), 7.14 (d, 1H), 4.80 (d, 2H), 4.48 (q, 2H), 2.65 (s, 3H), 1.84 (m, 1H), 1.42 (t, 3H)

Preparation Example 189-1

Synthesis of 1-isobutyl-7-methyl-3-morpholin-4-ylmethyl-1H-indazole-6-carboxylic acid methyl ester The compound (172 mg, 0.627 mmol) obtained from Preparation Example 170-2 and morpholine (82 mg, 0.941 mmol) were dissolved in dichloroethane (5 ml) and the mixture was stirred for 1 hour at room temperature. Sodium triacetoxyborohydride (199 mg, 0.941 mmol) and acetic acid (0.054 ml, 0.941 mmol) were added thereto and then the mixture was stirred for 16 hours at room temperature. After completion of the reaction, a saturated solution of sodium hydrogen carbonate was added and the mixture was extracted with dichloromethane. The organic layer was dried over anhydrous magnesium sulfate and filtered. Filtrate was distilled under reduced pressure and separated by column chromatography to obtain the title compound (60 mg, 28%).
NMR:$^1$H-NMR(500 HMz, CDCl$_3$); δ 7.72 (d, 1H), 7.47 (d, 1H), 4.42 (d, 2H), 3.93 (s, 3H), 3.86 (s, 2H), 3.69 (t, 4H), 2.86 (s, 3H), 2.50 (t, 4H), 2.19 (m, 1H), 0.88 (d, 6H)

Preparation Example 189-2

Synthesis of (1-isobutyl-7-methyl-3-morpholin-4-ylmethyl-1H-indazol-6-yl)-methanol According to the method described in Preparation Example 56, the compound (60 mg, 0.174 mmol) obtained from Preparation Example 189-1 was used to obtain the title compound (42 mg, 76%).
NMR:$^1$H-NMR(500 HMz, CDCl$_3$); δ 7.69 (d, 1H), 7.13 (d, 1H), 4.84 (d, 2H), 4.39 (d, 2H), 3.85 (s, 2H), 3.69 (t, 4H), 2.71 (s, 3H), 2.50 (t, 4H), 2.19 (m, 1H), 0.89 (d, 6H)

Preparation Example 190-1

Synthesis of 7-chloro-3-formyl-1H-indazole-6-carboxylic acid methyl ester

According to the method described in Preparation Example 170-1, the compound (2.57 g, 12.26 mmol) obtained from Preparation Example 7-2 was used to obtain the title compound (1.53 g, 52%).
NMR:$^1$H-NMR(500 HMz, CDCl$_3$); δ 10.29 (s, 1H), 8.24 (d, 1H), 7.88 (d, 1H), 4.00 (s, 3H)

Preparation Example 190-2

Synthesis of 7-chloro-3-formyl-1-isobutyl-1H-indazole-6-carboxylic acid methyl ester According to the method described in Preparation Example 55, the compound (597 mg, 2.5 mmol) obtained from Preparation Example 190-1 and isobutyl iodide (0.58 ml, 5.0 mmol) were used to obtain the title compound (340 mg, 46%).
NMR:$^1$H-NMR(500 HMz, CDCl$_3$); δ 10.22 (s, 1H), 8.27 (d, 1H), 7.65 (d, 1H), 4.72 (d, 2H), 3.98 (s, 3H), 2.39 (m, 1H), 0.96 (d, 6H)

Preparation Example 190-3

Synthesis of 7-chloro-1-isobutyl-3-morpholin-4-ylmethyl-1H-indazole-6-carboxylic acid methyl ester According to the method described in Preparation Example 189-1, the compound (109 mg, 0.37 mmol) obtained from Preparation Example 190-2 and morpholine (48 mg, 0.56 mmol) were used to obtain the title compound (103 mg, 76%).
NMR:$^1$H-NMR(500 HMz, CDCl$_3$); δ 7.82 (d, 1H), 7.43 (d, 1H), 4.58 (d, 2H), 3.99 (s, 3H), 3.86 (s, 2H), 3.69 (t, 4H), 2.49 (t, 4H), 2.29 (m, 1H), 0.89 (d, 6H)

Preparation Example 190-4

Synthesis of (7-chloro-1-isobutyl-3-morpholin-4-ylmethyl-1H-indazol-6-yl)-methanol According to the method described in Preparation Example 56, the compound (103 mg, 0.282 mmol) obtained from Preparation Example 190-3 was used to obtain the title compound (75 mg, 79%).
NMR:$^1$H-NMR(500 HMz, CDCl$_3$); δ 7.79 (d, 1H), 7.26 (d, 1H), 4.93 (d, 2H), 4.54 (d, 2H), 3.86 (s, 2H), 3.69 (t, 4H), 2.50 (t, 4H), 2.28 (m, 1H), 1.91 (t, 1H), 0.89 (d, 6H)

Preparation Example 191-1

Synthesis of 1-isobutyl-7-methyl-3-pyrrolidin-1-ylmethyl-1H-indazole-6-carboxylic acid methyl ester According to the method described in Preparation Example 189-1, the compound (192 mg, 0.7 mmol) obtained from Preparation Example 170-2 and pyrrolidine (75 mg, 1.05 mmol) were used to obtain the title compound (76 mg, 33%).
NMR:$^1$H-NMR(500 HMz, CDCl$_3$); δ 7.68 (d, 1H), 7.46 (d, 1H), 4.42 (d, 2H), 3.98 (br s, 2H), 3.93 (s, 3H), 2.87 (s, 3H), 2.58 (br s, 4H), 2.20 (m, 1H), 1.76 (br s, 4H), 0.88 (d, 6H)

Preparation Example 191-2

Synthesis of (1-isobutyl-7-methyl-3-pyrrolidin-1-ylmethyl-1H-indazol-6-yl)-methanol According to the method described in Preparation Example 56, the compound (76 mg, 0.231 mmol) obtained from Preparation Example 191-1 was used to obtain the title compound (59 mg, 84%).
NMR:$^1$H-NMR(500 HMz, CDCl$_3$); δ 7.65 (d, 1H), 7.11 (d, 1H), 4.83 (d, 2H), 4.39 (d, 2H), 3.97 (s, 2H), 2.70 (s, 3H), 2.58 (br s, 4H), 2.20 (m, 1H), 1.76 (br s, 4H), 0.89 (d, 6H)

Preparation Example 192-1

Synthesis of 1-isobutyl-7-methyl-3-piperidin-1-ylmethyl-1H-indazole-6-carboxylic acid methyl ester According to the method described in Preparation Example 189-1, the compound (192 mg, 0.7 mmol) obtained from Preparation Example 170-2 and piperidine (89 mg, 1.05 mmol) were used to obtain the title compound (99 mg, 41%).
NMR:$^1$H-NMR(500 HMz, CDCl$_3$); δ 7.73 (d, 1H), 7.46 (d, 1H), 4.42 (d, 2H), 3.93 (s, 3H), 3.84 (br s, 2H), 2.86 (s, 3H), 2.43 (br s, 4H), 2.19 (m, 1H), 1.68-1.34 (m, 64H), 0.88 (d, 6H)

Preparation Example 192-2

Synthesis of (1-isobutyl-7-methyl-3-piperidin-1-ylmethyl-1H-indazol-6-yl)-methanol According to the method described in Preparation Example 56, the compound (99 mg, 0.288 mmol) obtained from Preparation Example 192-1 was used to obtain the title compound (83 mg, 91%).
NMR:$^1$H-NMR(500 HMz, CDCl$_3$); δ 7.70 (d, 1H), 7.11 (d, 1H), 4.83 (d, 2H), 4.39 (d, 2H), 3.84 (s, 2H), 2.70 (s, 3H), 2.45 (br s, 4H), 2.19 (m, 1H), 1.64-1.33 (m, 6H), 0.89 (d, 6H)

Preparation Example 193-1

Synthesis of 3-morpholin-4-ylmethyl-indazole-1,6-dicarboxylic acid 1-t-butyl ester 6-methyl ester The compound (500 mg, 1.354 mmol) obtained from Preparation Example 162-2 was dissolved in acetonitrile (10 ml). Morpholine (0.24 ml, 2.708 mmol) was added dropwise thereto and the mixture was stirred at 60° C. for 16 hours. The mixture was cooled to room temperature, distilled under reduced pressure to remove the solvent. Water was added thereto and the residue was extracted with ethyl acetate. The extract was dried over anhydrous magnesium sulfate and filtered. The filtrate was distilled reduced pressure to obtain the title compound (486 mg, 96%).
NMR:$^1$H-NMR(500 HMz, CDCl$_3$); δ 8.81 (s, 1H), 8.07 (d, 1H), 7.97 (d 1H), 3.97 (s, 3H), 3.94 (s, 2H), 3.71 (t, 4H), 2.54 (br s, 4H), 1.74 (s, 9H)

Preparation Example 193-2

Synthesis of 3-morpholin-4-ylmethyl-1H-indazole-6-carboxylic acid methyl ester The compound (486 mg, 1.295 mmol) obtained from Preparation Example 193-1 was dissolved in dichloromethane (6 ml) and trifluoroacetic acid (3 ml) was added dropwise. The mixture was stirred for 2 hours and distilled under reduced pressure to remove the solvent. A saturated solution of sodium hydrogen carbonate was added thereto and the residue was extracted with dichloromethane. The organic layer was dried over anhydrous magnesium sulfate and filtered. The filtrate was distilled reduced pressure to obtain the title compound (335 mg, 94%).
NMR:$^1$H-NMR(500 HMz, CDCl$_3$); δ 10.12 (br s, 1H), 8.20 (s, 1H), 7.96 (d, 1H), 7.83 (d 1H), 3.96 (s, 3H), 3.93 (s, 2H), 3.72 (t, 4H), 2.54 (br s, 4H)

Preparation Example 193-3

Synthesis of 1-isobutyl-3-morpholin-4-ylmethyl-1H-indazole-6-carboxylic acid methyl ester According to the method described in Preparation Example 55, the compound (165 mg, 0.6 mmol) obtained from Preparation Example 193-2 and isobutyl iodide (0.14 ml, 1.2 mmol) were used to obtain the title compound (93 mg, 47%).
NMR:$^1$H-NMR(500 HMz, CDCl$_3$); δ 8.11 (s, 1H), 7.90 (d, 1H), 7.77 (d 1H), 4.19 (d, 2H), 3.97 (s, 3H), 3.91 (s, 2H), 3.71 (t, 4H), 2.52 (br s, 4H), 2.35 (m, 1H), 0.91 (d, 6H)

Preparation Example 193-4

Synthesis of (1-isobutyl-3-morpholin-4-ylmethyl-1H-indazol-6-yl)-methanol

According to the method described in Preparation Example 56, the compound (93 mg, 0.281 mmol) obtained from Preparation Example 193-3 was used to obtain the title compound (79 mg, 93%).
NMR:$^1$H-NMR(500 HMz, CDCl$_3$); δ 7.83 (d, 1H), 7.38 (s, 1H), 7.10 (d 1H), 4.84 (d, 2H), 4.13 (d, 2H), 3.88 (s, 2H), 3.70 (t, 4H), 2.51 (t, 4H), 2.34 (m, 1H), 1.75 (t, 1H), 0.91 (d, 6H)

Preparation Example 194

Synthesis of (1-isopropyl-7-methyl-1H-indazol-6-yl)-methanol

According to the methods described in Preparation Examples 55 and 56, the compound (2 g, 10.52 mmol) obtained from Preparation Example 185-2 and isopropyl iodide (2.1 ml, 21.04 mmol) were used to obtain the title compound (47.5 mg, 2%).
NMR:$^1$H-NMR(400 HMz, CDCl$_3$); δ 7.98 (s, 1H), 7.54 (d, 1H), 7.13 (d, 1H), 5.27-5.31 (m, 1H), 4.86 (d, 2H), 2.77 (s, 3H), 1.69 (t, 1H), 1.60 (d, 6H)

Preparation Example 195

Synthesis of (7-methyl-1-propyl-1H-indazol-6-yl)-methanol

According to the methods described in Preparation Examples 55 and 56, the compound (2 g, 10.52 mmol) obtained from Preparation Example 185-2 and propyl bromide (1.92 ml, 21.04 mmol) were used to obtain the title compound (32.4 mg, 1.5%).
NMR:$^1$H-NMR(400 HMz, CDCl$_3$); δ 7.93 (s, 1H), 7.54 (d, 1H), 7.14 (d, 1H), 4.86 (d, 2H), 4.59 (t, 2H), 2.75 (s, 3H), 1.87-1.93 (m, 2H), 0.96 (t, 3H)

Preparation Example 196-1

Synthesis of 3-fluoromethyl-1-isobutyl-7-methyl-1H-indazole-6-carboxylic acid methyl ester The compound (69 mg, 0.25 mmol) obtained from Preparation Example 170-3 was dissolved in dichloromethane (5 ml) and diethylamino-sulfur-trifluoride (DAST, 60.5 mg, 0.38 mmol) was added thereto. The mixture was stirred for 1 hour at room temperature and a saturated aqueous solution of sodiumbicarbonate was added thereto. The mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (56 mg, 80%).
NMR:$^1$H-NMR(400 HMz, CDCl$_3$); δ 7.66 (d, 1H), 7.56 (d, 1H), 5.75 (s, 1H), 5.63 (s, 1H), 4.45 (d, 2H), 3.94 (s, 3H), 2.89 (s, 3H), 2.23 (m, 1H), 0.92 (d, 6H)

Preparation Example 196-2

Synthesis of (3-fluoromethyl-1-isobutyl-7-methyl-1H-indazol-6-yl)-methanol

According to the method described in Preparation Example 56, the compound (12.8 mg, 0.046 mmol) obtained from Preparation Example 196-1 was used to obtain the title compound (11.5 mg, 100%).
NMR:$^1$H-NMR(400 HMz, CDCl$_3$); δ 7.63 (d, 1H), 7.20 (d, 1H), 5.72 (s, 1H), 5.62 (s, 1H), 4.84 (s, 2H), 4.39 (d, 2H), 2.71 (s, 3H), 2.22 (m, 1H), 0.91 (d, 6H)

Preparation Example 197

Synthesis of (1-isopropyl-7-methyl-1H-indazol-4-yl)-methanol

According to the methods described in Preparation Examples 55 and 56, 7-methyl-1H-indazole-4-carboxylic acid methyl ester (2.0 g, 10.52 mmol) obtained from Preparation Example 182-2 and isopropyl iodide (3.58 g, 21.04 mmol) were used to obtain the title compound (0.60 g, 28%).
NMR:$^1$H-NMR(400 HMz, CDCl$_3$); δ 8.14 (s, 1H), 7.06 (d, 1H), 7.00 (d, 1H), 5.24 (m, 1H), 4.98 (d, 2H), 2.74 (s, 3H), 1.76 (t, 1H), 1.60 (d, 6H)

Preparation Example 198

Synthesis of (1-isopropyl-1H-pyrrolo[2,3-b]pyridine-4-일)-methanol

According to the methods described in Preparation Examples 55 and 56, the compound (88 mg, 0.5 mmol) obtained from Preparation Example 178-2 and isopropyl iodide (0.1 ml, 1.0 mmol) were used to obtain the title compound (70 mg, 74%).
NMR:$^1$H-NMR(500 HMz, CDCl$_3$); δ 8.32 (d, 1H), 7.34 (d, 1H), 7.11 (d, 1H), 6.55 (d, 1H), 5.22 (m, 1H), 5.02 (d, 2H), 1.81 (t, 1H), 1.52 (d, 6H)

Preparation Example 199-1

Synthesis of 1-isobutyl-1H-pyrrolo[2,3-b]pyridine-4-carboxylic acid methyl ester According to the method described in Preparation Example 55, the compound (88 mg, 0.5 mmol) obtained from Preparation Example 178-2 and isobutyl iodide (0.12 ml, 1.0 mmol) were used to obtain the title compound (103 mg, 89%).
NMR:$^1$H-NMR(500 HMz, CDCl$_3$); δ 8.40 (d, 1H), 7.67 (d, 1H), 7.36 (d, 1H), 6.98 (d, 1H), 4.13 (d, 2H), 4.01 (s, 3H), 2.26 (m, 1H), 0.91 (d, 6H)

Preparation Example 199-2

Synthesis of 3-fluoro-1-isobutyl-1H-pyrrolo[2,3-b]pyridine-4-carboxylic acid methyl ester According to the method described in Preparation Example 163-2, the compound (103 mg, 0.443 mmol) obtained from Preparation Example 199-1 was used to obtain the title compound (44 mg, 40%).
NMR:$^1$H-NMR(500 HMz, CDCl$_3$); δ 8.40 (d, 1H), 7.61 (d, 1H), 7.16 (d, 1H), 4.09 (d, 2H), 4.01 (s, 3H), 2.20 (m, 1H), 0.91 (d, 6H)

Preparation Example 199-3

Synthesis of (3-fluoro-1-isobutyl-1H-pyrrolo[2,3-b]pyridin-4-yl)-methanol

According to the method described in Preparation Example 56, the compound (44 mg, 0.176 mmol) obtained from Preparation Example 199-2 was used to obtain the title compound (26 mg, 67%).
NMR:$^1$H-NMR(500 HMz, CDCl$_3$); δ 8.30 (d, 1H), 7.13 (d, 1H), 6.95 (d, 1H), 5.08 (d, 2H), 4.03 (d, 2H), 2.27-2.14 (m, 2H), 0.90 (d, 6H)

Preparation Example 200

Synthesis of (7-methyl-1-pyridin-3-ylmethyl-1H-indazol-6-yl)-methanol

According to the methods described in Preparation Examples 55 and 56, the compound (0.95 g, 5.0 mmol) obtained from Preparation Example 185-2 and 3-(bromomethyl)pyridine hydrobromide (1.52 g, 1.118 mmol) were used to obtain the title compound (40 mg, 3%).
NMR:$^1$H-NMR(500 HMz, CDCl$_3$); δ 8.49 (m, 1H), 8.38 (s, 1H), 8.04 (s, 1H), 7.58 (d, 1H), 7.26-7.16 (m, 3H), 5.90 (s, 2H), 4.79 (d, 2H), 2.59 (s, 3H)

Preparation Example 201-1

Synthesis of 3-(3,3-difluoro-piperidin-1-ylmethyl)-1-isobutyl-7-methyl-1H-indazole-6-carboxylic acid methyl ester The compound (150 mg, 0.55 mmol) obtained from Preparation Example 170-2 and 3,3-difluoro-piperidine (113 mg, 0.72 mmol) were dissolved in dichloroethane (10 ml). The mixture was stirred for 1 hour at room temperature. Sodium triacetoxyborohydride (174 mg, 0.82 mmol) and acetic acid (0.047 ml, 0.82 mmol) were added thereto and the mixture was stirred for 3 hours at room temperature. After completion of the reaction, a saturated sodium bicarbonate solution was added and the mixture was extracted with ethyl acetate. The extract was washed with saturated aqueous sodium chloride solution, dried over anhydrous magnesium sulfate and filtered. Filtrate was distilled under reduced pressure and separated by column chromatography to obtain the title compound (64.4 mg, 31%).
NMR:$^1$H-NMR(400 HMz, CDCl$_3$); δ 7.73 (d, 1H), 7.48 (d, 1H), 4.42 (d, 2H), 3.98 (s, 2H), 3.93 (s, 3H), 2.87 (s, 3H), 2.72 (t, 2H), 2.47-2.50 (m, 2H), 2.18-2.22 (m, 1H), 1.80-1.88 (m, 2H), 1.71-1.77 (m, 2H), 0.91 (d, 6H)

Preparation Example 201-2

Synthesis of [3-(3,3-difluoro-piperidin-1-ylmethyl)-1-isobutyl-7-methyl-1H-indazol-6-yl]-methanol According to the method described in Preparation Example 56, the compound (64.4 mg, 0.17 mmol) obtained from Preparation Example 201-1 was used to obtain the title compound (57 mg, 95%).
NMR:$^1$H-NMR(400 HMz, CDCl$_3$); δ 7.70 (d, 1H), 7.13 (d, 1H), 4.85 (d, 2H), 4.39 (d, 2H), 3.97 (s, 2H), 2.72 (m, 5H), 2.41-2.48 (m, 2H), 2.13-2.23 (m, 1H), 1.81-1.92 (m, 2H), 1.64-1.75 (m, 2H), 0.91 (d, 6H)

Preparation Example 202-1

Synthesis of 1-isobutyl-3-methanesulfonyloxymethyl-7-methyl-1H-indazole-6-carboxylic acid methyl ester The compound (107.3 mg, 0.39 mmol) obtained from Preparation Example 170-3 was dissolved in dichloromethane (5 ml). Methanesulfonylchloride (0.39 ml, 0.5 mmol) was added dropwise thereto at 0° C. and the mixture was stirred for 2 hours at room temperature. After completion of the reaction, a saturated sodium bicarbonate solution was added thereto and the mixture was extracted with dichloromethane. The extract was washed with saturated aqueous sodium chloride solution, dried over anhydrous magnesium sulfate and filtered. Filtrate was distilled under reduced pressure and separated by column chromatography to obtain the title compound (91.5 mg, 66%).
NMR:$^1$H-NMR(400 HMz, CDCl$_3$); δ 7.64 (d, 1H), 7.51 (d, 1H), 5.02 (s, 2H), 4.42 (d, 2H), 3.94 (s, 3H), 3.49 (s, 3H), 2.88 (s, 3H), 2.22 (m, 1H), 0.91 (d, 6H)

Preparation Example 202-2

Synthesis of 1-isobutyl-7-methyl-3-pyrazol-1-ylmethyl-1H-indazole-6-carboxylic acid methyl ester The compound (91.5 mg, 0.26 mmol) obtained from Preparation Example 202-1, pyrazol (17.6 mg, 0.26 mmol) and cesium carbonate (102 mg, 0.31 mmol) were dissolved in acetone (5 ml) and the mixture was stirred for 18 hours at 50° C. After completion of the reaction, the mixture was cooled to room temperature. Water was added thereto and the mixture was extracted with ethyl acetate. The extract was washed with saturated aqueous sodium chloride solution, dried over anhydrous magnesium sulfate and filtered. Filtrate was distilled under reduced pressure to obtain the title compound (71.3 mg, 84%).
NMR:$^1$H-NMR(400 HMz, CDCl$_3$); δ 7.52 (s, 1H), 7.38-7.45 (m, 3H), 6.23 (dd, 1H), 5.66 (s, 2H), 4.44 (d, 2H), 3.91 (s, 3H), 2.86 (s, 3H), 2.18-2.25 (m, 1H), 0.92 (d, 6H)

Preparation Example 202-3

Synthesis of (1-isobutyl-7-methyl-3-pyrazol-1-ylmethyl-1H-indazol-6-yl)-methanol According to the method described in Preparation Example 56, the compound (71.3 mg, 0.22 mmol) obtained from Preparation Example 202-2 was used to obtain the title compound (64.4 mg, 100%).

NMR:¹H-NMR(400 HMz, CDCl₃); δ 7.52 (s, 1H), 7.37 (dd, 2H), 7.09 (d, 1H), 6.22 (s, 1H), 5.65 (s, 2H), 4.81 (s, 2H), 4.41 (d, 2H), 2.70 (s, 3H), 2.19 (m, 1H), 0.93 (d, 6H)

Preparation Example 203-1

Synthesis of 3-(3,3-difluoro-pyrrolidin-1-ylmethyl)-1-isobutyl-7-methyl-1H-indazole-6-carboxylic acid methyl ester According to the method described in Preparation Example 189-1, the compound (153 mg, 0.558 mmol) obtained from Preparation Example 170-2 and 3,3-difluoropyrrolidine hydrochloride (80 mg, 0.558 mmol) were used to obtain the title compound (124 mg, 61%).

Preparation Example 203-2

Synthesis of [3-(3,3-difluoro-pyridin-1-ylmethyl)-1-isobutyl-7-methyl-1H-indazol-6-yl]-methanol According to the method described in Preparation Example 56, the compound (124 mg, 0.339 mmol) obtained from Preparation Example 203-1 was used to obtain the title compound (37 mg, 32%).
NMR:¹H-NMR(500 HMz, CDCl₃); δ 7.63 (d, 1H), 7.14 (d, 1H), 4.84 (d, 2H), 4.69 (d, 2H), 3.99 (s, 2H), 2.95 (t, 2H), 2.79 (t, 2H), 2.71 (s, 3H), 2.31-2.14 (m, 3H), 0.89 (d, 6H)

Preparation Example 204-1

Synthesis of 3-formyl-1H-pyrrolo[2,3-b]pyridine-6-carboxylic acid methyl ester 1H-pyrrolo[2,3-b]pyridine-6-carboxylic acid methyl ester (850 mg, 4.82 mmol) obtained from Preparation Example 53-2 was dissolved in acetic acid (5 ml) and water (10 ml). Hexamethylenetetramine (815 mg, 5.79 mmol) was added thereto, the mixture was stirred at 100° C. for 6 hours and then water was added. The resulting solid was filtered, washed with water and dried to obtain the title compound (420 mg, 43%).
NMR:¹H-NMR(400 HMz, CDCl₃); δ 13.10 (br s, 1H), 9.98 (s, 1H), 8.71 (s, 1H), 8.55 (d, 1H), 8.03 (d, 1H), 3.91 (s, 3H)

Preparation Example 204-2

Synthesis of 3-formyl-1-isobutyl-1H-pyrrolo[2,3-b]pyridine-6-carboxylic acid methyl ester According to the method described in Preparation Example 55, the compound (420 mg, 2.06 mmol) obtained from Preparation Example 204-1 and isobutyl iodide (0.36 ml, 3.09 mmol) were used to obtain the title compound (140 mg, 26%).
NMR:¹H-NMR(400 HMz, CDCl₃); δ 10.02 (s, 1H), 8.64 (d, 1H), 8.10 (d, 1H), 8.04 (s, 1H), 4.27 (d, 2H), 4.02 (s, 3H), 2.37 (m, 1H), 0.96 (d, 6H)

Preparation Example 204-3

Synthesis of 3-(3,3-difluoro-pyrrolidin-1-ylmethyl)-1-isobutyl-1H-pyrrolo[2,3-b]pyridine-6-carboxylic acid methyl ester According to the method described in Preparation Example 203-1, the compound (65 mg, 0.25 mmol) obtained from Preparation Example 204-2 was used to obtain the title compound (80 mg, 91%).
NMR:¹H-NMR(400 HMz, CDCl₃); δ 8.09 (d, 1H), 7.94 (d, 1H), 7.32 (s, 1H), 4.17 (d, 2H), 4.00 (s, 3H), 3.81 (s, 2H), 2.90 (t, 2H), 2.74 (t, 2H), 2.29 (m, 3H), 0.92 (d, 6H)

Preparation Example 204-4

Synthesis of [3-(3,3-difluoro-pyrrolidin-1-ylmethyl)-1-isobutyl-1H-pyrrolo[2,3-b]pyridin-6-yl]-methanol According to the method described in Preparation Example 56, the compound (80 mg, 0.23 mmol) obtained from Preparation Example 204-3 was used to obtain the title compound (65 mg, 87%).
NMR:¹H-NMR(400 HMz, CDCl₃); δ 7.97 (d, 1H), 7.08 (s, 1H), 6.96 (d, 1H), 4.84 (s, 2H), 4.06 (d, 2H), 3.79 (s, 2H), 2.89 (t, 2H), 2.74 (t, 2H), 2.28 (m, 3H), 2.26 (m, 2H), 0.92 (d, 6H)

Preparation Example 205-1

Synthesis of 3-(3,3-difluoro-piperidin-1-ylmethyl)-1-isobutyl-1H-pyrrolo[2,3-b]pyridine-6-carboxyl is acid methyl ester According to the method described in Preparation Example 201-1, the compound (65 mg, 2.06 mmol) obtained from Preparation Example 204-2 was used to obtain the title compound (70 mg, 77%).
NMR:¹H-NMR(400 HMz, CDCl₃); δ 8.10 (d, 1H), 7.94 (d, 1H), 7.31 (s, 1H), 4.17 (d, 2H), 3.99 (s, 3H), 3.81 (s, 2H), 2.65 (t, 2H), 2.47 (m, 2H), 2.29 (m, 1H), 1.88 (m, 2H), 1.78 (m, 2H), 0.93 (d, 6H)

Preparation Example 205-2

Synthesis of [3-(3,3-difluoro-piperidin-1-ylmethyl)-1-isobutyl-1H-pyrrolo[2,3-b]pyridin-6-yl]-methanol According to the method described in Preparation Example 56, the compound (70 mg, 0.19 mmol) obtained from Preparation Example 205-1 was used to obtain the title compound (55 mg, 84%).
NMR:¹H-NMR(400 HMz, CDCl₃); δ 8.00 (d, 1H), 7.07 (s, 1H), 6.95 (d, 1H), 4.83 (s, 2H), 4.06 (d, 2H), 3.77 (s, 2H), 2.65 (t, 2H), 2.46 (m, 2H), 2.26 (m, 1H), 1.87 (m, 2H), 1.76 (m. 2H), 0.92 (d, 6H)

Preparation Example 206-1

Synthesis of 3-((S)-3-fluoro-pyrrolidin-1-ylmethyl)-1-isobutyl-7-methyl-1H-indazole-6-carboxylic acid methyl ester According to the method described in Preparation Example 201-1, the compound (150 mg, 0.55 mmol) obtained from Preparation Example 170-2 and (S)-3-fluoropyrrolidine (103 mg, 0.82 mmol) were used to obtain the title compound (37 mg, 19%).
NMR:¹H-NMR(400 HMz, CDCl₃); δ 7.69 (d, 1H), 7.47 (d, 1H), 5.22 (br s, 0.5H), 5.08 (br s, 0.5H), 4.42 (d, 2H), 4.03 (s, 2H), 3.93 (s, 3H), 2.82-2.91 (m, 5H), 2.58 (m, 1H), 2.01-2.24 (m, 4H), 0.89 (d, 6H)

Preparation Example 206-2

Synthesis of [3-((S)-3-fluoro-pyrrolidin-1-ylmethyl)-1-isobutyl-7-methyl-1H-indazol-6-yl]-methanol According to the method described in Preparation Example 56, the compound (37 mg, 0.11 mmol) obtained from Preparation Example 206-1 was used to obtain the title compound (27.2 mg, 77%).

NMR:$^1$H-NMR(400 HMz, CDCl$_3$); δ 7.66 (d, 1H), 7.13 (d, 1H), 5.21 (br s, 0.5H), 5.03 (br s, 0.5H), 4.84 (s, 2H), 4.40 (d, 2H), 4.03 (s, 2H), 2.84-2.91 (m, 2H), 2.72 (s, 3H), 2.58 (m, 1H), 2.11(m, 1H), 2.04 (m, 1H), 1.82-1.85 (m, 2H), 0.91 (d, 6H)

Example 1

Synthesis of 3-{4-[(1-isopropyl-1H-indol-6-ylmethyl)-amino-phenyl}-propanoic acid

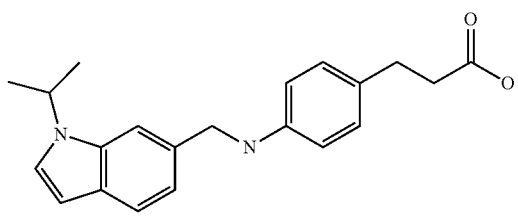 [SMILES: CC(C)n1ccc2ccc(CNc3ccc(CCC(=O)O)cc3)cc21]

1-Isopropyl-1H-indole-6-carbaldehyde (68 mg, 0.36 mmol) obtained from Preparation Example 1 and 3-(4-amino-phenyl)-propanoic acid (50 mg, 0.36 mmol) were dissolved in dichloroethane (10 mL). Sodium triacetoxyborohydride (96 mg, 0.45 mmol) was added thereto, and the mixture was stirred at room temperature for 8 hours. After completion of the reaction, water was added and the reaction mixture was extracted with ethylacetate, dried over anhydrous magnesium sulfate and filtered. Filtrate was distilled under reduced pressure, and the residue was purified via column chromatography to obtain the title compound (65 mg, 53%).

NMR:$^1$H-NMR(400 HMz, CDCl$_3$); δ 7.58 (dd, 1H), 7.39 (d, 1H), 7.20-7.23 (d, 1H), 7.10 (d, 1H), 7.02 (d, 2H), 6.63 (dd, 2H), 6.50 (s, 1H), 4.61-4.72 (m, 1H), 4.40 (d, 2H), 2.85 (t, 2H), 2.61 (t, 2H), 1.52 (d, 6H)

The following compounds of Examples 2 to 11 were prepared according to the method described in Example 1.

Example 2

Synthesis of 3-{4-[(1-benzyl-1H-indol-6-ylmethyl)-amino]-phenyl}-propanoic acid

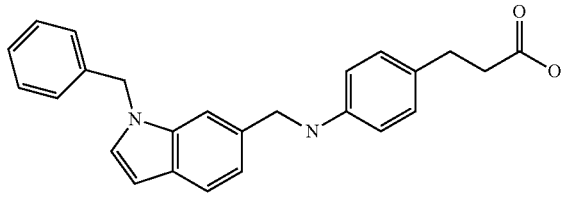 [SMILES: O=C(O)CCc1ccc(NCc2ccc3ccn(Cc4ccccc4)c3c2)cc1]

The compound (68 mg, 0.36 mmol) obtained from Preparation Example 2 and 3-(4-amino-phenyl)-propanoic acid (50 mg, 0.3 mmol) were used to obtain the title compound (65 mg, 54%).

NMR:$^1$H-NMR(400 HMz, CDCl$_3$); δ 7.64 (d, 1H), 7.21-7.28 (m, 4H), 7.06-7.11 (m, 4H), 6.98 (d, 2H), 6.56 (d, 2H), 6.52 (d, 1H), 5.26 (s, 2H), 4.33 (s, 2H), 2.83 (t, 2H), 2.59 (t, 2H)

Example 3

Synthesis of 3-{4-[(1-thiophen-3-yl-1H-indol-6-ylmethyl)-amino]-phenyl}-propanoic acid

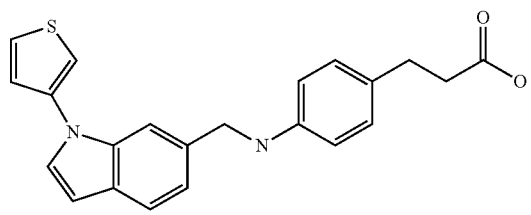 [SMILES: O=C(O)CCc1ccc(NCc2ccc3ccn(-c4ccsc4)c3c2)cc1]

The compound (76 mg, 0.33 mmol) obtained from Preparation Example 6-3 and 3-(4-amino-phenyl)-propanoic acid (55 mg, 0.33 mmol) were used to obtain the title compound (65 mg, 36%).

NMR:$^1$H-NMR(400 HMz, CDCl$_3$); δ 7.80 (d, 1H), 7.58 (s, 1H), 7.38 (dd, 1H), 7.26 (d, 1H), 7.21 (dd, 1H), 7.18 (dd, 1H), 7.14 (dd, 1H), 7.00 (d, 2H), 6.60 (dd, 2H), 6.57 (s, 1H), 4.35 (s, 2H), 2.82 (t, 2H), 2.57 (t, 2H)

Example 4

Synthesis of 3-{4-[(1-phenethyl-1H-indol-6-ylmethyl)-amino]-phenyl}-propanoic acid

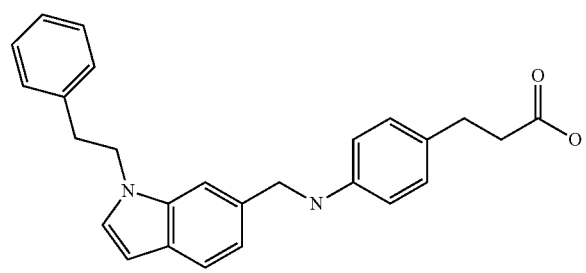 [SMILES: O=C(O)CCc1ccc(NCc2ccc3ccn(CCc4ccccc4)c3c2)cc1]

The compound (80 mg, 0.36 mmol) obtained from Preparation Example 5 and 3-(4-amino-phenyl)-propanoic acid (80 mg, 0.48 mmol) were used to obtain the title compound (90 mg, 63%).

NMR:$^1$H-NMR(500 HMz, CDCl$_3$); δ 7.59 (d, 1H), 7.29 (s, 1H), 7.22-7.27 (m, 2H), 7.10 (d, 2H), 7.05 (d, 2H), 7.03 (d, 2H), 6.93 (d, 1H), 6.64 (d, 2H), 6.43 (d, 1H), 4.40 (s, 2H), 4.32 (t, 2H), 3.06 (t, 2H), 2.86 (t, 2H), 2.92 (t, 2H)

Example 5

Synthesis of 3-{4-[(1-benzyl-3-chloro-1H-indol-6-ylmethyl)-amino]-phenyl}-propanoic acid

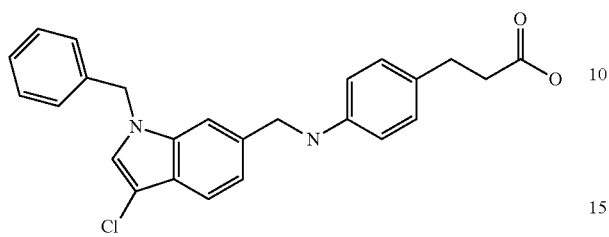

The compound (44 mg, 0.16 mmol) obtained from Preparation Example 3 and 3-(4-amino-phenyl)-propanoic acid (33 mg, 0.20 mmol) were used to obtain the title compound (30 mg, 45%).

NMR:$^1$H-NMR(500 HMz, CDCl$_3$); δ 7.59 (d, 1H), 7.26-7.32 (m, 4H), 7.18 (d, 1H), 7.09 (d, 2H), 7.05 (s, 1H), 7.00 (d, 2H), 6.57 (d, 2H), 5.22 (s, 2H), 4.37 (s, 2H), 2.84 (t, 2H), 2.61 (t, 2H)

Example 6

Synthesis of 3-{4-[(1-benzyl-2,3-dichloro-1H-indol-6-ylmethyl)-amino]-phenyl}-propanoic acid

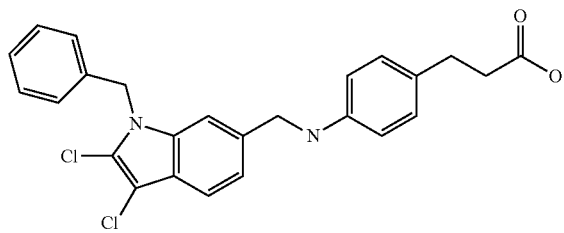 [SMILES: O=C(O)CCc1ccc(NCc2ccc3c(Cl)c(Cl)n(Cc4ccccc4)c3c2)cc1]

The compound (40 mg, 0.13 mmol) obtained from Preparation Example 4 and 3-(4-amino-phenyl)-propanoic acid (33 mg, 0.20 mmol) were used to obtain the title compound (22 mg, 37%).

NMR:$^1$H-NMR(500 HMz, CDCl$_3$); δ 7.53 (d, 1H), 7.23-7.28 (m, 5H), 7.05 (d, 1H), 7.04 (d, 1H), 6.98 (d, 2H), 6.54 (d, 2H), 5.34 (s, 2H), 4.35 (s, 2H), 2.84 (t, 2H), 2.60 (t, 2H)

Example 7

Synthesis of 3-{4-[(1-benzyl-7-chloro-1H-indol-6-ylmethyl)-amino]-phenyl}-propanoic acid

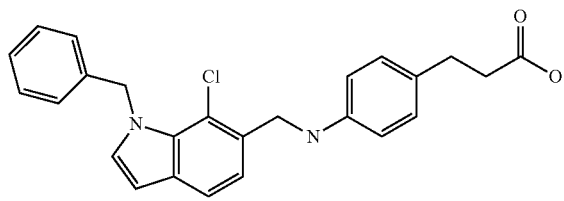 [SMILES: O=C(O)CCc1ccc(NCc2ccc3ccn(Cc4ccccc4)c3c2Cl)cc1]

The compound (50 mg, 0.19 mmol) obtained from Preparation Example 7-5 and 3-(4-amino-phenyl)-propanoic acid (37 mg, 0.22 mmol) were used to obtain the title compound (68 mg, 85%).

NMR:$^1$H-NMR(400 HMz, CDCl$_3$); δ 7.46 (d, 1H), 7.21-7.34 (m, 3H), 7.14 (d, 1H), 7.07 (d, 1H), 7.01 (d, 2H), 6.98 (d, 2H), 6.57 (d, 2H), 6.52 (d, 1H), 5.32(s, 2H), 4.44 (s, 2H), 2.83 (t, 2H), 2.59 (t, 2H)

Example 8

Synthesis of 3-{4-[(7-chloro-1-thiophen-3-yl-1H-indol-6-ylmethyl)-amino]-phenyl}-propanoic acid

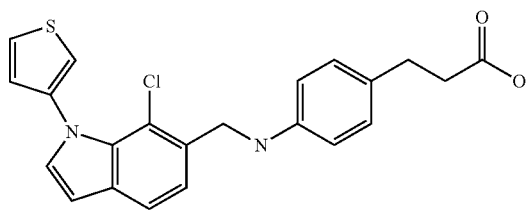 [SMILES: O=C(O)CCc1ccc(NCc2ccc3ccn(-c4ccsc4)c3c2Cl)cc1]

The compound (17 mg, 0.06 mmol) obtained from Preparation Example 8-2 and 3-(4-amino-phenyl)-propanoic acid (13 mg, 0.08 mmol) were used to obtain the title compound (10 mg, 41%).

NMR:$^1$H-NMR(400 HMz, CDCl$_3$); δ 7.50 (d, 1H), 7.33 (dd, 2H), 7.21 (d, 1H), 7.14 (dd, 1H), 7.13 (d, 1H), 7.00 (d, 2H), 6.59 (d, 2H), 6.57 (d, 1H), 4.46 (s, 2H), 2.83 (t, 2H), 2.60 (t, 2H)

Example 9

Synthesis of 3-(4-{[7-chloro-1-(4-fluoro-phenyl)-1H-indol-6-ylmethyl]-amino}-phenyl)-propanoic acid

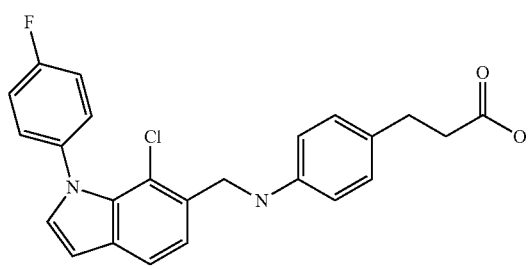 [SMILES: O=C(O)CCc1ccc(NCc2ccc3ccn(-c4ccc(F)cc4)c3c2Cl)cc1]

The compound (10 mg, 0.04 mmol) obtained from Preparation Example 9-2 and 3-(4-amino-phenyl)-propanoic acid (9 mg, 0.05 mmol) were used to obtain the title compound (8 mg, 47%).

NMR:$^1$H-NMR(400 HMz, CDCl$_3$); δ 7.64 (d, 1H), 7.35-7.38 (m, 2H), 7.22 (d, 1H), 7.11-7.15 (m, 3H), 7.00 (d, 2H), 6.60 (dd, 3H), 4.45 (s, 2H), 2.83 (t, 2H), 2.60 (t, 2H)

Example 10

Synthesis of 3-(4-{[1-(4-fluoro-phenyl)-1H-indol-6-ylmethyl]-amino}-phenyl)-propanoic acid

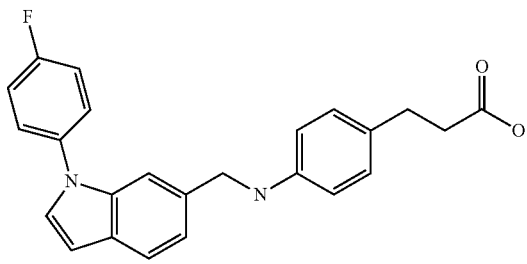

The compound (10 mg, 0.04 mmol) obtained from Preparation Example 139 and 3-(4-amino-phenyl)-propanoic acid (14 mg, 0.08 mmol) were used to obtain the title compound (12 mg, 77%).

NMR:$^1$H-NMR(400 HMz, CDCl$_3$); δ 7.64 (d, 1H), 7.53 (s, 1H), 7.39-7.45 (m, 2H), 7.25 (dd, 1H), 7.12-7.21 (m, 3H), 7.00 (d, 2H), 6.65 (d, 1H), 6.58 (d, 2H), 4.32 (s, 2H), 2.84 (t, 2H), 2.60 (t, 2H)

Example 11

Synthesis of 3-{4-[(7-chloro-1-cyclohexyl methyl-1H-indol-6-ylmethyl)-amino]-phenyl}-propanoic acid

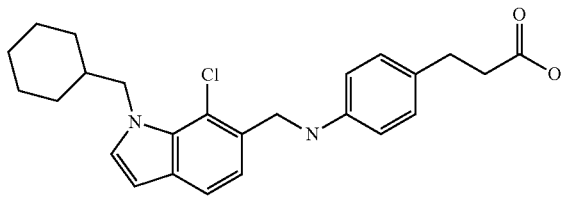 [SMILES: O=C(O)CCc1ccc(NCc2ccc3ccn(CC4CCCCC4)c3c2Cl)cc1]

The compound (32 mg, 0.12 mmol) obtained from Preparation Example 10-2 and 3-(4-amino-phenyl)-propanoic acid (29 mg, 0.17 mmol) were used to obtain the title compound (17 mg, 33%).

NMR:$^1$H-NMR(400 HMz, CDCl$_3$); δ 7.44 (d, 1H), 7.12 (d, 1H), 7.00 (d, 2H), 6.99 (d, 1H), 6.62 (d, 2H), 6.41 (d, 1H), 4.51 (s, 2H), 4.29 (d, 2H), 2.85 (t, 2H), 2.62 (t, 2H), 1.87-1.94 (m, 1H), 1.59-1.70 (m, 5H), 1.16-1.21 (m, 3H), 0.97-1.03 (m, 2H)

Example 12

Synthesis of [6-(1-benzyl-3-chloro-1H-indol-6-ylmethoxy)-2,3-dihydro-benzofuran-3-yl]-acetic acid

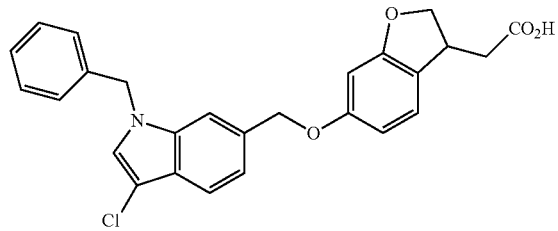 [SMILES: O=C(O)CC1COc2cc(OCc3ccc4c(Cl)cn(Cc5ccccc5)c4c3)ccc21]

(1-Benzyl-3-chloro-1H-indol-6-yl)-methanol (90 mg, 0.33 mmol) obtained from Preparation Example 140 and (6-hydroxy-2,3-dihydro-benzofuran-3-yl)-acetic acid methyl ester (60 mg, 0.29 mmol) obtained from Preparation Example 158 were dissolved in toluene (10 mL). 1,1'-(Azodicarbonyl)dipiperidine (ADD, 125 mg, 0.49 mmol) and tributylphosphine(Bu$_3$P, 100 mg, 0.49 mmol) were added thereto and the mixture was stirred for 1 hour. After completion of the reaction, resulting solids were removed by filteration with Celite and the filtrate was concentrated. The residue was purified via column chromatography to obtain the ester compound (130 mg, 86%).

The ester compound (130 mg, 0.28 mmol) was dissolved in a mixed solution of tetrahydrofuran and methanol (2/1, 9 ml) and then 1N NaOH solution (0.6 ml, 0.56 mmol) was added thereto. The mixture was stirred at room temperature for 4 hours, 1N hydrochloric acid solution was added thereto and extracted with ethylacetate. The extract was dried over anhydrous magnesium sulfate and filtered. The filtrate was distilled under reduced pressure. The residue was purified via column chromatography to obtain the title compound to obtain the title compound (100 mg, 79%).

NMR:$^1$H-NMR(400 HMz, MeOD-d$_3$); δ 7.62 (d, 1H), 7.36 (s, 1H), 7.29 (d, 3H), 7.22 (d, 1H), 7.12 (d, 2H), 7.09 (s, 1H), 7.03 (d, 1H), 6.49 (d, 1H), 6.46 (d, 1H), 5.38 (s, 2H), 5.09 (s, 2H), 4.76 (dd, 1H), 4.27 (dd, 1H), 3.79 (br s, 1H), 2.74 (dd, 1H), 2.54 (dd, 1H)

The following compounds of Examples 13 to 232 were prepared according to the method described in Example 12.

Example 13

Synthesis of 3-[4-(1-thiophen-3-yl-1H-indol-6-ylmethoxy)-phenyl]-propanoic acid

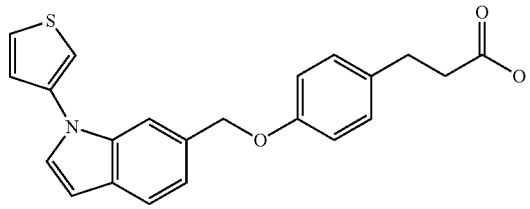 [SMILES: O=C(O)CCc1ccc(OCc2ccc3ccn(-c4ccsc4)c3c2)cc1]

According to the method described in Example 12, the compound (160 mg, 0.7 mmol) obtained from Preparation Example 6-2 and 3-(4-hydroxy-phenyl)-propanoic acid methyl ester (126 mg, 0.7 mmol) were used to obtain the title compound (200 mg, 76%).

NMR:$^1$H-NMR(400 HMz, CDCl$_3$); δ 7.66 (d, 1H), 7.62 (s, 1H), 7.44 (dd, 1H), 7.32 (d, 1H), 7.27 (d, 2H), 7.20 (dd, 1H), 7.11 (d, 2H), 6.92 (d, 2H), 6.64 (d, 1H), 4.94 (s, 2H), 2.89 (t, 2H), 2.64 (t, 2H)

Example 14

Synthesis of 3-{4-[1-(4-fluoro-phenyl)-7-methyl-1H-indol-6-ylmethoxy]-phenyl}-propanoic acid

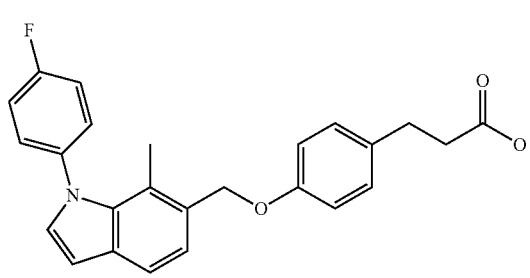 [SMILES: Cc1c(COc2ccc(CCC(=O)O)cc2)ccc2ccn(-c3ccc(F)cc3)c12]

The compound (96 mg, 0.38 mmol) obtained from Preparation Example 15-3 and 3-(4-hydroxy-phenyl)-propanoic acid methyl ester (68 mg, 0.38 mmol) were used to obtain the title compound (100 mg, 73%).

NMR:¹H-NMR(500 HMz, CDCl₃); δ 7.52 (d, 1H), 7.36 (dd, 1H), 7.35 (dd, 1H), 7.20 (d, 1H), 7.09-7.15 (m, 5H), 6.91 (d, 2H), 6.60 (d, 1H), 5.07 (s, 2H), 2.90 (t, 2H), 2.64 (t, 2H), 2.01 (s, 3H)

Example 15

Synthesis of 3-[4-(1-benzyl-7-methyl-1H-indol-6-ylmethoxy)-phenyl]-propanoic acid

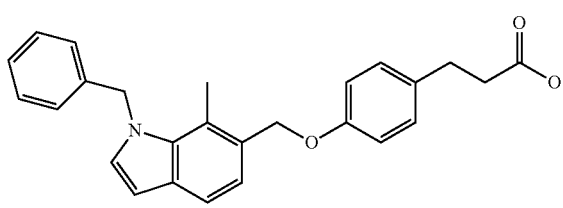 [SMILES: Cc1c(COc2ccc(CCC(=O)O)cc2)ccc2ccn(Cc3ccccc3)c12]

The compound (100 mg, 0.40 mmol) obtained from Preparation Example 17-2 and 3-(4-hydroxy-phenyl)-propanoic acid methyl ester (72 mg, 0.40 mmol) were used to obtain the title compound (70 mg, 44%).

NMR:¹H-NMR(500 HMz, CDCl₃); δ 7.48 (d, 1H), 7.21-7.29 (m, 3H), 7.08-7.14 (m, 4H), 6.89-6.94 (m, 4H), 6.54 (d, 1H), 5.63 (s, 2H), 5.04 (s, 2H), 2.89 (t, 2H), 2.64 (t, 2H), 2.50 (s, 3H)

Example 16

Synthesis of 3-[4-(7-methyl-1-thiophen-3-yl-1H-indol-6-ylmethoxy)-phenyl]-propanoic acid

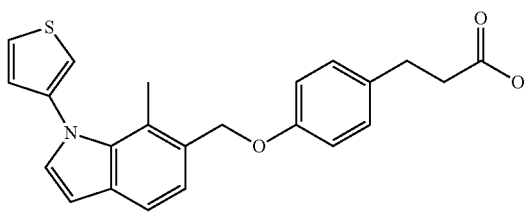 [SMILES: Cc1c(COc2ccc(CCC(=O)O)cc2)ccc2ccn(-c3ccsc3)c12]

The compound (30 mg, 0.12 mmol) obtained from Preparation Example 16 and 3-(4-hydroxy-phenyl)-propanoic acid methyl ester (22 mg, 0.12 mmol) were used to obtain the title compound (20 mg, 41%).

NMR:¹H-NMR(400 HMz, CDCl₃); δ 7.52 (d, 1H), 7.36 (dd, 1H), 7.30 (s, 1H), 7.19 (d, 1H), 7.11-7.13 (m, 4H), 6.92 (d, 2H), 6.58 (d, 1H), 5.08 (s, 2H), 2.90 (t, 2H), 2.64 (t, 2H), 2.10 (s, 3H)

Example 17

Synthesis of 3-{4-[1-(4-fluoro-2-methyl-phenyl)-1H-indol-6-ylmethoxy]-phenyl}-propanoic acid

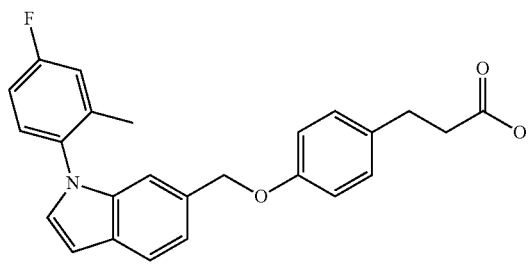 [SMILES: Cc1cc(F)ccc1-n1ccc2ccc(COc3ccc(CCC(=O)O)cc3)cc21]

The compound (52 mg, 0.20 mmol) obtained from Preparation Example 11-2 and 3-(4-hydroxy-phenyl)-propanoic acid methyl ester (36 mg, 0.20 mmol) were used to obtain the title compound (25 mg, 30%).

NMR:¹H-NMR(400 HMz, CDCl₃); δ 7.68 (d, 1H), 7.22 (dd, 1H), 7.13 (d, 1H), 7.04-7.10 (m, 5H), 7.00 (dd, 1H), 6.88 (d, 2H), 6.65 (d, 1H), 5.06 (s, 2H), 2.88 (t, 2H), 2.63 (t, 2H), 2.00 (s, 3H)

Example 18

Synthesis of 3-[4-(1-benzyl-7-chloro-1H-indol-6-ylmethoxy)-phenyl]-propanoic acid

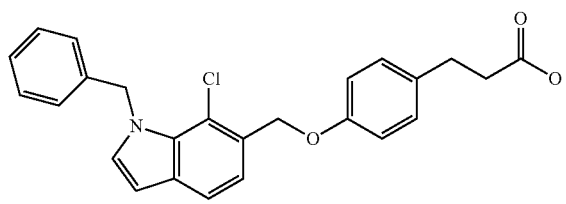 [SMILES: O=C(O)CCc1ccc(OCc2ccc3ccn(Cc4ccccc4)c3c2Cl)cc1]

The compound (158 mg, 0.72 mmol) obtained from Preparation Example 7-4 and 3-(4-hydroxy-phenyl)-propanoic acid methyl ester (105 mg, 0.58 mmol) were used to obtain the title compound (210 mg, 86%).

NMR:¹H-NMR(400 HMz, CDCl₃); δ 7.53 (d, 1H), 7.24-7.30 (m, 4H), 7.11 (d, 2H), 7.10 (s, 1H), 7.01 (d, 2H), 6.91 (d, 2H), 6.55 (d, 1H), 5.80 (s, 2H), 5.02 (s, 2H), 2.89 (t, 2H), 2.64 (t, 2H)

Example 19

Synthesis of 3-[4-(1-cyclohexyl methyl-1H-indol-6-ylmethoxy)-phenyl]-propanoic acid

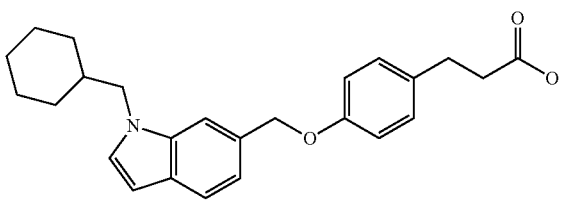 [SMILES: O=C(O)CCc1ccc(OCc2ccc3ccn(CC4CCCCC4)c3c2)cc1]

The compound (140 mg, 0.58 mmol) obtained from Preparation Example 14-2 and 3-(4-hydroxy-phenyl)-propanoic acid methyl ester (105 mg, 0.58 mmol) were used to obtain the title compound (35 mg, 16%)

NMR:$^1$H-NMR(400 HMz, CDCl$_3$); δ 7.66 (d, 1H), 7.43 (s, 1H), 7.14-7.20 (m, 3H), 7.11 (d, 1H), 7.00 (d, 2H), 6.51 (d, 1H), 5.21 (s, 2H), 3.97 (d, 2H), 2.95 (t, 2H), 2.70 (t, 2H), 1.85-1.91 (m, 1H), 1.64-1.73 (m, 5H), 1.19-1.26 (m, 3H), 0.92-1.04 (m, 2H)

Example 20

Synthesis of 3-[4-(3-benzyl-1-methyl-1H-indol-5-ylmethoxy)-phenyl]-propanoic acid

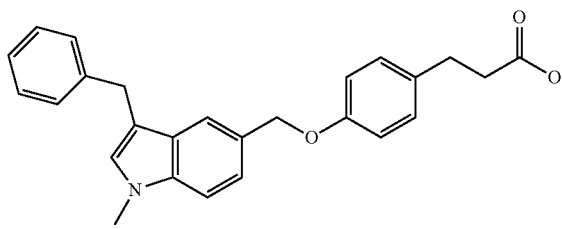 [SMILES: Cn1cc(Cc2ccccc2)c2cc(COc3ccc(CCC(=O)O)cc3)ccc21]

The compound (100 mg, 0.52 mmol) obtained from Preparation Example 50-3 and 3-(4-hydroxy-phenyl)-propanoic acid methyl ester (65 mg, 0.36 mmol) were used to obtain the title compound (7 mg, 3%).

NMR:$^1$H-NMR(400 HMz, CDCl$_3$); δ 7.56 (s, 1H), 7.26-7.29 (m, 6H), 7.18-7.21 (m, 1H), 7.11 (d, 2H), 6.92 (dt, 2H), 6.75 (s, 1H), 5.09 (s, 2H), 4.09 (s, 2H), 3.73 (s, 3H), 2.90 (t, 2H), 2.64 (t, 2H)

Example 21

Synthesis of 3-[4-(1-methyl-3-o-tolyl-1H-indol-5-ylmethoxy)-phenyl]-propanoic acid

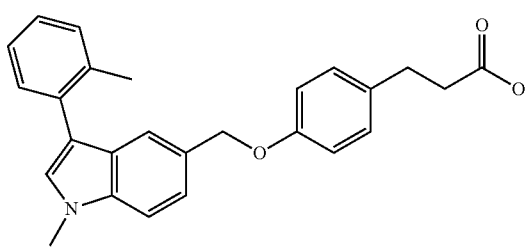 [SMILES: Cc1ccccc1-c1cn(C)c2ccc(COc3ccc(CCC(=O)O)cc3)cc12]

The compound (59 mg, 0.23 mmol) obtained from Preparation Example 51-3 and 3-(4-hydroxy-phenyl)-propanoic acid methyl ester (42 mg, 0.23 mmol) were used to obtain the title compound (65 mg, 67%).

NMR:$^1$H-NMR(400 HMz, CDCl$_3$); δ 7.55 (s, 1H), 7.38-7.41 (m, 1H), 7.37 (d, 1H), 7.35 (d, 1H), 7.30-7.33 (m, 1H), 7.24 (dd, 2H), 7.09 (d, 2H), 7.06 (s, 1H), 6.90 (d, 2H), 5.09 (s, 2H), 3.85 (s, 3H), 2.89 (t, 2H), 2.63 (t, 2H), 2.31 (s, 3H)

Example 22

Synthesis of 3-{4-[3-chloro-1-(4-fluoro-2-methyl-phenyl)-1H-indol-6-ylmethoxy)-phenyl]-propanoic acid

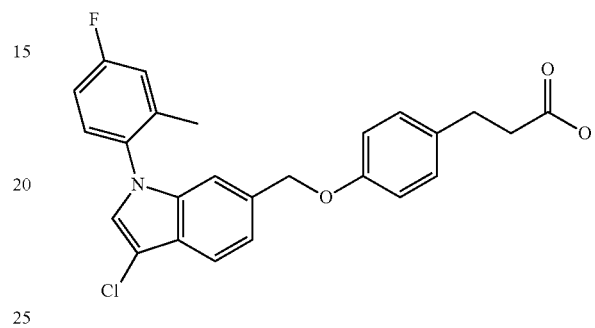

The compound (70 mg, 0.24 mmol) obtained from Preparation Example 12-2 and 3-(4-hydroxy-phenyl)-propanoic acid methyl ester (49 mg, 0.24 mmol) were used to obtain the title compound (70 mg, 66%).

NMR:$^1$H-NMR(400 HMz, CDCl$_3$); δ 7.72 (d, 1H), 7.33 (s, 1H), 7.27 (dd, 1H), 7.16 (s, 1H), 7.10-7.12 (m, 3H), 7.03-7.06 (m, 2H), 6.90 (d, 2H), 5.10 (s, 2H), 2.92 (t, 2H), 2.66 (t, 2H), 2.05 (s, 3H)

Example 23

Synthesis of 3-{4-[5-fluoro-1-(4-fluoro-2-methyl-phenyl)-1H-indol-6-ylmethoxy)-phenyl]-propanoic acid

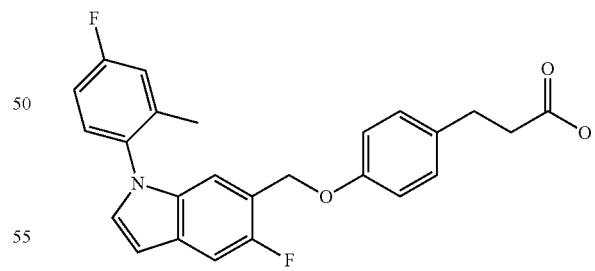

The compound (74 mg, 0.27 mmol) obtained from Preparation Example 13-5 and 3-(4-hydroxy-phenyl)-propanoic acid methyl ester (49 mg, 0.27 mmol) were used to obtain the title compound (70 mg, 61%).

NMR:$^1$H-NMR(400 HMz, CDCl$_3$); δ 7.35 (d, 1H), 7.23 (dd, 1H), 7.15 (d, 1H), 7.09 (d, 2H), 6.98-7.07 (m, 3H), 6.88 (d, 2H), 6.61 (d, 1H), 5.12 (s, 2H), 2.88 (t, 2H), 2.63 (t, 2H), 1.97 (s, 3H)

Example 24

Synthesis of {6-[1-(4-fluoro-2-methyl-phenyl)-1H-indol-6-ylmethoxy]-2,3-dihydro-benzofuran-3-yl}-acetic acid

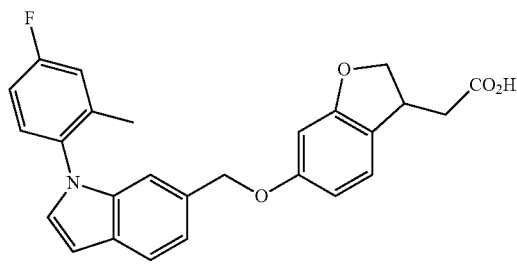 [SMILES: Cc1cc(F)ccc1-n1ccc2ccc(COc3ccc4c(c3)OCC4CC(=O)O)cc21]

The compound (75 mg, 0.29 mmol) obtained from Preparation Example 11-2 and the compound (61 mg, 0.29 mmol) obtained from Preparation Example 158 were used to obtain the title compound (91 mg, 72%).

NMR:$^1$H-NMR(400 HMz, CDCl$_3$); δ 7.73 (d, 1H), 7.30-7.33 (m, 1H), 7.26 (dd, 1H), 7.18 (d, 1H), 7.12 (dd, 1H), 7.07 (dd, 2H), 7.04 (d, 1H), 6.71 (d, 1H), 6.53 (dd, 1H), 5.49 (d, 1H), 5.09 (s, 2H), 4.79 (t, 1H), 4.31 (q, 1H), 3.84 (br t, 1H), 2.81-2.86 (m, 1H), 2.61-2.68 (m, 1H), 2.09 (s, 3H)

Example 25

Synthesis of (S)-3-[4-(1-benzyl-7-methyl-1H-indol-6-ylmethoxy)-phenyl]-hex-4-ynoic acid

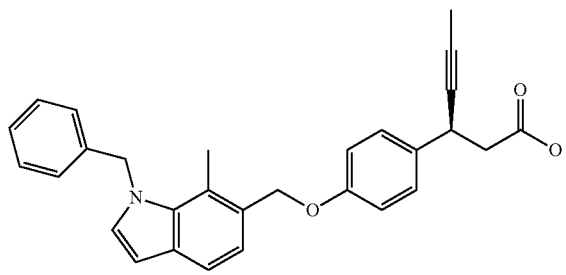 [SMILES: CC#C[C@@H](CC(=O)O)c1ccc(OCc2ccc3ccn(Cc4ccccc4)c3c2C)cc1]

The compound (500 mg, 1.99 mmol) obtained from Preparation Example 17-2 and the compound (435 mg, 1.99 mmol) obtained from Preparation Example 155 were used to obtain the title compound (550 mg, 63%).

NMR:$^1$H-NMR(400 HMz, DMSO-d$_6$); δ 7.48 (d, 1H), 7.42 (d, 1H), 7.26-7.32 (m, 5H), 7.10 (d, 1H), 6.90-6.96 (m, 4H), 6.53 (d, 1H), 5.71 (s, 2H), 5.08 (s, 2H), 3.95 (br s, 1H), 2.59 (m, 1H), 2.44 (s, 3H), 2.41 (m, 1H), 1.79 (s, 3H)

Example 26

Synthesis of (S)-3-{4-[1-(4-fluoro-2-methyl-phenyl)-1H-indol-6-ylmethoxy]-phenyl}-hex-4-ynoic acid

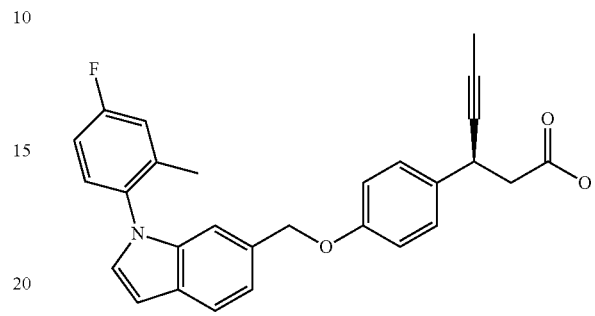

The compound (420 mg, 1.65 mmol) obtained from Preparation Example 11-2 and the compound (360 mg, 1.65 mmol) obtained from Preparation Example 155 were used to obtain the title compound (600 mg, 82%).

NMR:$^1$H-NMR(400 HMz, DMSO-d$_6$); δ 7.67 (d, 1H), 7.46 (d, 1H), 7.34-7.42 (m, 2H), 7.24 (d, 3H), 7.20 (d, 1H), 7.04 (s, 1H), 6.92 (dd, 2H), 6.69 (dd, 1H), 5.12 (s, 2H), 3.93 (br s, 1H), 2.59 (m, 1H), 2.57 (m, 1H), 1.97 (s, 3H), 1.78 (s, 3H)

Example 27

Synthesis of (S)-3-{4-[1-(4-methanesulfonyl-benzyl)-7-methyl-1H-indol-6-ylmethoxy]-phenyl}-hex-4-ynoic acid

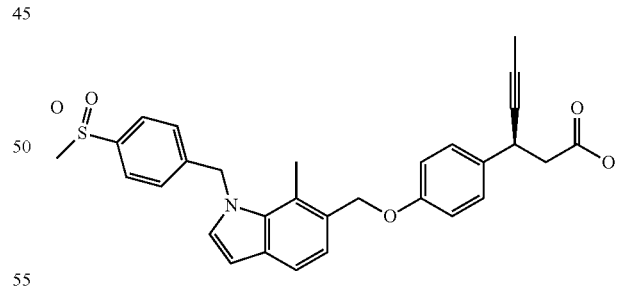

The compound (100 mg, 0.30 mmol) obtained from Preparation Example 32 and the compound (65 mg, 0.30 mmol) obtained from Preparation Example 155 were used to obtain the title compound (15 mg, 10%).

NMR:$^1$H-NMR(400 HMz, DMSO-d$_6$); δ 7.86 (d, 2H), 7.46 (d, 1H), 7.43 (d, 1H), 7.24 (d, 2H), 7.12 (dd, 3H), 6.92 (d, 2H), 6.56 (d, 1H), 5.81 (s, 2H), 5.06 (s, 2H), 3.16 (s, 3H), 2.57-2.59 (m, 1H), 2.52-2.53 (m, 1H), 2.39 (s, 3H), 1.76 (s, 3H)

Example 28

Synthesis of (S)-3-{4-[1-(4-methoxy-benzyl)-7-methyl-1H-indol-6-ylmethoxy]-phenyl}-hex-4-ynoic acid

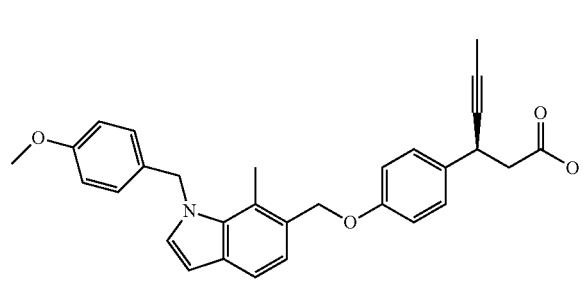 [SMILES: CC#C[C@@H](CC(=O)O)c1ccc(OCc2ccc3ccn(Cc4ccc(OC)cc4)c3c2C)cc1]

The compound (280 mg, 1.00 mmol) obtained from Preparation Example 30 and the compound (217 mg, 1.00 mmol) obtained from Preparation Example 155 were used to obtain the title compound (280 mg, 60%).

NMR:$^1$H-NMR(400 HMz, CDCl$_3$); δ 7.52 (d, 1H), 7.33 (dd, 2H), 7.17 (d, 1H), 7.12 (d, 1H), 6.98 (dd, 2H), 6.91 (d, 2H), 6.86 (dd, 2H), 6.56 (d, 1H), 5.59 (s, 2H), 5.12 (s, 2H), 4.10 (br s, 1H), 3.81 (s, 3H), 2.82-2.88 (m, 1H), 2.72-2.77 (m, 1H), 2.57 (s, 3H), 1.90 (s, 3H)

Example 29

Synthesis of (S)-3-{4-[7-methyl-1-(4-trifluoromethyl-benzyl)-1H-indol-6-ylmethoxy]-phenyl}-hex-4-ynoic acid

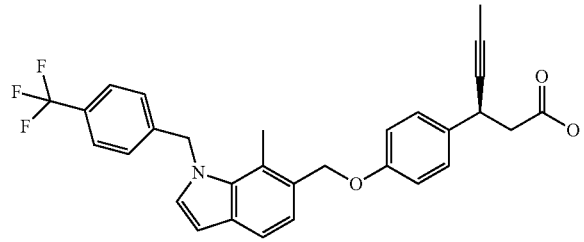 [SMILES: CC#C[C@@H](CC(=O)O)c1ccc(OCc2ccc3ccn(Cc4ccc(C(F)(F)F)cc4)c3c2C)cc1]

The compound (250 mg, 0.94 mmol) obtained from Preparation Example 28 and the compound (206 mg, 0.94 mmol) obtained from Preparation Example 155 were used to obtain the title compound (300 mg, 63%).

NMR:$^1$H-NMR(400 HMz, CDCl$_3$); δ 7.48 (d, 1H), 7.21-7.29 (m, 4H), 7.13 (d, 1H), 7.09 (d, 1H), 6.94 (d, 2H), 6.92 (d, 2H), 6.54 (d, 1H), 5.61 (s, 2H), 5.05 (s, 2H), 4.04 (br s, 1H), 2.77-2.83 (m, 1H), 2.67-2.73 (m, 1H), 2.50 (s, 3H), 1.82 (s, 3H)

Example 30

Synthesis of (S)-3-{4-[1-(3-methoxymethyl-benzyl)-7-methyl-1H-indol-6-ylmethoxy]-phenyl}-hex-4-ynoic acid

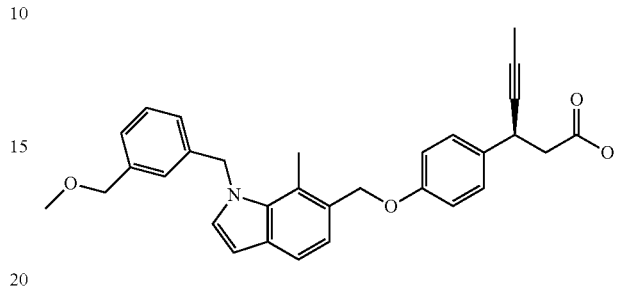

The compound (90 mg, 0.31 mmol) obtained from Preparation Example 31-4 and the compound (67 mg, 0.31 mmol) obtained from Preparation Example 155 were used to obtain the title compound (57 mg, 39%).

NMR:$^1$H-NMR(400 HMz, CDCl$_3$); δ 7.48 (d, 1H), 7.30 (d, 2H), 7.27 (s, 1H), 7.22 (d, 1H), 7.13 (d, 1H), 7.08 (d, 1H), 7.00 (s, 1H), 6.92 (dd, 2H), 6.80 (d, 1H), 6.54 (d, 1H), 5.61 (s, 2H), 5.06 (s, 2H), 4.39 (s, 2H), 4.05 (br s, 1H), 3.35 (s, 3H), 2.77-2.83 (m, 1H), 2.68-2.73 (m, 1H), 2.50 (s, 3H), 1.83 (s, 3H)

Example 31

Synthesis of (S)-3-[4-(1-benzyl-1H-indol-4-ylmethoxy)-phenyl]-hex-4-ynoic acid

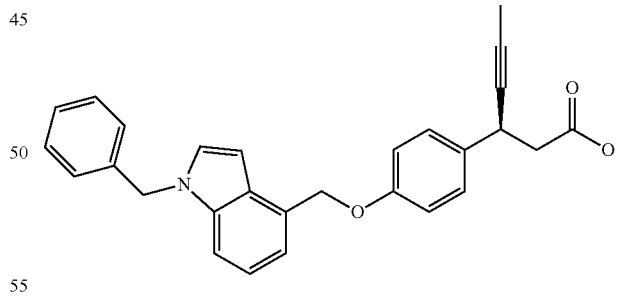

The compound (120 mg, 0.5 mmol) obtained from Preparation Example 131-2 and the compound (100 mg, 0.46 mmol) obtained from Preparation Example 155 were used to obtain the title compound (100 mg, 47%).

NMR:$^1$H-NMR(400 HMz, DMSO-d$_6$); δ 7.54 (d, 1H), 7.43 (dd, 1H), 7.32 (dd, 2H), 7.22-7.27 (m, 5H), 7.08-7.12 (m, 2H), 6.93 (d, 2H), 6.61 (d, 1H), 5.45 (s, 2H), 5.31 (s, 2H), 3.98 (br s, 1H), 2.24-2.29 (m, 1H), 2.09-2.14 (m, 1H), 1.76 (s, 3H)

Example 32

Synthesis of (S)-3-{4-[1-(4-fluoro-2-methyl-phenyl)-1H-indol-4-ylmethoxy]-phenyl}-hex-4-ynoic acid

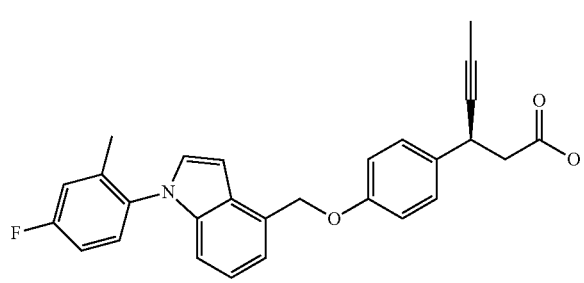 [SMILES: CC#C[C@@H](CC(=O)O)c1ccc(OCc2cccc3c2ccn3-c2ccc(F)cc2C)cc1]

The compound (100 mg, 0.4 mmol) obtained from Preparation Example 132-2 and the compound (85 mg, 0.39 mmol) obtained from Preparation Example 155 were used to obtain the title compound (100 mg, 57%).

NMR:$^1$H-NMR(400 HMz, CDCl$_3$); δ 7.33 (d, 2H), 7.24 (dd, 1H), 7.22 (dd, 1H), 7.18 (s, 1H), 7.15 (dd, 1H), 7.08 (dd, 1H), 6.96-7.02 (m, 4H), 6.76 (d, 1H), 5.44 (s, 2H), 4.07 (br t, 1H), 2.79-2.85 (m, 1H), 2.70-2.75 (m, 1H), 2.04 (s, 3H), 1.83 (s, 3H)

Example 33

Synthesis of (S)-3-{4-[1-(2,6-difluoro-benzyl)-7-methyl-1H-indol-6-ylmethoxy]-phenyl}-hex-4-ynoic acid

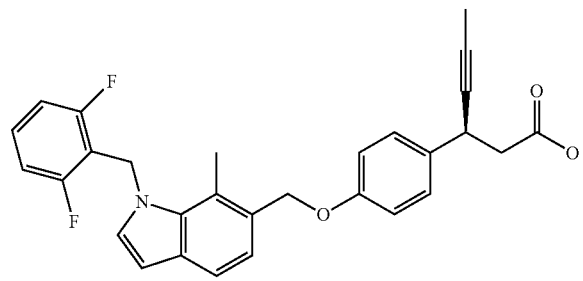

The compound (200 mg, 0.70 mmol) obtained from Preparation Example 22 and the compound (153 mg, 0.70 mmol) obtained from Preparation Example 155 were used to obtain the title compound (200 mg, 61%).

NMR:$^1$H-NMR(500 HMz, CDCl$_3$); δ 7.42 (d, 1H), 7.31 (d, 3H), 7.11 (d, 1H), 6.98 (d, 2H), 6.93 (d, 3H), 6.43 (d, 1H), 5.70 (s, 2H), 5.13 (s, 2H), 4.07 (br s, 1H), 2.79-2.84 (m, 1H), 2.81 (s, 3H), 2.70-2.75 (m, 1H), 1.83 (s, 3H)

Example 34

Synthesis of (S)-3-{4-[1-benzyl-2-(2-methoxy-ethyl)-1H-indol-6-ylmethoxy]-phenyl}-hex-4-ynoic acid

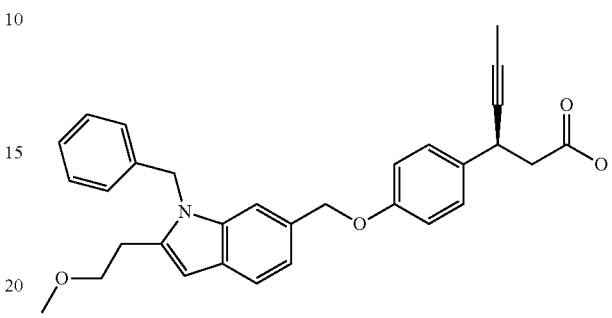

The compound (130 mg, 0.44 mmol) obtained from Preparation Example 52-5 and the compound (96 mg, 0.44 mmol) obtained from Preparation Example 155 were used to obtain the title compound (50 mg, 23%).

NMR:$^1$H-NMR(500 HMz, CDCl$_3$); δ 7.56 (d, 1H), 7.19-7.30 (m, 5H), 7.13 (d, 1H), 6.93 (d, 2H), 6.90 (d, 3H), 6.37 (s, 1H), 5.35 (s, 2H), 5.07 (s, 2H), 4.03 (br s, 1H), 3.64 (t, 2H), 3.31 (s, 3H), 2.94 (t, 2H), 2.76-2.81 (m, 1H), 2.67-2.71 (m, 1H), 1.82 (s, 3H)

Example 35

Synthesis of (S)-3-{4-[1-(3-methanesulfonylmethyl-benzyl)-7-methyl-1H-indol-6-ylmethoxy]-phenyl}-hex-4-ynoic acid

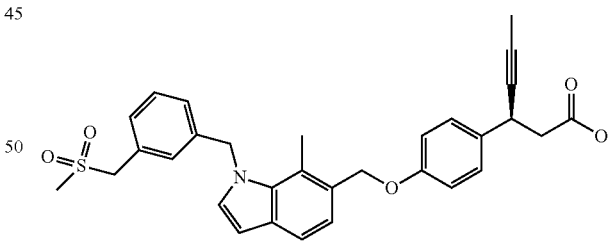

The compound (130 mg, 0.38 mmol) obtained from Preparation Example 33-2 and the compound (83 mg, 0.38 mmol) obtained from Preparation Example 155 were used to obtain the title compound (60 mg, 30%).

NMR:$^1$H-NMR(400 HMz, CDCl$_3$); δ 7.53 (d, 1H), 7.39 (dd, 1H), 7.31-7.34 (m, 4H), 7.18 (d, 1H), 7.15 (dd, 1H), 7.06 (d, 1H), 6.94 (dd, 1H), 6.76 (s, 1H), 6.61 (d, 1H), 5.67 (s, 2H), 5.09 (s, 2H), 4.14 (s, 2H), 4.08 (br s, 1H), 2.82-2.88 (m, 1H), 2.72-2.77 (m, 1H), 2.52 (s, 3H), 2.49 (s, 3H), 1.87 (s, 3H)

Example 36

Synthesis of (S)-3-{4-[7-methyl-1-(2-methyl-benzyl)-1H-indol-6-ylmethoxy]-phenyl}-hex-4-ynoic acid

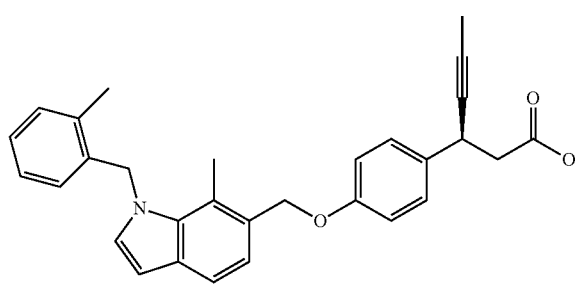 [SMILES: CC#C[C@@H](CC(=O)O)c1ccc(OCc2ccc3ccn(Cc4ccccc4C)c3c2C)cc1]

The compound (0.21 g, 0.70 mmol) obtained from Preparation Example 26-2 and the compound (0.20 g, 0.70 mmol) obtained from Preparation Example 155 were used to obtain the title compound (0.10 g, 35%).

NMR:$^1$H-NMR(400 HMz, CDCl$_3$); δ 7.49 (d, 1H), 7.27 (dd, 2H), 7.13-7.19 (m, 3H), 7.01-7.04 (m, 2H), 6.92 (d, 2H), 6.53 (dd, 1H), 6.41 (d, 1H), 5.52 (s, 2H), 5.06 (s, 2H), 4.11 (br s, 1H), 2.78-2.82 (m, 1H), 2.67-2.72 (m, 1H), 2.44 (s, 3H), 2.35 (s, 3H), 1.82 (s, 3H)

Example 37

Synthesis of (S)-3-{4-[1-(2-fluoro-benzyl)-7-methyl-1H-indol-6-ylmethoxy]-phenyl}-hex-4-ynoic acid

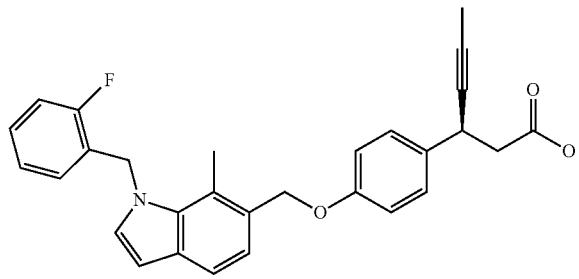 [SMILES: CC#C[C@@H](CC(=O)O)c1ccc(OCc2ccc3ccn(Cc4ccccc4F)c3c2C)cc1]

The compound (0.28 g, 0.94 mmol) obtained from Preparation Example 18-2 and the compound (0.20 g, 0.70 mmol) obtained from Preparation Example 155 were used to obtain the title compound (0.16 g, 37%).

NMR:$^1$H-NMR(400 HMz, CDCl$_3$); δ 7.48 (d, 1H), 7.28 (d, 2H), 7.21 (dd, 1H), 7.14 (d, 1H), 7.09 (dd, 2H), 6.98 (d, 2H), 6.92 (d, 2H), 6.55 (d, 1H), 5.64 (s, 2H), 5.06 (s, 2H), 4.04 (br t, 1H), 2.76-2.82 (m, 1H), 2.66-2.72 (m, 1H), 2.48 (s, 3H), 1.82 (s, 3H)

Example 38

Synthesis of (S)-3-{4-[1-(2-chloro-benzyl)-7-methyl-1H-indol-6-ylmethoxy]-phenyl}-hex-4-ynoic acid

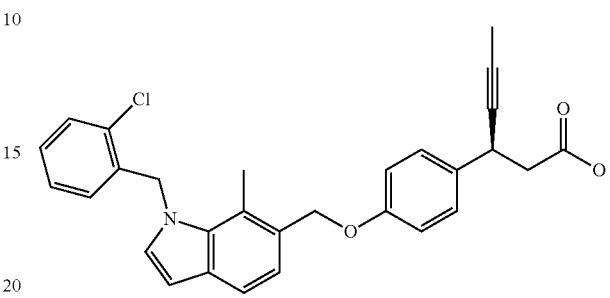

The compound (0.19 g, 0.64 mmol) obtained from Preparation Example 25-2 and the compound (0.18 g, 0.64 mmol) obtained from Preparation Example 155 were used to obtain the title compound (0.12 g, 42%).

NMR:$^1$H-NMR(400 HMz, CDCl$_3$); δ 7.50 (d, 1H), 7.39 (d, 1H), 7.27 (d, 2H), 7.12-7.21 (m, 2H), 7.06 (d, 2H), 6.91 (d, 2H), 6.56 (d, 1H), 6.38 (d, 1H), 5.63 (s, 2H), 5.06 (s, 2H), 4.04 (br t, 1H), 2.76-2.82 (m, 1H), 2.67-2.72 (m, 1H), 2.40 (s, 3H), 1.82 (s, 3H)

Example 39

Synthesis of (S)-3-{4-[1-(2,6-dimethyl-benzyl)-7-methyl-1H-indol-6-ylmethoxy]-phenyl}-hex-4-ynoic acid

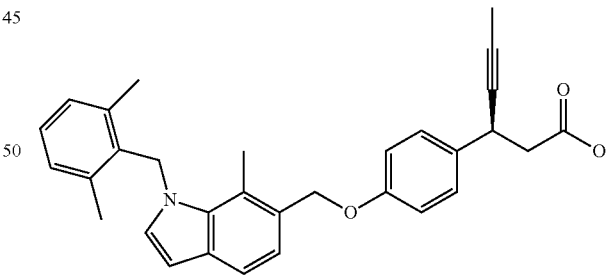

The compound (0.18 g, 0.62 mmol) obtained from Preparation Example 29-2 and the compound (0.17 g, 0.62 mmol) obtained from Preparation Example 155 were used to obtain the title compound (0.12 g, 42%).

NMR:$^1$H-NMR(400 HMz, CDCl$_3$); δ 7.43 (d, 1H), 7.35 (d, 2H), 7.20 (d, 1H), 7.12 (d, 3H), 7.01 (d, 2H), 6.48 (d, 1H), 6.30 (d, 1H), 5.67 (s, 2H), 5.16 (s, 2H), 4.08 (br t, 1H), 2.93 (s, 3H), 2.77-2.83 (m, 1H), 2.72-2.74 (m, 1H), 2.27 (s, 6H), 1.83 (s, 3H)

Example 40

Synthesis of (S)-3-[4-(1-benzyl-7-chloro-1H-indol-6-ylmethoxy)-phenyl]-hex-4-ynoic acid

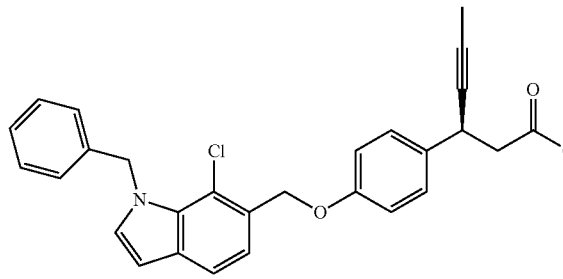

The compound (0.21 g, 0.71 mmol) obtained from Preparation Example 46 and the compound (0.18 g, 0.71 mmol) obtained from Preparation Example 155 were used to obtain the title compound (0.16 g, 49%).

NMR: $^1$H-NMR(400 HMz, CDCl$_3$); δ 7.52 (d, 1H), 7.21-7.30 (m, 6H), 7.10 (d, 1H), 7.01 (d, 2H), 6.93 (d, 2H), 6.54 (d, 1H), 5.83 (s, 2H), 5.20 (s, 2H), 4.06 (br t, 1H), 2.76-2.82 (m, 1H), 2.66-2.72 (m, 1H), 1.82 (s, 3H)

Example 41

Synthesis of (S)-3-[4-(1-benzyl-5-fluoro-1H-indol-6-ylmethoxy)-phenyl]-hex-4-ynoic acid

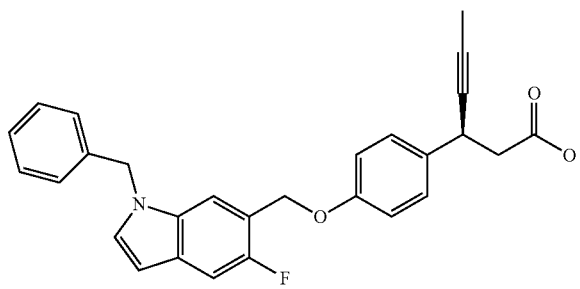

The compound (0.17 g, 0.59 mmol) obtained from Preparation Example 47-2 and the compound (0.15 g, 0.59 mmol) obtained from Preparation Example 155 were used to obtain the title compound (0.09 g, 32%).

NMR: $^1$H-NMR(400 HMz, CDCl$_3$); δ 7.64 (d, 1H), 7.60 (d, 1H), 7.36 (d, 1H), 7.30 (d, 1H), 7.18-7.26 (m, 4H), 7.08 (d, 1H), 6.88 (d, 2H), 6.63 (d, 1H), 6.49 (d, 1H), 5.42 (s, 2H), 5.10 (s, 2H), 3.99 (br s, 1H), 2.23-2.31 (m, 1H), 2.09-2.16 (m, 1H), 1.75 (s, 3H)

Example 42

Synthesis of (S)-3-{4-[1-(3-fluoro-benzyl)-7-methyl-1H-indol-6-ylmethoxy]-phenyl}-hex-4-ynoic acid

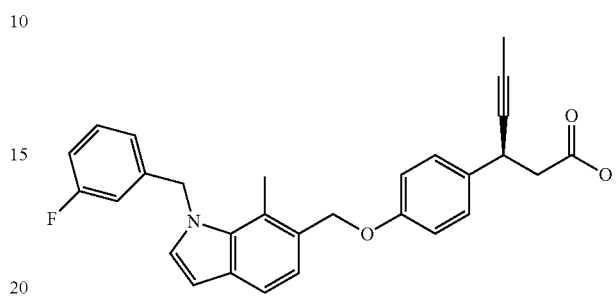

The compound (0.20 g, 0.68 mmol) obtained from Preparation Example 19-2 and the compound (0.18 g, 0.68 mmol) obtained from Preparation Example 155 were used to obtain the title compound (0.06 g, 19%).

NMR: $^1$H-NMR(400 HMz, CDCl$_3$); δ 7.49 (d, 1H), 7.28 (dd, 2H), 7.22 (dd, 1H), 7.14 (d, 1H), 7.08 (dd, 1H), 6.92-6.94 (m, 3H), 6.71 (d, 1H), 6.62 (d, 1H), 6.55 (dd, 1H), 5.59 (s, 2H), 5.07 (s, 2H), 4.05 (br s, 1H), 2.77-2.83 (m, 1H), 2.67-2.73 (m, 1H), 2.49 (s, 3H), 1.82 (s, 3H)

Example 43

Synthesis of (S)-3-{4-[7-methyl-1-(3-trifluoromethyl-benzyl)-1H-indol-6-ylmethoxy]-phenyl}-hex-4-ynoic acid

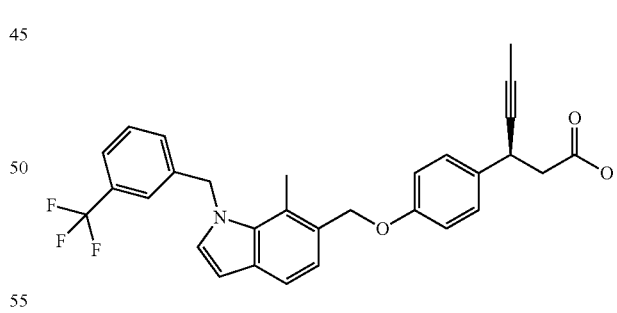

The compound (0.20 g, 0.68 mmol) obtained from Preparation Example 27-2 and the compound (0.18 g, 0.68 mmol) obtained from Preparation Example 155 were used to obtain the title compound (0.15 g, 49%).

NMR: $^1$H-NMR(400 HMz, CDCl$_3$); δ 7.70 (dd, 1H), 7.50 (d, 1H), 7.34 (dd, 2H), 7.26 (dd, 2H), 7.15 (d, 1H), 7.07 (d, 1H), 6.90 (d, 2H), 6.58 (d, 1H), 6.42 (dd, 1H), 5.80 (s, 2H), 5.04 (s, 2H), 4.11 (br t, 1H), 2.75-2.81 (m, 1H), 2.66-2.72 (m, 1H), 2.38 (s, 3H), 1.82 (s, 3H)

Example 44

Synthesis of (S)-3-{4-[7-methyl-1-(5-methyl-pyrazin-2-ylmethyl)-1H-indol-6-ylmethoxy]-phenyl}-hex-4-ynoic acid

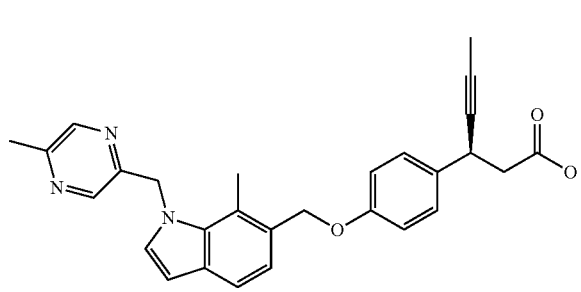 [SMILES: CC#C[C@@H](CC(=O)O)c1ccc(OCc2ccc3ccn(Cc4cnc(C)cn4)c3c2C)cc1]

The compound (0.09 g, 0.33 mmol) obtained from Preparation Example 42 and the compound (0.09 g, 0.33 mmol) obtained from Preparation Example 155 were used to obtain the title compound (0.07 g, 49%).

NMR:¹H-NMR(400 HMz, DMSO-d₆); δ 8.51 (s, 1H), 7.96 (s, 1H), 7.50 (d, 1H), 7.40 (d, 1H), 7.23 (d, 2H), 7.11 (d, 1H), 6.88 (d, 2H), 6.51 (d, 1H), 5.81 (s, 2H), 5.07 (s, 2H), 3.98 (br s, 1H), 2.48 (s, 3H), 2.47 (s, 3H), 2.23 (m, 1H), 2.12 (m, 1H), 1.76 (s, 3H)

Example 45

Synthesis of (S)-3-{4-[1-(4-methanesulfonylmethyl-benzyl)-7-methyl-1H-indol-6-ylmethoxy]-phenyl}-hex-4-ynoic acid

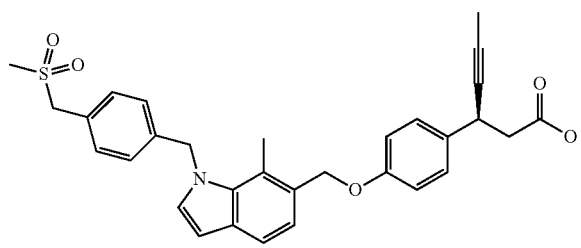 [SMILES: CC#C[C@@H](CC(=O)O)c1ccc(OCc2ccc3ccn(Cc4ccc(CS(C)(=O)=O)cc4)c3c2C)cc1]

The compound (240 mg, 0.70 mmol) obtained from Preparation Example 35 and the compound (153 mg, 0.70 mmol) obtained from Preparation Example 155 were used to obtain the title compound (90 mg, 24%).

NMR:¹H-NMR(400 HMz, CDCl₃); δ 7.53 (d, 1H), 7.31-7.37 (m, 4H), 7.18 (d, 1H), 7.12 (d, 1H), 7.00 (d, 2H), 6.96 (d, 2H), 6.60 (d, 1H), 5.66 (s, 2H), 5.11 (s, 2H), 4.29 (s, 2H), 4.09 (br s, 1H), 2.81-2.87 (m, 1H), 2.78 (s, 3H), 2.71-2.75 (m, 1H), 2.52 (s, 3H), 1.86 (s, 3H)

Example 46

Synthesis of (S)-3-{4-[1-(6-chloro-pyridin-3-ylmethyl)-7-methyl-1H-indol-6-ylmethoxy]-phenyl}-hex-4-ynoic acid

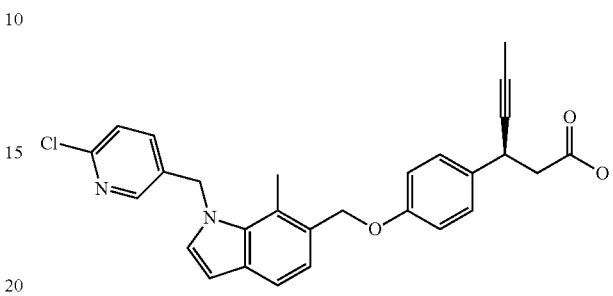

The compound (0.17 g, 0.57 mmol) obtained from Preparation Example 37-2 and the compound (0.15 g, 0.57 mmol) obtained from Preparation Example 155 were used to obtain the title compound (0.09 g, 35%).

NMR:¹H-NMR(400 HMz, CDCl₃); δ 8.13 (s, 1H), 7.48 (d, 1H), 7.29 (dd, 2H), 7.19 (d, 1H), 7.15 (d, 1H), 7.04 (d, 2H), 6.92 (d, 2H), 6.57 (d, 1H), 5.59 (s, 2H), 5.07 (s, 2H), 4.04 (br s, 1H), 2.78-2.84 (m, 1H), 2.66-2.72 (m, 1H), 2.44 (s, 3H), 1.82 (s, 3H)

Example 47

Synthesis of (S)-3-[4-(2-benzyl-2H-indazol-4-yl-methoxy)-phenyl]-hex-4-ynoic acid

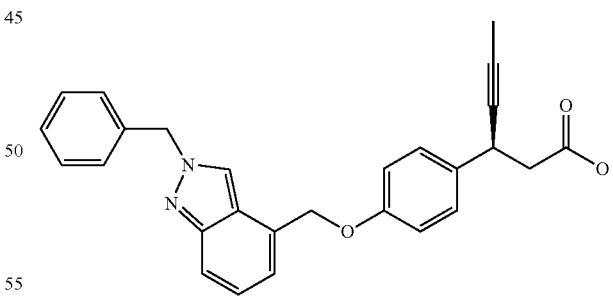

The compound (140 mg, 0.60 mmol) obtained from Preparation Example 134-2 and the compound (131 mg, 0.60 mmol) obtained from Preparation Example 155 were used to obtain the title compound (170 mg, 68%).

NMR:¹H-NMR(400 HMz, CDCl₃); δ 8.16 (s, 1H), 7.31-7.32 (m, 5H), 7.27-7.28 (m, 2H), 7.16-7.21 (m, 3H), 6.97 (dd, 2H), 5.61 (s, 2H), 5.36 (s, 2H), 4.05 (br s, 1H), 2.77-2.83 (m, 1H), 2.67-2.73 (m, 1H), 1.82 (s, 3H)

Example 48

Synthesis of (S)-3-[4-(1-benzyl-1H-indazol-4-yl-methoxy)-phenyl]-hex-4-ynoic acid

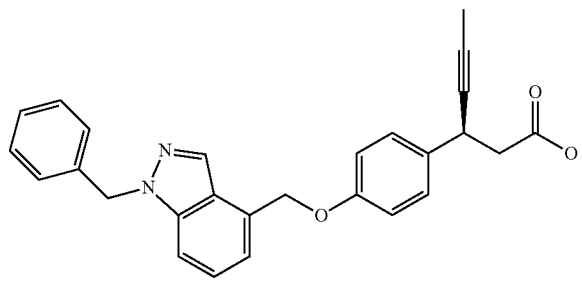 [SMILES: CC#C[C@@H](CC(=O)O)c1ccc(OCc2cccc3c2cnn3Cc2ccccc2)cc1]

The compound (90 mg, 0.38 mmol) obtained from Preparation Example 133-2 and the compound (83 mg, 0.38 mmol) obtained from Preparation Example 155 were used to obtain the title compound (100 mg, 95%).

NMR:$^1$H-NMR(400 HMz, CDCl$_3$); δ 8.01 (s, 1H), 7.69 (d, 1H), 7.32-7.35 (m, 3H), 7.25-7.27 (m, 5H), 7.08 (d, 1H), 6.91 (d, 2H), 5.59 (s, 2H), 5.24 (s, 2H), 4.04 (br s, 1H), 2.76-2.82 (m, 1H), 2.66-2.71 (m, 1H), 1.82 (s, 3H)

Example 49

Synthesis of (S)-3-[4-(1-benzyl-5-fluoro-7-methyl-1H-indol-6-ylmethoxy)-phenyl]-hex-4-ynoic acid

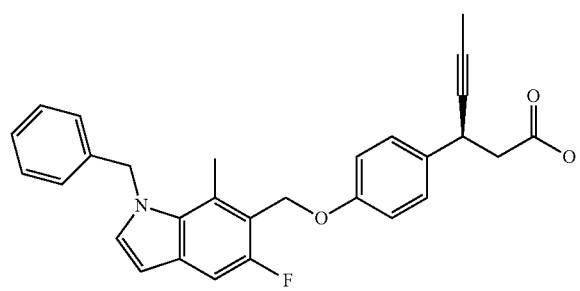 [SMILES: CC#C[C@@H](CC(=O)O)c1ccc(OCc2c(F)cc3ccn(Cc4ccccc4)c3c2C)cc1]

The compound (252 mg, 0.94 mmol) obtained from Preparation Example 48-4 and the compound (205 mg, 0.94 mmol) obtained from Preparation Example 155 were used to obtain the title compound (123 mg, 29%).

NMR:$^1$H-NMR(400 HMz, CDCl$_3$); δ 7.24-7.31 (m, 5H), 7.18 (d, 1H), 7.12 (d, 1H), 6.91 (m, 4H), 6.50 (d, 1H), 5.58 (s, 2H), 5.13 (d, 2H), 4.04 (m, 1H), 2.81 (dd, 1H), 2.72 (dd, 1H), 2.51 (s, 3H), 1.82 (s, 3H)

Example 50

Synthesis of (S)-3-{4-[1-(4-fluoro-benzyl)-7-methyl-1H-indol-6-ylmethoxy]-phenyl}-hex-4-ynoic acid

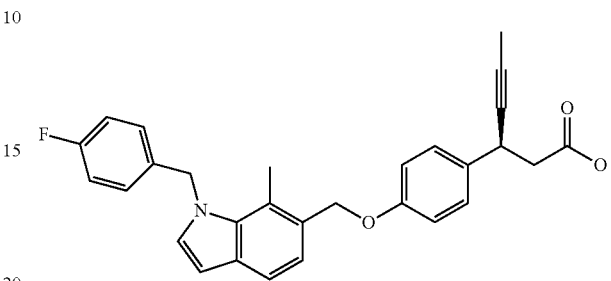

The compound (0.15 g, 0.51 mmol) obtained from Preparation Example 20-2 and the compound (0.13 g, 0.51 mmol) obtained from Preparation Example 155 were used to obtain the title compound (0.12 g, 52%).

NMR:$^1$H-NMR(400 HMz, CDCl$_3$); δ 7.48 (d, 1H), 7.28 (d, 2H), 7.14 (d, 1H), 7.07 (d, 1H), 6.87-6.99 (m, 6H), 6.54 (d, 1H), 5.57 (s, 2H), 5.06 (s, 2H), 4.05 (br s, 1H), 2.77-2.83 (m, 1H), 2.67-2.73 (m, 1H), 2.49 (s, 3H), 1.82 (s, 3H)

Example 51

Synthesis of (S)-3-{4-[1-(3,4-difluoro-benzyl)-7-methyl-1H-indol-6-ylmethoxy]-phenyl}-hex-4-ynoic acid

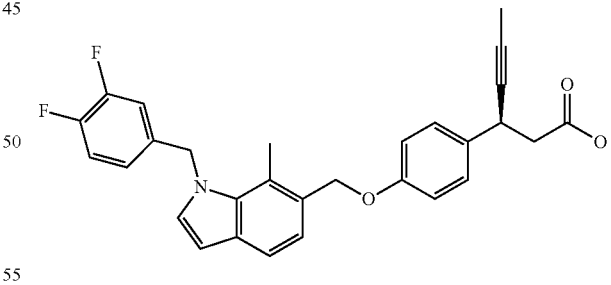

The compound (0.19 g, 0.64 mmol) obtained from Preparation Example 21-2 and the compound (0.17 g, 0.64 mmol) obtained from Preparation Example 155 were used to obtain the title compound (0.13 g, 44%).

NMR:$^1$H-NMR(400 HMz, CDCl$_3$); δ 7.48 (d, 1H), 7.29 (d, 2H), 7.14 (d, 1H), 7.06 (d, 2H), 6.92 (d, 2H), 6.70-6.75 (m, 1H), 6.65 (m, 1H), 6.56 (d, 1H), 5.55 (s, 2H), 5.07 (s, 2H), 4.05 (br s, 1H), 2.77-2.83 (m, 1H), 2.68-2.74 (m, 1H), 2.48 (s, 3H), 1.72 (s, 3H)

Example 52

Synthesis of (S)-3-{4-[1-(3,5-difluoro-benzyl)-7-methyl-1H-indol-6-ylmethoxy]-phenyl}-hex-4-ynoic acid

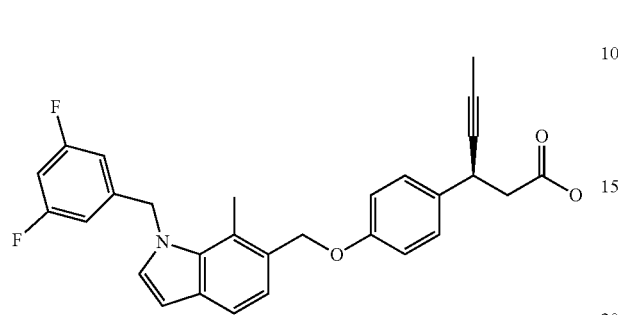

The compound (0.14 g, 0.49 mmol) obtained from Preparation Example 23 and the compound (0.13 g, 0.49 mmol) obtained from Preparation Example 155 were used to obtain the title compound (0.12 g, 54%).

NMR:¹H-NMR(400 HMz, CDCl₃); δ 7.49 (d, 1H), 7.31 (d, 2H), 7.15 (d, 1H), 7.05 (d, 1H), 6.93 (dd, 2H), 6.67 (dddd, 1H), 6.52 (d, 1H), 6.38 (d, 2H), 5.55 (s, 2H), 5.07 (s, 2H), 4.05 (br s, 1H), 2.77-2.83 (m, 1H), 2.68-2.73 (m, 1H), 2.47 (s, 3H), 1.82 (s, 3H)

Example 53

Synthesis of (S)-3-{4-[1-(2,4-difluoro-benzyl)-7-methyl-1H-indol-6-ylmethoxy]-phenyl}-hex-4-ynoic acid

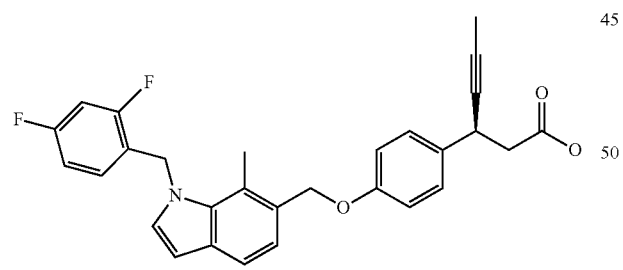

The compound (0.15 g, 0.49 mmol) obtained from Preparation Example 24 and the compound (0.13 g, 0.49 mmol) obtained from Preparation Example 155 were used to obtain the title compound (0.14 g, 63%).

NMR:¹H-NMR(400 HMz, CDCl₃); δ 7.49 (d, 1H), 7.28 (d, 2H), 7.15 (d, 1H), 7.06 (d, 1H), 6.92 (dd, 2H), 6.84 (dd, 1H), 6.70 (t, 1H), 6.55 (d, 1H), 6.44-6.47 (m, 1H), 5.59 (s, 2H), 5.07 (s, 2H), 4.05 (br s, 1H), 2.77-2.83 (m, 1H), 2.68-2.73 (m, 1H), 2.48 (s, 3H), 1.82 (s, 3H)

Example 54

Synthesis of 3-[4-(1-benzyl-1H-indol-4-ylmethoxy)-2-fluoro-phenyl]-propanoic acid

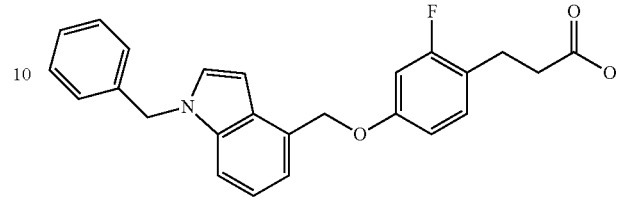

The compound (100 mg, 0.42 mmol) obtained from Preparation Example 131-2 and the compound (90 mg, 0.42 mmol) obtained from Preparation Example 149 were used to obtain the title compound (135 mg, 80%).

NMR:¹H-NMR(400 HMz, CDCl₃); δ 7.47 (d, 1H), 7.27 (m, 3H), 7.08 (m, 3H), 6.91 (d, 2H), 6.66 (m, 2H), 6.53 (d, 1H), 5.60 (s, 2H), 5.02 (s, 2H), 2.89 (t, 2H), 2.63 (t, 2H), 2.48 (s, 3H)

Example 55

Synthesis of 3-[4-(1-benzyl-7-methyl-1H-indol-6-ylmethoxy)-2-fluoro-phenyl]-propanoic acid

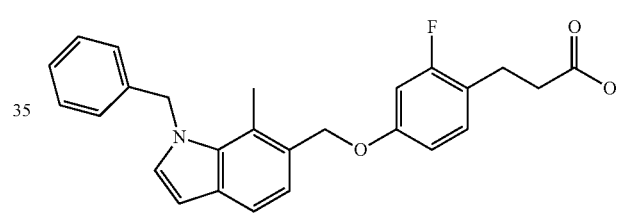

The compound (100 mg, 0.40 mmol) obtained from Preparation Example 17-2 and the compound (84 mg, 0.40 mmol) obtained from Preparation Example 149 were used to obtain the title compound (90.5 mg, 54%).

NMR:¹H-NMR(400 HMz, DMSO-d₆); δ 7.53 (d, 1H), 7.43 (m, 1H), 7.16-7.32 (m, 6H), 7.10 (m, 1H), 6.87 (m, 1H), 6.80 (m, 1H), 6.60 (m, 1H), 5.43 (s, 2H), 5.32 (s, 2H), 2.75 (t, 2H), 2.47 (t, 2H)

Example 56

Synthesis of (S)-3-[4-(7-methyl-1-thiazol-4-ylmethyl-1H-indol-6-ylmethoxy)-phenyl}-hex-4-ynoic acid

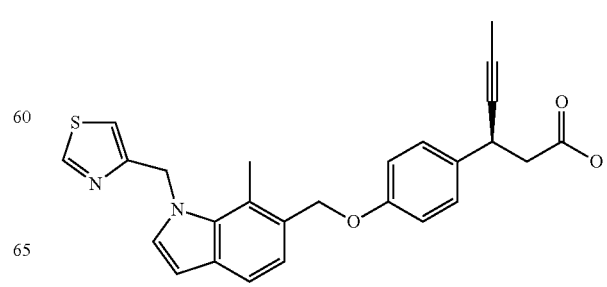

The compound (0.11 g, 0.38 mmol) obtained from Preparation Example 43-2 and the compound (0.10 g, 0.38 mmol) obtained from Preparation Example 155 were used to obtain the title compound (0.07 g, 43%).

NMR:$^1$H-NMR(400 HMz, CDCl$_3$); δ 8.82 (s, 1H), 7.47 (d, 1H), 7.28 (d, 2H), 7.12-7.14 (m, 2H), 6.92 (d, 2H), 6.54 (d, 2H), 5.75 (s, 2H), 5.10 (s, 2H), 4.04 (br s, 1H), 2.77-2.83 (m, 1H), 2.66-2.71 (m, 1H), 2.50 (s, 3H), 1.73 (s, 3H)

Example 57

Synthesis of (S)-3-{4-[7-methyl-1-(2-methyl-thiazol-4-ylmethyl)-1H-indol-6-ylmethoxy]-phenyl}-hex-4-ynoic acid

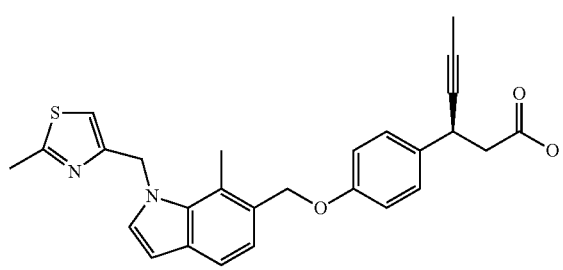 [SMILES: CC#C[C@@H](CC(=O)O)c1ccc(OCc2ccc3ccn(Cc4csc(C)n4)c3c2C)cc1]

The compound (0.10 g, 0.33 mmol) obtained from Preparation Example 44-2 and the compound (0.09 g, 0.33 mmol) obtained from Preparation Example 155 were used to obtain the title compound (0.08 g, 50%).

NMR:$^1$H-NMR(400 HMz, CDCl$_3$); δ 7.46 (d, 1H), 7.29 (d, 2H), 7.12 (d, 1H), 7.10 (d, 1H), 6.92 (d, 2H), 6.52 (d, 1H), 6.21 (s, 1H), 5.58 (s, 2H), 5.02 (s, 2H), 4.52 (t, 1H), 3.27-3.34 (m, 1H), 2.90-2.96 (m, 1H), 2.47 (s, 6H), 1.73 (s, 3H)

Example 58

Synthesis of (S)-3-[4-(2-benzyl-2H-indazol-6-ylmethoxy)-phenyl]-hex-4-ynoic acid

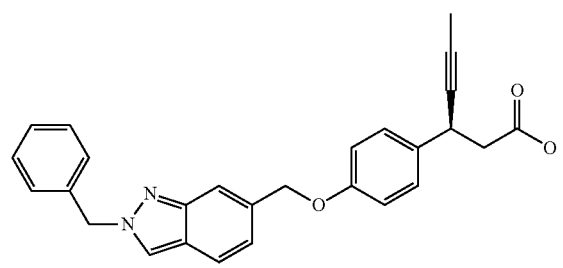 [SMILES: CC#C[C@@H](CC(=O)O)c1ccc(OCc2ccc3cn(Cc4ccccc4)nc3c2)cc1]

The compound (209 mg, 0.88 mmol) obtained from Preparation Example 57 and the compound (192 mg, 0.88 mmol) obtained from Preparation Example 155 were used to obtain the title compound (220 mg, 59%).

NMR:$^1$H-NMR(400 HMz, CDCl$_3$); δ 7.87 (s, 1H), 7.72 (s, 1H), 7.62 (d, 1H), 7.32-7.35 (m, 3H), 7.28-7.30 (m, 4H), 7.13 (dd, 1H), 6.94 (d, 2H), 5.59 (s, 2H), 5.13 (s, 2H), 4.04 (br s, 1H), 2.76-2.82 (m, 1H), 2.67-2.72 (m, 1H), 1.83 (s, 3H)

Example 59

Synthesis of (S)-3-[4-(1-benzyl-1H-indazol-6-ylmethoxy)-phenyl]-hex-4-ynoic acid

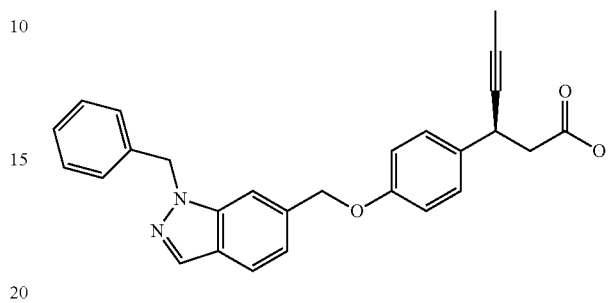

The compound (150 mg, 0.63 mmol) obtained from Preparation Example 56 and the compound (137 mg, 0.63 mmol) obtained from Preparation Example 155 were used to obtain the title compound (100 mg, 37%).

NMR:$^1$H-NMR(400 HMz, DMSO-d$_6$); δ 8.12 (s, 1H), 7.80 (d, 1H), 7.78 (s, 1H), 7.28-7.32 (m, 3H), 7.22-7.26 (m, 5H), 6.91 (d, 2H), 5.68 (s, 2H), 5.18 (s, 2H), 4.01 (br s, 1H), 2.21-2.23 (m, 1H), 2.09-2.10 (m, 1H), 1.76 (s, 3H)

Example 60

Synthesis of (S)-3-[4-(7-methyl-1-pyrazin-2-ylmethyl-1H-indol-6-ylmethoxy)-phenyl]-hex-4-ynoic acid

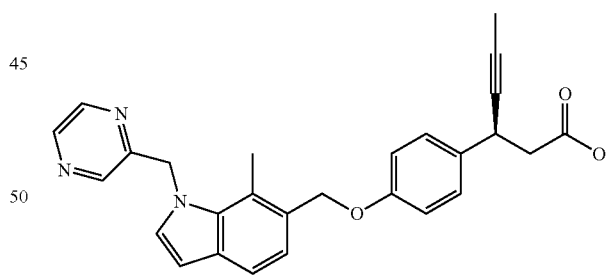

The compound (0.06 g, 0.21 mmol) obtained from Preparation Example 38-2 and the compound (0.05 g, 0.21 mmol) obtained from Preparation Example 155 were used to obtain the title compound (0.03 g, 31%).

NMR:$^1$H-NMR(500 MHz, DMSO-d$_6$); δ 8.57 (d, 1H), 8.51 (d, 1H), 8.02 (s, 1H), 7.46 (d, 1H), 7.36 (d, 1H), 7.17 (d, 1H), 7.16 (d, 1H), 7.06 (d, 1H), 6.83 (d, 1H), 6.81 (d, 1H), 6.48 (d, 1H), 5.81 (s, 2H), 5.00 (s, 2H), 3.92 (br s, 1H), 2.40 (s, 3H), 2.17-2.21 (m, 1H), 2.03-2.06 (m, 1H), 1.70 (s, 3H)

Example 61

Synthesis of (S)-3-[4-(7-methyl-1-pyrimidin-4-ylmethyl-1H-indol-6-ylmethoxy)-phenyl]-hex-4-ynoic acid

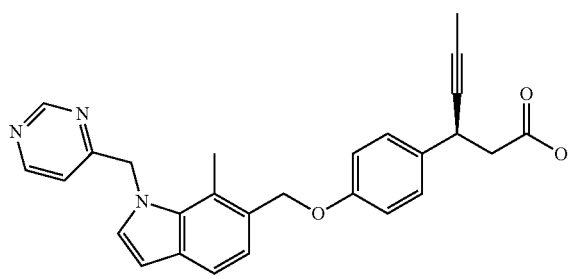 [SMILES: CC#C[C@@H](CC(=O)O)c1ccc(OCc2ccc3ccn(Cc4ccncn4)c3c2C)cc1]

The compound (0.08 g, 0.30 mmol) obtained from Preparation Example 39 and the compound (0.07 g, 0.30 mmol) obtained from Preparation Example 155 were used to obtain the title compound (0.02 g, 13%).

NMR: $^1$H-NMR(400 HMz, CDCl$_3$); δ 9.20 (s, 1H), 8.57 (d, 1H), 7.51 (d, 1H), 7.28 (d, 2H), 7.17 (d, 2H), 7.08 (d, 1H), 6.90 (d, 1H), 6.60 (d, 1H), 6.47 (d, 1H), 5.57 (s, 2H), 5.05 (s, 2H), 4.05 (br s, 1H), 2.77-2.83 (m, 1H), 2.67-2.73 (m, 1H), 2.41 (s, 3H), 1.72 (s, 3H)

Example 62

Synthesis of (S)-3-[4-(1-benzyl-3-fluoro-7-methyl-1H-indol-6-ylmethoxy)-phenyl]-hex-4-ynoic acid

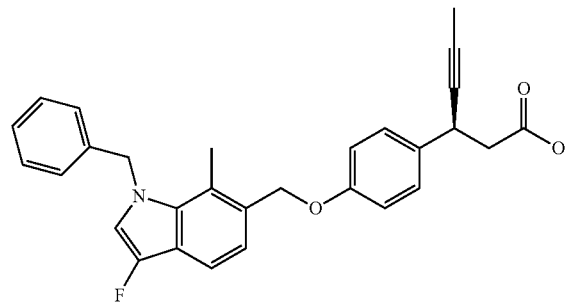 [SMILES: CC#C[C@@H](CC(=O)O)c1ccc(OCc2ccc3c(F)cn(Cc4ccccc4)c3c2C)cc1]

The compound (50 mg, 0.19 mmol) obtained from Preparation Example 49-2 and the compound (41 mg, 0.19 mmol) obtained from Preparation Example 155 were used to obtain the title compound (50 mg, 59%).

NMR: $^1$H-NMR(400 HMz, CDCl$_3$); δ 7.49 (d, 1H), 7.26-7.30 (m, 5H), 7.15 (d, 1H), 6.91-6.95 (m, 4H), 6.86 (d, 1H), 5.50 (s, 2H), 5.05 (s, 2H), 4.05 (br s, 1H), 2.77-2.83 (m, 1H), 2.68-2.73 (m, 1H), 2.49 (s, 3H), 1.82 (s, 3H)

Example 63

Synthesis of (S)-3-{4-[7-methyl-1-(1-methyl-1H-pyrazol-4-ylmethyl)-1H-indol-6-ylmethoxy)-phenyl]-hex-4-ynoic acid

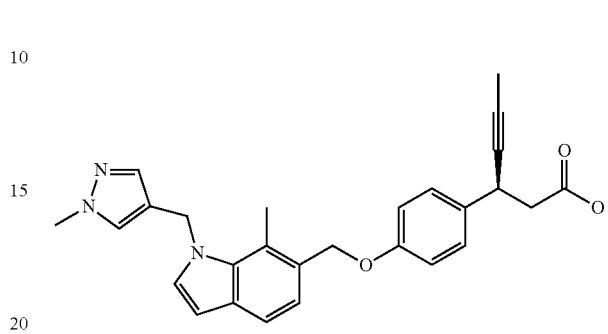

The compound (0.06 g, 0.24 mmol) obtained from Preparation Example 45 and the compound (0.05 g, 0.24 mmol) obtained from Preparation Example 155 were used to obtain the title compound (0.09 g, 82%).

NMR: $^1$H-NMR(400 HMz, CDCl$_3$); δ 7.53 (d, 1H), 7.30 (d, 2H), 7.29 (s, 1H), 7.11 (d, 1H), 7.06 (d, 1H), 6.90-6.95 (m, 3H), 6.47 (d, 1H), 5.47 (s, 2H), 5.09 (s, 2H), 4.09 (t, 1H), 3.77 (s, 3H), 2.73-2.82 (m, 1H), 2.62-2.72 (m, 1H), 2.57 (s, 3H), 1.81 (s, 3H)

Example 64

Synthesis of (S)-3-[4-(7-methyl-1-pyrimidin-2-ylmethyl-1H-indol-6-ylmethoxy)-phenyl]-hex-4-ynoic acid

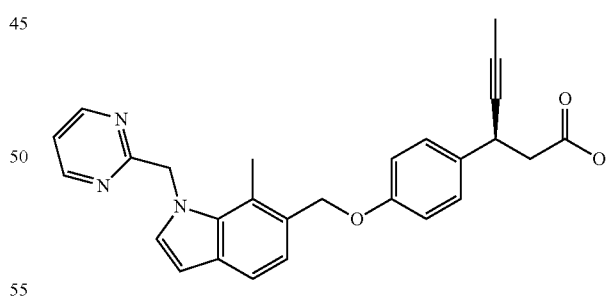

The compound (0.12 g, 0.45 mmol) obtained from Preparation Example 40 and the compound (0.10 g, 0.45 mmol) obtained from Preparation Example 155 were used to obtain the title compound (0.08 g, 37%).

NMR: $^1$H-NMR(400 HMz, CDCl$_3$); δ 8.67 (d, 2H), 7.45 (d, 1H), 7.27 (d, 2H), 7.20 (d, 1H), 7.16 (dd, 1H), 7.03 (d, 1H), 6.91 (d, 2H), 6.53 (d, 1H), 5.77 (s, 2H), 5.05 (s, 2H), 4.03 (t, 1H), 2.76-2.82 (m, 1H), 2.63-2.72 (m, 1H), 2.53 (s, 3H), 1.81 (s, 3H)

Example 65

Synthesis of 3-[4-(1-benzyl-1H-indazol-6-yl-methoxy)-phenyl]-3-(4,5-dihydro-isoxazol-3-yl)-propanoic acid

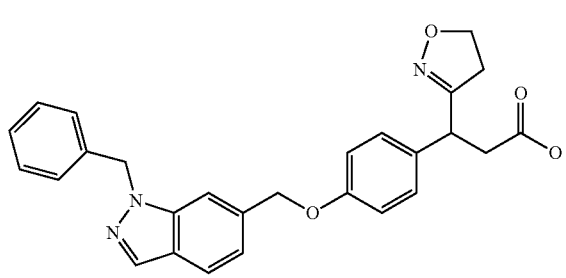 [SMILES: O=C(O)CC(C1=NOCC1)c1ccc(OCc2ccc3cnn(Cc4ccccc4)c3c2)cc1]

The compound (0.27 g, 1.20 mmol) obtained from Preparation Example 56 and the compound (0.20 g, 0.80 mmol) obtained from Preparation Example 156 were used to obtain the title compound (0.11 g, 29%).

NMR:$^1$H-NMR(400 HMz, DMSO-$d_6$, Na salt); δ 8.10 (s, 1H), 7.79 (d, 2H), 7.31 (m, 3H), 7.24 (d, 3H), 7.16 (d, 2H), 6.95 (d, 2H), 5.66 (s, 2H), 5.16 (s, 2H), 4.13 (t, 1H), 4.06 (t, 2H), 2.79 (t, 2H), 2.53 (dd, 1H), 2.32 (dd, 1H)

Example 66

Synthesis of (S)-3-{4-[1-(4-fluoro-benzyl)-1H-indazol-6-ylmethoxy]-phenyl}-hex-4-ynoic acid

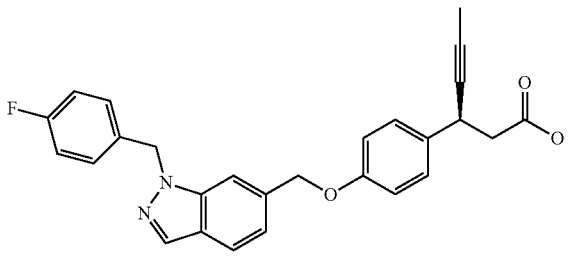

The compound (0.2 g, 0.76 mmol) obtained from Preparation Example 58 and the compound (0.15 g, 0.69 mmol) obtained from Preparation Example 155 were used to obtain the title compound (0.15 g, 47%).

NMR:$^1$H-NMR(400 HMz, DMSO-$d_6$, Na salt); δ 8.10 (s, 1H), 7.81 (s, 1H), 7.78 (d, 1H), 7.20-7.29 (m, 5H), 7.15 (t, 2H), 6.93 (d, 2H), 5.65 (s, 2H), 5.17 (s, 2H), 4.00 (m, 1H), 2.32 (dd, 1H), 2.19 (dd, 1H), 1.75 (s, 3H)

Example 67

Synthesis of (S)-3-{4-[2-(4-fluoro-benzyl)-2H-indazol-6-ylmethoxy]-phenyl}-hex-4-ynoic acid

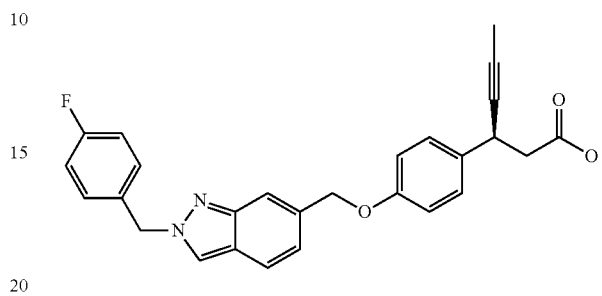

The compound (0.2 g, 0.76 mmol) obtained from Preparation Example 59 and the compound (0.15 g, 0.69 mmol) obtained from Preparation Example 155 were used to obtain the title compound (0.18 g, 48%).

NMR:$^1$H-NMR(400 HMz, DMSO-$d_6$, Na salt)); δ 8.47 (s, 1H), 7.72 (d, 1H), 7.64 (s, 1H), 7.39 (t, 2H), 7.15-7.24 (m, 4H), 7.10 (d, 1H), 6.91 (d, 2H), 5.62 (s, 2H), 5.12 (s, 2H), 3.97 (m, 1H), 2.30 (dd, 1H), 2.16 (dd, 1H), 1.74 (s, 3H)

Example 68

Synthesis of (S)-3-[4-(1-pyrimidin-2-ylmethyl-1H-indazol-6-ylmethoxy)-phenyl]-hex-4-ynoic acid

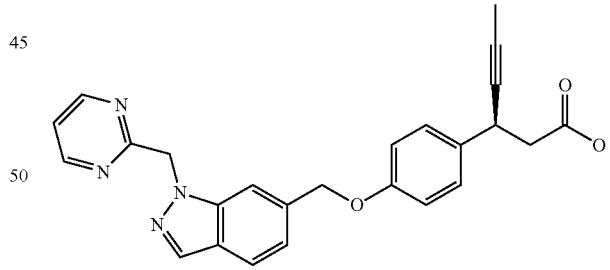 [SMILES: CC#C[C@@H](CC(=O)O)c1ccc(OCc2ccc3cnn(Cc4ccc(F)cc4)c3c2)cc1]

The compound (0.13 g, 0.55 mmol) obtained from Preparation Example 60-2 and the compound (0.14 g, 0.55 mmol) obtained from Preparation Example 155 were used to obtain the title compound (0.10 g, 39%).

NMR:$^1$H-NMR(400 HMz, DMSO-$d_6$); δ 8.73 (d, 2H), 8.10 (s, 1H), 7.80 (d, 1H), 7.72 (s, 1H), 7.43 (dd, 1H), 7.25 (d, 2H), 7.23 (d, 1H), 6.90 (d, 2H), 5.89 (s, 2H), 5.18 (s, 2H), 3.99 (br s, 1H), 2.26-2.31 (m, 1H), 2.10-2.16 (m, 1H), 1.77 (s, 3H)

Example 69

Synthesis of (S)-3-[4-(2-pyrimidin-2-ylmethyl-2H-indazol-6-ylmethoxy]-phenyl}-hex-4-ynoic acid

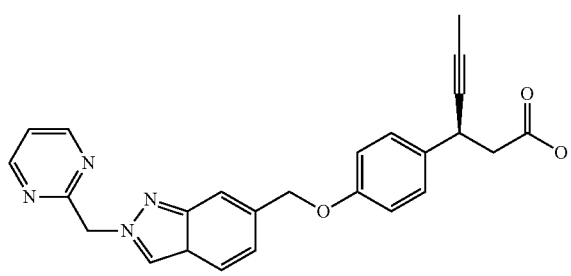

The compound (0.2 g, 0.83 mmol) obtained from Preparation Example 61 and the compound (0.15 g, 0.69 mmol) obtained from Preparation Example 155 were used to obtain the title compound (0.12 g, 27%).

NMR:$^1$H-NMR(400 HMz, DMSO-d$_6$); δ 8.79 (d, 2H), 8.52 (s, 1H), 7.76 (d, 1H), 7.62 (s, 1H), 7.46 (dd, 1H), 7.23 (d, 2H), 7.12 (d, 1H), 6.91 (d, 2H), 5.89 (s, 2H), 5.15 (s, 2H), 3.98 (br s, 1H), 2.23-2.28 (m, 1H), 2.08-2.11 (m, 1H), 1.75 (s, 3H)

Example 70

Synthesis of (S)-3-[4-(1-pyrazin-2-ylmethyl-1H-indazol-6-ylmethoxy]-phenyl}-hex-4-ynoic acid

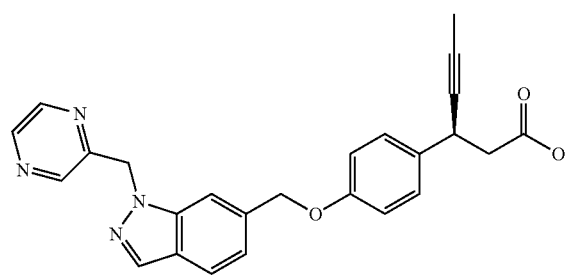

The compound (0.2 g, 0.83 mmol) obtained from Preparation Example 62 and the compound (0.15 g, 0.69 mmol) obtained from Preparation Example 155 were used to obtain the title compound (0.12 g, 27%)

NMR:$^1$H-NMR(400 HMz, DMSO-d$_6$, Na salt); δ 8.56 (d, 2H), 8.49 (s, 1H), 8.12 (s, 1H), 7.81 (s, 1H), 7.80 (d, 1H), 7.24 (m, 3H), 6.92 (d, 2H), 5.85 (s, 2H), 5.18 (s, 2H), 4.01 (m, 1H), 2.34 (dd, 1H), 2.17 (dd, 1H), 1.75 (s, 3H)

Example 71

Synthesis of (S)-3-{4-[1-(4-fluoro-benzyl)-1H-indazol-4-ylmethoxy]-phenyl}-hex-4-ynoic acid

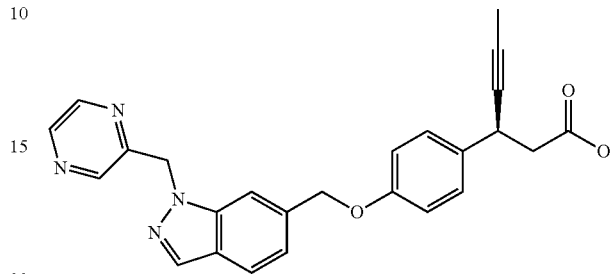

The compound (190 mg, 0.74 mmol) obtained from Preparation Example 135-2 and the compound (373 mg, 1.48 mmol) obtained from Preparation Example 155 were used to obtain the title compound (180 mg, 55%).

NMR:$^1$H-NMR(400 HMz, DMSO-d$_6$); δ 8.23 (s, 1H), 7.70 (d, 1H), 7.39 (d, 1H), 7.32 (d, 1H), 7.30 (d, 1H), 7.24 (d, 1H), 7.23 (d, 2H), 7.16 (d, 1H), 7.13 (d, 1H), 6.95 (d, 2H), 5.68 (s, 2H), 5.41 (s, 2H), 3.98 (br s, 1H), 2.23-2.28 (m, 1H), 2.08-2.11 (m, 1H), 1.75 (s, 3H)

Example 72

Synthesis of (S)-3-{4-[2-(4-fluoro-benzyl)-2H-indazol-4-ylmethoxy]-phenyl}-hex-4-ynoic acid

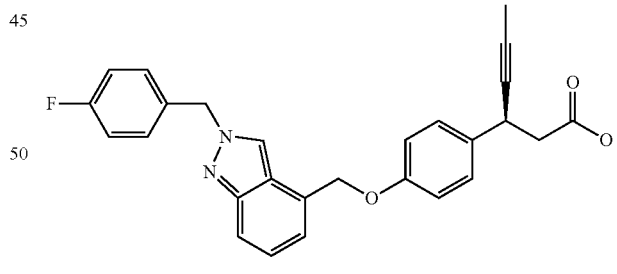

The compound (150 mg, 0.59 mmol) obtained from Preparation Example 136-2 and the compound (295 mg, 1.17 mmol) obtained from Preparation Example 155 were used to obtain the title compound (150 mg, 58%).

NMR:$^1$H-NMR(400 HMz, DMSO-d$_6$); δ 8.59 (s, 1H), 7.56 (d, 1H), 7.45 (d, 1H), 7.43 (d, 1H), 7.17-7.26 (m, 5H), 7.12 (d, 1H), 6.94 (d, 2H), 5.66 (s, 2H), 5.31 (s, 2H), 3.99 (br s, 1H), 2.25-2.30 (m, 1H), 2.09-2.15 (m, 1H), 1.76 (s, 3H)

Example 73

Synthesis of (S)-3-{4-[1-(5-methyl-pyrazin-2-ylmethyl)-1H-indazol-6-ylmethoxy]-phenyl}-hex-4-ynoic acid

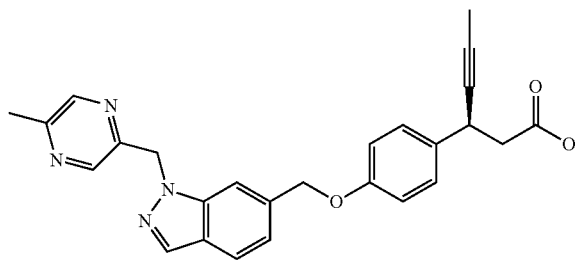 [SMILES: CC#C[C@@H](CC(=O)O)c1ccc(OCc2ccc3cnn(Cc4cnc(C)cn4)c3c2)cc1]

The compound (0.20 g, 0.82 mmol) obtained from Preparation Example 63 and the compound (0.16 g, 0.75 mmol) obtained from Preparation Example 155 were used to obtain the title compound (0.15 g, 18%).

NMR:$^1$H-NMR(400 HMz, DMSO-d$_6$, Na salt); δ 8.45 (s, 1H), 8.40 (s, 1H), 8.12 (s, 1H), 7.83 (s, 1H), 7.80 (d, 1H), 7.26 (m, 3H), 6.95 (d, 2H), 5.80 (s, 2H), 5.20 (s, 2H), 4.03 (m, 1H), 2.47 (s, 3H), 2.35 (dd, 1H), 2.22 (dd, 1H), 1.77 (s, 3H)

Example 74

Synthesis of (S)-3-{4-[2-(5-methyl-pyrazin-2-ylmethyl)-2H-indazol-6-ylmethoxy]-phenyl}-hex-4-ynoic acid

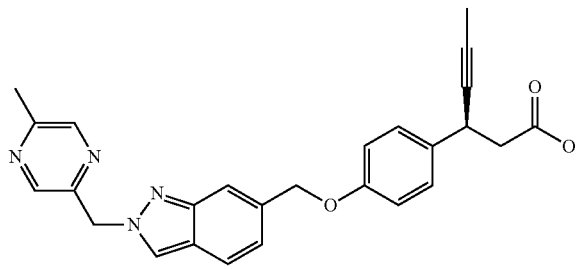 [SMILES: CC#C[C@@H](CC(=O)O)c1ccc(OCc2ccc3cn(Cc4cnc(C)cn4)nc3c2)cc1]

The compound (0.20 g, 0.82 mmol) obtained from Preparation Example 64 and the compound (0.16 g, 0.75 mmol) obtained from Preparation Example 155 were used to obtain the title compound (0.08 g, 22%).

NMR:$^1$H-NMR(400 HMz, DMSO-d$_6$, Na salt); δ 8.52 (d, 2H), 8.48 (s, 1H), 7.73 (d, 1H), 7.61 (s, 1H), 7.24 (d, 2H), 7.11 (d, 1H), 6.91 (d, 2H), 5.77 (s, 2H), 5.12 (s, 2H), 3.98 (m, 1H), 2.47 (s, 3H), 2.32 (dd, 1H), 2.16 (dd, 1H), 1.74 (s, 3H)

Example 75

Synthesis of (S)-3-[4-(1-pyrimidin-4-ylmethyl-1H-indazol-6-ylmethoxy)-phenyl]-hex-4-ynoic acid

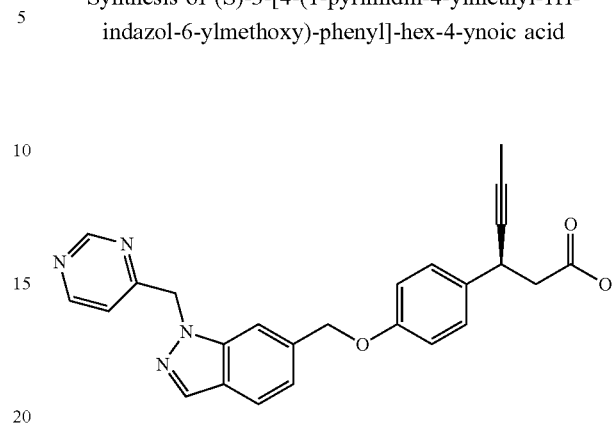

The compound (0.13 g, 0.55 mmol) obtained from Preparation Example 65 and the compound (0.14 g, 0.55 mmol) obtained from Preparation Example 155 were used to obtain the title compound (0.05 g, 21%).

NMR:$^1$H-NMR(400 HMz, DMSO-d$_6$); δ 9.12 (s, 1H), 8.72 (d, 1H), 8.18 (s, 1H), 7.83 (d, 1H), 7.78 (s, 1H), 7.28 (s, 1H), 7.24 (d, 2H), 7.00 (d, 1H), 6.91 (d, 2H), 5.83 (s, 2H), 5.18 (s, 2H), 3.99 (br s, 1H), 2.25-2.30 (m, 1H), 2.10-2.16 (m, 1H), 1.76 (s, 3H)

Example 76

Synthesis of (S)-3-[4-(2-pyrimidin-4-ylmethyl-2H-indazol-6-ylmethoxy]-phenyl}-hex-4-ynoic acid

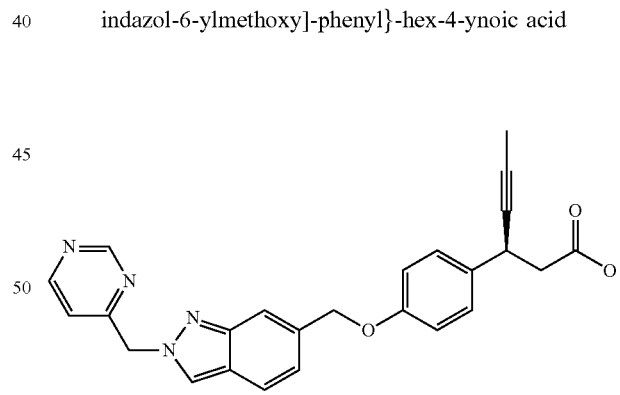

The compound (0.03 g, 0.13 mmol) obtained from Preparation Example 66 and the compound (0.03 g, 0.13 mmol) obtained from Preparation Example 155 were used to obtain the title compound (0.02 g, 30%).

NMR:$^1$H-NMR(400 HMz, DMSO-d$_6$); δ 9.16 (s, 1H), 8.77 (d, 1H), 8.57 (s, 1H), 7.78 (d, 1H), 7.67 (s, 1H), 7.24 (d, 2H), 7.16 (s, 1H), 7.14-7.16 (m, 1H), 6.92 (d, 2H), 5.83 (s, 2H), 5.16 (s, 2H), 3.99 (br s, 1H), 2.25-2.30 (m, 1H), 2.10-2.15 (m, 1H), 1.75 (s, 3H)

Example 77

Synthesis of (S)-3-{4-[1-(5-methyl-pyrazin-2-ylmethyl)-1H-indazol-4-ylmethoxy]-phenyl}-hex-4-ynoic acid

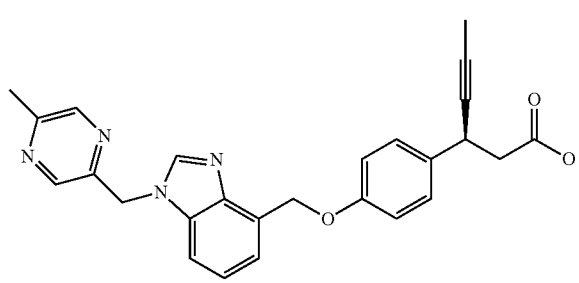 [SMILES: CC#C[C@@H](CC(=O)O)c1ccc(OCc2cccc3c2ncn3Cc2cnc(C)cn2)cc1]

The compound (180 mg, 0.71 mmol) obtained from Preparation Example 137-2 and the compound (155 mg, 0.71 mmol) obtained from Preparation Example 155 were used to obtain the title compound (220 mg, 70%).

NMR: $^1$H-NMR(400 HMz, DMSO-d$_6$); δ 8.46 (s, 1H), 8.42 (s, 1H), 8.22 (s, 1H), 7.70 (d, 1H), 7.40 (dd, 1H), 7.26 (d, 3H), 6.95 (d, 2H), 5.81 (s, 2H), 5.41 (s, 2H), 3.97 (br s, 1H), 2.46 (s, 3H), 2.23-2.78 (m, 1H), 2.07-2.13 (m, 1H), 1.75 (s, 3H)

Example 78

Synthesis of (S)-3-{4-[2-(5-methyl-pyrazin-2-ylmethyl)-2H-indazol-4-ylmethoxy]-phenyl}-hex-4-ynoic acid

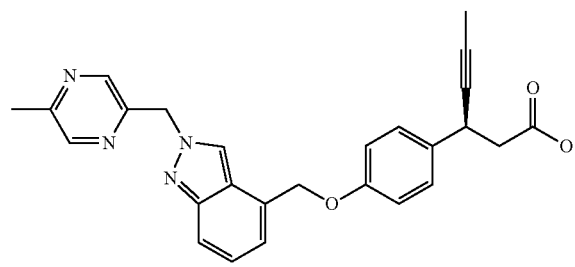 [SMILES: CC#C[C@@H](CC(=O)O)c1ccc(OCc2cccc3nn(Cc4cnc(C)cn4)cc23)cc1]

The compound (100 mg, 0.39 mmol) obtained from Preparation Example 138-2 and the compound (85 mg, 0.39 mmol) obtained from Preparation Example 155 were used to obtain the title compound (86 mg, 50%).

NMR: $^1$H-NMR(400 HMz, DMSO-d$_6$); δ 8.63 (s, 1H), 8.55 (s, 1H), 8.51 (d, 1H), 7.53 (d, 1H), 7.24 (d, 3H), 7.14 (d, 1H), 6.95 (d, 2H), 5.81 (s, 2H), 5.32 (s, 2H), 4.00 (br s, 1H), 2.73-2.80 (m, 1H), 2.87-2.94 (m, 1H), 1.76 (s, 3H)

Example 79

Synthesis of (S)-3-[4-(1-pyridin-3-ylmethyl-1H-indazol-6-ylmethoxy)-phenyl]-hex-4-ynoic acid

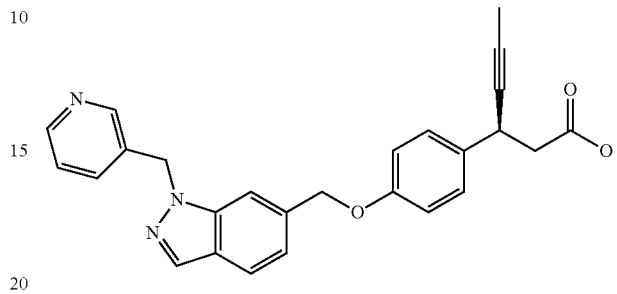

The compound (240 mg, 1.00 mmol) obtained from Preparation Example 67 and the compound (218 mg, 1.00 mmol) obtained from Preparation Example 155 were used to obtain the title compound (320 mg, 75%).

NMR: $^1$H-NMR(400 HMz, DMSO-d$_6$); δ 8.55 (d, 1H), 8.48 (dd, 1H), 8.14 (s, 1H), 7.89 (s, 1H), 7.79 (d, 1H), 7.59 (dd, 1H), 7.34 (dd, 1H), 7.25 (dd, 3H), 6.92 (d, 2H), 5.74 (s, 2H), 5.20 (s, 2H), 4.00 (br s, 1H), 2.24-2.30 (m, 1H), 2.09-2.14 (m, 1H), 1.76 (s, 3H)

Example 80

Synthesis of (S)-3-[4-(2-pyridin-3-ylmethyl-2H-indazol-6-ylmethoxy)-phenyl]-hex-4-ynoic acid

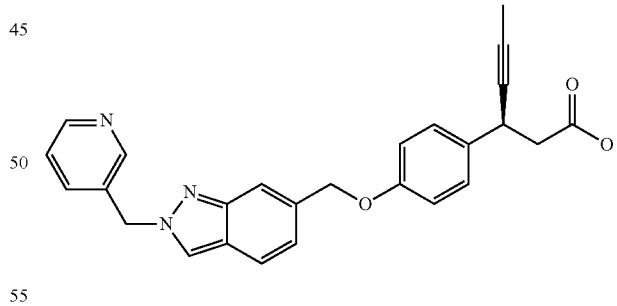

The compound (150 mg, 0.63 mmol) obtained from Preparation Example 68 and the compound (137 mg, 0.63 mmol) obtained from Preparation Example 155 were used to obtain the title compound (98 mg, 37%).

NMR: $^1$H-NMR(400 HMz, DMSO-d$_6$); δ 8.63 (s, 1H), 8.54 (s, 1H), 8.53 (d, 1H), 7.73 (d, 2H), 7.66 (s, 1H), 7.39 (d, 1H), 7.23 (d, 2H), 7.11 (d, 1H), 6.91 (d, 2H), 5.71 (s, 2H), 5.14 (s, 2H), 3.99 (br s, 1H), 2.25-2.31 (m, 1H), 2.10-2.16 (m, 1H), 1.76 (s, 3H)

Example 81

Synthesis of (S)-3-{4-[7-methyl-1-(6-methyl-pyridin-3-ylmethyl)-1H-indol-6-ylmethoxy]-phenyl}-hex-4-ynoic acid

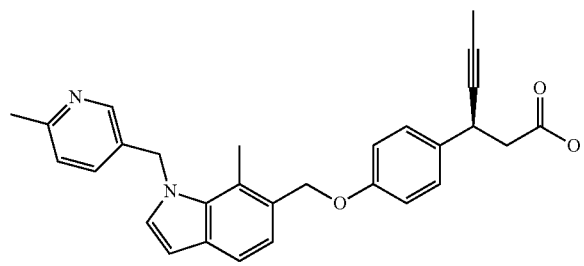 [SMILES: CC#C[C@@H](CC(=O)O)c1ccc(OCc2ccc3ccn(Cc4ccc(C)nc4)c3c2C)cc1]

The compound (0.12 g, 0.49 mmol) obtained from Preparation Example 36-2 and the compound (0.13 g, 0.49 mmol) obtained from Preparation Example 155 were used to obtain the title compound (0.07 g, 33%).

NMR: $^1$H-NMR(400 HMz, DMSO-d$_6$); δ 8.05 (s, 1H), 7.46 (d, 1H), 7.39 (d, 1H), 7.21 (d, 2H), 7.16 (d, 1H), 7.08-7.11 (m, 2H), 6.86 (d, 2H), 6.51 (d, 1H), 5.68 (s, 2H), 5.04 (s, 2H), 3.97 (br s, 1H), 2.43 (s, 3H), 2.41 (s, 3H), 2.27-2.30 (m, 1H), 2.10-2.13 (m, 1H), 1.74 (s, 3H)

Example 82

Synthesis of (S)-3-{4-[1-(1-methyl-1H-pyrazol-4-ylmethyl)-1H-indazol-6-ylmethoxy]-phenyl}-hex-4-ynoic acid

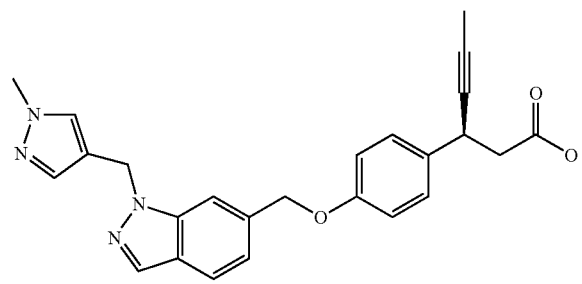 [SMILES: CC#C[C@@H](CC(=O)O)c1ccc(OCc2ccc3cnn(Cc4cnn(C)c4)c3c2)cc1]

The compound (0.16 g, 0.65 mmol) obtained from Preparation Example 69 and the compound (0.17 g, 0.65 mmol) obtained from Preparation Example 155 were used to obtain the title compound (0.19 g, 64%).

NMR: $^1$H-NMR(400 HMz, CDCl$_3$); δ 8.05 (s, 1H), 7.46 (d, 1H), 7.39 (d, 1H), 7.21 (d, 2H), 7.16 (d, 1H), 7.08-7.11 (m, 2H), 6.86 (d, 2H), 6.51 (d, 1H), 5.68 (s, 2H), 5.04 (s, 2H), 3.97 (br s, 1H), 2.43 (s, 3H), 2.41 (s, 3H), 2.27-2.30 (m, 1H), 2.10-2.13 (m, 1H), 1.74 (s, 3H)

Example 83

Synthesis of (S)-3-[4-(1-benzyl-7-methyl-1H-indol-6-ylmethoxy)-phenyl]-3-isoxazol-3-yl-propanoic acid

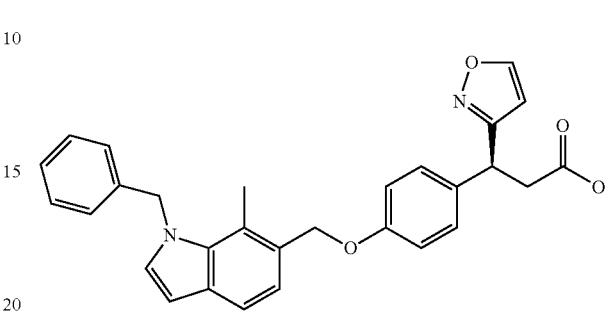

The compound (0.20 g, 0.80 mmol) obtained from Preparation Example 17-2 and the compound (0.18 g, 0.76 mmol) obtained from Preparation Example 157 were used to obtain the title compound (0.21 g, 57%).

NMR: $^1$H-NMR(400 HMz, DMSO-d$_6$, Na salt)); δ 8.65 (s, 1H), 7.45 (d, 1H), 7.40 (d, 1H), 7.29 (m, 2H), 7.22 (m, 1H), 7.16 (d, 2H), 7.08 (d, 1H), 6.89 (m, 4H), 6.50 (d, 1H), 6.41 (s, 1H), 5.68 (s, 2H), 5.01 (s, 2H), 4.51 (t, 1H), 2.62 (dd, 1H), 2.48 (dd, 1H), 2.40 (s, 3H)

Example 84

Synthesis of (S)-3-{4-[1-(4-fluoro-benzyl)-7-methyl-1H-indol-6-ylmethoxy]-phenyl}-3-isoxazol-3-yl-propanoic acid

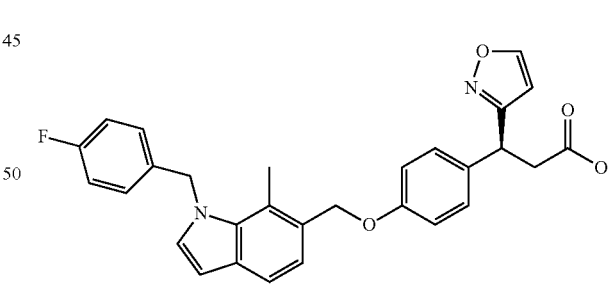

The compound (0.20 g, 0.80 mmol) obtained from Preparation Example 20-2 and the compound (0.18 g, 0.76 mmol) obtained from Preparation Example 157 were used to obtain the title compound (0.18 g, 43%).

NMR: $^1$H-NMR(400 HMz, DMSO-d$_6$, Na salt); δ 8.65 (s, 1H), 7.45 (d, 1H), 7.40 (d, 1H), 7.14 (m, 4H), 7.09 (d, 1H), 6.93 (m, 2H), 6.89 (d, 1H), 6.50 (d, 1H), 6.40 (s, 1H), 5.67 (s, 2H), 5.02 (s, 2H), 4.48 (t, 1H), 2.51 (dd, 1H), 2.40 (dd, 1H), 2.39 (s, 3H)

Example 85

Synthesis of (S)-3-[4-(1-benzyl-1H-indazol-6-yl-methoxy)-phenyl]-3-isoxazol-3-yl-propanoic acid

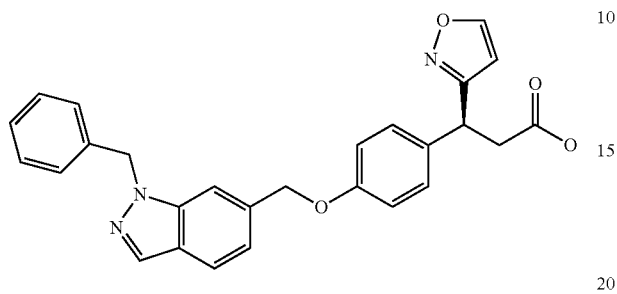

The compound (0.20 g, 0.84 mmol) obtained from Preparation Example 56 and the compound (0.18 g, 0.76 mmol) obtained from Preparation Example 157 were used to obtain the title compound (0.26 g, 72%).

NMR:$^1$H-NMR(400 HMz, DMSO-$d_6$, Na salt); δ 8.67 (s, 1H), 8.10 (s, 1H), 7.78 (d, 2H), 7.17-7.29 (m, 8H), 6.92 (d, 2H), 6.42 (s, 1H), 5.65 (s, 2H), 5.15 (s, 2H), 4.54 (t, 1H), 2.66 (dd, 1H), 2.50 (dd, 1H)

Example 86

Synthesis of (S)-3-{4-[1-(4-fluoro-benzyl)-1H-indazol-6-ylmethoxy]-phenyl}-3-isoxazol-3-yl-propanoic acid

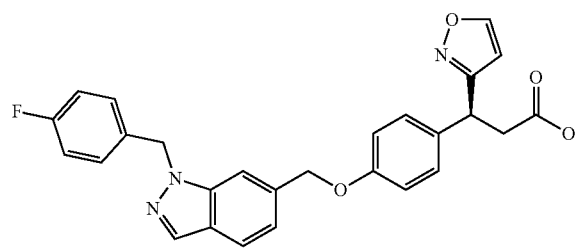 [SMILES: O=C(O)C[C@@H](c1ccc(OCc2ccc3cnn(Cc4ccc(F)cc4)c3c2)cc1)c1ccon1]

The compound (0.20 g, 0.80 mmol) obtained from Preparation Example 58 and the compound (0.18 g, 0.76 mmol) obtained from Preparation Example 157 were used to obtain the title compound (0.25 g, 67%).

NMR:$^1$H-NMR(400 HMz, DMSO-$d_6$, Na salt); δ 8.66 (s, 1H), 8.10 (s, 1H), 7.80 (s, 1H), 7.29 (m, 2H), 7.10-7.21 (m, 5H), 6.92 (d, 2H), 6.42 (s, 1H), 5.65 (s, 2H), 5.15 (s, 2H), 4.52 (t, 1H), 2.51 (dd, 1H), 2.47 (dd, 1H)

Example 87

Synthesis of (S)-3-[4-(1-isobutyl-1H-indazol-6-yl-methoxy)-phenyl]-3-isoxazol-3-yl-propanoic acid

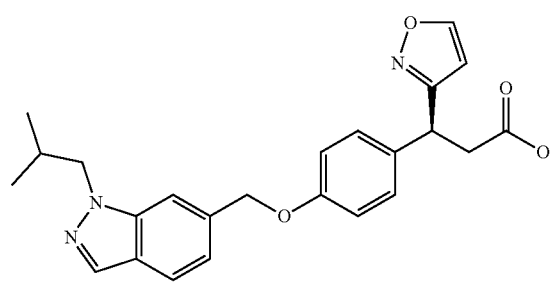 [SMILES: CC(C)Cn1ncc2ccc(COc3ccc([C@H](CC(=O)O)c4ccon4)cc3)cc21]

The compound (0.20 g, 0.80 mmol) obtained from Preparation Example 75-1 and the compound (0.18 g, 0.76 mmol) obtained from Preparation Example 157 were used to obtain the title compound (0.15 g, 45%).

NMR:$^1$H-NMR(400 HMz, DMSO-$d_6$, Na salt); δ 8.67 (s, 1H), 8.05 (s, 1H), 7.75 (d, 2H), 7.20 (d, 3H), 6.94 (d, 2H), 6.42 (s, 1H), 5.18 (s, 2H), 4.54 (t, 1H), 4.21 (d, 2H), 2.65 (dd, 1H), 2.55 (dd, 1H), 2.18 (m, 1H), 0.84 (d, 3H)

Example 88

Synthesis of (S)-3-[4-(2-isobutyl-2H-indazol-6-yl-methoxy)-phenyl]-3-isoxazol-3-yl-propanoic acid

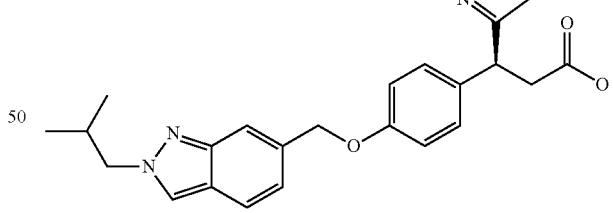

The compound (0.20 g, 0.80 mmol) obtained from Preparation Example 75-2 and the compound (0.18 g, 0.76 mmol) obtained from Preparation Example 157 were used to obtain the title compound (0.20 g, 60%).

NMR:$^1$H-NMR(400 HMz, DMSO-$d_6$, Na salt); δ 8.66 (s, 1H), 8.33 (s, 1H), 7.70 (d, 1H), 7.64 (s, 1H), 7.19 (d, 2H), 7.08 (d, 1H), 6.93 (d, 2H), 6.42 (s, 1H), 5.11 (s, 2H), 4.52 (t, 1H), 4.22 (d, 2H), 2.61 (dd, 1H), 2.51 (dd, 1H), 2.27 (m, 1H), 0.86 (d, 3H)

Example 89

Synthesis of (S)-3-isoxazol-3-yl-3-[4-(7-methyl-1-pyrazin-2-ylmethyl-1H-indol-6-ylmethoxy)-phenyl]-propanoic acid

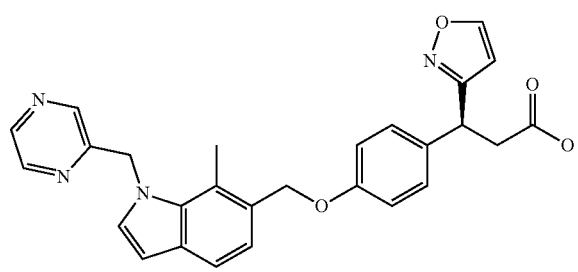 [SMILES: Cc1c(COc2ccc([C@H](CC(=O)O)c3ccon3)cc2)ccc2ccn(Cc3cnccn3)c12]

The compound (180 mg, 0.71 mmol) obtained from Preparation Example 38-2 and the compound (175 mg, 0.71 mmol) obtained from Preparation Example 157 were used to obtain the title compound (120 mg, 36%).

NMR:$^1$H-NMR(400 HMz, DMSO-$d_6$); δ 8.67 (d, 1H), 8.62 (d, 1H), 8.57 (d, 1H), 8.08 (s, 1H), 7.51 (d, 1H), 7.41 (d, 1H), 7.16 (d, 1H), 7.14 (d, 1H), 7.10 (d, 1H), 6.88 (d, 2H), 6.53 (d, 1H), 6.41 (d, 1H), 5.86 (s, 2H), 5.05 (s, 2H), 4.51 (br s, 1H), 2.50-2.52 (m, 1H), 2.45 (s, 3H), 2.40-2.42 (m, 1H)

Example 90

Synthesis of (S)-3-[4-(1-benzyl-1H-pyrrolo[2,3-b]pyridin-6-ylmethoxy)-phenyl]-hex-4-ynoic acid

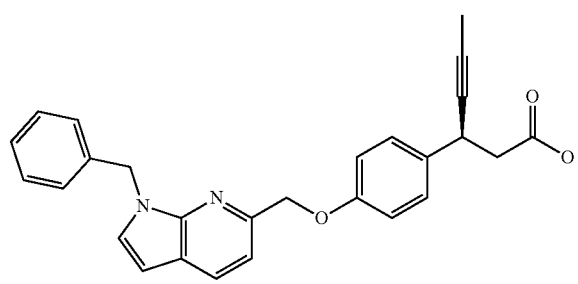 [SMILES: CC#C[C@@H](CC(=O)O)c1ccc(OCc2ccc3ccn(Cc4ccccc4)c3n2)cc1]

The compound (140 mg, 0.59 mmol) obtained from Preparation Example 54-2 and the compound (139 mg, 0.59 mmol) obtained from Preparation Example 155 were used to obtain the title compound (90 mg, 36%).

NMR:$^1$H-NMR(400 HMz, DMSO-$d_6$); δ 8.01 (d, 1H), 7.63 (d, 1H), 7.21-7.36 (m, 8H), 6.92 (d, 2H), 6.53 (d, 1H), 5.51 (s, 2H), 5.22 (s, 2H), 3.80 (br s, 1H), 2.22-2.27 (m, 1H), 2.07-2.12 (m, 1H)

Example 91

Synthesis of (S)-3-[4-(1-benzyl-1H-pyrrolo[2,3-b]pyridin-6-ylmethoxy)-phenyl]-3-isoxazol-3-yl-propanoic acid

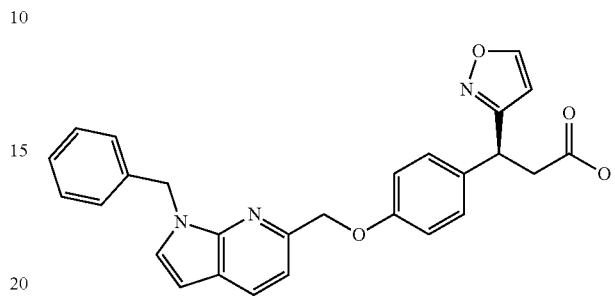

The compound (135 mg, 0.57 mmol) obtained from Preparation Example 54-2 and the compound (141 mg, 0.57 mmol) obtained from Preparation Example 157 were used to obtain the title compound (150 mg, 62%).

NMR:$^1$H-NMR(400 HMz, DMSO-$d_6$); δ 8.61 (s, 1H), 7.95 (d, 1H), 7.57 (d, 1H), 7.20-7.26 (m, 6H), 7.09 (d, 2H), 6.87 (d, 2H), 6.46 (dd, 1H), 6.36 (d, 1H), 5.44 (s, 2H), 5.15 (s, 2H), 4.45 (t, 1H), 2.46-2.49 (m, 1H), 2.37-2.40 (m, 1H)

Example 92

Synthesis of (S)-3-isoxazol-3-yl-3-{4-[7-methyl-1-(5-methyl-pyrazin-2-ylmethyl)-1H-indol-6-ylmethoxy]-phenyl}-propanoic acid

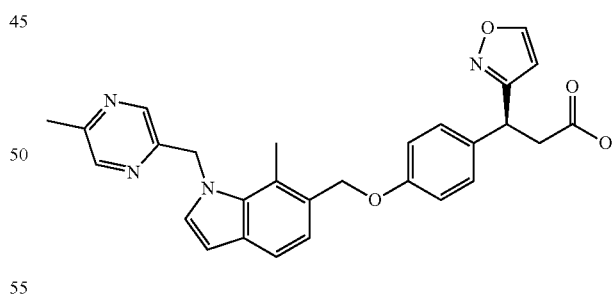

The compound (196 mg, 0.73 mmol) obtained from Preparation Example 42 and the compound (180 mg, 0.79 mmol) obtained from Preparation Example 157 were used to obtain the title compound (140 mg, 40%).

NMR:$^1$H-NMR(400 HMz, DMSO-$d_6$); δ 8.62 (s, 1H), 8.45 (s, 1H), 7.89 (s, 1H), 7.44 (d, 1H), 7.34 (d, 1H), 7.10 (d, 2H), 7.04 (d, 1H), 6.83 (d, 2H), 6.46 (d, 1H), 6.37 (s, 1H), 5.74 (s, 2H), 4.99 (s, 2H), 4.45 (t, 1H), 2.46-2.49 (m, 1H), 2.38-2.41 (m, 1H), 2.37 (s, 3H), 2.35 (s, 3H)

Example 93

Synthesis of (S)-3-{4-[1-(6-methyl-pyridin-3-ylmethyl)-1H-indazol-6-ylmethoxy]-phenyl}-hex-4-ynoic acid

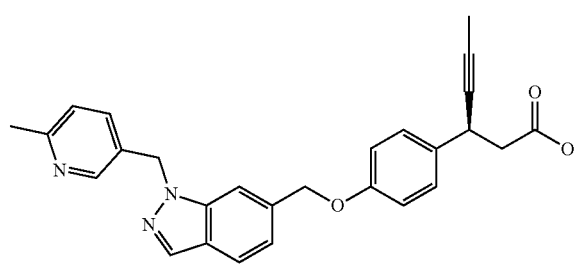 [SMILES: CC#C[C@@H](CC(=O)O)c1ccc(OCc2ccc3cnn(Cc4ccc(C)nc4)c3c2)cc1]

The compound (72.2 mg, 0.29 mmol) obtained from Preparation Example 147 and the compound (70.4 mg, 0.29 mmol) obtained from Preparation Example 155 were used to obtain the title compound (94 mg, 71%).

NMR:$^1$H-NMR(400 HMz, DMSO-d$_6$); δ 8.42 (s, 1H), 8.10 (s, 1H), 7.86 (s, 1H), 7.77 (d, 1H), 7.48 (dd, 1H), 7.24 (d, 2H), 7.21 (d, 1H), 7.16 (d, 1H), 6.91 (d, 2H), 5.66 (s, 2H), 5.17 (s, 2H), 3.98 (br s, 1H), 2.40 (s, 3H), 2.24-2.30 (m, 1H), 2.09-2.15 (m, 1H), 1.75 (s, 3H)

Example 94

Synthesis of (S)-3-[4-(1-benzyl-1H-indazol-4-ylmethoxy)-phenyl]-3-isoxazol-3-yl-propanoic acid

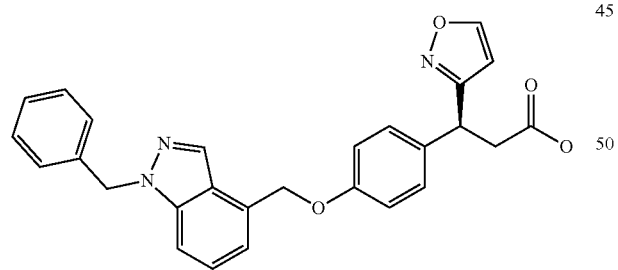

The compound (150 mg, 0.63 mmol) obtained from Preparation Example 133-2 and the compound (56 mg, 0.63 mmol) obtained from Preparation Example 157 were used to obtain the title compound (180 mg, 63%).

NMR:$^1$H-NMR(400 HMz, DMSO-d$_6$); δ 8.62 (s, 1H), 8.16 (s, 1H), 7.62 (d, 1H), 7.12-7.32 (m, 9H), 6.89 (d, 2H), 6.38 (d, 1H), 5.62 (s, 2H), 5.33 (s, 2H), 4.46 (t, 1H), 2.50-2.52 (m, 1H), 2.42-2.46 (m, 1H)

Example 95

Synthesis of (S)-3-{4-[1-(4-fluoro-benzyl)-1H-pyrrolo[2,3-b]pyridin-6-ylmethoxy]-phenyl}-3-isoxazol-3-yl-propanoic acid

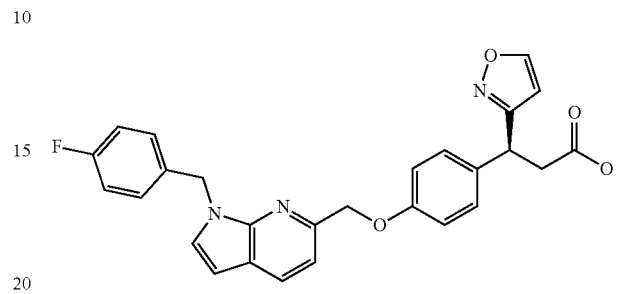

The compound (70 mg, 0.27 mmol) obtained from Preparation Example 53-4 and the compound (70 mg, 0.27 mmol) obtained from Preparation Example 157 were used to obtain the title compound (80 mg, 62%).

NMR:$^1$H-NMR(400 HMz, DMSO-d$_6$); δ 8.62 (br s, 1H), 7.95 (d, 1H), 7.58 (br s, 1H), 7.26 (br s, 1H), 7.20 (d, 2H), 7.10 (br s, 4H), 6.87 (d, 2H), 6.45 (d, 1H), 6.36 (d, 1H), 5.42 (s, 2H), 5.14 (s, 2H), 4.52 (br s, 1H)

Example 96

Synthesis of (S)-3-[4-(1-isopropyl-1H-indazol-6-ylmethoxy)-phenyl]-3-isoxazol-3-yl-propanoic acid

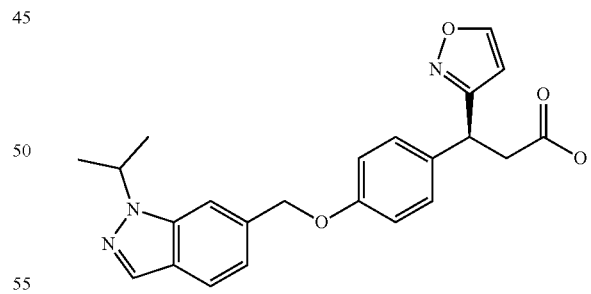

The compound (0.19 g, 0.98 mmol) obtained from Preparation Example 72 and the compound (0.24 g, 0.98 mmol) obtained from Preparation Example 157 were used to obtain the title compound (0.28 g, 63%).

NMR:$^1$H-NMR(400 HMz, DMSO-d$_6$); δ 8.59 (s, 1H), 7.98 (s, 1H), 7.68 (s, 1H), 7.66 (s, 1H), 7.11 (d, 3H), 6.86 (d, 2H), 6.35 (d, 1H), 5.10 (s, 2H), 4.87-4.94 (m, 1H), 4.45 (t, 1H), 2.49-2.55 (m, 1H), 2.37-2.41 (m, 1H), 1.40 (d, 6H)

Example 97

Synthesis of (S)-3-[4-(1-cyclopropylmethyl-1H-indazol-6-ylmethoxy)-phenyl]-3-isoxazol-3-yl-propanoic acid

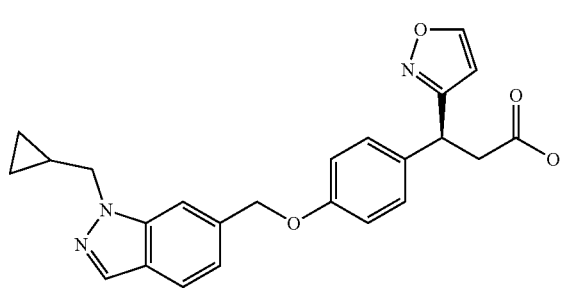 [SMILES: O=C(O)C[C@@H](c1ccc(OCc2ccc3cnn(CC4CC4)c3c2)cc1)c1ccon1]

The compound (0.16 g, 0.81 mmol) obtained from Preparation Example 74 and the compound (0.20 g, 0.81 mmol) obtained from Preparation Example 157 were used to obtain the title compound (0.26 g, 71%).

NMR:$^1$H-NMR(400 HMz, DMSO-d$_6$); δ 8.67 (s, 1H), 8.05 (s, 1H), 7.76 (s, 1H), 7.73 (s, 1H), 7.18-7.20 (m, 3H), 6.93 (d, 2H), 6.43 (s, 1H), 5.18 (s, 2H), 4.54 (t, 1H), 4.29 (d, 2H), 2.62-2.68 (m, 1H), 2.50-2.54 (m, 1H), 1.25 (br s, 1H), 0.44-0.46 (m, 2H), 0.36-0.37 (m, 2H)

Example 98

Synthesis of (S)-3-[4-(1-isobutyl-1H-pyrrolo[2,3-b]pyridin-6-ylmethoxy)-phenyl]-3-isoxazol-3-yl-propanoic acid

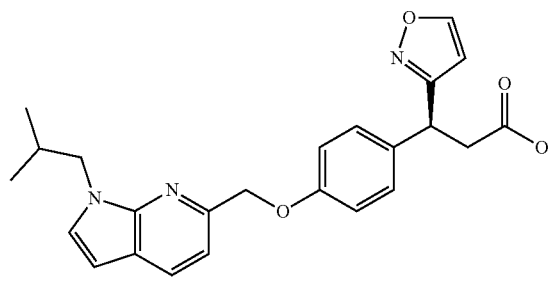 [SMILES: CC(C)Cn1ccc2ccc(COc3ccc([C@H](CC(=O)O)c4ccon4)cc3)nc21]

The compound (190 mg, 0.93 mmol) obtained from Preparation Example 142-2 and the compound (230 mg, 0.93 mmol) obtained from Preparation Example 157 were used to obtain the title compound (220 mg, 56%).

NMR:$^1$H-NMR(400 HMz, DMSO-d$_6$); δ 8.66 (d, 1H), 7.97 (d, 1H), 7.55 (d, 1H), 7.22 (d, 1H), 7.15 (d, 2H), 6.93 (d, 2H), 6.47 (d, 1H), 6.41 (d, 1H), 5.18 (s, 2H), 4.50 (t, 1H), 4.08 (d, 2H), 2.54-2.68 (m, 1H), 2.40-2.46 (m, 1H), 2.21-2.26 (m, 1H), 0.84 (d, 6H)

Example 99

Synthesis of (S)-3-[4-(2-isopropyl-2H-indazol-6-ylmethoxy)-phenyl]-3-isoxazol-3-yl-propanoic acid

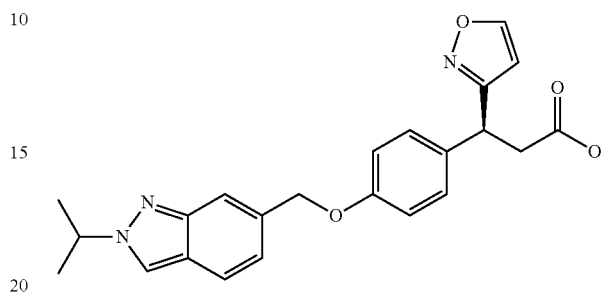

The compound (0.14 g, 0.72 mmol) obtained from Preparation Example 73 and the compound (0.18 g, 0.72 mmol) obtained from Preparation Example 157 were used to obtain the title compound (0.34 g, 100%).

NMR:$^1$H-NMR(400 HMz, DMSO-d$_6$); δ 8.66 (s, 1H), 8.38 (s, 1H), 7.66 (dd, 2H), 7.16 (d, 2H), 7.07 (d, 1H), 6.90 (d, 2H), 6.41 (s, 1H), 5.12 (s, 2H), 4.77-4.84 (m, 1H), 4.50 (t, 1H), 2.55-2.61 (m, 1H), 2.43-2.47 (m, 1H), 1.54 (d, 6H)

Example 100

Synthesis of [6-(1-isopropyl-1H-indazol-6-ylmethoxy)-2,3-dihydro-benzofuran-3-yl]-acetic acid

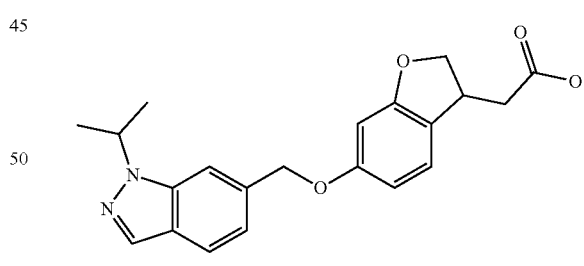

The compound (0.13 g, 0.67 mmol) obtained from Preparation Example 72 and the compound (0.14 g, 0.67 mmol) obtained from Preparation Example 158 were used to obtain the title compound (0.08 g, 27%).

NMR:$^1$H-NMR(400 HMz, DMSO-d$_6$); δ 8.05 (s, 1H), 7.75 (s, 1H), 7.73 (s, 1H), 7.18 (d, 1H), 7.09 (d, 1H), 6.47 (d, 1H), 6.44 (d, 1H), 5.15 (s, 2H), 4.95-5.02 (m, 1H), 4.66 (t, 1H), 4.13 (t, 1H), 3.59 (br t, 1H), 2.31-2.36 (m, 1H), 1.98-2.04 (m, 1H), 1.47 (d, 6H)

Example 101

Synthesis of (S)-3-isoxazol-3-yl-3-[4-(1-methyl-1H-indazol-6-ylmethoxy)-phenyl]-propanoic acid

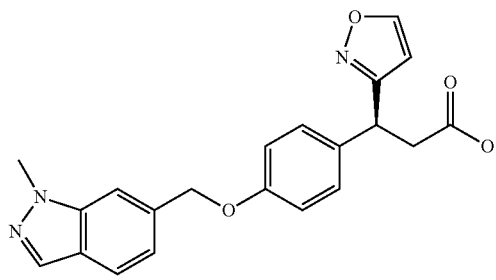 [SMILES: Cn1ncc2ccc(COc3ccc([C@H](CC(=O)O)c4ccon4)cc3)cc21]

The compound (0.15 g, 0.92 mmol) obtained from Preparation Example 71 and the compound (0.23 g, 0.92 mmol) obtained from Preparation Example 157 were used to obtain the title compound (0.15 g, 36%).

NMR:$^1$H-NMR(400 HMz, DMSO-d$_6$); δ 8.67 (s, 1H), 8.03 (s, 1H), 7.74 (d, 1H), 7.71 (s, 1H), 7.17-7.21 (m, 3H), 6.93 (d, 2H), 6.42 (s, 1H), 5.18 (s, 2H), 4.52 (t, 1H), 4.04 (s, 3H), 2.59-2.62 (m, 1H), 2.45-2.50 (m, 1H)

Example 102

Synthesis of (S)-3-[4-(1H-indazol-6-ylmethoxy)-phenyl]-3-isoxazol-3-yl-propanoic acid

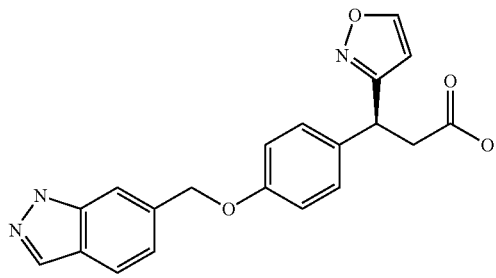 [SMILES: O=C(O)C[C@@H](c1ccc(OCc2ccc3cn[nH]c3c2)cc1)c1ccon1]

The compound (0.15 g, 1.00 mmol) obtained from Preparation Example 70 and the compound (0.25 g, 1.00 mmol) obtained from Preparation Example 157 were used to obtain the title compound (0.06 g, 14%).

NMR:$^1$H-NMR(400 HMz, DMSO-d$_6$); δ 8.65 (s, 1H), 8.04 (s, 1H), 7.75 (d, 1H), 7.57 (s, 1H), 7.14-7.18 (m, 3H), 6.91 (d, 2H), 6.41 (s, 1H), 5.18 (s, 2H), 4.50 (t, 1H), 2.50-2.58 (m, 1H), 2.41-2.47 (m, 1H)

Example 103

Synthesis of (S)-3-[4-(1-cyclopentylmethyl-1H-indazol-6-ylmethoxy)-phenyl]-3-isoxazol-3-yl-propanoic acid

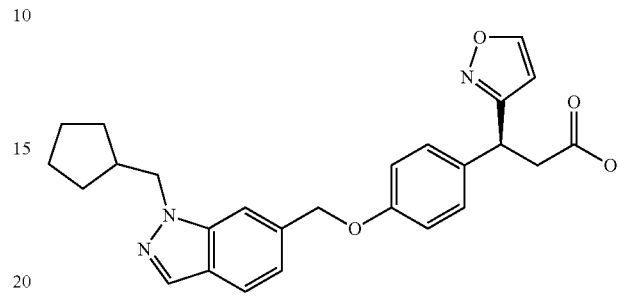

The compound (0.24 g, 1.05 mmol) obtained from Preparation Example 77 and the compound (0.26 g, 1.05 mmol) obtained from Preparation Example 157 were used to obtain the title compound (0.23 g, 48%).

NMR:$^1$H-NMR(400 HMz, DMSO-d$_6$); δ 8.66 (s, 1H), 8.03 (s, 1H), 7.74 (d, 2H), 7.17 (dd, 3H), 6.93 (d, 2H), 6.42 (s, 1H), 5.18 (s, 2H), 4.52 (t, 1H), 4.31 (d, 2H), 2.50-2.59 (m, 1H), 2.41-2.48 (m, 1H), 1.46-1.60 (m, 6H), 1.24-1.28 (m, 2H)

Example 104

Synthesis of (S)-3-isoxazol-3-yl-3-[4-(1-pyrazin-2-ylmethyl-1H-pyrrolo[2,3-b]pyridin-6-ylmethoxy)-phenyl]-propanoic acid

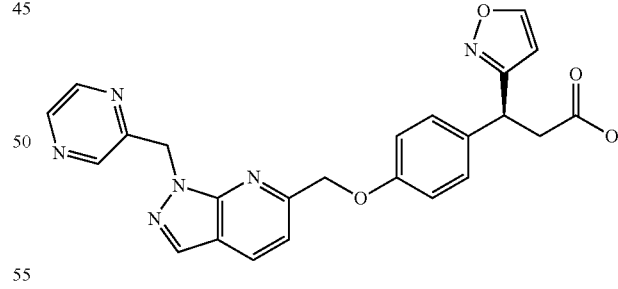

The compound (140 mg, 0.58 mmol) obtained from Preparation Example 141 and the compound (160 mg, 0.58 mmol) obtained from Preparation Example 157 were used to obtain the title compound (60 mg, 23%).

NMR:$^1$H-NMR(400 HMz, DMSO-d$_6$); δ 8.67 (d, 1H), 8.58 (d, 2H), 8.51 (s, 1H), 8.02 (d, 1H), 7.68 (d, 1H), 7.26 (d, 1H), 7.13 (d, 2H), 6.89 (d, 2H), 6.56 (d, 1H), 6.42 (d, 1H), 5.68 (s, 2H), 5.15 (s, 2H), 2.54-2.60 (m, 1H), 2.42-2.48 (m, 1H)

Example 105

Synthesis of [6-(1-benzyl-1H-indazol-6-ylmethoxy)-2,3-dihydro-benzofuran-3-yl]-acetic acid

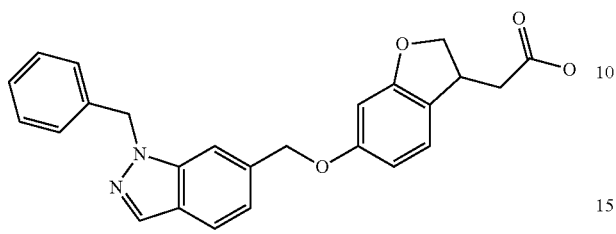

The compound (200 mg, 0.84 mmol) obtained from Preparation Example 56 and the compound (157 mg, 0.76 mmol) obtained from Preparation Example 158 were used to obtain the title compound (187 mg, 67%).

NMR: $^1$H-NMR(400 HMz, DMSO-$d_6$); δ 8.10 (s, 1H), 7.77 (d, 2H), 7.18-7.31 (m, 6H), 7.07 (d, 1H), 6.41-6.45 (m, 2H), 5.66 (s, 2H), 5.13 (s, 2H), 4.66 (t, 1H), 4.13 (t, 1H), 3.59 (pent, 1H), 2.33 (dd, 1H), 2.01 (dd, 1H)

Example 106

Synthesis of 3-[4-(1-benzyl-1H-indazol-6-yl-methoxy)-2-fluoro-phenyl]-propanoic acid

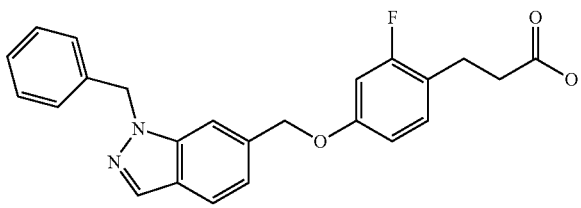 [SMILES: O=C(O)CCc1ccc(OCc2ccc3cnn(Cc4ccccc4)c3c2)cc1F]

The compound (200 mg, 0.84 mmol) obtained from Preparation Example 56 and the compound (161 mg, 0.76 mmol) obtained from Preparation Example 149 were used to obtain the title compound (205 mg, 66%).

NMR: $^1$H-NMR(400 HMz, DMSO-$d_6$); δ 8.04 (s, 1H), 7.73 (d, 1H), 7.70 (s, 1H), 7.08-7.24 (m, 7H), 6.75 (d, 1H), 6.68 (d, 1H), 5.59 (s, 2H), 5.11 (s, 2H), 2.60 (t, 2H), 2.01 (t, 2H)

Example 107

Synthesis of 3-[4-(1-cyclopentylmethyl-1H-indazol-6-ylmethoxy)-2-fluoro-phenyl]-propanoic acid

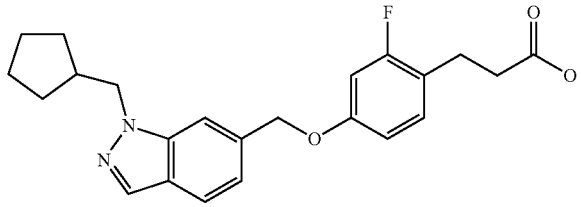 [SMILES: O=C(O)CCc1ccc(OCc2ccc3cnn(CC4CCCC4)c3c2)cc1F]

The compound (200 mg, 0.87 mmol) obtained from Preparation Example 77 and the compound (166 mg, 0.78 mmol) obtained from Preparation Example 149 were used to obtain the title compound (260 mg, 84%).

NMR: $^1$H-NMR(400 HMz, DMSO-$d_6$); δ 8.04 (s, 1H), 7.75 (d, 2H), 7.17 (dd, 2H), 6.83 (d, 1H), 6.76 (d, 1H), 5.20 (s, 2H), 4.32 (d, 2H), 2.65 (t, 2H), 2.42-2.49 (m, 1H), 2.04 (t, 2H), 1.51-1.53 (m, 6H), 1.25 (m, 2H)

Example 108

Synthesis of [6-(1-cyclopentylmethyl-1H-indazol-6-ylmethoxy)-2,3-dihydro-benzofuran-3-yl]-acetic acid

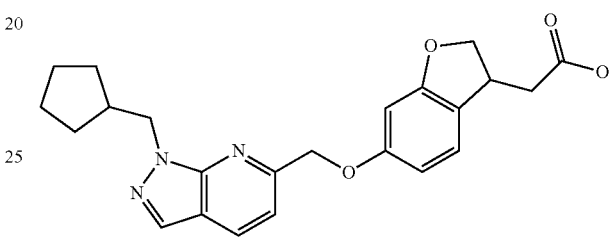

The compound (200 mg, 0.87 mmol) obtained from Preparation Example 77 and the compound (162 mg, 0.78 mmol) obtained from Preparation Example 158 were used to obtain the title compound (154 mg, 46%).

NMR: $^1$H-NMR(400 HMz, DMSO-$d_6$); δ 8.03 (s, 1H), 7.74 (d, 2H), 7.17 (d, 1H), 7.07 (d, 1H), 6.42-6.46 (m, 2H), 5.16 (s, 2H), 4.65 (t, 1H), 4.31 (d, 2H), 4.12 (t, 1H), 3.57 (m, 1H), 2.42-2.49 (m, 1H), 2.31 (dd, 1H), 1.99 (dd, 1H), 1.49-1.60 (m, 6H), 1.24-1.26 (m, 2H)

Example 109

Synthesis of [5-(1-benzyl-1H-indazol-6-ylmethoxy)-indan-1-yl]-acetic acid

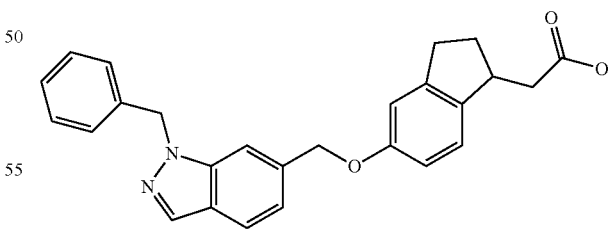

The compound (200 mg, 0.84 mmol) obtained from Preparation Example 56 and the compound (177 mg, 0.76 mmol) obtained from Preparation Example 159 were used to obtain the title compound (210 mg, 56%).

NMR: $^1$H-NMR(400 HMz, CDCl$_3$); δ 8.09 (s, 1H), 7.78 (m, 1H), 7.27 (m, 2H), 7.20 (m, 3H), 7.10 (m, 1H), 6.82 (m, 1H), 6.72 (m, 1H), 5.66 (s, 2H), 5.14 (s, 2H), 3.29 (m, 1H), 2.68 (m, 2H), 2.20 (m, 2H), 1.89 (dd, 1H), 1.56 (m, 1H)

Example 110

Synthesis of [6-(1-benzyl-1H-indazol-6-ylmethoxy)-1,2,3,4-tetrahydro-naphthalen-1-yl]-acetic acid

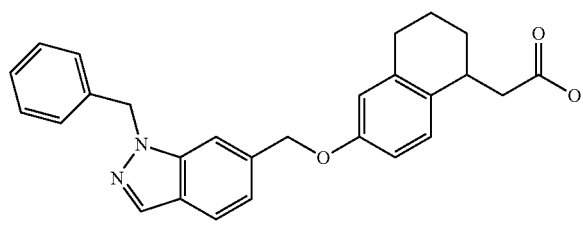 [SMILES: O=C(O)CC1CCCc2cc(OCc3ccc4cnn(Cc5ccccc5)c4c3)ccc21]

The compound (200 mg, 0.84 mmol) obtained from Preparation Example 56 and the compound (177 mg, 0.76 mmol) obtained from Preparation Example 161 were used to obtain the title compound (224 mg, 63%).

NMR:$^1$H-NMR(400 HMz, DMSO-d$_6$); δ 8.10 (s, 1H), 7.78 (m, 2H), 7.29 (m, 2H), 7.21 (m, 3H), 7.08 (d, 1H), 6.71 (m, 1H), 6.65 (m, 1H), 5.66 (s, 2H), 5.13 (s, 2H), 3.07 (m, 1H), 2.62 (m, 2H), 2.16 (dd, 1H), 1.95 (dd, 1H), 1.70 (m, 2H), 1.59 (m, 2H)

Example 111

Synthesis of (S)-3-[4-(1-benzyl-1H-indazol-5-yl-methoxy)-phenyl]-hex-4-ynoic acid

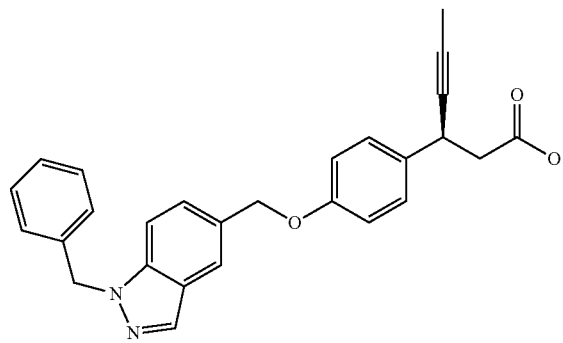

The compound (200 mg, 0.84 mmol) obtained from Preparation Example 91 and the compound (165 mg, 0.76 mmol) obtained from Preparation Example 155 were used to obtain the title compound (185 mg, 57%).

NMR:$^1$H-NMR(400 HMz, DMSO-d$_6$); δ 8.11 (s, 1H), 7.83 (s, 1H), 7.70 (d, 1H), 7.44 (d, 1H), 7.20-7.32 (m, 7H), 6.90 (d, 2H), 5.66 (s, 2H), 5.13 (s, 2H), 3.97 (br s, 1H), 2.08-2.29 (m, 2H), 1.74 (s, 3H)

Example 112

Synthesis of (S)-3-[4-(2-benzyl-2H-indazol-5-yl-methoxy)-phenyl]-hex-4-ynoic acid

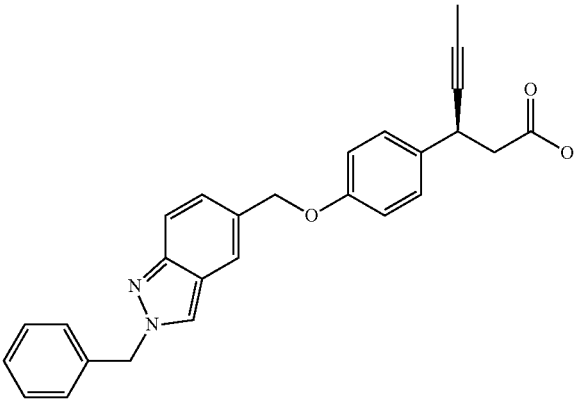 [SMILES: CC#C[C@@H](CC(=O)O)c1ccc(OCc2ccc3nn(Cc4ccccc4)cc3c2)cc1]

The compound (160 mg, 0.67 mmol) obtained from Preparation Example 92 and the compound (132 mg, 0.60 mmol) obtained from Preparation Example 155 were used to obtain the title compound (178 mg, 73%).

NMR:$^1$H-NMR(400 HMz, DMSO-d$_6$); δ 8.41 (s, 1H), 7.69 (s, 1H), 7.53 (d, 1H), 7.14-7.28 (m, 8H), 6.82 (d, 2H), 5.56 (s, 2H), 5.01 (s, 2H), 3.89 (br s, 1H), 2.01-2.20 (m, 2H), 1.67 (s, 3H)

Example 113

Synthesis of [6-(2-benzyl-2H-indazol-6-ylmethoxy)-2,3-dihydro-benzofuran-3-yl]-acetic acid

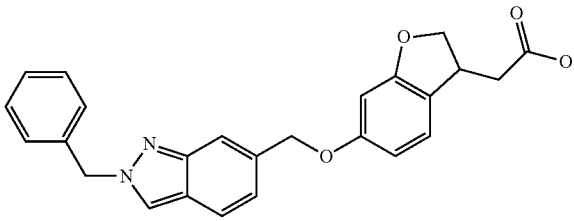 [SMILES: O=C(O)CC1COc2cc(OCc3ccc4cn(Cc5ccccc5)nc4c3)ccc21]

The compound (245 mg, 1.03 mmol) obtained from Preparation Example 57 and the compound (193 mg, 0.93 mmol) obtained from Preparation Example 158 were used to obtain the title compound (292 mg, 76%).

NMR:$^1$H-NMR(400 HMz, DMSO-d$_6$); δ 8.40 (s, 1H), 7.63 (d, 1H), 7.55 (s, 1H), 7.21-7.30 (m, 5H), 6.70 (d, 2H), 6.33-6.38 (m, 2H), 5.56 (s, 2H), 5.02 (s, 2H), 4.59 (dd, 1H), 4.06 (dd, 1H), 3.50-3.56 (m, 1H), 2.27 (dd, 1H), 1.69-1.98 (m, 1H)

Example 114

Synthesis of (S)-3-[4-(1-isobutyl-1H-indazol-6-yl-methoxy)-phenyl]-hex-4-ynoic acid

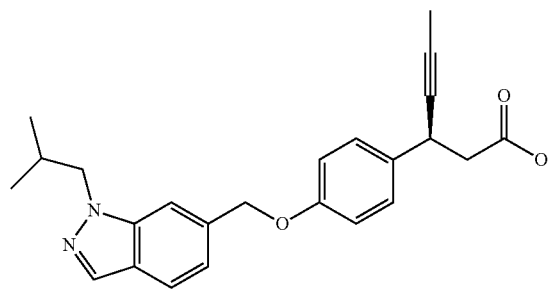 [SMILES: CC#C[C@@H](CC(=O)O)c1ccc(OCc2ccc3cnn(CC(C)C)c3c2)cc1]

The compound (0.20 g, 0.98 mmol) obtained from Preparation Example 75-1 and the compound (0.19 g, 0.88 mmol) obtained from Preparation Example 155 were used to obtain the title compound (0.29 g, 76%).

NMR:$^1$H-NMR(500 HMz, CDCl$_3$); δ 7.99 (s, 1H), 7.73 (d, 1H), 7.45 (s, 1H), 7.32 (d, 2H), 7.18 (d, 1H), 6.96 (d, 2H), 5.18 (s, 2H), 4.17 (d, 2H), 4.06 (m, 1H), 2.79 (dd, 1H), 2.72 (dd, 1H), 2.33 (m, 1H), 1.82 (s, 3H), 0.91 (d, 6H)

Example 115

Synthesis of (S)-3-[4-(1-isobutyl-1H-pyrrolo[2,3-b]pyridin-6-ylmethoxy)-phenyl]-hex-4-ynoic acid

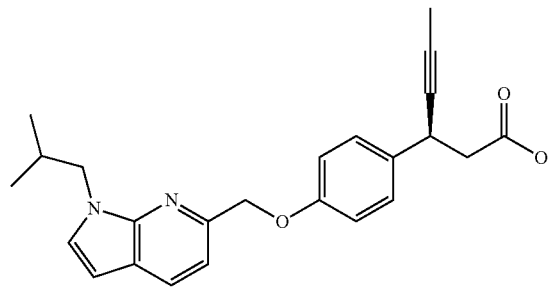 [SMILES: CC#C[C@@H](CC(=O)O)c1ccc(OCc2ccc3ccn(CC(C)C)c3n2)cc1]

The compound (0.20 g, 0.98 mmol) obtained from Preparation Example 142-2 and the compound (0.19 g, 0.88 mmol) obtained from Preparation Example 155 were used to obtain the title compound (0.20 g, 53%).

NMR:$^1$H-NMR(500 HMz, CDCl$_3$); δ 7.89 (d, 1H), 7.27 (m, 3H), 7.17 (s, 1H), 6.98 (d, 2H), 6.42 (s, 1H), 5.29 (s, 2H), 4.09 (d, 2H), 4.03 (m, 1H), 2.75 (dd, 1H), 2.66 (dd, 1H), 2.26 (m, 1H), 1.81 (s, 3H), 0.91 (d, 6H)

Example 116

Synthesis of (S)-3-[4-(1-isopropyl-1H-indazol-5-ylmethoxy)-phenyl]-hex-4-ynoic acid

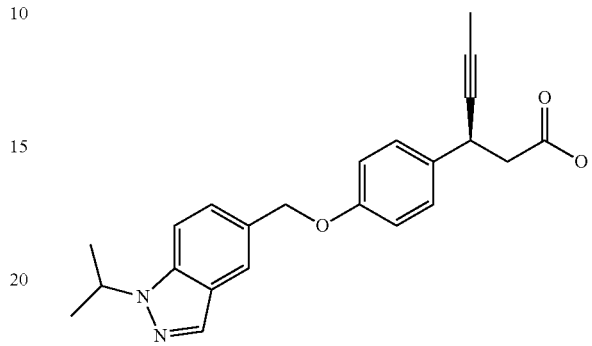

The compound (150 mg, 0.79 mmol) obtained from Preparation Example 96 and the compound (155 mg, 0.71 mmol) obtained from Preparation Example 155 were used to obtain the title compound (32 mg, 12%).

NMR:$^1$H-NMR(400 HMz, CDCl$_3$); δ 8.00 (s, 1H), 7.77 (s, 1H), 7.45-7.48 (m, 2H), 7.31 (d, 2H), 6.96 (d, 2H), 5.13 (s, 2H), 4.84-4.87 (m, 1H), 4.06 (br s, 1H), 2.69-2.84 (m, 2H), 1.84 (s, 3H), 1.60 (d, 6H)

Example 117

Synthesis of 3-[4-(1-benzyl-1H-indazol-6-yl-methoxy)-phenyl]-butyric acid

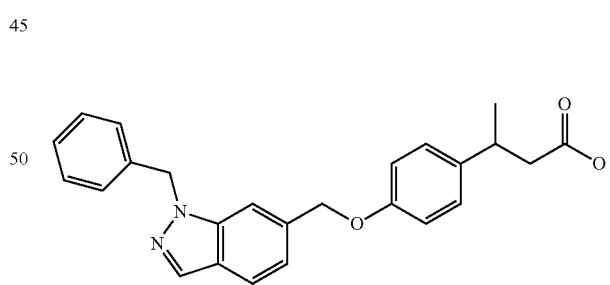

The compound (200 mg, 0.84 mmol) obtained from Preparation Example 56 and the compound (157 mg, 0.76 mmol) obtained from Preparation Example 150 were used to obtain the title compound (217 mg, 71%).

NMR:$^1$H-NMR(400 HMz, CDCl$_3$); δ 8.03 (s, 1H), 7.73 (d, 1H), 7.42 (s, 1H), 7.13-7.25 (m, 8H), 6.90 (d, 2H), 5.59 (s, 2H), 5.12 (s, 2H), 3.20-3.26 (m, 1H), 2.51-2.65 (m, 2H), 1.29 (d, 3H)

Example 118

Synthesis of [5-(1-benzyl-1H-indazol-5-ylmethoxy)-indan-1-yl]-acetic acid

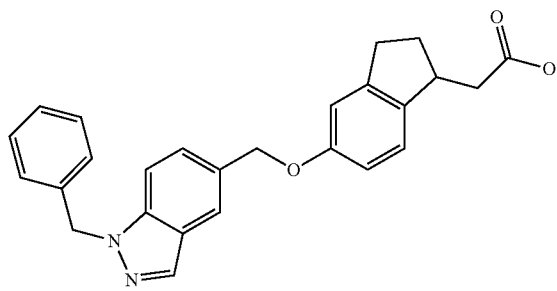 [SMILES: O=C(O)CC1CCc2cc(OCc3ccc4c(cnn4Cc4ccccc4)c3)ccc21]

The compound (200 mg, 0.84 mmol) obtained from Preparation Example 91 and the compound (166 mg, 0.76 mmol) obtained from Preparation Example 159 were used to obtain the title compound (224 mg, 65%).

NMR: $^1$H-NMR(400 HMz, CDCl$_3$); δ 8.04 (s, 1H), 7.79 (s, 1H), 7.37 (m, 2H), 7.27 (m, 3H), 7.19 (m, 2H), 7.09 (d, 1H), 6.88 (m, 1H), 6.80 (m, 1H), 5.61 (s, 2H), 5.11 (s, 2H), 3.54 (m, 1H), 2.84 (m, 3H), 2.45 (m, 2H), 1.81 (m, 1H)

Example 119

Synthesis of [6-(1-benzyl-1H-indazol-5-ylmethoxy)-1,2,3,4-tetrahydro-naphthalen-1-yl]-acetic acid

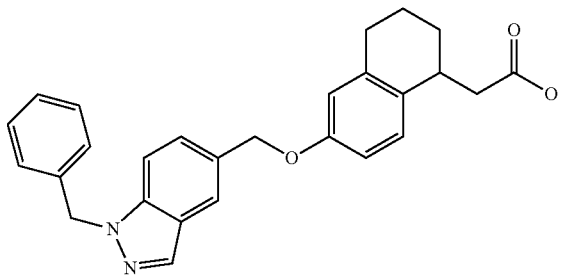 [SMILES: O=C(O)CC1CCCc2cc(OCc3ccc4c(cnn4Cc4ccccc4)c3)ccc21]

The compound (200 mg, 0.84 mmol) obtained from Preparation Example 91 and the compound (177 mg, 0.76 mmol) obtained from Preparation Example 161 were used to obtain the title compound (160 mg, 45%).

NMR: $^1$H-NMR(400 HMz, CDCl$_3$); δ 8.04 (s, 1H), 7.78 (s, 1H), 7.39 (m, 2H), 7.27 (m, 3H), 7.19 (m, 2H), 7.09 (d, 1H), 6.79 (m, 1H), 6.71 (d, 1H), 5.60 (s, 2H), 5.09 (s, 2H), 3.31 (m, 1H), 2.74 (m, 3H), 2.55 (dd, 1H), 1.95 (m, 1H), 1.77 (m, 3H)

Example 120

Synthesis of [7-(1-benzyl-1H-indazol-5-ylmethoxy)-chroman-4-yl]-acetic acid

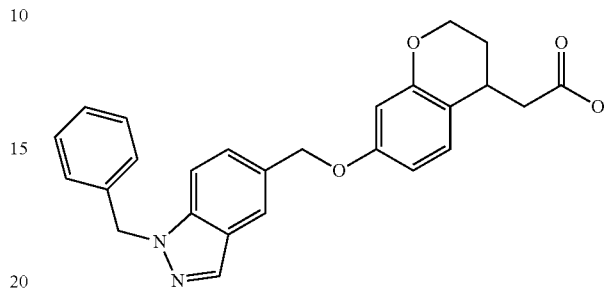

The compound (130 mg, 0.55 mmol) obtained from Preparation Example 91 and the compound (116 mg, 0.49 mmol) obtained from Preparation Example 160 were used to obtain the title compound (53 mg, 23%).

NMR: $^1$H-NMR(400 HMz, CDCl$_3$); δ 8.04 (s, 1H), 7.78 (s, 1H), 7.36 (m, 2H), 7.27 (m, 3H), 7.19 (m, 2H), 7.02 (d, 1H), 6.54 (m, 1H), 6.45 (d, 1H), 5.60 (s, 2H), 5.08 (s, 2H), 4.17 (m, 2H), 3.30 (m, 1H), 2.81 (dd, 1H), 2.55 (dd, 1H), 2.12 (m, 1H), 1.87 (m, 1H)

Example 121

Synthesis of [6-(1-benzyl-1H-pyrrolo[2,3-b]pyridin-6-ylmethoxy)-2,3-dihydro-benzofuran-3-yl]-acetic acid

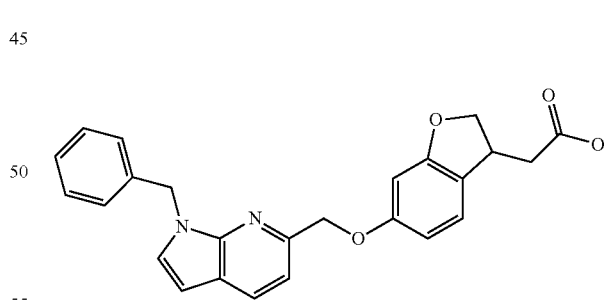

The compound (210 mg, 0.88 mmol) obtained from Preparation Example 54-2 and the compound (167 mg, 0.80 mmol) obtained from Preparation Example 158 were used to obtain the title compound (287 mg, 86%).

NMR: $^1$H-NMR(400 HMz, CDCl$_3$+CD$_3$OD); δ 7.93 (d, 1H), 6.87-7.40 (m, 8H), 6.40-6.60 (m, 3H), 5.50 (s, 2H), 5.24 (s, 2H), 4.75 (t, 2H), 4.27 (t, 2H), 3.78 (m, 1H), 2.45-2.88 (m, 2H)

Example 122

Synthesis of (S)-3-[4-(1-benzyl-5-fluoro-1H-indazol-6-ylmethoxy)-phenyl]-hex-4-ynoic acid

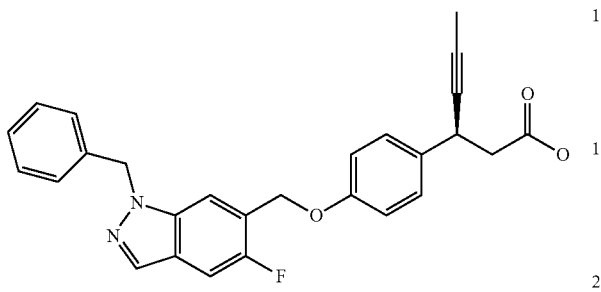

The compound (113 mg, 0.44 mmol) obtained from Preparation Example 84 and the compound (87 mg, 0.40 mmol) obtained from Preparation Example 155 were used to obtain the title compound (119 mg, 67%).

NMR: $^1$H-NMR(400 HMz, CDCl$_3$); δ 7.99 (s, 1H), 7.12-7.48 (m, 9H), 5.61 (s, 2H), 5.17 (s, 2H), 4.06 (m, 1H), 2.64-2.86 (m, 2H), 1.82 (d, 3H)

Example 123

Synthesis of (S)-3-[4-(1-benzyl-1H-indol-5-yl-methoxy)-phenyl]-hex-4-ynoic acid

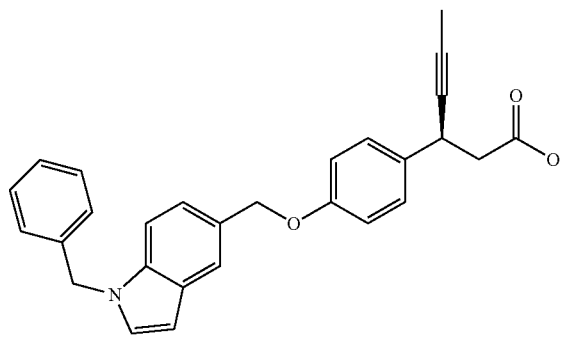 [SMILES: CC#C[C@@H](CC(=O)O)c1ccc(OCc2ccc3c(ccn3Cc3ccccc3)c2)cc1]

The compound (131 mg, 0.55 mmol) obtained from Preparation Example 90 and the compound (109 mg, 0.50 mmol) obtained from Preparation Example 155 were used to obtain the title compound (89 mg, 42%).

NMR: $^1$H-NMR(500 HMz, CDCl$_3$); δ 7.71 (s, 1H), 7.07-7.34 (m, 10H), 6.97 (d, 2H), 6.56 (d, 1H), 5.32 (s, 2H), 5.12 (s, 2H), 4.06 (m, 1H), 2.66-2.86 (m, 2H), 1.83 (d, 3H)

Example 124

Synthesis of (S)-3-[4-(1-benzyl-1H-benzotriazol-5-ylmethoxy)-phenyl]-hex-4-ynoic acid

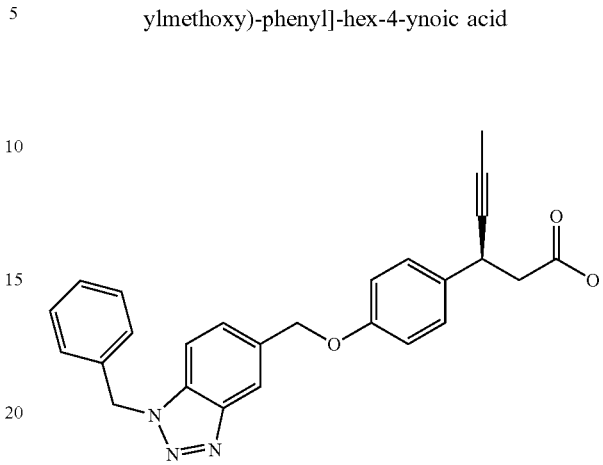

The compound (100 mg, 0.42 mmol) obtained from Preparation Example 125-4 and the compound (82 mg, 0.38 mmol) obtained from Preparation Example 155 were used to obtain the title compound (60 mg, 37%).

NMR: $^1$H-NMR(400 HMz, CDCl$_3$); δ 8.09 (s, 1H), 7.47 (d, 1H), 7.26-7.36 (m, 8H), 6.92 (d, 2H), 5.84 (s, 2H), 5.15 (s, 2H), 4.05 (br s, 1H), 2.67-2.83 (m, 2H), 1.82 (s, 3H)

Example 125

Synthesis of (S)-3-[4-(1-benzyl-1H-benzoimidazol-5-ylmethoxy)-phenyl]-hex-4-ynoic acid

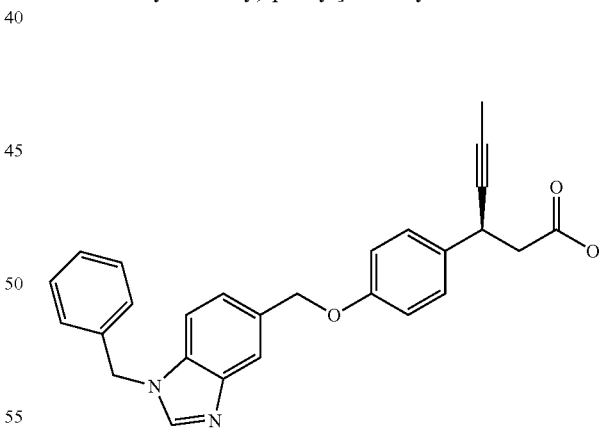

The compound (100 mg, 0.42 mmol) obtained from Preparation Example 126-2 and the compound (82 mg, 0.38 mmol) obtained from Preparation Example 155 were used to obtain the title compound (34 mg, 20%).

NMR: $^1$H-NMR(400 HMz, CDCl$_3$); δ 8.08 (s, 1H), 7.82 (s, 1H), 7.26-7.33 (m, 7H), 7.16-7.18 (m, 2H), 6.90 (d, 2H), 5.34 (s, 2H), 5.11 (s, 2H), 4.09 (br s, 1H), 2.68-2.85 (m, 2H), 1.81 (s, 3H)

Example 126

Synthesis of (S)-3-[4-(1-benzyl-7-methyl-1H-indazol-5-ylmethoxy)-phenyl]-hex-4-ynoic acid

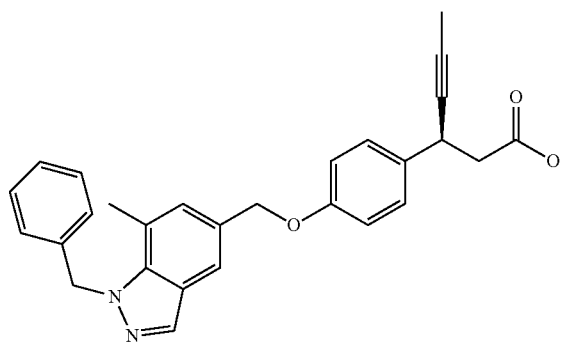 [SMILES: CC#C[C@@H](CC(=O)O)c1ccc(OCc2cc(C)c3c(cnn3Cc3ccccc3)c2)cc1]

The compound (110 mg, 0.44 mmol) obtained from Preparation Example 110 and the compound (86 mg, 0.39 mmol) obtained from Preparation Example 155 were used to obtain the title compound (73 mg, 44%).

NMR:$^1$H-NMR(400 HMz, CDCl$_3$); δ 8.04 (s, 1H), 7.62 (s, 1H), 7.21-7.31 (m, 5H), 7.14 (s, 1H), 6.93-6.95 (m, 4H), 5.84 (s, 2H), 5.06 (s, 2H), 4.06 (br s, 1H), 2.67-2.83 (m, 2H), 2.40 (s, 3H), 1.82 (s, 3H)

Example 127

Synthesis of (S)-3-[4-(2-benzyl-7-methyl-2H-indazol-5-ylmethoxy)-phenyl]-hex-4-ynoic acid

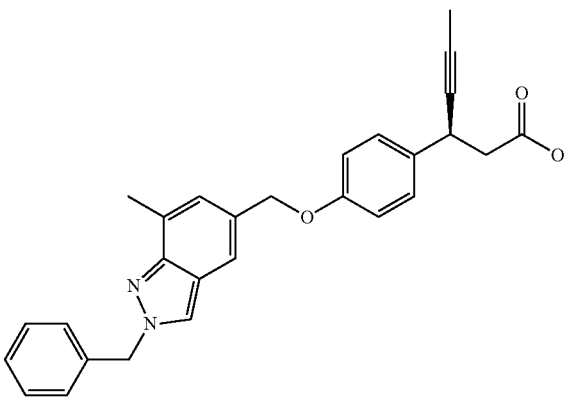 [SMILES: CC#C[C@@H](CC(=O)O)c1ccc(OCc2cc(C)c3nn(Cc4ccccc4)cc3c2)cc1]

The compound (150 mg, 0.59 mmol) obtained from Preparation Example 111 and the compound (117 mg, 0.54 mmol) obtained from Preparation Example 155 were used to obtain the title compound (71 mg, 30%).

NMR:$^1$H-NMR(400 HMz, CDCl$_3$); δ 7.78 (s, 1H), 7.46 (s, 1H), 7.17-7.33 (m, 7H), 7.10 (s, 1H), 6.93 (d, 2H), 5.61 (s, 2H), 5.02 (s, 2H), 4.05 (br s, 1H), 2.66-2.82 (m, 2H), 2.62 (s, 3H), 1.81 (s, 3H)

Example 128

Synthesis of [6-(1-benzyl-7-methyl-1H-indazol-5-ylmethoxy)-2,3-dihydro-benzofuran-3-yl]-acetic acid

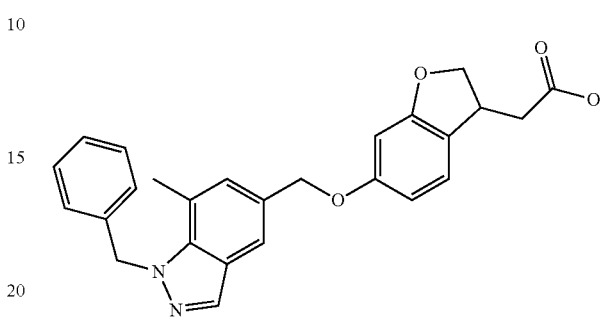

The compound (0.17 g, 0.66 mmol) obtained from Preparation Example 110 and the compound (0.12 g, 0.59 mmol) obtained from Preparation Example 158 were used to obtain the title compound (0.10 g, 39%).

NMR:$^1$H-NMR(400 HMz, CDCl$_3$); δ 8.04 (s, 1H), 7.62 (s, 1H), 7.25 (m, 3H), 7.13 (s, 1H), 7.07 (d, 1H), 6.96 (d, 2H), 6.53 (m, 2H), 5.84 (s, 2H), 5.03 (s, 2H), 4.78 (t, 1H), 4.28 (q, 1H), 3.82 (m, 1H), 2.81 (dd, 1H), 2.64 (dd, 1H), 2.57 (s, 3H)

Example 129

Synthesis of [7-(1-benzyl-7-methyl-1H-indazol-5-ylmethoxy)-chroman-4-yl]-acetic acid

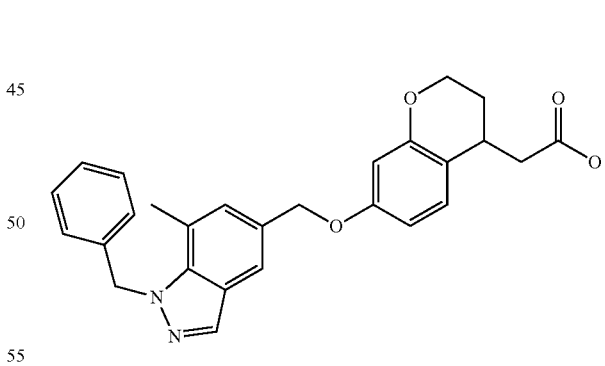

The compound (0.17 g, 0.66 mmol) obtained from Preparation Example 110 and the compound (0.14 g, 0.59 mmol) obtained from Preparation Example 160 were used to obtain the title compound (0.10 g, 43%).

NMR:$^1$H-NMR(400 HMz, CDCl$_3$); δ 8.04 (s, 1H), 7.62 (s, 1H), 7.25 (m, 3H), 7.13 (s, 1H), 7.05 (d, 1H), 6.96 (d, 2H), 6.58 (dd, 1H), 6.47 (s, 1H), 4.18 (m, 2H), 3.34 (m, 1H), 2.85 (dd, 1H), 2.58 (s, 3H), 2.52 (m, 1H), 2.18 (m, 1H), 1.84 (m, 1H)

Example 130

Synthesis of (S)-3-[4-(1-isobutyl-7-methyl-1H-indazol-5-ylmethoxy)-phenyl]-hex-4-ynoic acid

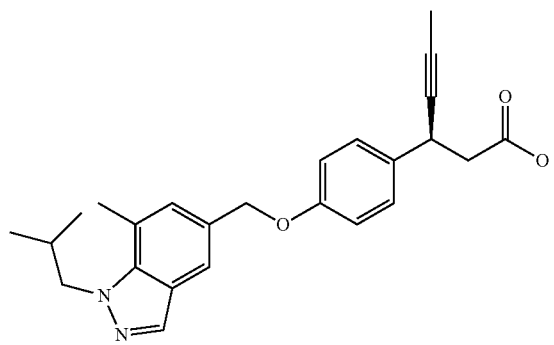 [SMILES: CC#C[C@@H](CC(=O)O)c1ccc(OCc2cc(C)c3c(cnn3CC(C)C)c2)cc1]

The compound (141 mg, 0.65 mmol) obtained from Preparation Example 112 and the compound (127 mg, 0.58 mmol) obtained from Preparation Example 155 were used to obtain the title compound (171 mg, 73%).

NMR:$^1$H-NMR(400 HMz, CDCl$_3$); δ 7.91 (s, 1H), 7.73 (s, 1H), 7.31 (d, 2H), 7.21 (s, 1H), 6.95 (d, 2H), 5.05 (s, 2H), 4.37 (d, 2H), 4.08 (br s, 1H), 2.68-2.84 (m, 2H), 2.61 (s, 3H), 1.82 (s, 3H), 0.87 (d, 6H)

Example 131

Synthesis of [7-(1-isobutyl-7-methyl-1H-indazol-5-ylmethoxy)-chroman-4-yl]-acetic acid

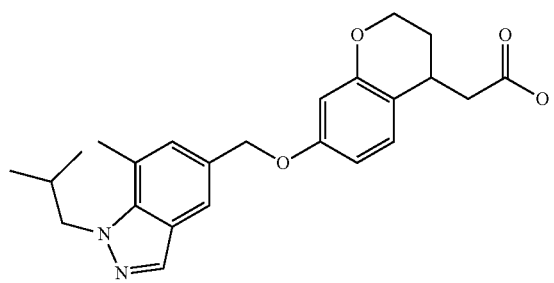 [SMILES: Cc1cc(COc2ccc3c(c2)OCCC3CC(=O)O)cc2cnn(CC(C)C)c12]

The compound (141 mg, 0.65 mmol) obtained from Preparation Example 112 and the compound (138 mg, 0.58 mmol) obtained from Preparation Example 160 were used to obtain the title compound (102 mg, 43%).

NMR:$^1$H-NMR(400 HMz, CDCl$_3$); δ 7.97 (s, 1H), 7.59 (s, 1H), 7.16 (s, 1H), 7.05 (d, 1H), 6.57 (d, 1H), 6.48 (s, 1H), 5.03 (s, 2H), 4.38 (d, 2H), 4.18 (br s, 2H), 3.33 (br s, 1H), 2.82-2.86 (m, 1H), 2.71 (s, 3H), 2.51-2.58 (m, 1H), 2.18-2.23 (m, 1H), 1.88 (m, 1H), 0.92 (d, 6H)

Example 132

Synthesis of (S)-3-[4-(1-isobutyl-1H-indazol-5-ylmethoxy)-phenyl]-hex-4-ynoic acid

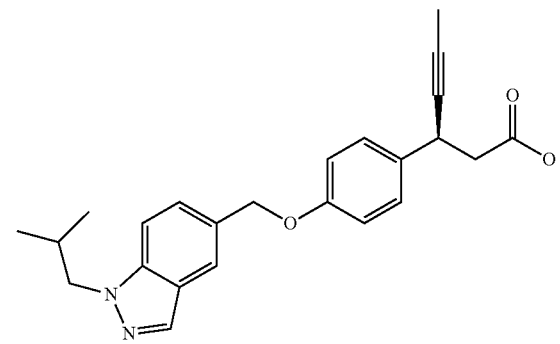

The compound (100 mg, 0.48 mmol) obtained from Preparation Example 97 and the compound (95 mg, 0.43 mmol) obtained from Preparation Example 155 were used to obtain the title compound (69 mg, 37%).

NMR:$^1$H-NMR(400 HMz, CDCl$_3$); δ 8.00 (s, 1H), 7.76 (s, 1H), 7.39-7.45 (m, 2H), 7.30-7.32 (m, 2H), 6.95 (d, 2H), 5.11 (s, 2H), 4.18 (d, 2H), 4.07 (br s, 1H), 2.68-2.84 (m, 2H), 2.30-2.36 (m, 1H), 1.98 (s, 3H), 0.92 (d, 6H)

Example 133

Synthesis of [7-(1-isobutyl-1H-indazol-5-ylmethoxy)-chroman-4-yl]-acetic acid

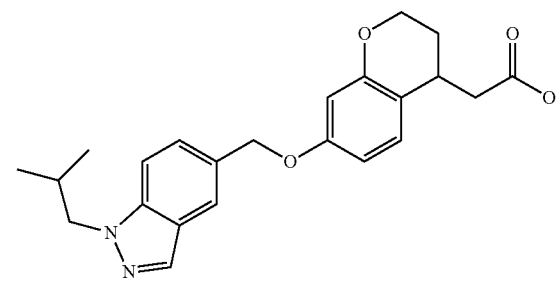 [SMILES: CC(C)Cn1ncc2cc(COc3ccc4c(c3)OCCC4CC(=O)O)ccc21]

The compound (100 mg, 0.48 mmol) obtained from Preparation Example 97 and the compound (102 mg, 0.43 mmol) obtained from Preparation Example 160 were used to obtain the title compound (41 mg, 24%).

NMR:$^1$H-NMR(400 HMz, CDCl$_3$); δ 7.99 (s, 1H), 7.76 (s, 1H), 7.40-7.45 (m, 2H), 7.05 (d, 1H), 6.57 (d, 1H), 6.48 (s, 1H), 5.09 (s, 2H), 4.18 (d, 2H), 3.31-3.34 (m, 1H), 2.81-2.86 (m, 1H), 2.52-2.58 (m, 1H), 2.31-2.38 (m, 1H), 2.17-2.19 (m, 1H), 1.86-1.88 (m, 1H), 0.93 (d, 6H)

Example 134

Synthesis of (S)-3-[4-(1-phenethyl-1H-indazol-5-ylmethoxy)-phenyl]-hex-4-ynoic acid

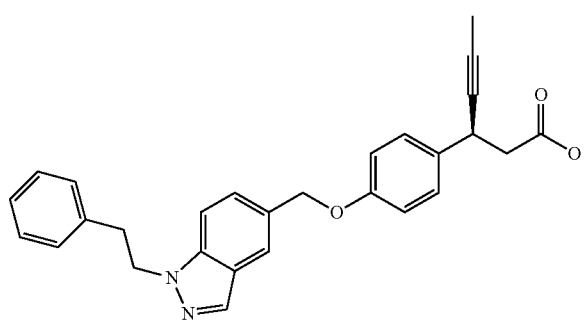 [SMILES: CC#C[C@@H](CC(=O)O)c1ccc(OCc2ccc3c(cnn3CCc3ccccc3)c2)cc1]

The compound (117 mg, 0.47 mmol) obtained from Preparation Example 93 and the compound (92 mg, 0.42 mmol) obtained from Preparation Example 155 were used to obtain the title compound (64 mg, 35%).

NMR:$^1$H-NMR(400 HMz, CDCl$_3$); δ 8.01 (s, 1H), 7.74 (s, 1H), 7.35 (dd, 1H), 7.30 (d, 2H), 7.16-7.25 (m, 4H), 7.11 (dd, 2H), 6.93 (d, 2H), 5.09 (s, 2H), 4.58 (t, 2H), 4.07 (br t, 1H), 3.19 (t, 2H), 2.78-2.84 (m, 1H), 2.63-2.72 (m, 1H), 1.81 (s, 3H)

Example 135

Synthesis of [7-(1-phenethyl-1H-indazol-5-ylmethoxy)-chroman-4-yl]-acetic acid

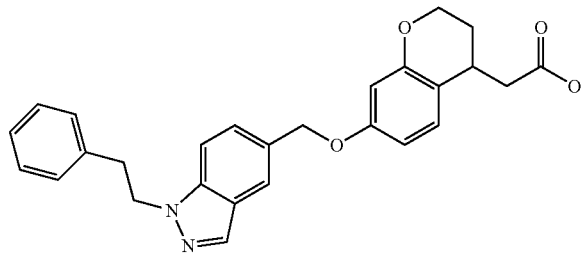 [SMILES: O=C(O)CC1CCOc2cc(OCc3ccc4c(cnn4CCc4ccccc4)c3)ccc21]

The compound (117 mg, 0.47 mmol) obtained from Preparation Example 93 and the compound (100 mg, 0.42 mmol) obtained from Preparation Example 160 were used to obtain the title compound (69 mg, 37%).

NMR:$^1$H-NMR(400 HMz, CDCl$_3$); δ 8.01 (s, 1H), 7.74 (s, 1H), 7.35 (d, 1H), 7.20-7.25 (m, 4H), 7.11 (d, 2H), 7.04 (d, 1H), 6.55 (dd, 1H), 6.46 (d, 1H), 5.06 (s, 2H), 4.59 (t, 2H), 4.13-4.20 (m, 2H), 3.30-3.34 (m, 1H), 3.19 (t, 2H), 2.83 (dd, 1H), 2.54 (dd, 1H), 2.13-2.21 (m, 1H), 1.84-1.88 (m, 1H)

Example 136

Synthesis of (S)-3-{4-[1-(3-methyl-butyl)-1H-indazol-5-ylmethoxy]-phenyl}-hex-4-ynoic acid

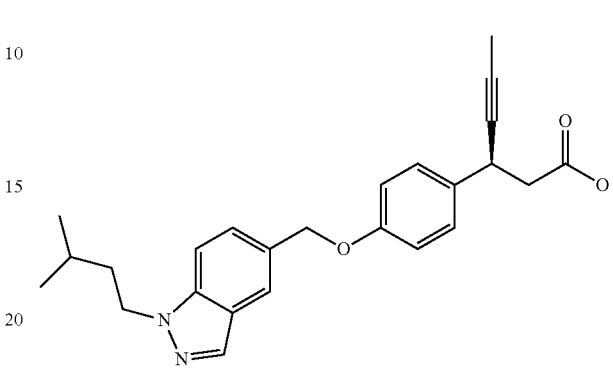

The compound (96 mg, 0.44 mmol) obtained from Preparation Example 98 and the compound (87 mg, 0.40 mmol) obtained from Preparation Example 155 were used to obtain the title compound (109 mg, 68%).

NMR:$^1$H-NMR(400 HMz, CDCl$_3$); δ 7.98 (s, 1H), 7.76 (s, 1H), 7.38-7.48 (m, 2H), 7.31 (d, 2H), 6.95 (d, 2H), 5.12 (s, 2H), 4.40 (t, 2H), 4.06 (m, 1H), 2.67-2.87 (m, 2H), 1.75-1.88 (m, 5H), 1.56 (m, 1H), 0.96 (d, 6H)

Example 137

Synthesis of {7-[1-(3-methyl-butyl)-1H-indazol-5-ylmethoxy]-chroman-4-yl}-acetic acid

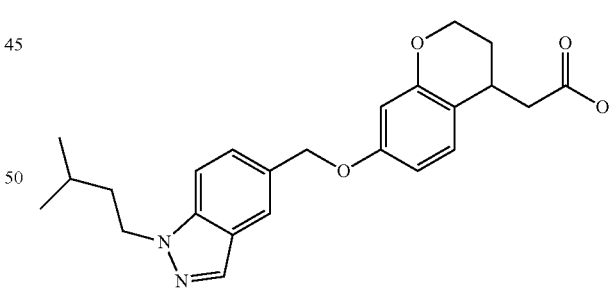

The compound (96 mg, 0.44 mmol) obtained from Preparation Example 98 and the compound (95 mg, 0.40 mmol) obtained from Preparation Example 160 were used to obtain the title compound (100 mg, 61%).

NMR:$^1$H-NMR(400 HMz, CDCl$_3$); δ 8.03 (s, 1H), 7.76 (s, 1H), 7.38-7.48 (m, 2H), 7.04 (d, 2H), 6.56 (dd, 1H), 6.47 (d, 1H), 5.09 (s, 2H), 4.40 (t, 2H), 4.10-4.24 (m, 2H), 3.32 (m, 1H), 2.83 (dd, 1H), 2.55 (dd, 1H), 2.17 (m, 1H), 1.75-1.93 (m, 3H), 1.58 (m, 1H), 0.96 (d, 6H)

Example 138

Synthesis of (S)-3-[4-(1-cyclohexyl methyl-1H-indazol-5-ylmethoxy)-phenyl]-hex-4-ynoic acid

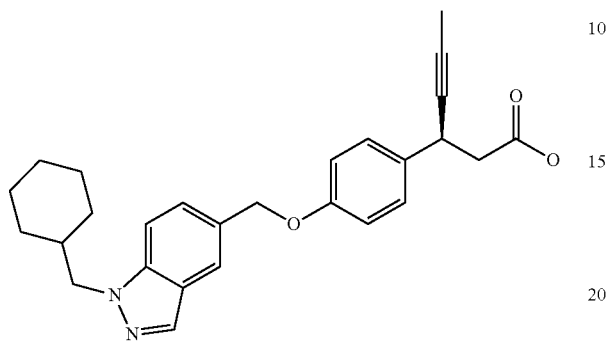

The compound (108 mg, 0.44 mmol) obtained from Preparation Example 102 and the compound (87 mg, 0.40 mmol) obtained from Preparation Example 155 were used to obtain the title compound (120 mg, 70%).

NMR:$^1$H-NMR(400 HMz, CDCl$_3$); δ 7.98 (s, 1H), 7.76 (s, 1H), 7.38-7.47 (m, 2H), 7.31 (d, 2H), 6.96 (d, 2H), 5.12 (s, 2H), 4.20 (d, 2H), 4.06 (m, 1H), 2.65-2.87 (m, 2H), 1.99 (m, 1H), 1.83 (d, 3H), 1.53-1.77 (m, 5H), 0.96-1.28 (m, 5H)

Example 139

Synthesis of [7-(1-cyclohexyl methyl-1H-indazol-5-ylmethoxy)-chroman-4-yl]-acetic acid

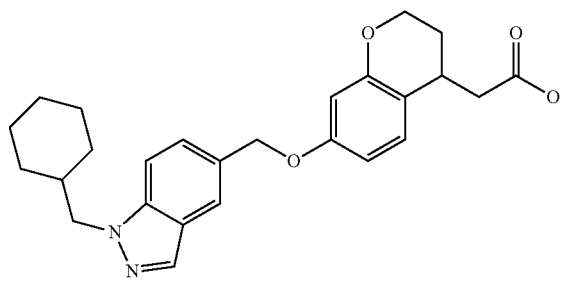 [SMILES: O=C(O)CC1CCOc2cc(OCc3ccc4c(cnn4CC4CCCCC4)c3)ccc21]

The compound (108 mg, 0.44 mmol) obtained from Preparation Example 102 and the compound (95 mg, 0.40 mmol) obtained from Preparation Example 160 were used to obtain the title compound (111 mg, 64%).

NMR:$^1$H-NMR(400 HMz, CDCl$_3$); δ 7.98 (s, 1H), 7.75 (s, 1H), 7.38-7.47 (m, 2H), 7.04 (d, 1H), 6.57 (dd, 1H), 6.48 (d, 1H), 5.09 (s, 2H), 4.10-4.26 (m, 4H), 3.32 (m, 1H), 2.84 (m, 1H), 2.55 (m, 1H), 2.17 (m, 1H), 2.00 (m, 1H), 1.87 (m, 1H), 1.52-1.77 (m, 5H), 0.96-1.30 (m, 5H)

Example 140

Synthesis of (S)-3-[4-(2-isobutyl-7-methyl-2H-indazol-5-ylmethoxy)-phenyl]-hex-4-ynoic acid

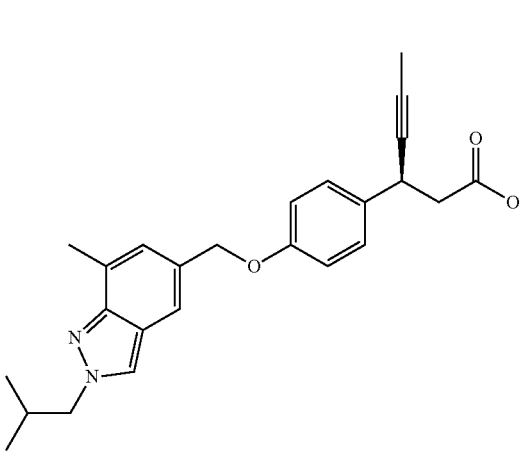 [SMILES: CC#C[C@@H](CC(=O)O)c1ccc(OCc2cc(C)c3nn(CC(C)C)cc3c2)cc1]

The compound (150 mg, 0.69 mmol) obtained from Preparation Example 113 and the compound (135 mg, 0.62 mmol) obtained from Preparation Example 155 were used to obtain the title compound (55 mg, 22%).

NMR:$^1$H-NMR(400 HMz, CDCl$_3$); δ 7.84 (s, 1H), 7.51 (s, 1H), 7.31 (d, 2H), 7.09 (s, 1H), 6.95 (d, 2H), 5.05 (s, 2H), 4.22 (d, 2H), 4.07 (br t, 1H), 2.68-2.83 (m, 2H), 2.62 (s, 3H), 2.33-2.40 (m, 1H), 1.83 (s, 3H), 0.88 (d, 6H)

Example 141

Synthesis of (S)-3-[4-(1-pyridine-2-ylmethyl-1H-indazol-5-ylmethoxy)-phenyl]-hex-4-ynoic acid

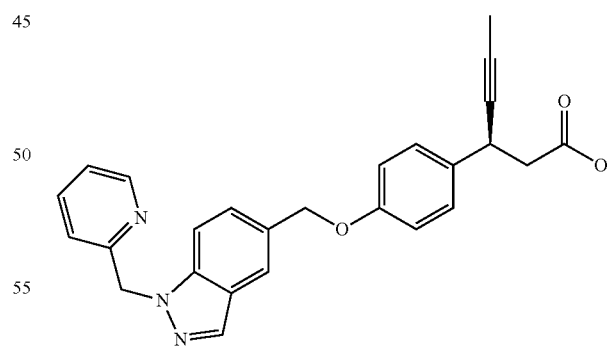

The compound (111 mg, 0.46 mmol) obtained from Preparation Example 94 and the compound (91 mg, 0.42 mmol) obtained from Preparation Example 155 were used to obtain the title compound (90 mg, 50%).

NMR:$^1$H-NMR(400 HMz, CDCl$_3$); δ 8.58 (d, 1H), 8.07 (s, 1H), 7.77 (s, 1H), 7.55-7.58 (m, 1H), 7.18-7.40 (m, 4H), 6.91 (d, 1H), 6.83 (d, 3H), 5.75 (s, 2H), 5.06 (s, 2H), 4.09 (br s, 1H), 2.68-2.85 (m, 2H), 1.81 (s, 3H)

Example 142

Synthesis of [7-(1-pyridine-2-ylmethyl-1H-indazol-5-ylmethoxy)-chroman-4-yl]-acetic acid

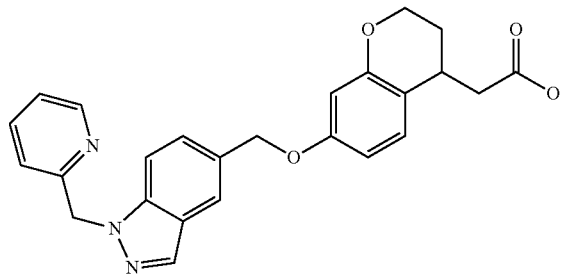

The compound (111 mg, 0.46 mmol) obtained from Preparation Example 94 and the compound (99 mg, 0.42 mmol) obtained from Preparation Example 160 were used to obtain the title compound (26 mg, 15%).

NMR:$^1$H-NMR(400 HMz, CDCl$_3$); δ 8.60 (d, 1H), 8.08 (s, 1H), 7.79 (s, 1H), 7.56-7.60 (m, 1H), 7.42 (s, 2H), 7.20-7.23 (m, 1H), 7.05 (d, 1H), 6.84 (d, 1H), 6.55 (dd, 1H), 6.46 (s, 1H), 5.78 (s, 2H), 5.07 (s, 2H), 4.17 (br t, 2H), 3.30-3.34 (m, 1H), 2.80-2.84 (m, 1H), 2.50-2.57 (m, 1H), 2.16-2.19 (m, 1H), 1.85-1.89 (m, 1H)

Example 143

Synthesis of (S)-3-[4-(1-benzyl-1H-pyrrolo[2,3-b]pyridin-5-ylmethoxy)-phenyl]-hex-4-ynoic acid

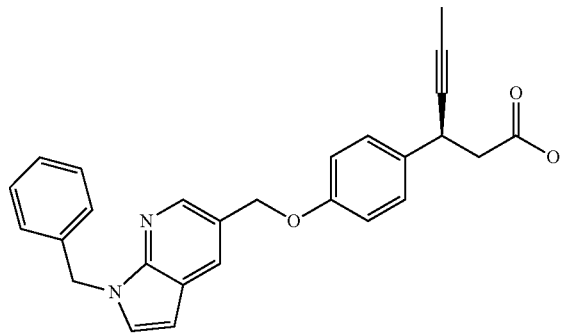 [SMILES: CC#C[C@@H](CC(=O)O)c1ccc(OCc2cnc3c(ccn3Cc3ccccc3)c2)cc1]

The compound (0.12 g, 0.53 mmol) obtained from Preparation Example 123 and the compound (0.10 g, 0.48 mmol) obtained from Preparation Example 155 were used to obtain the title compound (0.10 g, 49%).

NMR:$^1$H-NMR(400 HMz, CDCl$_3$); δ 8.41 (s, 1H), 8.01 (s, 1H), 7.26-7.32 (m, 5H), 7.20 (m, 3H), 6.96 (d, 2H), 6.48 (d, 1H), 5.49 (s, 2H), 5.13 (s, 2H), 4.09 (m, 1H), 2.84 (dd, 1H), 2.72 (dd, 1H), 1.83 (s, 3H)

Example 144

Synthesis of (S)-3-[4-(1-isobutyl-1H-pyrrolo[2,3-b]pyridin-5-ylmethoxy)-phenyl]-hex-4-ynoic acid

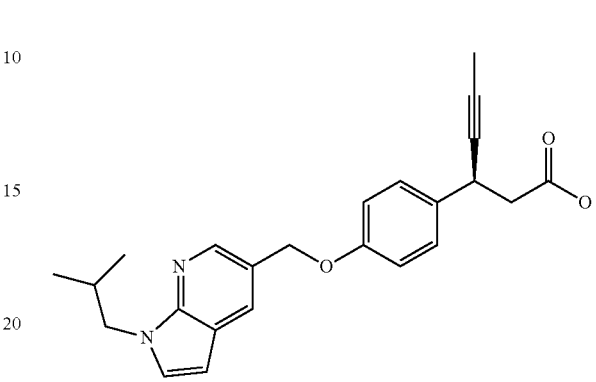

The compound (0.10 g, 0.47 mmol) obtained from Preparation Example 124 and the compound (0.09 g, 0.42 mmol) obtained from Preparation Example 155 were used to obtain the title compound (0.07 g, 42%).

NMR:$^1$H-NMR(400 HMz, CDCl$_3$); δ 8.38 (s, 1H), 7.99 (s, 1H), 7.33 (d, 2H), 7.20 (d, 1H), 6.96 (d, 2H), 6.45 (d, 1H), 5.12 (s, 2H), 4.08 (d, 2H), 4.06 (m, 1H), 2.85 (dd, 1H), 2.74 (dd, 1H), 2.25 (m, 1H), 1.83 (s, 3H), 0.91 (d, 6H)

Example 145

Synthesis of [7-(1-benzyl-7-methyl-1H-indol-6-ylmethoxy)-chroman-4-yl]-acetic acid

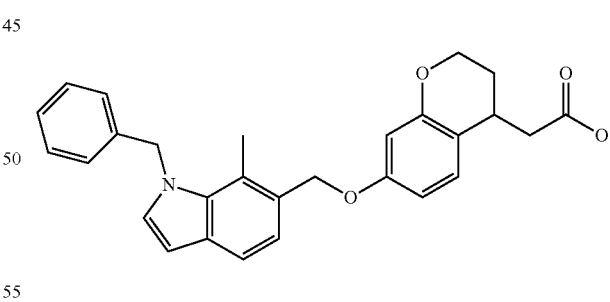

The compound (117 mg, 0.47 mmol) obtained from Preparation Example 17-2 and the compound (100 mg, 0.42 mmol) obtained from Preparation Example 160 were used to obtain the title compound (18 mg, 9%).

NMR:$^1$H-NMR(400 HMz, CDCl$_3$); δ 7.48 (d, 1H), 7.28 (m, 3H), 7.12 (d, 1H), 7.08 (d, 1H), 7.00 (d, 1H), 6.92 (d, 1H), 6.54 (m, 2H), 6.46 (m, 1H), 5.61 (s, 2H), 5.03 (s, 2H), 4.16 (m, 2H), 3.30 (m, 1H), 2.81 (dd, 1H), 2.53 (m, 4H), 2.16 (m, 1H), 1.85 (m, 1H)

Example 146

Synthesis of [8-(2-benzyl-7-methyl-2H-indazol-5-ylmethoxy)-chroman-4-yl]-acetic acid

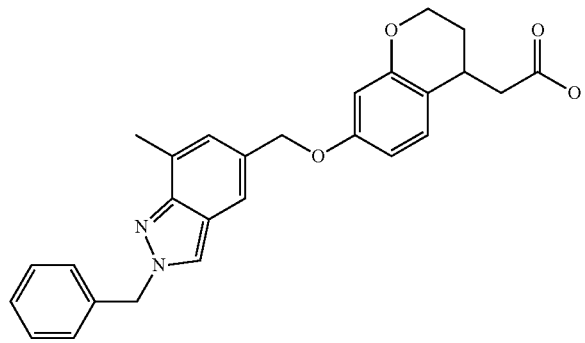 [SMILES: Cc1cc(COc2ccc3c(c2)OCCC3CC(=O)O)cc2cn(Cc3ccccc3)nc12]

The compound (107 mg, 0.47 mmol) obtained from Preparation Example 111 and the compound (100 mg, 0.42 mmol) obtained from Preparation Example 160 were used to obtain the title compound (40 mg, 22%).

NMR:$^1$H-NMR(400 HMz, CDCl$_3$); δ 7.81 (s, 1H), 7.47 (s, 1H), 7.32 (m, 3H), 7.24 (m, 3H), 7.09 (s, 1H), 7.02 (d, 1H), 6.56 (m, 1H), 6.45 (d, 1H), 5.63 (s, 2H), 5.01 (s, 2H), 4.17 (m, 2H), 3.30 (m, 1H), 2.81 (dd, 1H), 2.65 (s, 3H), 2.53 (dd, 1H), 2.16 (m, 1H), 1.85 (m, 1H)

Example 147

Synthesis of (S)-3-[4-(1-pyridin-3-ylmethyl-1H-indazol-5-ylmethoxy)-phenyl]-hex-4-ynoic acid

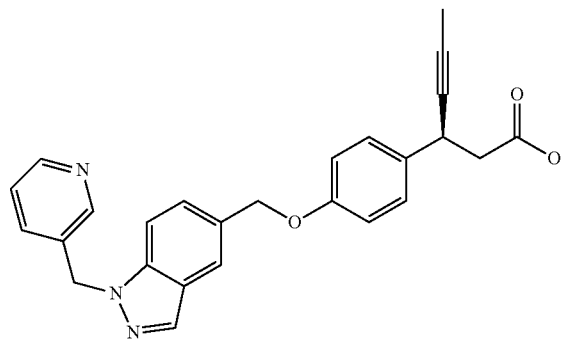

The compound (96 mg, 0.40 mmol) obtained from Preparation Example 95 and the compound (96 mg, 0.44 mmol) obtained from Preparation Example 155 were used to obtain the title compound (88 mg, 52%).

NMR:$^1$H-NMR(400 HMz, CDCl$_3$); δ 8.51 (d, 1H), 8.43 (s, 1H), 8.04 (s, 1H), 7.78 (s, 1H), 7.20-7.60 (m, 6H), 6.90 (d, 2H), 5.61 (s, 2H), 5.13 (s, 2H), 4.05 (m, 1H), 2.63-2.87 (m, 2H), 1.81 (d, 3H)

Example 148

Synthesis of [7-(1-pyridin-3-ylmethyl-1H-indazol-5-ylmethoxy)-chroman-4-yl]-acetic acid

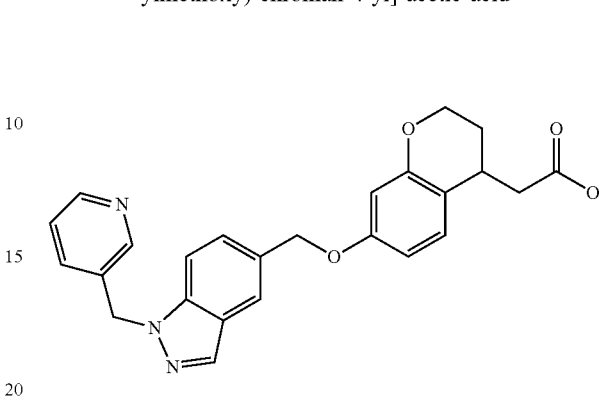

The compound (96 mg, 0.40 mmol) obtained from Preparation Example 95 and the compound (104 mg, 0.44 mmol) obtained from Preparation Example 160 were used to obtain the title compound (91 mg, 53%).

NMR:$^1$H-NMR(400 HMz, DMSO-d$_6$); δ 12.25 (br s, 1H), 8.53 (s, 1H), 8.46 (s, 1H), 8.13 (s, 1H), 7.82 (s, 1H), 7.78 (d, 1H), 7.59 (d, 1H), 7.45 (d, 1H), 7.32 (dd, 1H), 7.07 (d, 1H), 6.51 (dd, 1H), 6.39 (d, 1H), 5.71 (s, 2H), 5.11 (s, 2H), 4.09 (t, 2H), 3.12 (m, 1H), 2.67 (dd, 1H), 2.38 (dd, 1H), 1.99 (m, 1H), 1.71 (m, 1H)

Example 149

Synthesis of {7-[1-(2-ethoxy-ethyl)-1H-indazol-5-ylmethoxy]-chroman-4-yl}-acetic acid

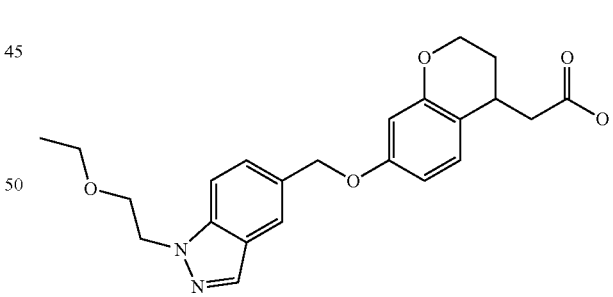

The compound (103 mg, 0.47 mmol) obtained from Preparation Example 106 and the compound (100 mg, 0.42 mmol) obtained from Preparation Example 160 were used to obtain the title compound (70 mg, 36%).

NMR:$^1$H-NMR(400 HMz, CDCl$_3$); δ 7.99 (s, 1H), 7.75 (s, 1H), 7.50 (m, 1H), 7.42 (m, 1H), 7.03 (d, 1H), 6.55 (m, 1H), 6.46 (d, 1H), 5.09 (s, 2H), 4.55 (t, 2H), 4.18 (m, 2H), 3.85 (t, 2H), 3.41 (q, 1H), 3.33 (m, 1H), 2.82 (dd, 1H), 2.55 (dd, 1H), 2.18 (m, 1H), 1.76 (m, 1H), 1.09 (t, 3H)

Example 150

Synthesis of (S)-3-[4-(5-fluoro-1-isobutyl-1H-indazol-6-ylmethoxy)-phenyl]-hex-4-ynoic acid

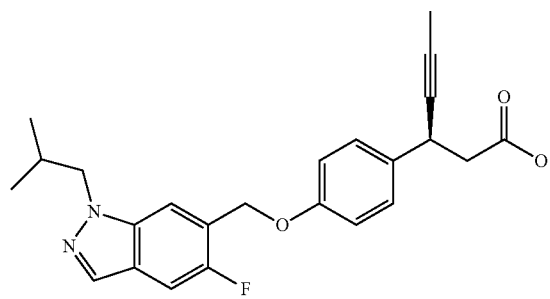 [SMILES: CC#C[C@@H](CC(=O)O)c1ccc(OCc2cc3c(cnn3CC(C)C)cc2F)cc1]

The compound (78 mg, 0.35 mmol) obtained from Preparation Example 85 and the compound (69 mg, 0.32 mmol) obtained from Preparation Example 155 were used to obtain the title compound (100 mg, 76%).

NMR:$^1$H-NMR(400 HMz, CDCl$_3$); δ 8.05 (s, 1H), 7.51 (d, 1H), 7.29-7.35 (m, 3H), 6.99 (d, 2H), 5.28 (s, 2H), 4.09 (d, 2H), 5.07 (br t, 1H), 2.64-2.80 (m, 2H), 2.25-2.32 (m, 1H), 1.82 (s, 3H), 0.90 (d, 6H)

Example 151

Synthesis of (S)-3-{4-[1-(tetrahydrofuran-2-ylmethyl)-1H-indazol-5-ylmethoxy]-phenyl}-hex-4-ynoic acid

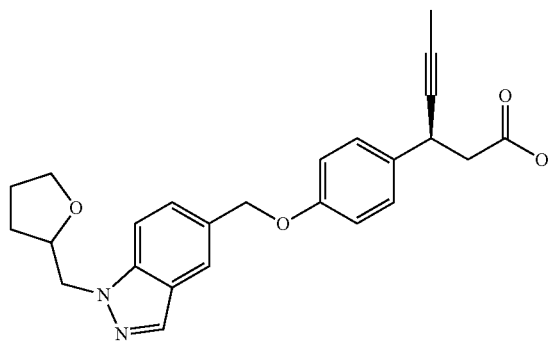

The compound (150 mg, 0.65 mmol) obtained from Preparation Example 103 and the compound (127 mg, 0.58 mmol) obtained from Preparation Example 155 were used to obtain the title compound (141 mg, 58%).

NMR:$^1$H-NMR(400 HMz, CDCl$_3$); δ 7.99 (s, 1H), 7.65 (s, 1H), 7.53 (d, 1H), 7.43 (d, 1H), 7.31 (d, 2H), 6.94 (d, 2H), 5.10 (s, 2H), 4.84 (d, 2H), 4.34-4.48 (m, 1H), 4.07 (br s, 2H), 3.69-3.76 (m, 2H), 2.67-2.82 (m, 2H), 1.94-1.97 (m, 1H), 1.82 (s, 3H), 1.66-1.78 (m, 2H)

Example 152

Synthesis of (S)-3-{4-[1-(3-methanesulfonyl-propyl)-1H-indazol-5-ylmethoxy]-phenyl}-hex-4-ynoic acid

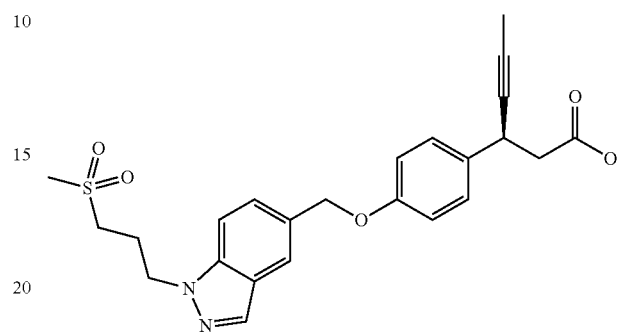

The compound (74 mg, 0.28 mmol) obtained from Preparation Example 79-2 and the compound (55 mg, 0.25 mmol) obtained from Preparation Example 155 were used to obtain the title compound (6 mg, 5%).

NMR:$^1$H-NMR(400 HMz, CDCl$_3$); δ 8.01 (s, 1H), 7.78 (s, 1H), 7.41-7.50 (m, 2H), 7.31 (d, 2H), 6.94 (d, 2H), 5.14 (s, 2H), 4.58 (t, 2H), 4.06 (br t, 1H), 2.99 (t, 2H), 2.87 (s, 3H), 2.68-2.84 (m, 2H), 2.51 (pent, 2H), 1.83 (s, 3H)

Example 153

Synthesis of (S)-3-{4-[1-(tetrahydrofuran-3-ylmethyl)-1H-indazol-5-ylmethoxy]-phenyl}-hex-4-ynoic acid

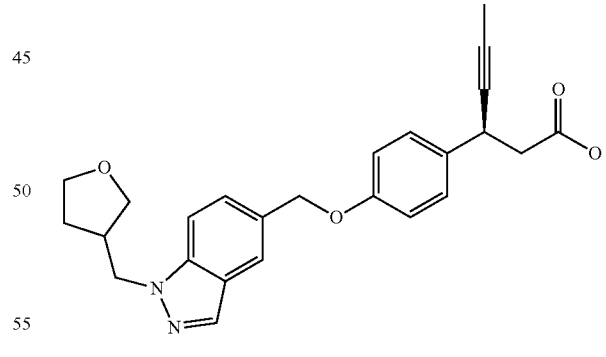

The compound (0.17 g, 0.73 mmol) obtained from Preparation Example 104 and the compound (0.14 g, 0.66 mmol) obtained from Preparation Example 155 were used to obtain the title compound (0.19 g, 70%).

NMR:$^1$H-NMR(400 HMz, CDCl$_3$); δ 8.00 (s, 1H), 7.77 (s, 1H), 7.47 (q, 2H), 7.32 (d, 2H), 6.96 (d, 2H), 5.12 (s, 2H), 4.37 (d, 2H), 4.07 (m, 1H), 3.99 (m, 1H), 3.79 (m, 2H), 3.66 (m, 1H), 2.97 (m, 1H), 2.83 (dd, 1H), 2.73 (dd, 1H), 2.02 (m, 1H), 1.82 (s, 3H), 1.73 (m, 1H)

Example 154

Synthesis of (S)-3-{4-[2-(tetrahydrofuran-3-ylmethyl)-2H-indazol-5-ylmethoxy]-phenyl}-hex-4-ynoic acid

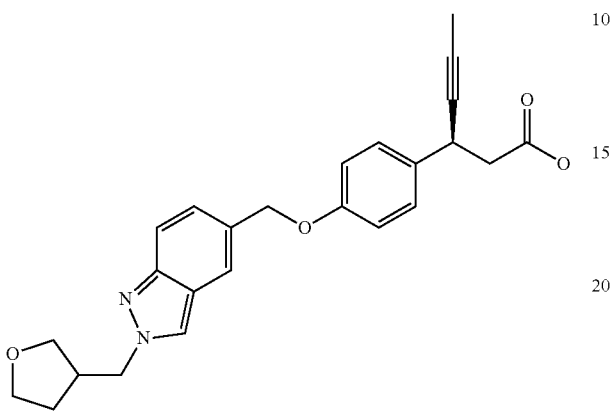

The compound (0.17 g, 0.73 mmol) obtained from Preparation Example 105 and the compound (0.14 g, 0.66 mmol) obtained from Preparation Example 155 were used to obtain the title compound (0.10 g, 37%).

NMR:$^1$H-NMR(400 HMz, CDCl$_3$); δ 7.89 (s, 1H), 7.71 (d, 1H), 7.67 (s, 1H), 7.35 (m, 2H), 6.95 (d, 2H), 5.08 (s, 2H), 4.39 (d, 2H), 4.07 (m, 1H), 3.96 (m, 1H), 3.79 (m, 2H), 3.62 (m, 1H), 3.03 (m, 1H), 2.83 (dd, 1H), 2.73 (dd, 1H), 2.06 (m, 1H), 1.82 (s, 3H), 1.70 (m, 1H)

Example 155

Synthesis of 3-[4-(1-benzyl-1H-indazol-5-ylmethoxy)-phenyl]-3-methoxy-propanoic acid

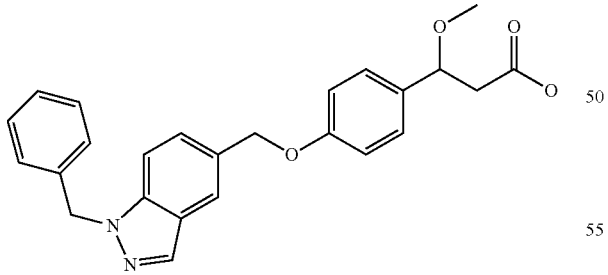

The compound (117 mg, 0.49 mmol) obtained from Preparation Example 91 and the compound (100 mg, 0.44 mmol) obtained from Preparation Example 153-3 were used to obtain the title compound (164 mg, 91%).

NMR:$^1$H-NMR(400 HMz, CDCl$_3$); δ 8.05 (s, 1H), 7.73 (s, 1H), 7.17-7.49 (m, 9H), 6.98 (d, 2H), 5.59 (s, 2H), 5.15 (s, 2H), 4.57-4.60 (m, 1H), 3.20 (s, 3H), 2.84 (dd, 1H), 2.61 (dd, 1H)

Example 156

Synthesis of (S)-3-[4-(1-isobutyl-1H-pyrazolo[3,4-b]pyridin-5-ylmethoxy)-phenyl]-hex-4-ynoic acid

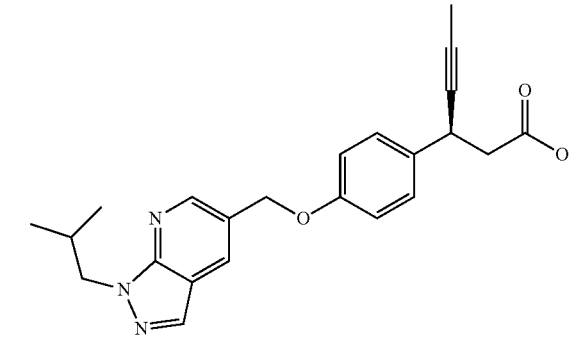 [SMILES: CC#C[C@@H](CC(=O)O)c1ccc(OCc2cnc3c(cnn3CC(C)C)c2)cc1]

The compound (87 mg, 0.47 mmol) obtained from Preparation Example 130 and the compound (92 mg, 0.42 mmol) obtained from Preparation Example 155 were used to obtain the title compound (95 mg, 55%).

NMR:$^1$H-NMR(400 HMz, CDCl$_3$); δ 8.61 (m, 1H), 8.13 (m, 1H), 8.02 (s, 1H), 7.32 (d, 2H), 6.95 (d, 2H), 5.16 (s, 2H), 4.34 (d, 2H), 4.06 (m, 1H), 2.83 (dd, 1H), 2.71 (dd, 1H), 1.83 (d, 3H), 0.92 (d, 6H)

Example 157

Synthesis of (S)-3-{4-[1-(2-ethoxy-ethyl)-1H-indazol-5-ylmethoxy]-phenyl}-hex-4-ynoic acid

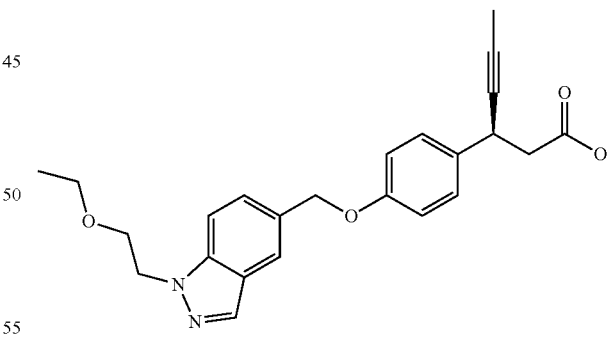

The compound (103 mg, 0.47 mmol) obtained from Preparation Example 106 and the compound (92 mg, 0.42 mmol) obtained from Preparation Example 155 were used to obtain the title compound (85 mg, 45%).

NMR:$^1$H-NMR(400 HMz, CDCl$_3$); δ 7.99 (s, 1H), 7.75 (s, 1H), 7.51 (m, 1H), 7.43 (m, 1H), 7.30 (d, 2H), 6.94 (d, 2H), 5.13 (s, 2H), 4.55 (t, 2H), 4.06 (m, 1H), 3.86 (t, 2H), 3.43 (q, 2H), 2.81 (dd, 1H), 2.70 (dd, 1H), 1.83 (d, 3H), 1.09 (t, 3H)

Example 158

Synthesis of 3-[4-(1-benzyl-1H-indazol-5-yl-methoxy)-phenyl]-butyric acid

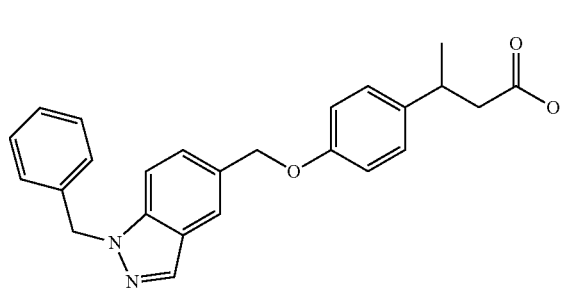 [SMILES: CC(CC(=O)O)c1ccc(OCc2ccc3c(cnn3Cc3ccccc3)c2)cc1]

The compound (105 mg, 0.44 mmol) obtained from Preparation Example 91 and the compound (83 mg, 0.40 mmol) obtained from Preparation Example 150 were used to obtain the title compound (124 mg, 78%).

NMR:$^1$H-NMR(400 HMz, CDCl$_3$); δ 8.04 (s, 1H), 7.79 (s, 1H), 7.10-7.46 (m, 9H), 6.93 (d, 2H), 5.60 (s, 2H), 5.10 (s, 2H), 3.24 (m, 1H), 2.52-2.68 (m, 2H), 1.30 (d, 3H)

Example 159

Synthesis of 3-[4-(1-benzyl-1H-indazol-5-yl-methoxy)-phenyl]-pentanoic acid

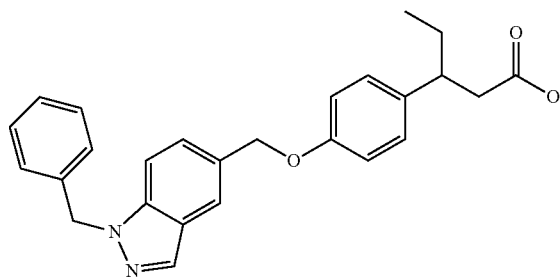 [SMILES: CCC(CC(=O)O)c1ccc(OCc2ccc3c(cnn3Cc3ccccc3)c2)cc1]

The compound (114 mg, 0.48 mmol) obtained from Preparation Example 91 and the compound (89 mg, 0.40 mmol) obtained from Preparation Example 151 were used to obtain the title compound (141 mg, 86%).

NMR:$^1$H-NMR(400 HMz, CDCl$_3$); δ 8.04 (s, 1H), 7.79 (s, 1H), 7.16-7.44 (m, 7H), 7.10 (d, 2H), 6.92 (d, 2H), 5.60 (s, 2H), 5.10 (s, 2H), 2.95 (m, 1H), 2.52-2.70 (m, 2H), 1.49-1.78 (m, 2H), 0.79 (t, 3H)

Example 160

Synthesis of (S)-3-{4-[2-(2-ethoxy-ethyl)-2H-indazol-5-ylmethoxy]-phenyl}-hex-4-ynoic acid

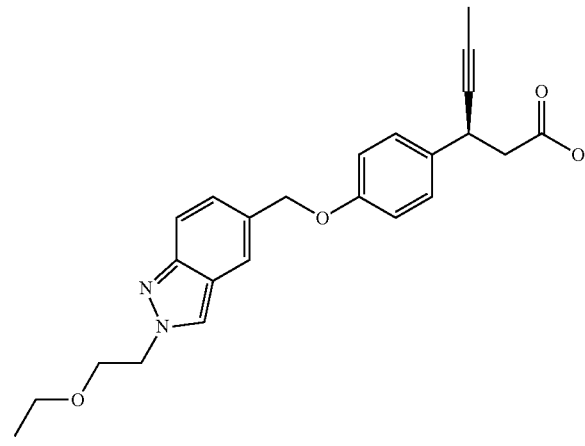 [SMILES: CC#C[C@@H](CC(=O)O)c1ccc(OCc2ccc3nn(CCOCC)cc3c2)cc1]

The compound (103 mg, 0.47 mmol) obtained from Preparation Example 107 and the compound (92 mg, 0.42 mmol) obtained from Preparation Example 155 were used to obtain the title compound (67 mg, 35%).

NMR:$^1$H-NMR(400 HMz, CDCl$_3$); δ 8.02 (s, 1H), 7.69 (m, 2H), 7.31 (m, 4H), 6.95 (d, 2H), 4.57 (t, 2H), 4.06 (m, 1H), 3.90 (t, 2H), 3.47 (q, 2H), 2.78 (dd, 1H), 2.73 (dd, 1H), 1.83 (d, 3H), 1.14 (t, 3H)

Example 161

Synthesis of (S)-3-[4-(1-benzyl-3-methyl-2-oxo-2,3-dihydro-1H-benzoimidazol-5-ylmethoxy)-phenyl]-hex-4-ynoic acid

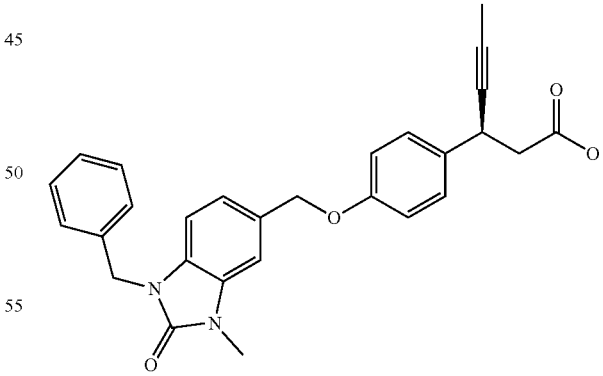

The compound (0.20 g, 0.75 mmol) obtained from Preparation Example 127-2 and the compound (0.14 g, 0.68 mmol) obtained from Preparation Example 155 were used to obtain the title compound (0.16 g, 41%).

NMR:$^1$H-NMR(400 HMz, CDCl$_3$); δ 7.23-7.30 (m, 7H), 7.07 (s, 1H), 7.06 (d, 1H), 6.92 (d, 2H), 6.86 (d, 1H), 5.07 (s, 2H), 5.02 (s, 2H), 4.06 (m, 1H), 3.46 (s, 3H), 2.82 (dd, 1H), 2.72 (dd, 1H), 1.82 (s, 3H)

Example 162

Synthesis of 3-[4-(1-benzyl-1H-indazol-5-yl-methoxy)-phenyl]-3-cyano-propanoic acid

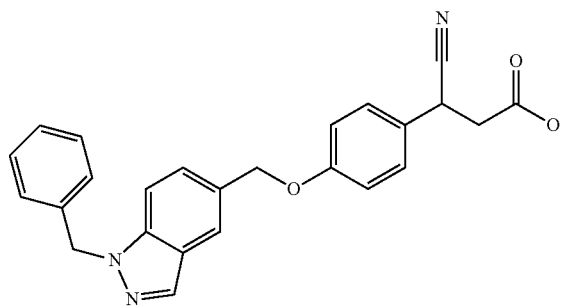 [SMILES: N#CC(CC(=O)O)c1ccc(OCc2ccc3c(cnn3Cc3ccccc3)c2)cc1]

The compound (0.12 g, 0.51 mmol) obtained from Preparation Example 91 and the compound (0.10 g, 0.46 mmol) obtained from Preparation Example 154 were used to obtain the title compound (0.06 g, 33%).

NMR:$^1$H-NMR(400 HMz, CDCl$_3$); δ 8.05 (s, 1H), 7.77 (s, 1H), 7.41 (q, 2H), 7.29 (m, 5H), 7.19 (d, 2H), 6.99 (d, 2H), 5.60 (s, 2H), 5.11 (s, 2H), 4.22 (m, 1H), 3.05 (dd, 1H), 2.88 (dd, 1H)

Example 163

Synthesis of (S)-3-[4-(1-cyclopentylmethyl-1H-indazol-5-ylmethoxy)-phenyl]-hex-4-ynoic acid

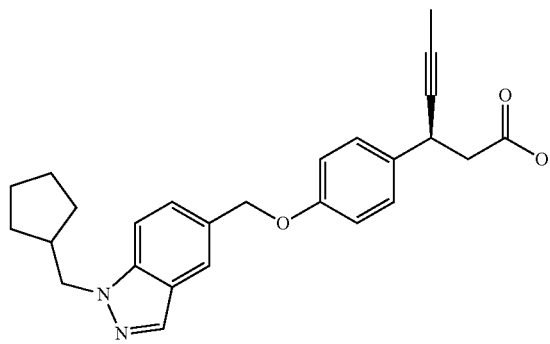 [SMILES: CC#C[C@@H](CC(=O)O)c1ccc(OCc2ccc3c(cnn3CC3CCCC3)c2)cc1]

The compound (150 mg, 0.65 mmol) obtained from Preparation Example 101 and the compound (128 mg, 0.59 mmol) obtained from Preparation Example 155 were used to obtain the title compound (145 mg, 59%).

NMR:$^1$H-NMR(400 HMz, CDCl$_3$); δ 8.03 (s, 1H), 7.75 (s, 1H), 7.40-7.48 (m, 2H), 7.33 (dd, 2H), 6.92 (dd, 2H), 5.15 (s, 2H), 4.29 (d, 2H), 4.05-4.10 (m, 1H), 2.75-2.81 (m, 1H), 2.66-2.71 (m, 1H), 2.49-2.56 (m, 1H), 1.81 (s, 3H), 1.63-1.66 (m, 4H), 1.32-1.59 (m, 2H), 1.23-1.30 (m, 2H)

Example 164

Synthesis of (S)-3-[4-(1-cyclopentyl-1H-indazol-5-ylmethoxy)-phenyl]-hex-4-ynoic acid

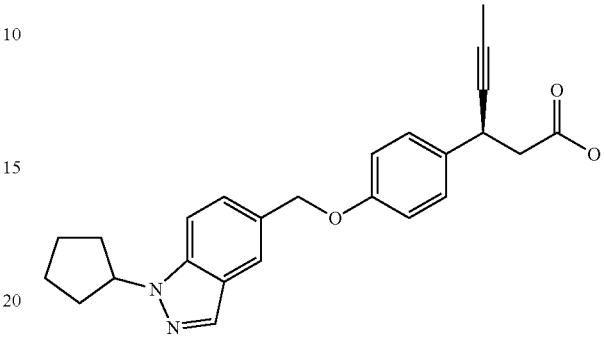

The compound (150 mg, 0.69 mmol) obtained from Preparation Example 100 and the compound (136 mg, 0.62 mmol) obtained from Preparation Example 155 were used to obtain the title compound (145 mg, 58%).

NMR:$^1$H-NMR(400 HMz, CDCl$_3$); δ 7.93 (s, 1H), 7.75 (s, 1H), 7.41-7.47 (m, 2H), 7.28 (dd, 2H), 6.91 (dd, 2H), 5.11 (s, 2H), 4.96-5.02 (m, 1H), 4.06 (br s, 1H), 2.77-2.83 (m, 1H), 2.67-2.73 (m, 1H), 2.16-2.17 (m, 4H), 1.97-2.09 (m, 2H), 1.82 (s, 3H), 1.73-1.75 (m, 2H)

Example 165

Synthesis of (S)-3-[4-(1-cyclopropylmethyl-1H-indazol-5-ylmethoxy)-phenyl]-hex-4-ynoic acid

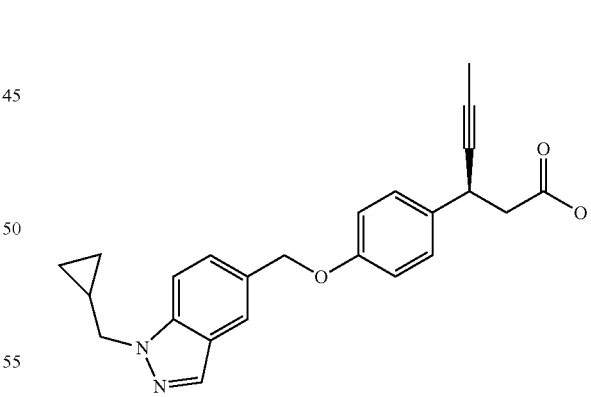

The compound (0.17 g, 0.87 mmol) obtained from Preparation Example 99 and the compound (0.17 g, 0.78 mmol) obtained from Preparation Example 155 were used to obtain the title compound (0.10 g, 34%).

NMR:$^1$H-NMR(400 HMz, CDCl$_3$); δ 8.00 (s, 1H), 7.76 (s, 1H), 7.44 (s, 2H), 7.32 (d, 2H), 6.96 (d, 2H), 5.11 (s, 2H), 4.27 (d, 2H), 4.08 (m, 1H), 2.84 (dd, 1H), 2.73 (dd, 1H), 1.82 (s, 3H), 0.57 (m, 2H), 0.40 (m, 2H)

Example 166

Synthesis of (S)-3-[4-(3-isobutyl-3H-benzotriazol-5-ylmethoxy)-phenyl]-hex-4-ynoic acid

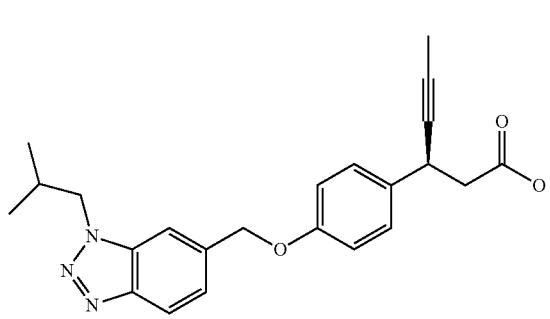 [SMILES: CC#C[C@@H](CC(=O)O)c1ccc(OCc2ccc3nnn(CC(C)C)c3c2)cc1]

The compound (95 mg, 0.47 mmol) obtained from Preparation Example 128-2 and the compound (92 mg, 0.42 mmol) obtained from Preparation Example 155 were used to obtain the title compound (60 mg, 33%).

NMR:$^1$H-NMR(400 HMz, CDCl$_3$); δ 8.05 (d, 1H), 7.58 (s, 1H), 7.40 (d, 1H), 7.32 (d, 2H), 6.95 (d, 2H), 5.22 (s, 2H), 4.43 (d, 2H), 4.07 (m, 1H), 2.83 (dd, 1H), 2.71 (dd, 1H), 2.40 (m, 1H), 1.83 (d, 3H), 0.96 (d, 6H)

Example 167

Synthesis of 2-[4-(1-benzyl-1H-indazol-6-yl-methoxy)-phenyl]-cyclopropane carboxylic acid

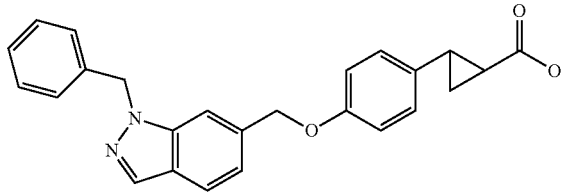 [SMILES: O=C(O)C1CC1c1ccc(OCc2ccc3cnn(Cc4ccccc4)c3c2)cc1]

The compound (100 mg, 0.42 mmol) obtained from Preparation Example 56 and the compound (73 mg, 0.38 mmol) obtained from Preparation Example 152 were used to obtain the title compound (76 mg, 51%).

NMR:$^1$H-NMR(400 HMz, CDCl$_3$); δ 8.13 (s, 1H), 7.72 (d, 1H), 7.40 (s, 1H), 7.20-7.26 (m, 3H), 7.14-7.17 (m, 3H), 7.01 (d, 2H), 6.86 (d, 2H), 5.57 (s, 2H), 5.11 (s, 2H), 2.51-2.56 (m, 1H), 1.79-1.83 (m, 1H), 1.56-1.62 (m, 2H), 1.26-1.32 (m, 2H)

Example 168

Synthesis of (S)-3-[4-(1-isopropyl-7-methyl-1H-indazol-5-ylmethoxy)-phenyl]-hex-4-ynoic acid

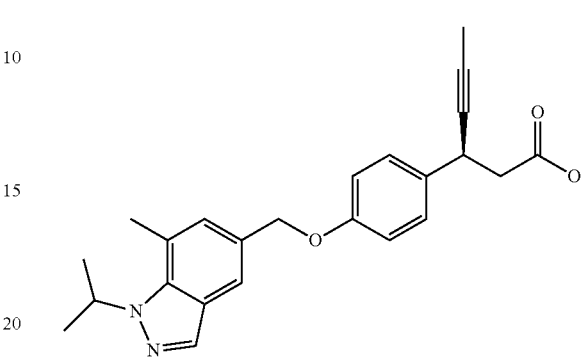

The compound (150 mg, 0.73 mmol) obtained from Preparation Example 114 and the compound (144 mg, 0.66 mmol) obtained from Preparation Example 155 were used to obtain the title compound (150 mg, 58%).

NMR:$^1$H-NMR(400 HMz, CDCl$_3$); δ 8.25 (s, 1H), 7.55 (s, 1H), 7.30 (d, 2H), 7.16 (s, 1H), 6.94 (d, 2H), 5.15-5.22 (m, 1H), 5.06 (s, 2H), 4.07 (br s, 1H), 2.77-2.83 (m, 1H), 2.73 (s, 3H), 2.57-2.70 (m, 1H), 1.82 (s, 3H), 1.58 (d, 6H)

Example 169

Synthesis of (S)-3-[4-(1-cyclopentylmethyl-7-methyl-1H-indazol-5-ylmethoxy)-phenyl]-hex-4-ynoic acid

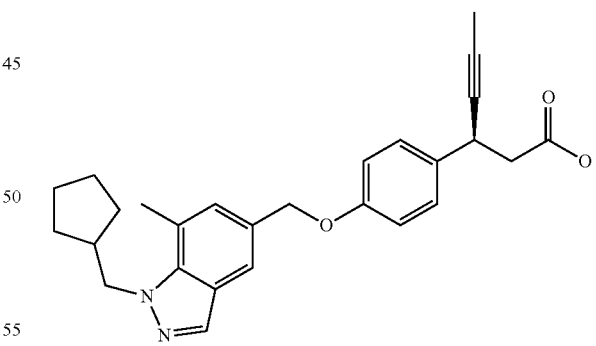

The compound (150 mg, 0.61 mmol) obtained from Preparation Example 116 and the compound (121 mg, 0.55 mmol) obtained from Preparation Example 155 were used to obtain the title compound (106 mg, 45%).

NMR:$^1$H-NMR(400 HMz, CDCl$_3$); δ 7.96 (s, 1H), 7.58 (s, 1H), 7.31 (d, 2H), 7.16 (s, 1H), 6.95 (d, 2H), 5.05 (s, 2H), 4.50 (d, 2H), 4.07 (br s, 1H), 2.73-2.81 (m, 1H), 2.72 (s, 3H), 2.68 (m, 1H), 2.38-2.45 (m, 1H), 1.82 (s, 3H), 1.61-1.64 (m, 2H), 1.52-1.53 (m, 2H), 1.43 (m, 2H), 1.33-1.35 (m, 2H)

Example 170

Synthesis of (S)-3-[4-(1-isobutyl-3-methyl-1H-indazol-5-ylmethoxy)-phenyl]-hex-4-ynoic acid

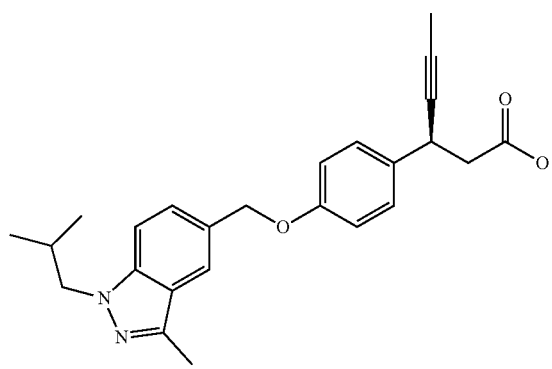 [SMILES: CC#C[C@@H](CC(=O)O)c1ccc(OCc2ccc3c(c2)c(C)nn3CC(C)C)cc1]

The compound (101 mg, 0.47 mmol) obtained from Preparation Example 118 and the compound (92 mg, 0.42 mmol) obtained from Preparation Example 155 were used to obtain the title compound (30 mg, 16%).

NMR:$^1$H-NMR(400 HMz, CDCl$_3$); δ 7.69 (s, 1H), 7.43 (m, 1H), 7.32 (m, 3H), 6.96 (m, 2H), 5.12 (s, 2H), 4.08 (m, 3H), 2.75 (m, 1H), 2.57 (s, 3H), 2.32 (m, 1H), 1.84 (d, 3H), 0.91 (d, 6H)

Example 171

Synthesis of (S)-3-[4-(1-cyclopentyl-7-methyl-1H-indazol-5-ylmethoxy)-phenyl]-hex-4-ynoic acid

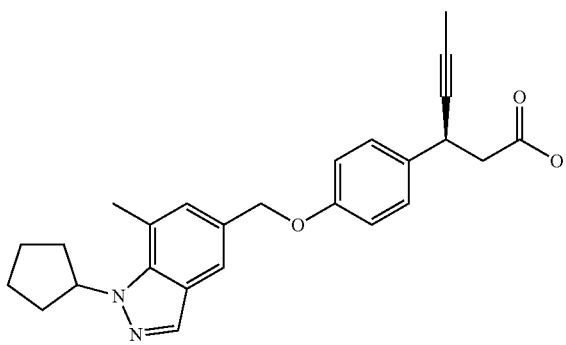 [SMILES: CC#C[C@@H](CC(=O)O)c1ccc(OCc2cc(C)c3c(cnn3C3CCCC3)c2)cc1]

The compound (146 mg, 0.57 mmol) obtained from Preparation Example 115 and the compound (111 mg, 0.51 mmol) obtained from Preparation Example 155 were used to obtain the title compound (123 mg, 57%).

NMR:$^1$H-NMR(400 HMz, CDCl$_3$); δ 8.03 (s, 1H), 7.57 (s, 1H), 7.30 (d, 2H), 7.19 (s, 1H), 6.88 (d, 2H), 5.34 (pent, 1H), 5.06 (s, 2H), 4.06 (br t, 1H), 2.77-2.83 (m, 1H), 2.75 (s, 3H), 2.68-2.73 (m, 1H), 2.18-2.23 (m, 2H), 2.08-2.13 (m, 2H), 1.95-1.98 (m, 2H), 1.83 (s, 3H), 1.69-1.73 (m, 2H)

Example 172

Synthesis of (S)-3-[4-(1-cyclopentyl-1H-indazol-6-ylmethoxy)-phenyl]-hex-4-ynoic acid

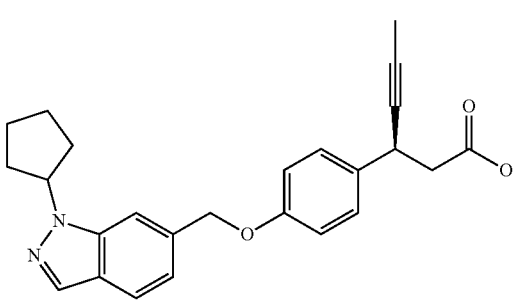 [SMILES: CC#C[C@@H](CC(=O)O)c1ccc(OCc2ccc3cnn(C4CCCC4)c3c2)cc1]

The compound (130 mg, 0.60 mmol) obtained from Preparation Example 76 and the compound (118 mg, 0.54 mmol) obtained from Preparation Example 155 were used to obtain the title compound (160 mg, 73%).

NMR:$^1$H-NMR(400 HMz, CDCl$_3$); δ 7.99 (s, 1H), 7.71 (d, 1H), 7.52 (s, 1H), 7.32 (d, 2H), 7.16 (d, 1H), 6.87 (d, 2H), 5.18 (s, 2H), 4.99 (br t, 1H), 4.06 (br s, 1H), 2.78-2.84 (m, 1H), 2.68-2.74 (m, 1H), 2.16-2.18 (m, 4H), 1.98 (m, 2H), 1.83 (s, 3H), 1.74 (m, 2H)

Example 173

Synthesis of (S)-3-[4-(1-cyclopentylmethyl-1H-indazol-6-ylmethoxy)-phenyl]-hex-4-ynoic acid

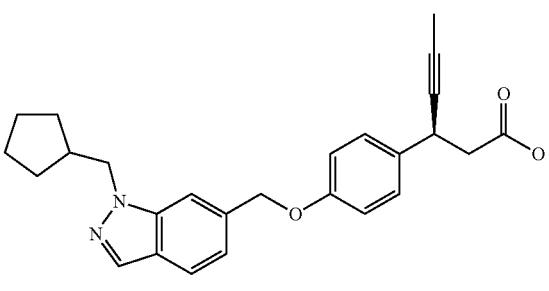 [SMILES: CC#C[C@@H](CC(=O)O)c1ccc(OCc2ccc3cnn(CC4CCCC4)c3c2)cc1]

The compound (130 mg, 0.56 mmol) obtained from Preparation Example 77 and the compound (111 mg, 0.51 mmol) obtained from Preparation Example 155 were used to obtain the title compound (94 mg, 44%).

NMR:$^1$H-NMR(400 HMz, CDCl$_3$); δ 8.04 (s, 1H), 7.71 (d, 1H), 7.47 (s, 1H), 7.24 (d, 2H), 7.16 (d, 1H), 6.95 (d, 2H), 5.25 (s, 2H), 4.29 (d, 2H), 4.07 (br t, 1H), 2.78-2.84 (m, 1H), 2.68-2.73 (m, 1H), 2.53 (pent, 1H), 1.82 (s, 3H), 1.63-1.64 (m, 4H), 1.53-1.57 (m, 2H), 1.26-1.31 (m, 2H)

Example 174

Synthesis of (S)-3-{4-[1-(2-methanesulfonyl-ethyl)-1H-indazol-5-ylmethoxy]-phenyl}-hex-4-ynoic acid

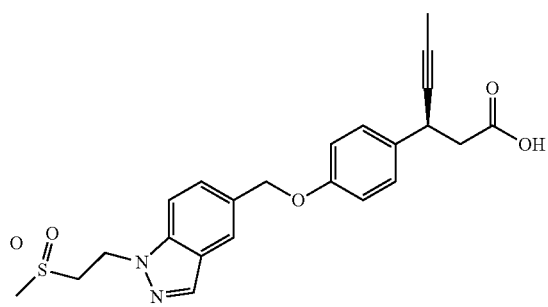

The compound (102 mg, 0.40 mmol) obtained from Preparation Example 79-1 and the compound (105 mg, 0.48 mmol) obtained from Preparation Example 155 were used to obtain the title compound (87 mg, 49%).

NMR:$^1$H-NMR(400 HMz, DMSO-$d_6$); δ 8.15 (s, 1H), 7.84 (s, 1H), 7.73 (d, 1H), 7.50 (d, 1H), 7.27 (d, 2H), 6.97 (d, 2H), 5.17 (s, 2H), 4.82 (t, 2H), 3.93 (m, 1H), 3.74 (t, 2H), 2.89 (s, 3H), 2.55-2.63 (m, 2H), 1.77 (d, 3H)

Example 175

Synthesis of (S)-3-{4-[1-(2-methoxy-ethyl)-1H-indazol-5-ylmethoxy]-phenyl}-hex-4-ynoic acid

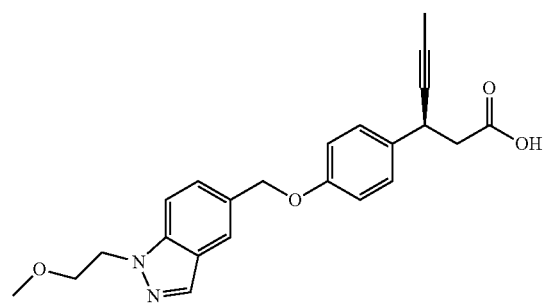 [SMILES: CC#C[C@@H](CC(=O)O)c1ccc(OCc2ccc3c(cnn3CCOC)c2)cc1]

The compound (99 mg, 0.48 mmol) obtained from Preparation Example 80 and the compound (87 mg, 0.40 mmol) obtained from Preparation Example 155 were used to obtain the title compound (114 mg, 73%).

NMR:$^1$H-NMR(400 HMz, CDCl$_3$); δ 8.05 (s, 1H), 7.48 (s, 1H), 7.40-7.52 (m, 2H), 7.31 (d, 2H), 6.94 (d, 2H), 5.11 (s, 2H), 4.55 (t, 2H), 4.06 (m, 1H), 3.82 (t, 2H), 3.28 (s, 3H), 2.66-2.86 (dd, 1H), 1.82 (d, 3H)

Example 176

Synthesis of (S)-3-{4-[1-(3-methoxy-propyl)-1H-indazol-5-ylmethoxy]-phenyl}-hex-4-ynoic acid

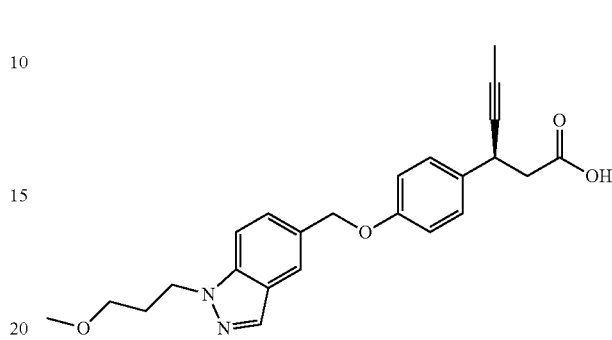

The compound (106 mg, 0.48 mmol) obtained from Preparation Example 81 and the compound (87 mg, 0.40 mmol) obtained from Preparation Example 155 were used to obtain the title compound (121 mg, 75%).

NMR:$^1$H-NMR(400 HMz, CDCl$_3$); δ 8.01 (s, 1H), 7.76 (s, 1H), 7.42-7.52 (m, 2H), 7.31 (d, 2H), 6.95 (d, 2H), 5.12 (s, 2H), 4.50 (t, 2H), 4.07 (m, 1H), 3.29 (s, 3H), 3.28 (t, 2H), 2.66-2.86 (m, 2H), 2.12-2.23 (m, 2H), 1.83 (d, 3H)

Example 177

Synthesis of (S)-3-{4-[1-(3-methyl-oxetan-3-ylmethyl)-1H-indazol-6-ylmethoxy]-phenyl}-hex-4-ynoic acid

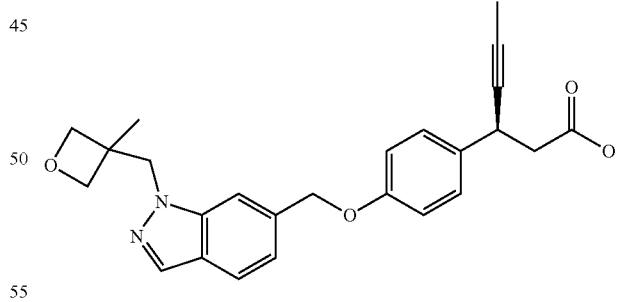

The compound (135 mg, 0.58 mmol) obtained from Preparation Example 82 and the compound (114 mg, 0.52 mmol) obtained from Preparation Example 155 were used to obtain the title compound (81 mg, 37%).

NMR:$^1$H-NMR(400 HMz, CDCl$_3$); δ 8.00 (s, 1H), 7.71 (d, 1H), 7.45 (s, 1H), 7.30 (d, 2H), 7.16 (d, 1H), 6.93 (d, 2H), 5.18 (s, 2H), 4.77 (d, 2H), 4.54 (s, 2H), 4.39 (d, 2H), 4.06 (br s, 1H), 2.76-2.82 (m, 1H), 2.66-2.71 (m, 1H), 1.81 (s, 3H), 1.22 (s, 3H)

Example 178

Synthesis of (S)-3-[4-(1-isobutyl-3-methyl-1H-indazol-6-ylmethoxy)-phenyl]-hex-4-ynoic acid

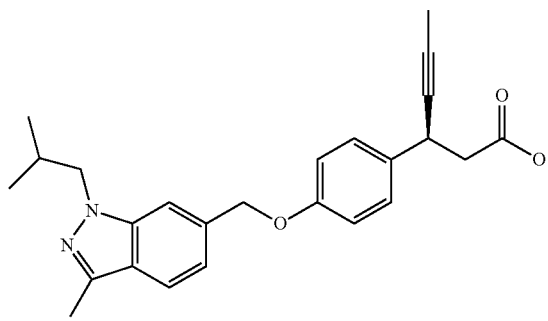 [SMILES: CC#C[C@@H](CC(=O)O)c1ccc(OCc2ccc3c(C)nn(CC(C)C)c3c2)cc1]

The compound (150 mg, 0.69 mmol) obtained from Preparation Example 87 and the compound (136 mg, 0.62 mmol) obtained from Preparation Example 155 were used to obtain the title compound (183 mg, 74%).

NMR:$^1$H-NMR(400 HMz, CDCl$_3$); δ 7.62 (d, 1H), 7.38 (s, 3H), 7.32 (d, 1H), 7.13 (d, 1H), 6.95 (d, 2H), 5.25 (s, 2H), 4.09 (d, 3H), 2.77-2.83 (m, 1H), 2.67-2.73 (m, 1H), 2.56 (s, 3H), 2.25-2.31 (m, 1H), 1.82 (s, 3H), 0.89 (d, 6H)

Example 179

Synthesis of (S)-3-[4-(2-isobutyl-3-methyl-2H-indazol-6-ylmethoxy)-phenyl]-hex-4-ynoic acid

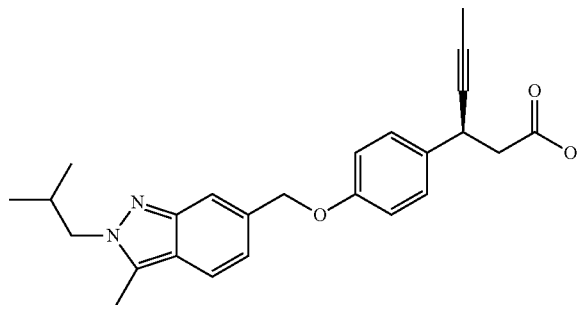 [SMILES: CC#C[C@@H](CC(=O)O)c1ccc(OCc2ccc3c(C)n(CC(C)C)nc3c2)cc1]

The compound (100 mg, 0.46 mmol) obtained from Preparation Example 88 and the compound (90 mg, 0.41 mmol) obtained from Preparation Example 155 were used to obtain the title compound (120 mg, 73%).

NMR:$^1$H-NMR(400 HMz, CDCl$_3$); δ 7.63 (s, 1H), 7.55 (d, 1H), 7.29 (d, 2H), 7.08 (d, 1H), 6.94 (d, 2H), 5.12 (s, 2H), 4.14 (d, 2H), 4.06 (br t, 1H), 2.77-2.83 (m, 1H), 2.67-2.73 (m, 1H), 2.59 (s, 3H), 2.34-2.43 (m, 1H), 1.83 (s, 3H), 0.93 (d, 6H)

Example 180

Synthesis of (S)-3-[4-(1-isopropyl-1H-indazol-6-ylmethoxy)-phenyl]-hex-4-ynoic acid

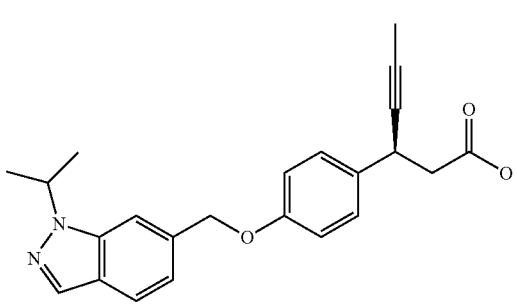 [SMILES: CC#C[C@@H](CC(=O)O)c1ccc(OCc2ccc3cnn(C(C)C)c3c2)cc1]

The compound (0.17 g, 0.92 mmol) obtained from Preparation Example 72 and the compound (0.18 g, 0.83 mmol) obtained from Preparation Example 155 were used to obtain the title compound (0.17 g, 54%).

NMR:$^1$H-NMR(400 HMz, CDCl$_3$); δ 8.02 (s, 1H), 7.73 (d, 1H), 7.51 (s, 1H), 7.33 (d, 2H), 7.18 (d, 1H), 6.98 (d, 2H), 5.18 (s, 2H), 4.88 (m, 1H), 4.07 (m, 1H), 2.84 (dd, 1H), 2.74 (dd, 1H), 1.83 (s, 3H), 1.59 (d, 6H)

Example 181

Synthesis of (S)-3-[4-(3-isobutyl-benzo[d]isoxazol-5-ylmethoxy)-phenyl]-hex-4-ynoic acid

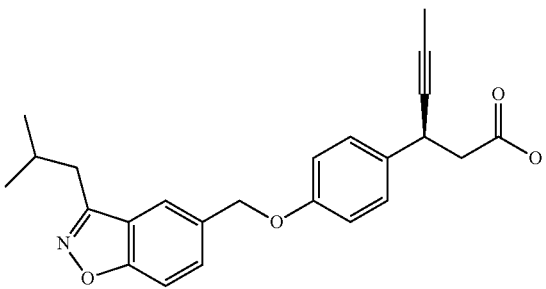

The compound (40 mg, 0.19 mmol) obtained from Preparation Example 89-4 and the compound (37 mg, 0.17 mmol) obtained from Preparation Example 155 were used to obtain the title compound (45 mg, 59%).

NMR:$^1$H-NMR(400 HMz, CDCl$_3$); δ 7.76 (s, 1H), 7.68 (d, 1H), 7.58 (d, 1H), 7.32 (d, 2H), 6.95 (dd, 2H), 5.14 (s, 2H), 4.08 (br t, 1H), 2.91 (d, 2H), 2.78-2.84 (m, 1H), 2.68-2.73 (m, 1H), 2.20-2.28 (m, 1H), 1.83 (s, 3H), 1.00 (d, 6H)

Example 182

Synthesis of (S)-3-{4-[1-(2,2-dimethyl-propyl)-1H-indazol-6-ylmethoxy]-phenyl}-hex-4-ynoic acid

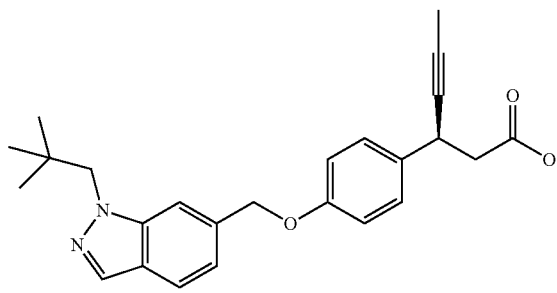 [SMILES: CC#C[C@@H](CC(=O)O)c1ccc(OCc2ccc3cnn(CC(C)(C)C)c3c2)cc1]

The compound (220 mg, 1.01 mmol) obtained from Preparation Example 78 and the compound (198 mg, 0.91 mmol) obtained from Preparation Example 155 were used to obtain the title compound (250 mg, 68%).

NMR:$^1$H-NMR(400 HMz, CDCl$_3$); δ 7.99 (s, 1H), 7.72 (d, 1H), 7.45 (s, 1H), 7.30 (d, 2H), 7.16 (d, 1H), 6.95 (d, 2H), 5.19 (s, 2H), 4.16 (s, 2H), 3.97 (br s, 1H), 2.78-2.80 (m, 1H), 2.68-2.73 (m, 1H), 1.84 (s, 3H), 1.00 (s, 9H)

Example 183

Synthesis of (S)-3-[4-(1-isobutyl-6-methyl-1H-indazol-5-ylmethoxy)-phenyl]-hex-4-ynoic acid

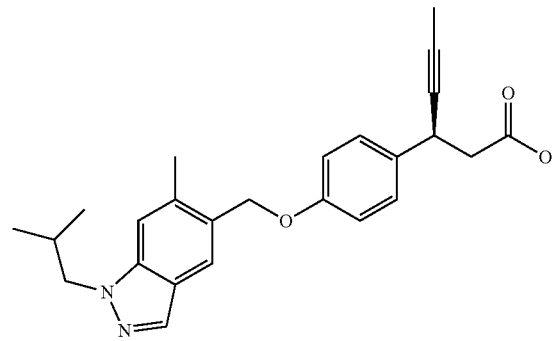 [SMILES: CC#C[C@@H](CC(=O)O)c1ccc(OCc2cc3cnn(CC(C)C)c3cc2C)cc1]

The compound (96 mg, 0.44 mmol) obtained from Preparation Example 120 and the compound (87 mg, 0.40 mmol) obtained from Preparation Example 155 were used to obtain the title compound (109 mg, 67%).

NMR:$^1$H-NMR(500 HMz, CDCl$_3$); δ 7.94 (s, 1H), 7.73 (s, 1H), 7.33 (d, 2H), 7.23 (s, 1H), 6.97 (d, 2H), 5.07 (s, 2H), 4.14 (d, 2H), 4.08 (m, 1H), 2.68-2.86 (m, 2H), 2.50 (s, 3H), 2.33 (m, 1H), 1.83 (d, 3H), 0.92 (d, 6H)

Example 184

Synthesis of (S)-3-[4-(1-isobutyl-1H-indazol-4-ylmethoxy)-phenyl]-hex-4-ynoic acid

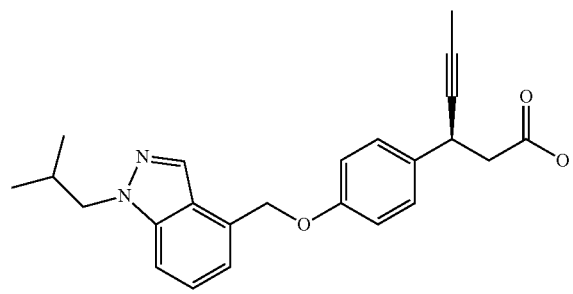 [SMILES: CC#C[C@@H](CC(=O)O)c1ccc(OCc2cccc3c2cnn3CC(C)C)cc1]

The compound (257 mg, 1.26 mmol) obtained from Preparation Example 145 and the compound (247 mg, 1.13 mmol) obtained from Preparation Example 155 were used to obtain the title compound (140 mg, 32%).

NMR:$^1$H-NMR(400 HMz, CDCl$_3$); δ 8.10 (s, 1H), 7.36 (d, 2H), 7.31 (d, 2H), 7.18 (d, 1H), 6.98 (d, 2H), 5.36 (s, 2H), 4.19 (d, 2H), 4.06 (br s, 1H), 2.78-2.84 (m, 1H), 2.69-2.74 (m, 1H), 2.34-2.35 (m, 1H), 1.83 (s, 3H), 0.94 (d, 6H)

Example 185

Synthesis of (S)-3-[4-(1-isopropyl-3-methyl-1H-indazol-6-ylmethoxy)-phenyl]-hex-4-ynoic acid

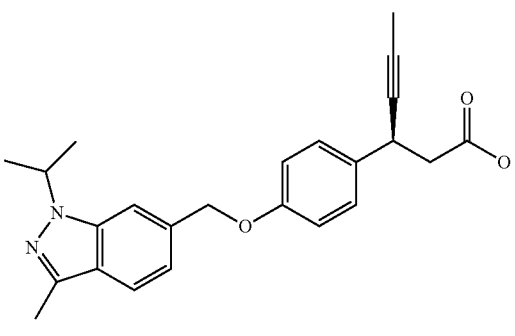 [SMILES: CC#C[C@@H](CC(=O)O)c1ccc(OCc2ccc3c(C)nn(C(C)C)c3c2)cc1]

The compound (0.25 g, 1.29 mmol) obtained from Preparation Example 143 and the compound (0.25 g, 1.16 mmol) obtained from Preparation Example 155 were used to obtain the title compound (0.3 g, 66%).

NMR:$^1$H-NMR(400 HMz, CDCl$_3$); δ 7.64 (d, 1H), 7.43 (s, 1H), 7.32 (d, 2H), 7.14 (d, 1H), 6.98 (d, 2H), 5.18 (s, 2H), 4.81 (m, 1H), 4.09 (m, 1H), 2.84 (dd, 1H), 2.74 (dd, 1H), 2.57 (s, 3H), 1.84 (s, 3H), 1.56 (d, 6H)

Example 186

Synthesis of (S)-3-[4-(3-isobutyl-1-methyl-1H-indazol-5-ylmethoxy)-phenyl]-hex-4-ynoic acid

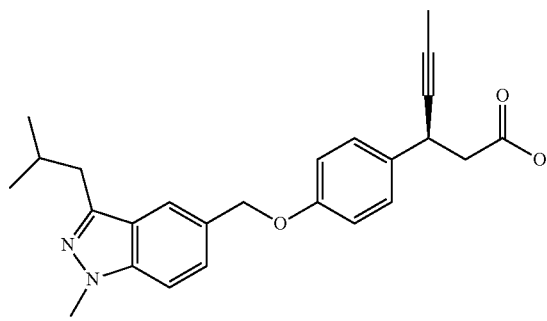

The compound (96 mg, 0.44 mmol) obtained from Preparation Example 108-5 and the compound (87 mg, 0.40 mmol) obtained from Preparation Example 155 were used to obtain the title compound (101 mg, 62%).

NMR:$^1$H-NMR(400 HMz, CDCl$_3$); δ 7.69 (s, 1H), 7.28-7.47 (m, 4H), 6.96 (d, 2H), 5.12 (s, 2H), 4.06 (m, 1H), 4.01 (s, 3H), 2.66-2.87 (m, 4H), 2.14 (m, 1H), 1.84 (d, 3H), 0.97 (d, 6H)

Example 187

Synthesis of (S)-3-[4-(1-isopropyl-3-methyl-1H-indazol-5-ylmethoxy)-phenyl]-hex-4-ynoic acid

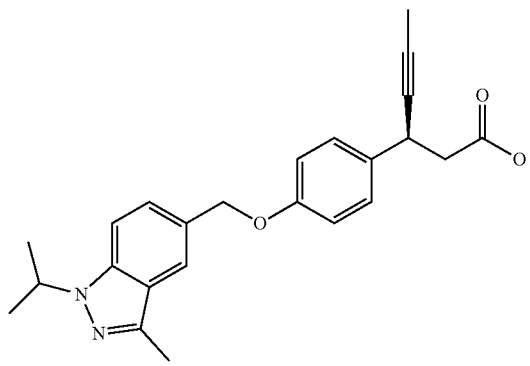 [SMILES: CC#C[C@@H](CC(=O)O)c1ccc(OCc2ccc3c(c2)c(C)nn3C(C)C)cc1]

The compound (111 mg, 0.47 mmol) obtained from Preparation Example 148 and the compound (92 mg, 0.42 mmol) obtained from Preparation Example 155 were used to obtain the title compound (30 mg, 14%).

NMR:$^1$H-NMR(400 HMz, CDCl$_3$); δ 7.69 (s, 1H), 7.40 (m, 2H), 7.30 (m, 1H), 6.95 (m, 2H), 5.12 (s, 2H), 4.78 (m, 1H), 2.82 (dd, 1H), 2.71 (dd, 1H), 2.58 (s, 3H), 1.83 (d, 3H), 1.56 (d, 6H)

Example 188

Synthesis of (S)-3-[4-(1-isobutyl-3-methoxymethyl-1H-indazol-6-ylmethoxy)-phenyl]-hex-4-ynoic acid

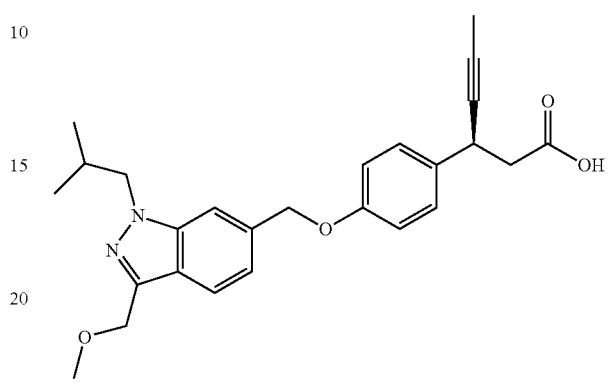

The compound (90 mg, 0.632 mmol) obtained from Preparation Example 162-4 and the compound (72 mg, 0.329 mmol) obtained from Preparation Example 155 were used to obtain the title compound (104 mg, 72%).

NMR:$^1$H-NMR(500 HMz, CDCl$_3$); δ 7.80 (d, 1H), 7.42 (s, 1H), 7.30 (d, 2H), 7.17 (d, 1H), 6.95 (d, 2H), 5.18 (s, 2H), 4.82 (s, 2H), 4.13 (d, 2H), 4.05 (m, 1H), 3.39 (s, 3H), 2.83-2.66 (m, 2H), 2.32 (m, 1H), 1.82 (d, 3H), 0.90 (d, 6H)

Example 189

Synthesis of (S)-3-[4-(3-fluoro-1-isobutyl-1H-indazol-4-ylmethoxy)-phenyl]-hex-4-ynoic acid

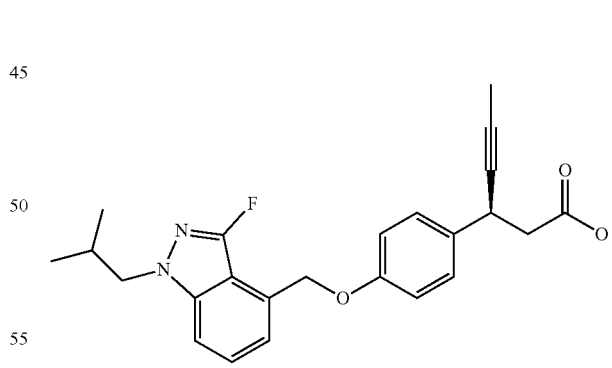

The compound (64.7 mg, 0.29 mmol) obtained from Preparation Example 163-3 and the compound (57.2 mg, 0.26 mmol) obtained from Preparation Example 155 were used to obtain the title compound (52 mg, 49%).

NMR:$^1$H-NMR(500 HMz, CDCl$_3$); δ 7.36 (dd, 1H), 7.30 (d, 1H), 7.25 (s, 2H), 7.21 (d, 1H), 6.96 (d, 2H), 5.37 (s, 2H), 4.05 (br s, 1H), 4.00 (d, 2H), 2.79 (m, 1H), 2.72 (m, 1H), 2.28 (m, 1H), 1.82 (s, 3H), 0.92 (d, 6H)

Example 190

Synthesis of (S)-3-[4-(1-isopropyl-1H-indazol-4-ylmethoxy)-phenyl]-hex-4-ynoic acid

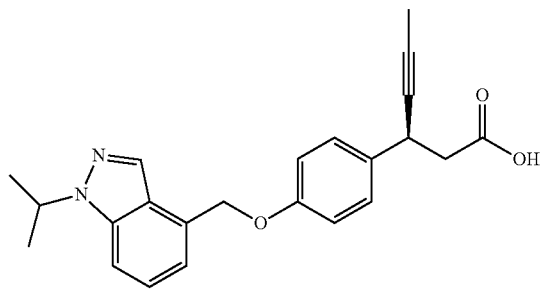 [SMILES: CC#C[C@@H](CC(=O)O)c1ccc(OCc2cccc3c2cnn3C(C)C)cc1]

The compound (42 mg, 0.22 mmol) obtained from Preparation Example 164-2 and the compound (44 mg, 0.20 mmol) obtained from Preparation Example 155 were used to obtain the title compound (61 mg, 81%).

NMR: $^1$H-NMR(500 HMz, DMSO-d$_6$); δ 12.25 (br s), 8.12(s, 1H), 7.62 (d, 1H), 7.32 (t, 1H), 7.23 (d, 2H), 7.16 (d, 1H), 6.96 (d, 2H), 5.36 (s, 2H), 4.96 (m, 1H), 3.89 (m, 1H), 2.62-2.49 (m, 2H), 1.72 (d, 3H), 1.44 (d, 6H)

Example 191

Synthesis of (S)-3-[4-(3-ethoxymethyl-1-isobutyl-1H-indazol-6-ylmethoxy)-phenyl]-hex-4-ynoic acid

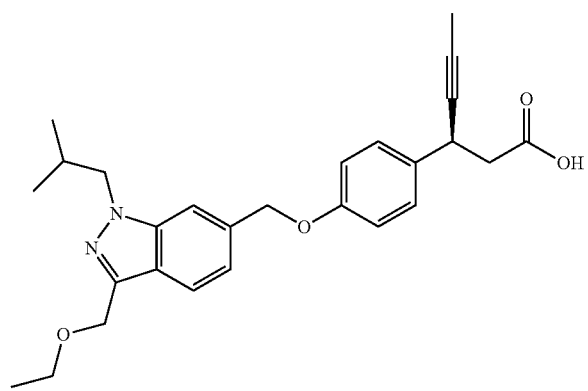 [SMILES: CC#C[C@@H](CC(=O)O)c1ccc(OCc2ccc3c(COCC)nn(CC(C)C)c3c2)cc1]

The compound (92 mg, 0.351 mmol) obtained from Preparation Example 165-2 and the compound (70 mg, 0.319 mmol) obtained from Preparation Example 155 were used to obtain the title compound (112 mg, 78%).

NMR: $^1$H-NMR(500 HMz, CDCl$_3$); δ 7.83 (d, 1H), 7.41 (s, 1H), 7.30 (d, 2H), 7.17 (d, 1H), 6.95 (d, 2H), 5.17 (s, 2H), 4.86 (s, 2H), 4.12 (d, 2H), 4.05 (m, 1H), 3.56 (q, 2H), 2.83-2.66 (m, 2H), 2.31 (m, 1H), 1.82 (d, 3H), 1.22 (t, 3H), 0.90 (d, 6H)

Example 192

Synthesis of (S)-3-[4-(3-chloro-1-isobutyl-1H-indazol-4-ylmethoxy)-phenyl]-hex-4-ynoic acid

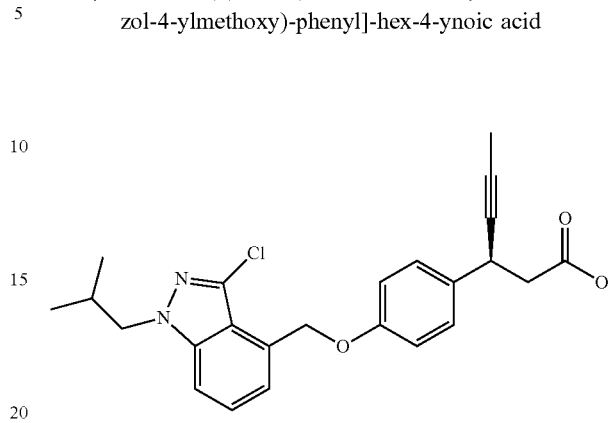

The compound (111.4 mg, 0.47 mmol) obtained from Preparation Example 166-2 and the compound (92 mg, 0.42 mmol) obtained from Preparation Example 155 were used to obtain the title compound (87 mg, 49%).

NMR: $^1$H-NMR(500 HMz, CDCl$_3$); δ 7.37 (dd, 1H), 7.31 (dd, 3H), 7.25 (d, 1H), 6.98 (d, 2H), 5.55 (s, 2H), 4.10 (d, 2H), 4.07 (br s, 1H), 2.80 (m, 1H), 2.72 (m, 1H), 2.31-2.35 (m, 1H), 1.83 (s, 3H), 0.93 (d, 6H)

Example 193

Synthesis of (S)-3-[4-(1-isobutyl-3-isopropoxymethyl-1H-indazol-6-ylmethoxy)-phenyl]-hex-4-ynoic acid

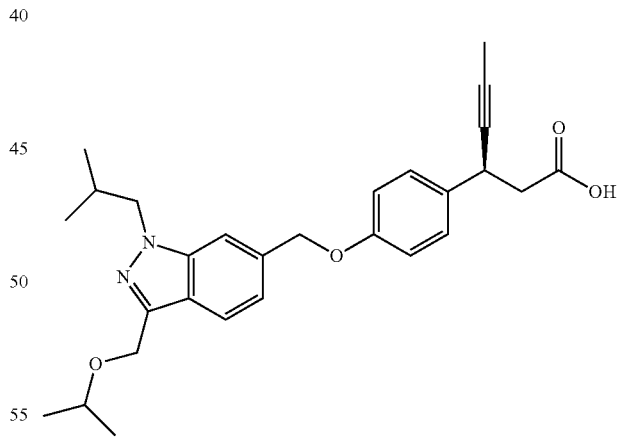

The compound (85 mg, 0.308 mmol) obtained from Preparation Example 167-2 and the compound (61 mg, 0.280 mmol) obtained from Preparation Example 155 were used to obtain the title compound (100 mg, 77%).

NMR: $^1$H-NMR(500 HMz, CDCl$_3$); δ 7.84 (d, 1H), 7.39 (s, 1H), 7.30 (d, 2H), 7.16 (d, 1H), 6.94 (d, 2H), 5.17 (s, 2H), 4.86 (s, 2H), 4.11 (d, 2H), 4.05 (m, 1H), 3.73 (m, 1H), 2.83-2.66 (m, 2H), 2.30 (m, 1H), 1.82 (d, 3H), 1.21 (d, 6H), 0.90 (d, 6H)

Example 194

Synthesis of (S)-3-[4-(3-fluoro-1-isopropyl-1H-indazol-4-ylmethoxy)-phenyl]-hex-4-ynoic acid

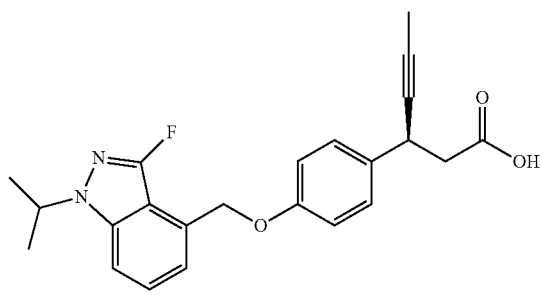 [SMILES: CC#C[C@@H](CC(=O)O)c1ccc(OCc2cccc3c2c(F)nn3C(C)C)cc1]

The compound (73 mg, 0.350 mmol) obtained from Preparation Example 168-2 and the compound (69 mg, 0.318 mmol) obtained from Preparation Example 155 were used to obtain the title compound (90 mg, 71%).

NMR:$^1$H-NMR(400 HMz, CDCl$_3$); δ 7.40-7.26(m, 4H), 7.22 (d, 1H), 6.97 (d, 2H), 5.37 (s, 2H), 4.72 (m, 1H), 4.06 (m, 1H), 2.85-2.66 (m, 2H), 1.83 (d, 3H), 1.53 (d, 6H)

Example 195

Synthesis of (S)-3-[4-(3-bromo-1-methyl-1H-indazol-7-ylmethoxy)-phenyl]-hex-4-ynoic acid

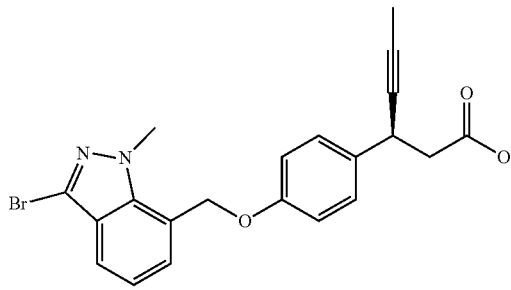 [SMILES: CC#C[C@@H](CC(=O)O)c1ccc(OCc2cccc3c(Br)nn(C)c23)cc1]

The compound (33 mg, 0.15 mmol) obtained from Preparation Example 169-4 and the compound (40 mg, 0.17 mmol) obtained from Preparation Example 155 were used to obtain the title compound (41.5 mg, 65%).

NMR:$^1$H-NMR(500 HMz, CDCl$_3$); δ 7.62 (d, 1H), 7.39 (d, 1H), 7.34 (d, 2H), 7.16 (dd, 1H), 6.96 (d, 2H), 5.29 (s, 2H), 4.19 (s, 3H), 4.07 (br s, 1H), 2.81 (m, 1H), 2.72 (m, 1H), 1.83 (s, 3H)

Example 196

Synthesis of (S)-3-[4-(1-isobutyl-3-methoxymethyl-7-methyl-1H-indazol-6-ylmethoxy)-phenyl]-hex-4-ynoic acid

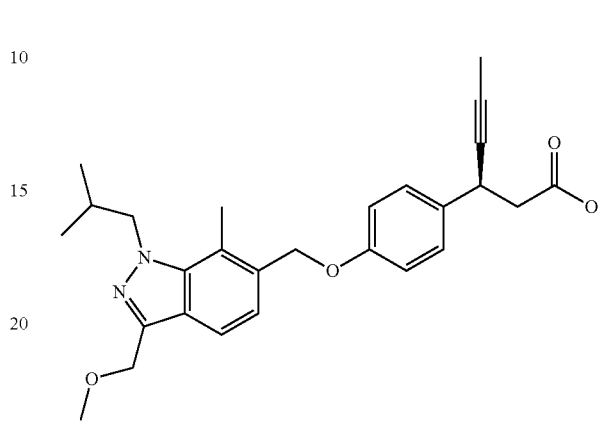

The compound (66.5 mg, 0.25 mmol) obtained from Preparation Example 170-5 and the compound (50 mg, 0.23 mmol) obtained from Preparation Example 155 were used to obtain the title compound (76.7 mg, 74%).

NMR:$^1$H-NMR(400 HMz, CDCl$_3$); δ 7.65 (d, 1H), 7.32 (d, 2H), 7.18 (d, 1H), 6.96 (d, 2H), 5.15 (s, 2H), 4.80 (s, 2H), 4.40 (d, 2H), 4.07 (br s, 1H), 3.37 (s, 3H), 2.83 (m, 1H), 2.73 (m, 1H), 2.69 (s, 3H), 2.23 (m, 1H), 1.84 (s, 3H), 0.92 (d, 6H)

Example 197

Synthesis of (S)-3-[4-(1-butyl-1H-indazol-4-ylmethoxy)-phenyl]-hex-4-ynoic acid

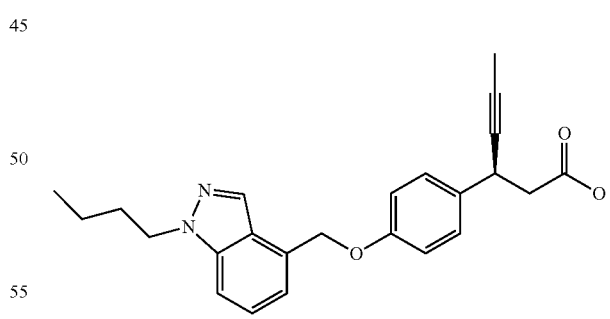

The compound (56 mg, 0.27 mmol) obtained from Preparation Example 171-2 and the compound (54 mg, 0.25 mmol) obtained from Preparation Example 155 were used to obtain the title compound (34.1 mg, 35%).

NMR:$^1$H-NMR(400 HMz, CDCl$_3$); δ 8.11 (s, 1H), 7.37 (dd, 2H), 7.30 (d, 2H), 7.17 (d, 1H), 6.98 (d, 2H), 5.36 (s, 2H), 4.40 (t, 2H), 4.04 (br s, 1H), 2.81 (m, 1H), 2.71(m, 1H), 1.87-1.95 (m, 2H), 1.83 (s, 3H), 1.30-1.43 (m, 2H), 0.94 (t, 3H)

Example 198

Synthesis of (S)-3-[4-(1-butyl-3-fluoro-1H-indazol-4-ylmethoxy)-phenyl]-hex-4-ynoic acid

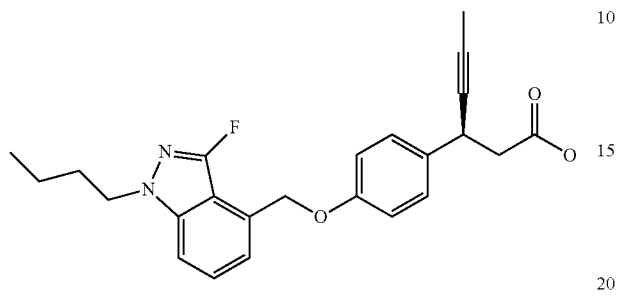

The compound (73.6 mg, 0.33 mmol) obtained from Preparation Example 172 and the compound (65 mg, 0.30 mmol) obtained from Preparation Example 155 were used to obtain the title compound (54 mg, 44%).

NMR:$^1$H-NMR(400 HMz, CDCl$_3$); δ 7.36 (dd, 1H), 7.31 (d, 3H), 7.22 (d, 1H), 6.97 (d, 2H), 5.38 (s, 2H), 4.21 (t, 2H), 4.18 (br s, 1H), 2.79 (m, 1H), 2.74 (m, 1H), 1.84-1.87 (m, 2H), 1.83 (s, 3H), 1.33-1.35 (m, 2H), 0.94 (t, 3H)

Example 199

Synthesis of (S)-3-[4-(1-cyclopropylmethyl-1H-indazol-4-ylmethoxy)-phenyl]-hex-4-ynoic acid

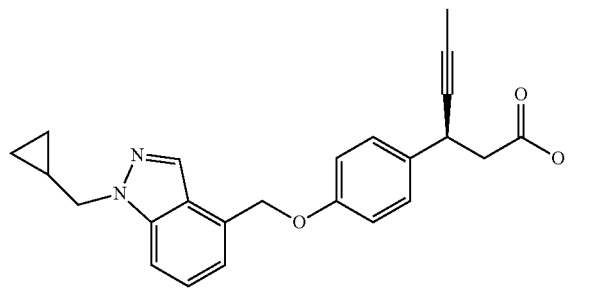 [SMILES: CC#C[C@@H](CC(=O)O)c1ccc(OCc2cccc3c2cnn3CC2CC2)cc1]

The compound (65.2 mg, 0.32 mmol) obtained from Preparation Example 173-2 and the compound (63.3 mg, 0.29 mmol) obtained from Preparation Example 155 were used to obtain the title compound (64.8 mg, 58%).

NMR:$^1$H-NMR(400 HMz, CDCl$_3$); δ 8.12 (s, 1H), 7.34-7.42 (m, 2H), 7.31 (d, 2H), 7.18 (d, 1H), 6.98 (d, 2H), 5.37 (s, 2H), 4.29 (d, 2H), 4.06 (br s, 1H), 2.81 (m, 1H), 2.71 (m, 1H), 1.83 (s, 3H), 1.35 (m, 1H), 0.56-0.61 (m, 2H), 0.40-0.44 (m, 2H)

Example 200

Synthesis of (S)-3-[4-(1-cyclopropylmethyl-3-fluoro-1H-indazol-4-ylmethoxy)-phenyl]-hex-4-ynoic acid

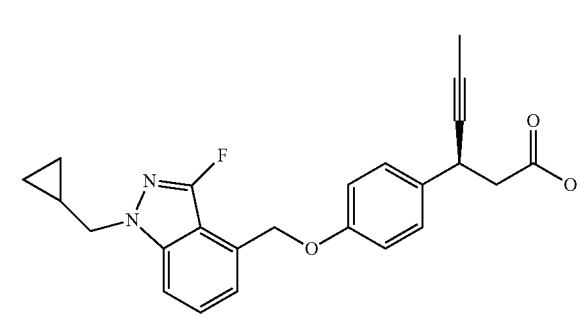 [SMILES: CC#C[C@@H](CC(=O)O)c1ccc(OCc2cccc3c2c(F)nn3CC2CC2)cc1]

The compound (89.4 mg, 0.41 mmol) obtained from Preparation Example 174 and the compound (80 mg, 0.37 mmol) obtained from Preparation Example 155 were used to obtain the title compound (82 mg, 30%).

NMR:$^1$H-NMR(500 HMz, CDCl$_3$); δ 7.37 (dd, 1H), 7.30 (d, 2H), 7.28 (d, 1H), 7.22 (d, 1H), 6.96 (d, 2H), 5.38 (s, 2H), 4.10 (d, 2H), 4.06 (br s, 1H), 2.80 (m, 1H), 2.71 (m, 1H), 1.83 (s, 3H), 1.27 (m, 1H), 0.57-0.58 (m, 2H), 0.39-0.40 (m, 2H)

Example 201

Synthesis of (S)-3-[4-(3-chloro-1-methyl-1H-indazol-7-ylmethoxy)-methyl]-hex-4-ynoic acid

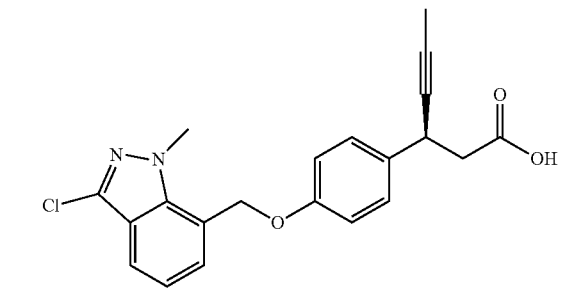 [SMILES: CC#C[C@@H](CC(=O)O)c1ccc(OCc2cccc3c(Cl)nn(C)c23)cc1]

The compound (66 mg, 0.336 mmol) obtained from Preparation Example 175-2 and the compound (67 mg, 0.305 mmol) obtained from Preparation Example 155 were used to obtain the title compound (87 mg, 74%).

NMR:$^1$H-NMR(500 HMz, CDCl$_3$); δ 7.68 (d, 1H), 7.38 (d, 1H), 7.34 (d, 2H), 7.15 (m, 1H), 6.96 (d, 2H), 5.28 (s, 2H), 4.16 (s, 3H), 4.07 (m, 1H), 2.85-2.67 (m, 2H), 1.83 (d, 3H)

Example 202

Synthesis of (S)-3-[4-(1-isopropyl-3-pyrazol-1-ylmethyl-1H-indazol-6-ylmethoxy)-phenyl]-hex-4-ynoic acid

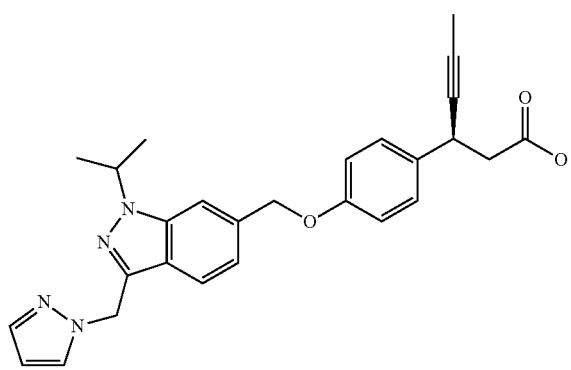 [SMILES: CC#C[C@@H](CC(=O)O)c1ccc(OCc2ccc3c(Cn4cccn4)nn(C(C)C)c3c2)cc1]

The compound (0.26 g, 0.96 mmol) obtained from Preparation Example 176-2 and the compound (0.18 g, 0.86 mmol) obtained from Preparation Example 155 were used to obtain the title compound (0.21 g, 54%).

NMR: $^1$H-NMR(500 HMz, CDCl$_3$); δ 7.55 (s, 1H), 7.46 (d, 2H), 7.41 (s, 1H), 7.31 (d, 2H), 7.09 (d, 1H), 6.93 (d, 2H), 6.24 (d, 1H), 5.70 (s, 2H), 5.12 (s, 2H), 4.83 (m, 1H), 4.06 (m, 1H), 2.79 (dd, 1H), 2.72 (dd, 1H), 1.81 (s, 3H), 1.58 (d, 6H)

Example 203

Synthesis of (S)-3-[4-(3-fluoro-1-methyl-1H-indazol-7-ylmethoxy)-phenyl]-hex-4-ynoic acid

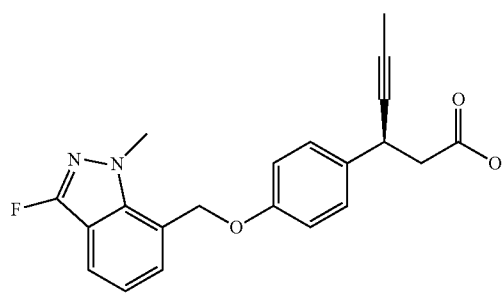 [SMILES: CC#C[C@@H](CC(=O)O)c1ccc(OCc2cccc3c(F)nn(C)c23)cc1]

The compound (40 mg, 0.19 mmol) obtained from Preparation Example 177-2 and the compound (38 mg, 0.17 mmol) obtained from Preparation Example 155 were used to obtain the title compound (36.1 mg, 58%).

NMR: $^1$H-NMR(500 HMz, CDCl$_3$); δ 7.66 (d, 1H), 7.38 (d, 1H), 7.34 (d, 2H), 7.10 (dd, 1H), 6.97 (d, 2H), 5.28 (s, 2H), 4.06 (s, 3H), 3.75 (br s, 1H), 2.81 (m, 1H), 2.72 (m, 1H), 1.84 (s, 3H)

Example 204

Synthesis of (S)-3-[4-(1-isobutyl-1H-pyrrolo[2,3-b]pyridin-4-ylmethoxy)-phenyl]-hex-4-ynoic acid

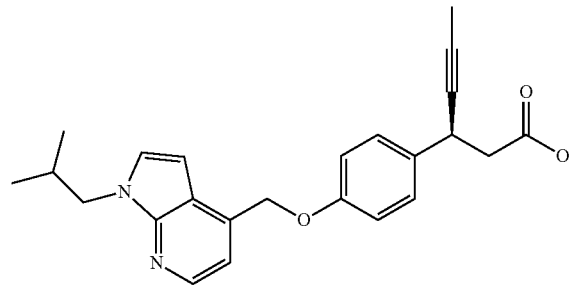 [SMILES: CC#C[C@@H](CC(=O)O)c1ccc(OCc2ccnc3c2ccn3CC(C)C)cc1]

The compound (0.19 g, 0.93 mmol) obtained from Preparation Example 178-3 and the compound (0.14 g, 0.66 mmol) obtained from Preparation Example 155 were used to obtain the title compound (0.13 g, 50%).

NMR: $^1$H-NMR(400 HMz, CDCl$_3$); δ 8.35 (d, 1H), 7.32 (d, 2H), 7.23 (d, 1H), 7.17 (d, 1H), 6.97 (d, 2H), 6.57 (d, 1H), 5.37 (s, 2H), 4.13 (d, 2H), 4.07 (m, 1H), 2.85 (dd, 1H), 2.74 (dd, 1H), 2.30 (m, 1H), 1.83 (s, 3H), 0.94 (d, 6H)

Example 205

Synthesis of (S)-3-[4-(1-butyl-3-methyl-1H-indazol-4-ylmethoxy)-phenyl]-hex-4-ynoic acid

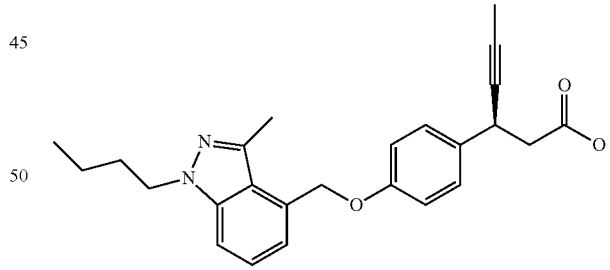

The compound (31 mg, 0.14 mmol) obtained from Preparation Example 179-3 and the compound (28 mg, 0.13 mmol) obtained from Preparation Example 155 were used to obtain the title compound (13.1 mg, 25%).

NMR: $^1$H-NMR(500 HMz, CDCl$_3$); δ 7.28-7.33 (m, 4H), 7.11 (d, 1H), 6.97 (dd, 2H), 5.33 (s, 2H), 4.30 (t, 2H), 4.07 (br s, 1H), 2.81 (m, 1H), 2.72 (m, 1H), 2.63 (s, 3H), 1.84-1.88 (m, 2H), 1.83 (s, 3H), 1.34-1.38 (m, 2H), 0.93 (t, 3H)

Example 206

Synthesis of (S)-3-[4-(3-butyl-1-methyl-1H-indazol-7-ylmethoxy)-phenyl]-hex-4-ynoic acid

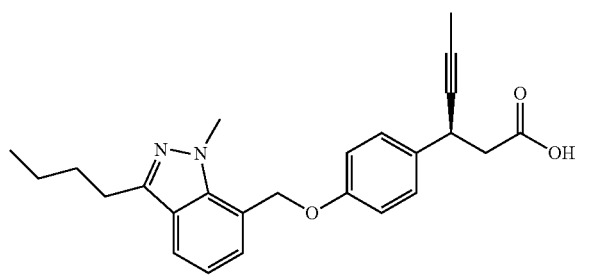 [SMILES: CC#C[C@@H](CC(=O)O)c1ccc(OCc2cccc3c(CCCC)nn(C)c23)cc1]

The compound (332 mg, 1.521 mmol) obtained from Preparation Example 180-5 and the compound (302 mg, 1.383 mmol) obtained from Preparation Example 155 were used to obtain the title compound (454 mg, 81%).

NMR:$^1$H-NMR(500 HMz, CDCl$_3$); δ 7.69 (d, 1H), 7.37-7.29 (m, 3H), 7.06 (t, 1H), 6.97 (d, 2H), 5.29 (s, 2H), 4.15 (s, 3H), 4.08 (m, 1H), 2.94 (t, 2H), 2.86-2.68 (m, 2H), 1.83 (d, 3H), 1.81-1.73 (m, 2H), 1.48-1.39 (m, 2H), 0.95 (t, 3H)

Example 207

Synthesis of (S)-3-[4-(3-isobutyl-1-methyl-1H-indazol-7-ylmethoxy)-phenyl]-hex-4-ynoic acid

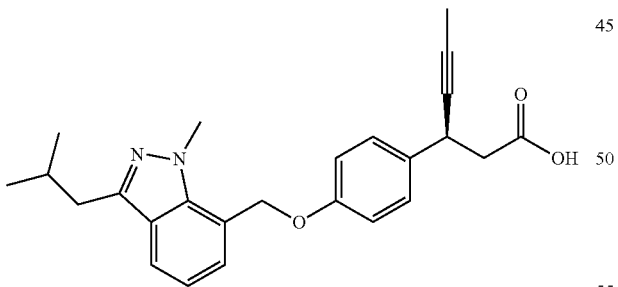

The compound (72 mg, 0.33 mmol) obtained from Preparation Example 181-5 and the compound (65 mg, 0.30 mmol) obtained from Preparation Example 155 were used to obtain the title compound (71 mg, 59%).

NMR:$^1$H-NMR(500 HMz, CDCl$_3$); δ 7.67 (d, 1H), 7.37-7.29 (m, 3H), 7.06 (t, 1H), 6.98 (d, 2H), 5.29 (s, 2H), 4.16 (s, 3H), 4.08 (m, 1H), 2.86-2.68 (m, 4H), 2.13 (m, 1H), 1.83 (d, 3H), 0.98 (d, 6H)

Example 208

Synthesis of (S)-3-[4-(1-isobutyl-7-methyl-1H-indazol-4-ylmethoxy)-phenyl]-hex-4-ynoic acid

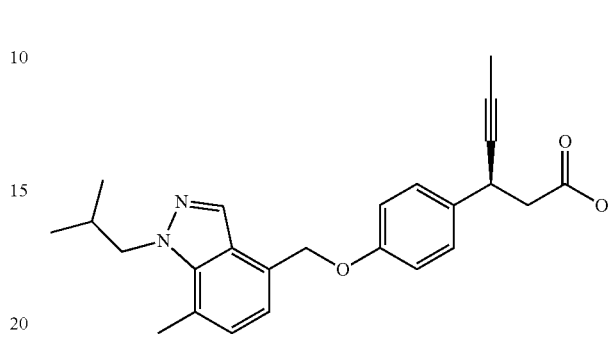

The compound (0.70 g, 3.21 mmol) obtained from Preparation Example 182-3 and the compound (0.70 g, 3.21 mmol) obtained from Preparation Example 155 were used to obtain the title compound (0.59 g, 46%).

NMR:$^1$H-NMR(400 HMz, CDCl$_3$); δ 8.06 (s, 1H), 7.31 (d, 2H), 7.06 (d, 1H), 6.98 (d, 2H), 5.31 (s, 2H), 4.40 (d, 2H), 4.06 (m, 1H), 2.80 (dd, 1H), 2.74 (dd, 1H), 2.71 (s, 3H), 2.24 (m, 1H), 1.83 (s, 3H), 0.95 (d, 6H)

Example 209

Synthesis of (S)-3-[4-(3-isopropyl-1-methyl-1H-indazol-7-ylmethoxy)-phenyl]-hex-4-ynoic acid

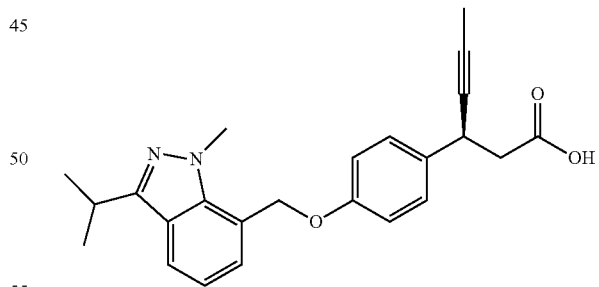

The compound (67 mg, 0.33 mmol) obtained from Preparation Example 183-5 and the compound (65 mg, 0.3 mmol) obtained from Preparation Example 155 were used to obtain the title compound (65 mg, 55%).

NMR:$^1$H-NMR(500 HMz, CDCl$_3$); δ 7.75 (d, 1H), 7.34 (d, 2H), 7.31 (d, 1H), 7.05 (t, 1H), 6.97 (d, 2H), 5.29 (s, 2H), 4.15 (s, 3H), 4.08 (m, 1H), 3.39 (m, 1H), 2.86-2.68 (m, 2H), 1.83 (d, 3H), 1.44 (d, 6H)

Example 210

Synthesis of (S)-3-[4-(1-methyl-3-propyl-1H-indazol-7-ylmethoxy)-phenyl]-hex-4-ynoic acid

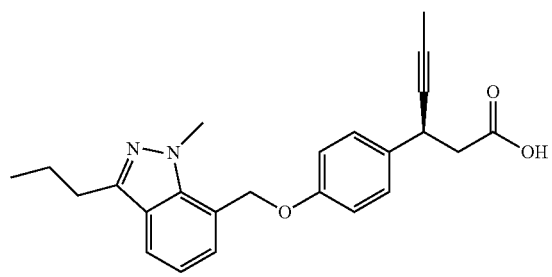 [SMILES: CC#C[C@@H](CC(=O)O)c1ccc(OCc2cccc3c(CCC)nn(C)c23)cc1]

The compound (67 mg, 0.33 mmol) obtained from Preparation Example 184-5 and the compound (65 mg, 0.3 mmol) obtained from Preparation Example 155 were used to obtain the title compound (67 mg, 57%).

NMR:$^1$H-NMR(500 HMz, CDCl$_3$); δ 7.68 (d, 1H), 7.34 (d, 2H), 7.32 (d, 1H), 7.06 (t, 1H), 6.97 (d, 2H), 5.29 (s, 2H), 4.15 (s, 3H), 4.08 (m, 1H), 2.92 (t, 2H), 2.86-2.68 (m, 2H), 1.87-1.76 (m, 5H), 1.01 (t, 3H)

Example 211

Synthesis of (S)-3-[4-(1-isobutyl-7-methyl-1H-indazol-6-ylmethoxy)-phenyl]-hex-4-ynoic acid

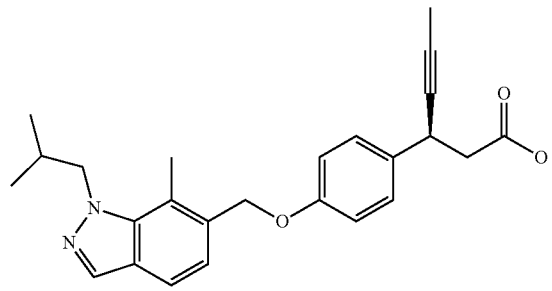 [SMILES: CC#C[C@@H](CC(=O)O)c1ccc(OCc2ccc3cnn(CC(C)C)c3c2C)cc1]

The compound (0.10 g, 0.41 mmol) obtained from Preparation Example 185-3 and the compound (0.13 g, 0.41 mmol) obtained from Preparation Example 155 were used to obtain the title compound (0.12 g, 76%).

NMR:$^1$H-NMR(400 HMz, CDCl$_3$); δ 7.94 (s, 1H), 7.54 (d, 1H), 7.33 (d, 2H), 7.18 (d, 1H), 6.97 (d, 3H), 5.14 (s, 2H), 4.43 (d, 2H), 4.07 (m, 1H), 2.79 (dd, 1H), 2.70 (dd, 1H), 2.69 (s, 3H), 2.24 (m, 1H), 1.83 (s, 3H), 0.92 (d, 6H)

Example 212

Synthesis of (S)-3-[4-(1-isobutyl-3,7-dimethyl-1H-indazol-6-ylmethoxy)-phenyl]-hex-4-ynoic acid

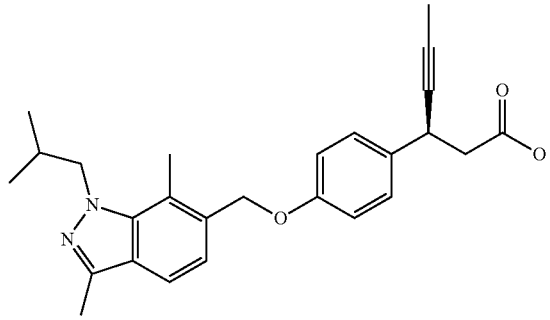 [SMILES: CC#C[C@@H](CC(=O)O)c1ccc(OCc2ccc3c(C)nn(CC(C)C)c3c2C)cc1]

The compound (70 mg, 0.30 mmol) obtained from Preparation Example 186-2 and the compound (59.2 mg, 0.27 mmol) obtained from Preparation Example 155 were used to obtain the title compound (44.8 mg, 40%).

NMR:$^1$H-NMR(500 HMz, CDCl$_3$); δ 7.46 (d, 1H), 7.32 (d, 2H), 7.14 (d, 1H), 6.96 (d, 2H), 5.13 (s, 2H), 4.34 (d, 2H), 4.07 (br s, 1H), 2.81 (m, 1H), 2.70-2.75 (m, 1H), 2.66 (s, 3H), 2.52 (s, 3H), 2.18-2.22 (m, 1H), 1.83 (s, 3H), 0.91 (d, 6H)

Example 213

Synthesis of (S)-3-[4-(3-fluoro-1-isobutyl-7-methyl-1H-indazol-4-ylmethoxy)-phenyl]-hex-4-ynoic acid

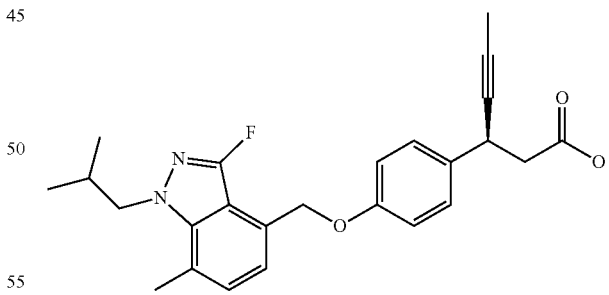

The compound (0.09 g, 0.38 mmol) obtained from Preparation Example 187-2 and the compound (0.08 g, 0.38 mmol) obtained from Preparation Example 155 were used to obtain the title compound (0.04 g, 27%).

NMR:$^1$H-NMR(500 HMz, CDCl$_3$); δ 7.31 (d, 2H), 7.09 (s, 2H), 6.97 (d, 2H), 5.33 (s, 2H), 4.21 (d, 2H), 4.05 (m, 1H), 2.79 (dd, 1H), 2.72 (dd, 1H), 2.65 (s, 3H), 2.23 (m, 1H), 1.83 (s, 3H), 0.93 (d, 6H)

Example 214

Synthesis of (S)-3-[4-(1-ethyl-3-fluoro-7-methyl-1H-indazol-6-ylmethoxy)-phenyl]-hex-4-ynoic acid

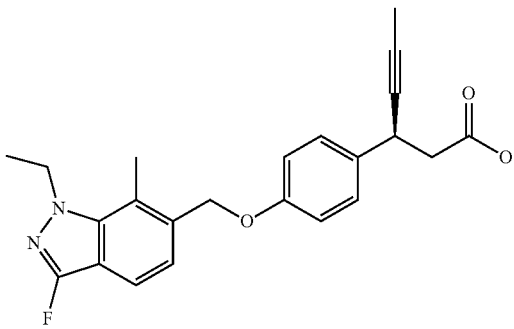 [SMILES: CC#C[C@@H](CC(=O)O)c1ccc(OCc2ccc3c(F)nn(CC)c3c2C)cc1]

The compound (0.08 g, 0.36 mmol) obtained from Preparation Example 188-2 and the compound (0.08 g, 0.36 mmol) obtained from Preparation Example 155 were used to obtain the title compound (0.07 g, 54%).

NMR:$^1$H-NMR(400 HMz, CDCl$_3$); δ 7.46 (d, 1H), 7.32 (d, 2H), 7.19 (d, 1H), 6.96 (d, 2H), 5.12 (s, 2H), 4.51 (q, 2H), 4.07 (m, 1H), 2.81 (dd, 1H), 2.73 (dd, 1H), 2.66 (s, 3H), 1.83 (s, 3H), 1.44 (t, 3H)

Example 215

Synthesis of (S)-3-[4-(1-isobutyl-7-methyl-3-morpholin-4-ylmethyl-1H-indazol-6-ylmethoxy)-phenyl]-hex-4-ynoic acid

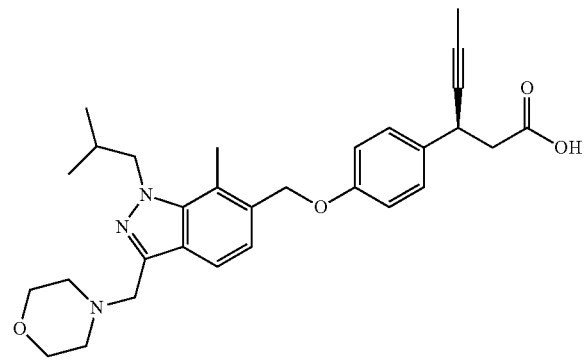 [SMILES: CC#C[C@@H](CC(=O)O)c1ccc(OCc2ccc3c(CN4CCOCC4)nn(CC(C)C)c3c2C)cc1]

The compound (42 mg, 0.132 mmol) obtained from Preparation Example 189-2 and the compound (26 mg, 0.12 mmol) obtained from Preparation Example 155 were used to obtain the title compound (17 mg, 28%).

NMR:$^1$H-NMR(500 HMz, CDCl$_3$); δ 7.62 (d, 1H), 7.32 (d, 2H), 7.10 (d, 1H), 6.94 (d, 2H), 5.11 (s, 2H), 4.39 (d, 2H), 4.06 (m, 1H), 4.00-3.90 (m, 2H), 3.71 (t, 4H), 2.82-2.58 (m, 9H), 2.20 (m, 1H), 1.81 (d, 3H), 0.90 (d, 6H)

Example 216

Synthesis of (S)-3-[4-(7-chloro-1-isobutyl-3-morpholin-4-ylmethyl-1H-indazol-6-ylmethoxy)-phenyl]-hex-4-ynoic acid

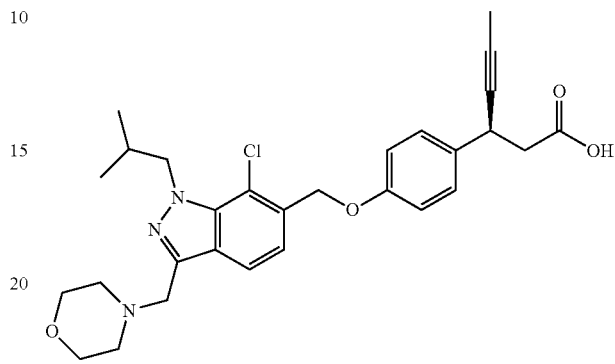

The compound (75 mg, 0.222 mmol) obtained from Preparation Example 190-4 and the compound (53 mg, 0.244 mmol) obtained from Preparation Example 155 were used to obtain the title compound (88 mg, 76%).

NMR:$^1$H-NMR(500 HMz, CDCl$_3$); δ 7.71 (d, 1H), 7.31 (d, 2H), 7.26 (d, 1H), 6.93 (d, 2H), 5.24 (s, 2H), 4.55 (d, 2H), 4.04 (m, 1H), 3.91 (s, 2H), 3.70 (t, 4H), 2.79-2.54 (m, 6H), 2.29 (m, 1H), 1.81 (d, 3H), 0.90 (d, 6H)

Example 217

Synthesis of (S)-3-[4-(1-isobutyl-7-methyl-3-pyrrolidin-1-ylmethyl-1H-indazol-6-ylmethoxy)-phenyl]-hex-4-ynoic acid

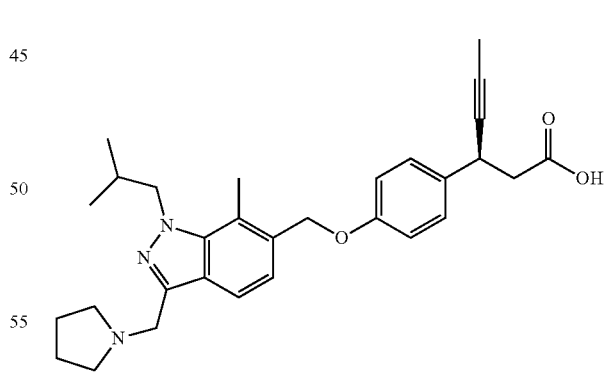

The compound (59 mg, 0.196 mmol) obtained from Preparation Example 191-2 and the compound (47 mg, 0.216 mmol) obtained from Preparation Example 155 were used to obtain the title compound (63 mg, 66%).

NMR:$^1$H-NMR(500 HMz, CDCl$_3$); δ 7.64 (d, 1H), 7.32 (d, 2H), 7.16 (d, 1H), 6.89 (d, 2H), 5.09 (s, 2H), 4.52-4.37 (m, 4H), 4.07 (m, 1H), 3.31 (br s, 4H), 2.80-2.59 (m, 5H), 2.20 (m, 1H), 1.93 (br s, 4H), 1.79 (d, 3H), 0.91 (d, 6H)

Example 218

Synthesis of (S)-3-[4-(1-isobutyl-7-methyl-3-piperidin-1-ylmethyl-1H-indazol-6-ylmethoxy)-phenyl]-hex-4-ynoic acid

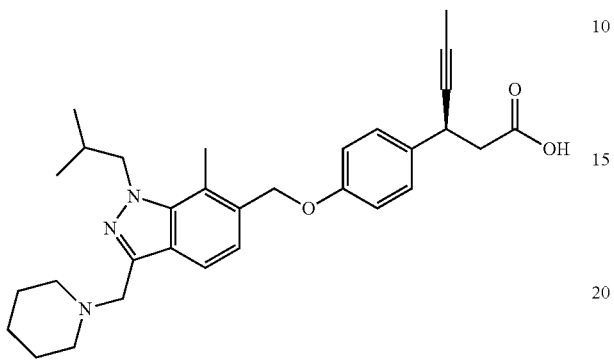

The compound (78 mg, 0.247 mmol) obtained from Preparation Example 192-2 and the compound (59 mg, 0.272 mmol) obtained from Preparation Example 155 were used to obtain the title compound (76 mg, 61%).

NMR:$^1$H-NMR(500 HMz, CDCl$_3$); δ 7.56 (d, 1H), 7.37 (d, 2H), 7.09 (d, 1H), 6.90 (d, 2H), 5.08-5.01 (m, 2H), 4.39 (d, 2H), 4.31-4.07 (m, 5H), 2.92 (br s, 4H), 2.83-2.59 (m, 5H), 2.19 (m, 1H), 1.86-1.82 (m, 7H), 1.40 (br s, 2H), 0.90 (d, 6H)

Example 219

Synthesis of (S)-3-[4-(1-isobutyl-3-morpholin-4-ylmethyl-1H-indazol-6-ylmethoxy)-phenyl]-hex-4-ynoic acid

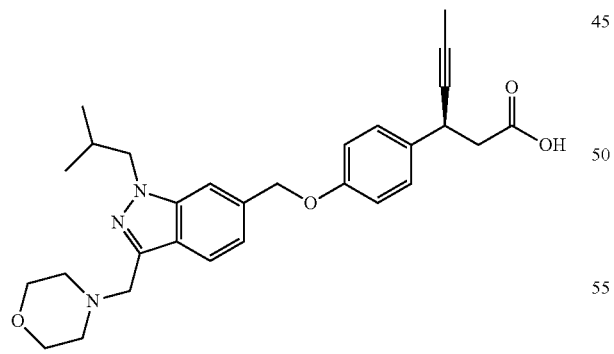

The compound (79 mg, 0.260 mmol) obtained from Preparation Example 193-4 and the compound (62 mg, 0.286 mmol) obtained from Preparation Example 155 were used to obtain the title compound (89 mg, 70%).

NMR:$^1$H-NMR(500 HMz, CDCl$_3$); δ 7.79 (d, 1H), 7.39 (s, 1H), 7.30 (d, 2H), 7.11 (d, 1H), 6.93 (d, 2H), 5.15 (s, 2H), 4.12 (d, 2H), 4.05 (m, 1H), 4.00-3.90 (m, 2H), 3.71 (t, 4H), 2.80-2.56 (m, 6H), 2.30 (m, 1H), 1.81 (d, 3H), 0.89 (d, 6H)

Example 220

Synthesis of (S)-3-[4-(1-isopropyl-7-methyl-1H-indazol-6-ylmethoxy)-phenyl]-hex-4-ynoic acid

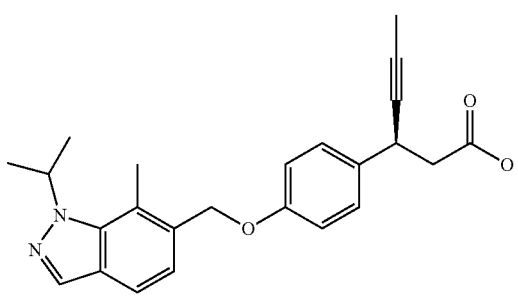 [SMILES: CC#C[C@@H](CC(=O)O)c1ccc(OCc2ccc3cnn(C(C)C)c3c2C)cc1]

The compound (47.5 mg, 0.23 mmol) obtained from Preparation Example 194 and the compound (51 mg, 0.23 mmol) obtained from Preparation Example 155 were used to obtain the title compound (32.3 mg, 36%).

NMR:$^1$H-NMR(500 HMz, CDCl$_3$); δ 7.99 (s, 1H), 7.55 (d, 1H), 7.32 (d, 2H), 7.16 (d, 1H), 6.97 (d, 2H), 5.29 (m, 1H), 5.15 (s, 2H), 4.07 (br s, 1H), 2.81 (m, 1H), 2.70-2.75 (m, 4H), 1.83 (s, 3H), 1.65 (d, 6H)

Example 221

Synthesis of (S)-3-[4-(7-methyl-1-propyl-1H-indazol-6-ylmethoxy)-phenyl]-hex-4-ynoic acid

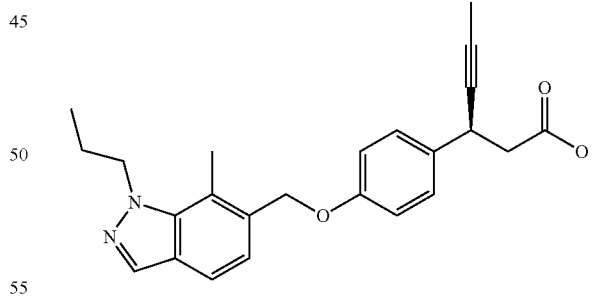

The compound (32.4 mg, 0.16 mmol) obtained from Preparation Example 195 and the compound (35 mg, 0.16 mmol) obtained from Preparation Example 155 were used to obtain the title compound (32.8 mg, 52%).

NMR:$^1$H-NMR(500 HMz, CDCl$_3$); δ 7.94 (s, 1H), 7.54 (d, 1H), 7.32 (d, 2H), 7.16 (d, 1H), 6.96 (d, 2H), 5.14 (s, 2H), 4.59 (t, 2H), 4.07 (br s, 1H), 2.77 (m, 1H), 2.70 (m, 4H), 1.89-1.92 (m, 2H), 1.83 (s, 3H), 0.96 (t, 3H)

Example 222

Synthesis of (S)-3-[4-(3-fluoromethyl-1-isobutyl-7-methyl-1H-indazol-6-ylmethoxy)-phenyl]-hex-4-ynoic acid

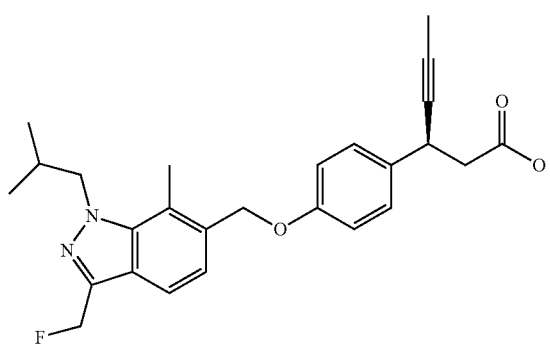 [SMILES: CC#C[C@@H](CC(=O)O)c1ccc(OCc2ccc3c(CF)nn(CC(C)C)c3c2C)cc1]

The compound (11.5 mg, 0.043 mmol) obtained from Preparation Example 196-2 and the compound (9.4 mg, 0.043 mmol) obtained from Preparation Example 155 were used to obtain the title compound (12.4 mg, 66%).

NMR:$^1$H-NMR(400 HMz, CDCl$_3$); δ 7.73 (d, 1H), 7.31 (d, 2H), 7.25 (d, 1H), 6.95 (d, 2H), 5.28 (s, 2H), 4.82 (q, 2H), 4.02 (br s, 1H), 3.86 (s, 2H), 3.71 (dd, 4H), 2.76-2.78 (m, 1H), 2.69-2.71 (m, 1H), 2.55 (br s, 4H), 1.83 (s, 3H), 1.48 (t, 3H)

Example 223

Synthesis of (S)-3-[4-(1-isopropyl-7-methyl-1H-indazol-4-ylmethoxy)-phenyl]-hex-4-ynoic acid

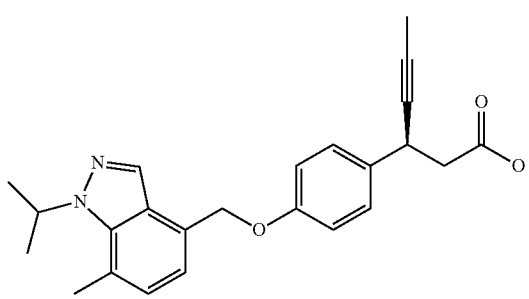 [SMILES: CC#C[C@@H](CC(=O)O)c1ccc(OCc2ccc(C)c3c2cnn3C(C)C)cc1]

The compound (0.60 g, 2.94 mmol) obtained from Preparation Example 197 and the compound (0.64 g, 2.94 mmol) obtained from Preparation Example 155 were used to obtain the title compound (0.72 g, 63%).

NMR:$^1$H-NMR(400 HMz, CDCl$_3$); δ 8.12 (s, 1H), 7.31 (d, 2H), 7.07 (s, 2H), 6.98 (d, 2H), 5.31 (s, 2H), 5.24 (m, 1H), 4.05 (m, 1H), 2.83 (dd, 1H), 2.74 (s, 3H), 2.72 (dd, 1H), 1.83 (s, 3H), 1.60 (d, 6H)

Example 224

Synthesis of (S)-3-[4-(1-isopropyl-1H-pyrrolo[2,3-b]pyridin-4-ylmethoxy)-phenyl]-hex-4-ynoic acid

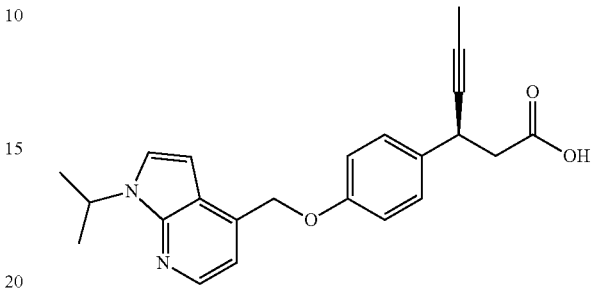

The compound (70 mg, 0.368 mmol) obtained from Preparation Example 198 and the compound (88 mg, 0.405 mmol) obtained from Preparation Example 155 were used to obtain the title compound (98 mg, 70%).

NMR:$^1$H-NMR(500 HMz, CDCl$_3$); δ 8.31 (d, 1H), 7.34 (d, 1H), 7.30 (d, 2H), 7.13 (d, 1H), 6.95 (d, 2H), 6.56 (d, 1H), 5.34 (s, 2H), 4.21 (m, 1H), 4.05 (m, 1H), 2.84-2.65 (m, 2H), 1.82 (d, 3H), 1.52 (d, 6H)

Example 225

Synthesis of (S)-3-[4-(3-fluoro-1-isobutyl-1H-pyrrolo[2,3-b]pyridin-4-ylmethoxy)-phenyl]-hex-4-ynoic acid

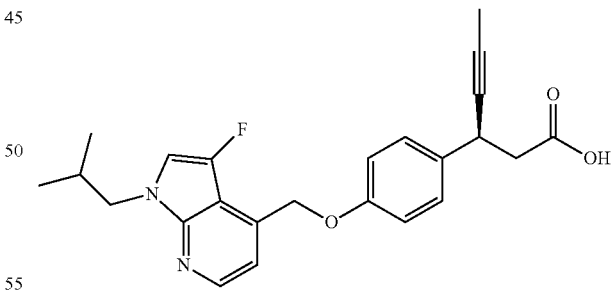

The compound (26 mg, 0.117 mmol) obtained from Preparation Example 199-3 and the compound (28 mg, 0.129 mmol) obtained from Preparation Example 155 were used to obtain the title compound (22 mg, 46%).

NMR:$^1$H-NMR(500 HMz, CDCl$_3$); δ 8.31 (d, 1H), 7.31 (d, 2H), 7.21 (d, 1H), 6.98-6.93 (m, 3H), 4.06 (m, 1H), 4.03 (d, 2H), 2.84-2.66 (m, 2H), 2.19 (m, 1H), 1.82 (d, 3H), 0.91 (d, 6H)

Example 226

Synthesis of (S)-3-[4-(7-methyl-1-pyridin-3-ylmethyl-1H-indazol-6-ylmethoxy)-phenyl]-hex-4-ynoic acid

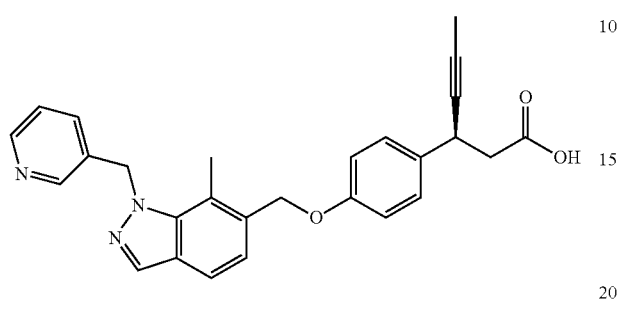

The compound (40 mg, 0.158 mmol) obtained from Preparation Example 200 and the compound (41 mg, 0.190 mmol) obtained from Preparation Example 155 were used to obtain the title compound (37 mg, 53%)

NMR:$^1$H-NMR(500 HMz, CDCl$_3$); δ 8.50 (br s, 1H), 8.30 (br s, 1H), 8.04 (s, 1H), 7.58 (d, 1H), 7.33-7.18 (m, 5H), 6.88 (d, 2H), 5.89 (s, 2H), 5.10 (s, 2H), 4.05 (m, 1H), 2.84-2.64 (m, 2H), 2.54 (s, 3H), 1.81 (d, 3H)

Example 227

Synthesis of (S)-3-{4-[3-(3,3-difluoro-piperidin-1-ylmethyl)-1-isobutyl-7-methyl-1H-indazol-6-yl-methoxy]-phenyl}-hex-4-ynoic acid

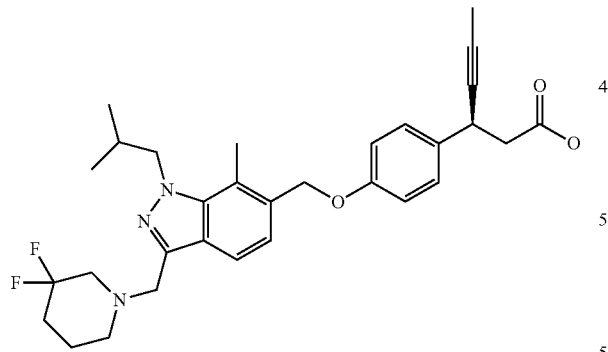

The compound (57 mg, 0.16 mmol) obtained from Preparation Example 201-2 and the compound (35.4 mg, 0.16 mmol) obtained from Preparation Example 155 were used to obtain the title compound (51.2 mg, 60%).

NMR:$^1$H-NMR(400 HMz, CDCl$_3$); δ 7.71 (d, 1H), 7.33 (d, 2H), 7.16 (d, 1H), 6.97 (d, 2H), 5.14 (s, 2H), 4.39 (d, 2H), 4.02 (br s, 1H), 3.98 (s, 2H), 2.81 (m, 1H), 2.68-2.76 (m, 5H), 2.48-2.51 (m, 2H), 2.21 (m, 1H), 1.84 (s, 5H), 1.71-1.74 (m, 2H), 0.89 (d, 6H)

Example 228

Synthesis of (S)-3-[4-(1-isobutyl-7-methyl-3-pyrazol-1-ylmethyl-1H-indazol-6-ylmethoxy)-phenyl]-hex-4-ynoic acid

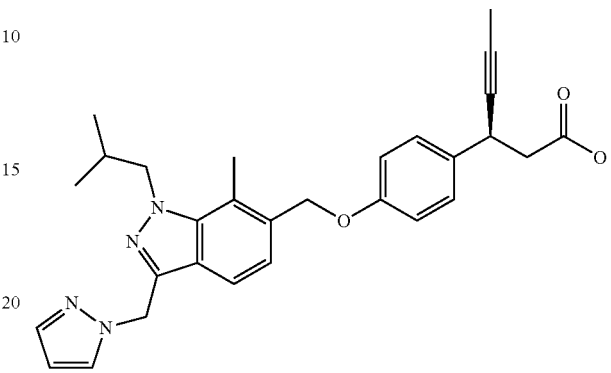

The compound (64.4 mg, 0.22 mmol) obtained from Preparation Example 202-3 and the compound (49 mg, 0.22 mmol) obtained from Preparation Example 155 were used to obtain the title compound (72.5 mg, 68%).

NMR:$^1$H-NMR(400 HMz, CDCl$_3$); δ 7.52 (d, 1H), 7.37 (d, 2H), 7.31 (d, 2H), 7.11 (d, 1H), 6.93 (d, 2H), 6.22 (d, 1H), 5.65 (s, 2H), 5.11 (s, 2H), 4.41 (d, 2H), 4.02 (br s, 1H), 2.79 (m, 1H), 2.72 (m, 1H), 2.67 (s, 3H), 2.22 (m, 1H), 1.83 (s, 3H), 0.93 (d, 6H)

Example 229

Synthesis of (S)-3-{4-[3-((S)-3-fluoro-pyrrolidin-1-ylmethyl)-1-isobutyl-7-methyl-1H-indazol-6-yl-methoxy]-phenyl}-hex-4-ynoic acid

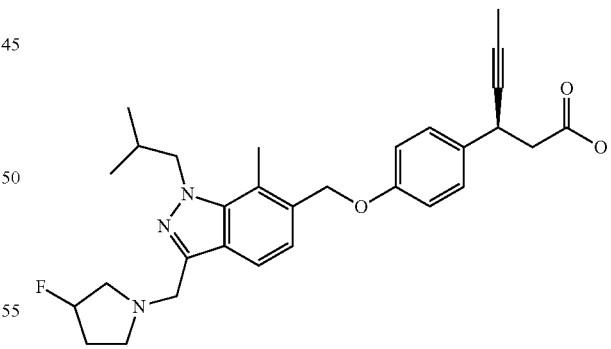

The compound (27.2 mg, 0.09 mmol) obtained from Preparation Example 206-2 and the compound (18.6 mg, 0.09 mmol) obtained from Preparation Example 155 were used to obtain the title compound (22.7 mg, 50%).

NMR:$^1$H-NMR(400 HMz, CDCl$_3$); δ 7.64 (d, 1H), 7.33 (d, 2H), 7.15 (d, 1H), 6.94 (d, 2H), 5.22 (br s, 0.5H), 5.12 (s, 2H), 5.08 (br s, 0.5H), 4.40 (d, 2H), 4.09 (s, 2H), 3.38-3.40 (m, 4H), 2.73 (m, 1H), 2.68 (s, 3H), 2.65 (m, 1H), 2.23 (m, 1H), 1.98-2.08 (m, 2H), 1.81 (s, 3H), 0.95 (d, 6H)

Example 230

Synthesis of (S)-3-{4-[3-(3,3-difluoro-pyrrolidin-1-ylmethyl)-1-isobutyl-7-methyl-1H-indazol-6-yl-methoxy]-phenyl}-hex-4-ynoic acid

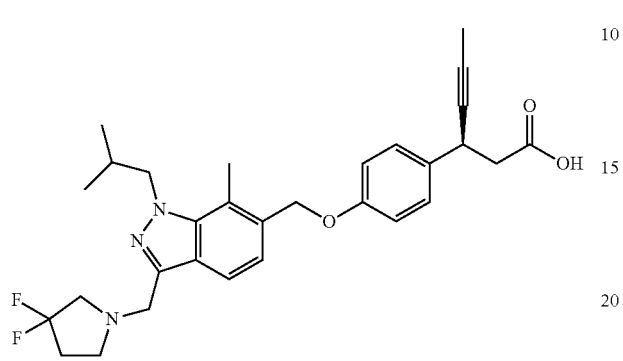

The compound (37 mg, 0.110 mmol) obtained from Preparation Example 203-2 and the compound (26 mg, 0.121 mmol) obtained from Preparation Example 155 were used to obtain the title compound (38 mg, 65%).

NMR:$^1$H-NMR(500 HMz, CDCl$_3$); δ 7.61 (d, 1H), 7.32 (d, 2H), 7.14 (d, 1H), 6.95 (d, 2H), 5.13 (s, 2H), 4.39 (d, 2H), 4.06 (m, 1H), 4.00 (s, 2H), 2.99 (t, 2H), 2.86-2.63 (m, 7H), 2.31-2.15 (m, 3H), 1.82 (d, 3H), 0.90 (d, 6H)

Example 231

Synthesis of (S)-3-{4-[3-(3,3-difluoro-pyrrolidin-1-ylmethyl)-1-isobutyl-1H-pyrrolo[2,3-b]pyridin-6-ylmethoxy]-phenyl}-hex-4-ynoic acid

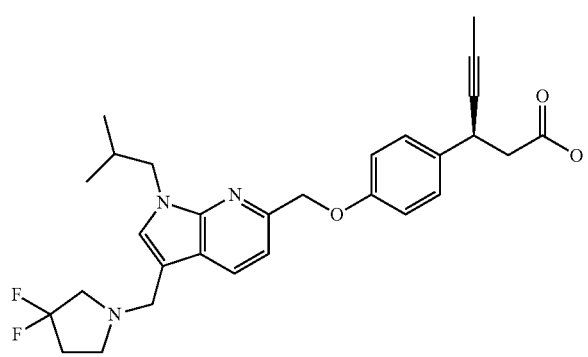 [SMILES: CC#C[C@@H](CC(=O)O)c1ccc(OCc2ccc3c(CN4CCC(F)(F)C4)cn(CC(C)C)c3n2)cc1]

The compound (65 mg, 0.20 mmol) obtained from Preparation Example 204-4 and the compound (48 mg, 0.22 mmol) obtained from Preparation Example 155 were used to obtain the title compound (42 mg, 37%).

NMR:$^1$H-NMR(400 HMz, CDCl$_3$); δ 7.95 (d, 1H), 7.29 (d, 2H), 7.25 (d, 1H), 7.13 (s, 1H), 6.96 (d, 2H), 5.22 (s, 2H), 4.04 (m, 3H), 3.82 (2H), 2.99 (t, 2H), 2.83 (t, 2H), 2.66 (m, 2H), 2.28 (m, 3H), 1.80 (s, 3H), 0.91 (d, 6H)

Example 232

Synthesis of (S)-3-{4-[3-(3,3-difluoro-piperidin-1-ylmethyl)-1-isobutyl-1H-pyrrolo[2,3-b]pyridin-6-ylmethoxy]-phenyl}-hex-4-ynoic acid

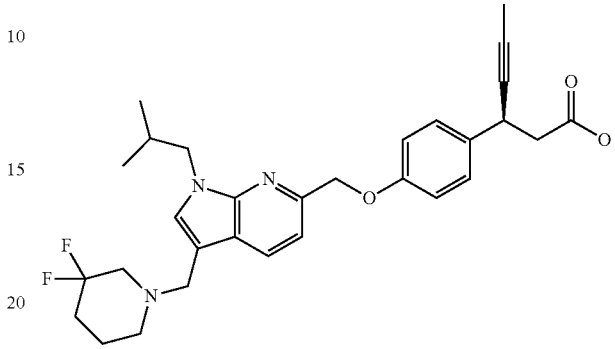

The compound (55 mg, 0.16 mmol) obtained from Preparation Example 205-2 and the compound (39 mg, 0018 mmol) obtained from Preparation Example 155 were used to obtain the title compound (39 mg, 47%).

NMR:$^1$H-NMR(400 HMz, CDCl$_3$); δ 7.97 (d, 1H), 7.29 (d, 1H), 7.24 (d, 1H), 7.11 (s, 1H), 6.98 (d, 2H), 5.24 (s, 2H), 4.06 (m, 3H), 3.81 (s, 2H), 2.73 (m, 2H), 2.64 (m, 2H), 2.51 (m, 2H), 2.23 (m, 1H), 1.84 (m, 2H), 1.80 (s, 3H), 1.75 (m, 2H), 0.91 (d, 6H)

Experimental Example 1

Evaluation of the Test Compounds for Induction of Ca$^{2+}$ Using Human GPR40 Expression Cell Line (1) Cell Line The cell line expressing human GPR40 was generated by transfection of the GPR40 expression vector into CHO-K1 cell, and used in the following calcium flux assay.

(2) Preparation of Cell-Culture Medium and Cell Culture

The cell line was cultured in cell-culture medium (F-12 (Invitrogen) supplemented with 10% (v/v) FBS (Fetal Bovine Serum; Invitrogen), 0.5 mg/ml Geneticin (Invitrogen) and 1% (v/v) Antibiotic-Antimycotic solution (Invitrogen)) under the condition of 5% CO$_2$ and 37° C. For calcium flux assay, the cells were diluted with the cell-culture medium to a concentration of 5×10$^5$ cells/ml, and the diluted cell suspension was dispensed in amount of 100 μl/well to a 96-well transparent bottom black polystyrene cell culture plate (Corning) and then cultured for 24 hours. The following concentrations of test compounds were added to these cells, and then the changes in intracellular calcium concentration were measured by FlexStation II384 (Molecular Devices). The following solution was prepared before the measurement.

(3) Preparation of Buffer Solution for Measurement of Calcium Concentration Change in FlexStation II$^{384}$ First, a buffer solution for assay was prepared for use in the manufacture of fluorescent dye solution. This buffer solution was prepared by adding 1M HEPES solution (Invitrogen) to HBSS (Hanks' Balanced Salt Solution) (Invitrogen) and then adding 1M NaOH (Nacalai Tesque) to adjust pH to 7.4. Then the fluorescent dye solution was prepared according to the manufacturer's instruction attached to Calcium 5 Assay Kit (Molecular Devices), and the final DMSO concentration was adjusted to 2%.

(4) Pre-Treatment for Measurement by FlexStation II$^{384}$

The fluorescent dye solution was added in an amount of 100 μl/well to supernatant of the cell culture plate cultured for 24 hours. The plate was cultured for 1 hour under the condition of 5% $CO_2$ and 37° C. so that the fluorescent dye was inserted into the cell.

Test compounds (i.e., the compounds prepared in the Examples) dissolved in dimethyl sulfoxide (DMSO ACROS) were diluted 200-fold in the buffer solution for assay to prepare compound solutions corresponding to the respective concentrations. As a positive-control solution, the compound of TAK-875 was diluted 200-fold in the buffer solution for assay. TAK-875 is a GPR40 receptor agonist disclosed in WO 2008/001931 (Applicant: to Takeda Pharmaceuticals Company), and it was prepared according to the method described in ACS Med. Chem. Lett., 2010, 290. 50 μl of the prepared sample solutions was added to each well of 96-well polypropylene plates (NUNC), and thereby a compound plate was prepared. Finally, the compound plate and the cell culture plate cultured for 1 hour with the fluorescent dye were placed in FlexStation II384.

(5) Measurement by FlexStation II$^{384}$

After the above pre-treatment, the change in the intracellular calcium concentration when each concentration of the test compound solutions was added at 50 μl was measured by FlexStation II$^{384}$.

GPR40 agonist activity of the test compound solutions in each concentration was calculated as relative activity value (%) when the change in intracellular calcium concentration induced by 10 μM of TAK-875 compound which was used as a positive control is 100%. Then, the relative activity values depending on the concentration of the compound were plotted using Prism 4 software (GraphPad) to calculate the $EC_{0.5}$ value. The $EC_{0.5}$ value represents the concentration of the compound that exhibits 50% activity compared to the positive control and was used to compare the agonist activities between the test compounds.

(6) Results

The results are shown in Table 1. In the table, "+++" indicates that $EC_{0.5}$ value is greater than or equal to 0.001 μM to less than 0.05 μM, "++" indicates that $EC_{0.5}$ value is greater than or equal to 0.05 μM to less than 0.5 μM, and "+" indicates that $EC_{0.5}$ value is greater than or equal to 0.5 μM.

TABLE 1

| Example | $EC_{0.5}$ | Example | $EC_{0.5}$ | Example | $EC_{0.5}$ | Example | $EC_{0.5}$ | Example | $EC_{0.5}$ |
|---|---|---|---|---|---|---|---|---|---|
| 1 | 0.1 | 2 | 0.03 | 3 | 0.01 | 4 | 0.05 | 5 | 0.03 |
| 6 | 0.1 | 7 | 0.02 | 8 | + | 9 | 0.3 | 10 | 0.7 |
| 11 | 0.4 | 12 | 0.16 | 13 | 0.02 | 14 | 0.03 | 15 | 0.01 |
| 16 | 0.02 | 17 | 0.007 | 18 | 0.09 | 19 | 0.4 | 20 | 0.07 |
| 21 | + | 22 | 0.04 | 23 | 0.004 | 24 | 0.02 | 25 | 0.02 |
| 26 | 0.02 | 27 | 0.03 | 28 | 0.01 | 29 | 0.07 | 30 | 0.04 |
| 31 | 0.03 | 32 | 0.04 | 33 | 0.02 | 34 | 0.04 | 35 | 0.01 |
| 36 | 0.06 | 37 | 0.04 | 38 | 0.09 | 39 | 0.2 | 40 | 0.06 |
| 41 | +++ | 42 | ++ | 43 | ++ | 44 | +++ | 45 | +++ |
| 46 | +++ | 47 | +++ | 48 | +++ | 49 | ++ | 50 | ++ |
| 51 | ++ | 52 | ++ | 53 | ++ | 54 | ++ | 55 | +++ |
| 56 | +++ | 57 | +++ | 58 | +++ | 59 | +++ | 60 | +++ |
| 61 | +++ | 62 | ++ | 63 | +++ | 64 | ++ | 65 | 0.05 |
| 66 | 0.01 | 67 | 0.07 | 68 | ++ | 69 | + | 70 | ++ |
| 71 | 0.02 | 72 | 0.03 | 73 | ++ | 74 | + | 75 | ++ |
| 76 | + | 77 | ++ | 78 | ++ | 79 | +++ | 80 | + |
| 81 | +++ | 82 | ++ | 83 | 0.01 | 84 | 0.05 | 85 | 0.01 |
| 86 | 0.01 | 87 | 0.01 | 88 | 0.4 | 89 | 0.03 | 90 | 0.01 |
| 91 | 0.03 | 92 | +++ | 93 | ++ | 94 | 0.06 | 95 | 0.1 |
| 96 | 0.03 | 97 | 0.05 | 98 | +++ | 99 | 1.3 | 100 | 0.6 |
| 101 | 0.09 | 102 | 0.4 | 103 | 0.01 | 104 | 0.8 | 105 | 0.4 |
| 106 | +++ | 107 | 0.2 | 108 | 0.5 | 109 | 0.4 | 110 | 0.2 |
| 111 | +++ | 112 | +++ | 113 | 9.1 | 114 | +++ | 115 | +++ |
| 116 | +++ | 117 | 0.05 | 118 | 0.2 | 119 | 0.06 | 120 | 0.04 |
| 121 | 0.3 | 122 | +++ | 123 | +++ | 124 | 0.05 | 125 | 0.02 |
| 126 | +++ | 127 | +++ | 128 | ++ | 129 | 0.08 | 130 | +++ |
| 131 | ++ | 132 | +++ | 133 | 0.4 | 134 | 0.004 | 135 | 0.2 |
| 136 | +++ | 137 | ++ | 138 | 0.01 | 139 | 0.3 | 140 | 0.004 |
| 141 | +++ | 142 | + | 143 | +++ | 144 | +++ | 145 | 0.04 |
| 146 | ++ | 147 | +++ | 148 | + | 149 | + | 150 | 0.003 |
| 151 | +++ | 152 | + | 153 | +++ | 154 | + | 155 | ++ |
| 156 | 0.02 | 157 | +++ | 158 | 0.05 | 159 | 0.1 | 160 | ++ |
| 161 | 0.005 | 162 | 0.02 | 163 | +++ | 164 | +++ | 165 | +++ |
| 166 | ++ | 167 | 0.06 | 168 | +++ | 169 | +++ | 170 | +++ |
| 171 | +++ | 172 | +++ | 173 | +++ | 174 | + | 175 | ++ |
| 176 | 0.04 | 177 | +++ | 178 | +++ | 179 | +++ | 180 | +++ |
| 181 | 0.006 | 182 | +++ | 183 | +++ | 184 | +++ | 185 | +++ |
| 186 | +++ | 187 | +++ | 188 | 0.005 | 189 | +++ | 190 | 0.04 |
| 191 | 0.010 | 192 | 0.030 | 193 | 0.003 | 194 | +++ | 195 | 0.006 |
| 196 | 0.005 | 197 | 0.005 | 198 | 0.016 | 199 | 0.017 | 200 | 0.009 |
| 201 | 0.010 | 202 | 0.008 | 203 | +++ | 204 | 0.009 | 205 | 0.016 |
| 206 | +++ | 207 | +++ | 208 | 0.005 | 209 | +++ | 210 | 0.008 |
| 211 | 0.004 | 212 | 0.002 | 213 | +++ | 214 | 0.002 | 215 | 0.010 |
| 216 | 0.006 | 217 | 0.020 | 218 | 0.014 | 219 | 0.023 | 220 | 0.003 |
| 221 | 0.005 | 222 | 0.005 | 223 | 0.011 | 224 | 0.027 | 225 | 0.013 |
| 226 | 0.009 | 227 | 0.005 | 228 | +++ | 229 | 0.035 | 230 | +++ |
| 231 | +++ | 232 | 0.012 | TAK-875 | 0.01 | | | | |

The invention claimed is:

1. A compound of Formula (1), or a pharmaceutically acceptable salt or stereoisomer thereof:

[Formula (1)]

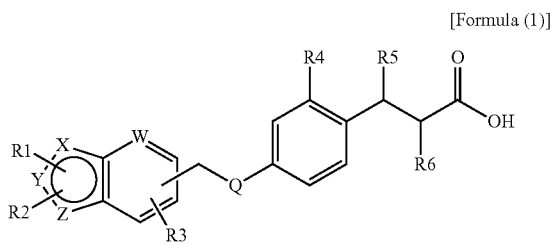

wherein,
Q represents O, or NH,
R1 represents H, alkyl, heteroalkyl, heterocycle, or heterocycle-alkyl,
R2 represents H, alkyl, heteroalkyl, or halogen,
R3 represents H, alkyl, or halogen,
R4 represents H, alkyl, or halogen, or represents O, when R4 is connected with R5,
R5 represents alkoxy, CN, heterocycle, or C≡C-Me, or
R4 and R5 can be connected together to form 5- or 6-membered ring,
R6 represents H, or alkyl, or
R5 and R6 can be connected together to form 3-membered ring,
wherein the structure of

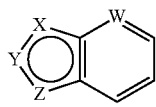

is selected from the following structures:

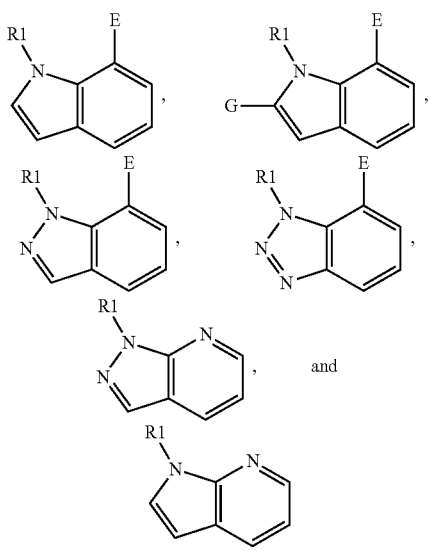

wherein, E represents H, alkyl or halogen, and G represents alkyl, heteroalkyl or halogen, wherein if the structure is

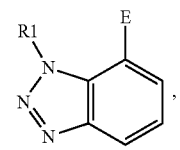

R2 is absent.

2. A compound, or a pharmaceutically acceptable salt or stereoisomer thereof, wherein the compound is selected from the group consisting of the following compounds
3-{4-[(1-isopropyl-1H-indol-6-ylmethyl)-amino-phenyl}-propanoic acid,
3-{4-[(1-benzyl-1H-indol-6-ylmethyl)-amino]-phenyl}-propanoic acid,
3-{4-[(1-thiophen-3-yl-1H-indol-6-ylmethyl)-amino]-phenyl}-propanoic acid,
3-{4-[(1-phenethyl-1H-indol-6-ylmethyl)-aminol]-phenyl}-propanoic acid,
3-{4-[(1-benzyl-3-chloro-1H-indol-6-ylmethyl)-amino]-phenyl}-propanoic acid,
3-{4-[(1-benzyl-2,3-dichloro-1H-indol-6-ylmethyl)-amino]-phenyl}-propanoic acid,
3-{4-[(1-benzyl-7-chloro-1H-indol-6-ylmethyl)-amino]-phenyl}-propanoic acid,
3-{4-[(7-chloro-1-thiophen-3-yl-1H-indol-6-ylmethyl)-amino]-phenyl}-propanoic acid,
3-(4-{[7-chloro-1-(4-fluoro-phenyl)-1H-indol-6-ylmethyl]-amino}-phenyl)-propanoic acid,
3-(4-{[1-(4-fluoro-phenyl)-1H-indol-6-ylmethyl]-amino}-phenyl)-propanoic acid,
3-{4-[(7-chloro-1-cyclohexyl methyl-1H-indol-6-ylmethyl)-amino]-phenyl}-propanoic acid,
[6-(1-benzyl-3-chloro-1H-indol-6-ylmethoxy)-2,3-dihydro-benzofuran-3-yl]-acetic acid,
3-[4-(1-thiophen-3-yl-1H-indol-6-ylmethoxy)-phenyl]-propanoic acid,
3-{4-[1-(4-fluoro-phenyl)-7-methyl-1H-indol-6-ylmethoxy]-phenyl}-propanoic acid,
3-[4-(1-benzyl-7-methyl-1H-indol-6-ylmethoxy)-phenyl]-propanoic acid,
3-[4-(7-methyl-1-thiophen-3-yl-1H-indol-6-ylmethoxy)-phenyl]-propanoic acid,
3-{4-[1-(4-fluoro-2-methyl-phenyl)-1H-indol-6-ylmethoxy]-phenyl}-propanoic acid,
3-[4-(1-benzyl-7-chloro-1H-indol-6-ylmethoxy)-phenyl]-propanoic acid,
3-[4-(1-cyclohexyl methyl-1H-indol-6-ylmethoxy)-phenyl]-propanoic acid,
3-[4-(3-benzyl-1-methyl-1H-indol-5-ylmethoxy)-phenyl]-propanoic acid,
3-[4-(1-methyl-3-o-tolyl-1H-indol-5-ylmethoxy)-phenyl]-propanoic acid,
3-{4-[3-chloro-1-(4-fluoro-2-methyl-phenyl)-1H-indol-6-ylmethoxy)-phenyl]-propanoic acid,
3-{4-[5-fluoro-1-(4-fluoro-2-methyl-phenyl)-1H-indol-6-ylmethoxy)-phenyl]-propanoic acid,
{6-[1-(4-fluoro-2-methyl-phenyl)-1H-indol-6-ylmethoxy]-2,3-dihydro-benzofuran-3-yl}-acetic acid,
(S)-3-[4-(1-benzyl-7-methyl-1H-indol-6-ylmethoxy)-phenyl]-hex-4-ynoic acid,
(S)-3-{4-[1-(4-fluoro-2-methyl-phenyl)-1H-indol-6-ylmethoxy]-phenyl}-hex-4-ynoic acid, (S)-3-{4-[1-(4-methanesulfonyl-benzyl)-7-methyl-1H-indol-6-ylmethoxy]-phenyl}-hex-4-ynoic acid,
(S)-3-{4-[1-(4-methoxy-benzyl)-7-methyl-1H-indol-6-ylmethoxy]-phenyl}-hex-4-ynoic acid,
(S)-3-{4-[7-methyl-1-(4-trifluoromethyl-benzyl)-1H-indol-6-ylmethoxy]-phenyl}-hex-4-ynoic acid,
(S)-3-{4-[1-(3-methoxymethyl-benzyl)-7-methyl-1H-indol-6-ylmethoxy]-phenyl}-hex-4-ynoic acid,
(S)-3-[4-(1-benzyl-1H-indol-4-ylmethoxy)-phenyl]-hex-4-ynoic acid,
(S)-3-{4-[1-(4-fluoro-2-methyl-phenyl)-1H-indol-4-ylmethoxy]-phenyl}-hex-4-ynoic acid,
(S)-3-{4-[1-(2,6-difluoro-benzyl)-7-methyl-1H-indol-6-ylmethoxy]-phenyl}-hex-4-ynoic acid,
(S)-3-{4-[1-benzyl-2-(2-methoxy-ethyl)-7-methyl-1H-indol-6-ylmethoxy]-phenyl}-hex-4-ynoic acid,
(S)-3-{4-[1-(3-methanesulfonylmethyl-benzyl)-7-methyl-1H-indol-6-ylmethoxy]-phenyl}-hex-4-ynoic acid,
(S)-3-{4-[7-methyl-1-(2-methyl-benzyl)-1H-indol-6-ylmethoxy]-phenyl}-hex-4-ynoic acid,
(S)-3-{4-[1-(2-fluoro-benzyl)-7-methyl-1H-indol-6-ylmethoxy]-phenyl}-hex-4-ynoic acid,
(S)-3-{4-[1-(2-chloro-benzyl)-7-methyl-1H-indol-6-ylmethoxy]-phenyl}-hex-4-ynoic acid,
(S)-3-{4-[1-(2,6-dimethyl-benzyl)-7-methyl-1H-indol-6-ylmethoxy]-phenyl}-hex-4-ynoic acid,
(S)-3-[4-(1-benzyl-7-chloro-1H-indol-6-ylmethoxy)-phenyl]-hex-4-ynoic acid,
(S)-3-[4-(1-benzyl-5-fluoro-1H-indol-6-ylmethoxy)-phenyl]-hex-4-ynoic acid,
(S)-3-{4-[1-(3-fluoro-benzyl)-7-methyl-1H-indol-6-ylmethoxy]-phenyl}-hex-4-ynoic acid,
(S)-3-{4-[7-methyl-1-(3-trifluoromethyl-benzyl)-1H-indol-6-ylmethoxy]-phenyl}-hex-4-ynoic acid,
(S)-3-{4-[7-methyl-1-(5-methyl-pyrazin-2-ylmethyl)-1H-indol-6-ylmethoxy]-phenyl}-hex-4-ynoic acid,
(S)-3-{4-[1-(4-methanesulfonylmethyl-benzyl)-7-methyl-1H-indol-6-ylmethoxy]-phenyl}-hex-4-ynoic acid,
(S)-3-{4-[1-(6-chloro-pyridin-3-ylmethyl)-7-methyl-1H-indol-6-ylmethoxy]-phenyl}-hex-4-ynoic acid,
(S)-3-[4-(2-benzyl-2H-indazol-4-ylmethoxy)-phenyl]-hex-4-ynoic acid,
(S)-3-[4-(1-benzyl-1H-indazol-4-ylmethoxy)-phenyl]-hex-4-ynoic acid,
(S)-3-[4-(1-benzyl-5-fluoro-7-methyl-1H-indol-6-ylmethoxy)-phenyl]-hex-4-ynoic acid,
(S)-3-{4-[1-(4-fluoro-benzyl)-7-methyl-1H-indol-6-ylmethoxy]-phenyl}-hex-4-ynoic acid,
(S)-3-{4-[1-(3,4-difluoro-benzyl)-7-methyl-1H-indol-6-ylmethoxy]-phenyl}-hex-4-ynoic acid,
(S)-3-{4-[1-(3,5-difluoro-benzyl)-7-methyl-1H-indol-6-ylmethoxy]-phenyl}-hex-4-ynoic acid,
(S)-3-{4-[1-(2,4-difluoro-benzyl)-7-methyl-1H-indol-6-ylmethoxy]-phenyl}-hex-4-ynoic acid,
3-[4-(1-benzyl-1H-indol-4-ylmethoxy)-2-fluoro-phenyl]-propanoic acid,
3-[4-(1-benzyl-7-methyl-1H-indol-6-ylmethoxy)-2-fluoro-phenyl]-propanoic acid,
(S)-3-[4-(7-methyl-1-thiazol-4-ylmethyl-1H-indol-6-ylmethoxy)-phenyl]-hex-4-ynoic acid,
(S)-3-{4-[7-methyl-1-(2-methyl-thiazol-4-ylmethyl)-1H-indol-6-ylmethoxy]-phenyl}-hex-4-ynoic acid,
(S)-3-[4-(2-benzyl-2H-indazol-6-ylmethoxy)-phenyl]-hex-4-ynoic acid,
(S)-3-[4-(1-benzyl-1H-indazol-6-ylmethoxy)-phenyl]-hex-4-ynoic acid,
(S)-3-[4-(7-methyl-1-pyrazin-2-ylmethyl-1H-indol-6-ylmethoxy)-phenyl]-hex-4-ynoic acid,
(S)-3-[4-(7-methyl-1-pyrimidin-4-ylmethyl-1H-indol-6-ylmethoxy)-phenyl]-hex-4-ynoic acid,
(S)-3-[4-(1-benzyl-3-fluoro-7-methyl-1H-indol-6-ylmethoxy)-phenyl]-hex-4-ynoic acid,
(S)-3-{4-[7-methyl-1-(1-methyl-1H-pyrazol-4-ylmethyl)-1H-indol-6-ylmethoxy]-phenyl]-hex-4-ynoic acid,
(S)-3-[4-(7-methyl-1-pyrimidin-2-ylmethyl-1H-indol-6-ylmethoxy)-phenyl]-hex-4-ynoic acid,
3-[4-(1-benzyl-1H-indazol-6-ylmethoxy)-phenyl]-3-(4,5-dihydro-isoxazol-3-yl)-propanoic acid,
(S)-3-{4-[1-(4-fluoro-benzyl)-1H-indazol-6-ylmethoxy]-phenyl}-hex-4-ynoic acid,
(S)-3-{4-[2-(4-fluoro-benzyl)-2H-indazol-6-ylmethoxy]-phenyl}-hex-4-ynoic acid,
(S)-3-[4-(1-pyrimidin-2-ylmethyl-1H-indazol-6-ylmethoxy)-phenyl]-hex-4-ynoic acid,
(S)-3-[4-(2-pyrimidin-2-ylmethyl-2H-indazol-6-ylmethoxy)-phenyl]-hex-4-ynoic acid,
(S)-3-[4-(1-pyrazin-2-ylmethyl-1H-indazol-6-ylmethoxy)-phenyl]-hex-4-ynoic acid,
(S)-3-{4-[1-(4-fluoro-benzyl)-1H-indazol-4-ylmethoxy]-phenyl}-hex-4-ynoic acid,
(S)-3-{4-[2-(4-fluoro-benzyl)-2H-indazol-4-ylmethoxy]-phenyl}-hex-4-ynoic acid,
(S)-3-{4-[1-(5-methyl-pyrazin-2-ylmethyl)-1H-indazol-6-ylmethoxy]-phenyl}-hex-4-ynoic acid,
(S)-3-{4-[2-(5-methyl-pyrazin-2-ylmethyl)-2H-indazol-6-ylmethoxy]-phenyl}-hex-4-ynoic acid,
(S)-3-[4-(1-pyrimidin-4-ylmethyl-1H-indazol-6-ylmethoxy)-phenyl]-hex-4-ynoic acid,
(S)-3-[4-(2-pyrimidin-4-ylmethyl-2H-indazol-6-ylmethoxy)-phenyl]-hex-4-ynoic acid,
(S)-3-{4-[1-(5-methyl-pyrazin-2-ylmethyl)-1H-indazol-4-ylmethoxy]-phenyl}-hex-4-ynoic acid,
(S)-3-{4-[2-(5-methyl-pyrazin-2-ylmethyl)-2H-indazol-4-ylmethoxy]-phenyl}-hex-4-ynoic acid,
(S)-3-[4-(1-pyridin-3-ylmethyl-1H-indazol-6-ylmethoxy)-phenyl]-hex-4-ynoic acid,
(S)-3-[4-(2-pyridin-3-ylmethyl-2H-indazol-6-ylmethoxy)-phenyl]-hex-4-ynoic acid,
(S)-3-{4-[7-methyl-1-(6-methyl-pyridin-3-ylmethyl)-1H-indol-6-ylmethoxy]-phenyl}-hex-4-ynoic acid,
(S)-3-{4-[1-(1-methyl-1H-pyrazol-4-ylmethyl)-1H-indazol-6-ylmethoxy]-phenyl}-hex-4-ynoic acid,
(S)-3-[4-(1-benzyl-7-methyl-1H-indol-6-ylmethoxy)-phenyl]-3-isoxazol-3-yl-propanoic acid,
(S)-3-{4-[1-(4-fluoro-benzyl)-7-methyl-1H-indol-6-ylmethoxy]-phenyl}-3-isoxazol-3-yl-propanoic acid,
(S)-3-[4-(1-benzyl-1H-indazol-6-ylmethoxy)-phenyl]-3-isoxazol-3-yl-propanoic acid,
(S)-3-{4-[1-(4-fluoro-benzyl)-1H-indazol-6-ylmethoxy]-phenyl}-3-isoxazol-3-yl-propanoic acid,
(S)-3-[4-(1-isobutyl-1H-indazol-6-ylmethoxy)-phenyl]-3-isoxazol-3-yl-propanoic acid,
(S)-3-[4-(2-isobutyl-2H-indazol-6-ylmethoxy)-phenyl]-3-isoxazol-3-yl-propanoic acid,
(S)-3-isoxazol-3-yl-3-[4-(7-methyl-1-pyrazin-2-ylmethyl-1H-indol-6-ylmethoxy)-phenyl]-propanoic acid,
(S)-3-[4-(1-benzyl-1H-pyrrolo[2,3-b]pyridin-6-ylmethoxy)-phenyl]-hex-4-ynoic acid,
(S)-3-[4-(1-benzyl-1H-pyrrolo[2,3-b]pyridin-6-ylmethoxy)-phenyl]-3-isoxazol-3-yl-propanoic acid, (S)-3-isoxazol-3-yl-3-{4-[7-methyl-1-(5-methyl-pyrazin-2-ylmethyl)-1H-indol-6-ylmethoxy]-phenyl}-propanoic acid,
(S)-3-{4-[1-(6-methyl-pyridin-3-ylmethyl)-1H-indazol-6-ylmethoxy]-phenyl}-hex-4-ynoic acid,
(S)-3-[4-(1-benzyl-1H-indazol-4-ylmethoxy)-phenyl]-3-isoxazol-3-yl-propanoic acid,
(S)-3-{4-[1-(4-fluoro-benzyl)-1H-pyrrolo[2,3-b]pyridin-6-ylmethoxy]-phenyl}-3-isoxazol-3-yl-propanoic acid,
(S)-3-[4-(1-isopropyl-1H-indazol-6-ylmethoxy)-phenyl]-3-isoxazol-3-yl-propanoic acid,
(S)-3-[4-(1-cyclopropylmethyl-1H-indazol-6-ylmethoxy)-phenyl]-3-isoxazol-3-yl-propanoic acid,
(S)-3-[4-(1-isobutyl-1H-pyrrolo[2,3-b]pyridin-6-ylmethoxy)-phenyl]-3-isoxazol-3-yl-propanoic acid,
(S)-3-[4-(2-isopropyl-2H-indazol-6-ylmethoxy)-phenyl]-3-isoxazol-3-yl-propanoic acid,
[6-(1-isopropyl-1H-indazol-6-ylmethoxy)-2,3-dihydro-benzofuran-3-yl]-acetic acid,
(S)-3-isoxazol-3-yl-3-[4-(1-methyl-1H-indazol-6-ylmethoxy)-phenyl]-propanoic acid,
(S)-3-[4-(1H-indazol-6-ylmethoxy)-phenyl]-3-isoxazol-3-yl-propanoic acid,
(S)-3-[4-(1-cyclopentylmethyl-1H-indazol-6-ylmethoxy)-phenyl]-3-isoxazol-3-yl-propanoic acid,
(S)-3-isoxazol-3-yl-3-[4-(1-pyrazin-2-ylmethyl-1H-pyrrolo[2,3-b]pyridin-6-ylmethoxy)-phenyl]-propanoic acid,
[6-(1-benzyl-1H-indazol-6-ylmethoxy)-2,3-dihydro-benzofuran-3-yl]-acetic acid,
3-[4-(1-benzyl-1H-indazol-6-ylmethoxy)-2-fluoro-phenyl]-propanoic acid,
3-[4-(1-cyclopentylmethyl-1H-indazol-6-ylmethoxy)-2-fluoro-phenyl]-propanoic acid,
[6-(1-cyclopentylmethyl-1H-indazol-6-ylmethoxy)-2,3-dihydro-benzofuran-3-yl]-acetic acid,
[5-(1-benzyl-1H-indazol-6-ylmethoxy)-indan-1-yl]-acetic acid,
[6-(1-benzyl-1H-indazol-6-ylmethoxy)-1,2,3,4-tetrahydro-naphthalen-1-yl]-acetic acid,
(S)-3-[4-(1-benzyl-1H-indazol-5-ylmethoxy)-phenyl]-hex-4-ynoic acid,
(S)-3-[4-(2-benzyl-2H-indazol-5-ylmethoxy)-phenyl]-hex-4-ynoic acid,
[6-(2-benzyl-2H-indazol-6-ylmethoxy)-2,3-dihydro-benzofuran-3-yl]-acetic acid,
(S)-3-[4-(1-isobutyl-1H-indazol-6-ylmethoxy)-phenyl]-hex-4-ynoic acid,
(S)-3-[4-(1-isobutyl-1H-pyrrolo[2,3-b]pyridin-6-ylmethoxy)-phenyl]-hex-4-ynoic acid,
(S)-3-[4-(1-isopropyl-1H-indazol-5-ylmethoxy)-phenyl]-hex-4-ynoic acid,
3-[4-(1-benzyl-1H-indazol-6-ylmethoxy)-phenyl]-butyric acid,
[5-(1-benzyl-1H-indazol-5-ylmethoxy)-indan-1-yl]-acetic acid,
[6-(1-benzyl-1H-indazol-5-ylmethoxy)-1,2,3,4-tetrahydro-naphthalen-1-yl]-acetic acid,
[7-(1-benzyl-1H-indazol-5-ylmethoxy)-chroman-4-yl]-acetic acid,
[6-(1-benzyl-1H-pyrrolo[2,3-b]pyridin-6-ylmethoxy)-2,3-dihydro-benzofuran-3-yl]-acetic acid,
(S)-3-[4-(1-benzyl-5-fluoro-1H-indazol-6-ylmethoxy)-phenyl]-hex-4-ynoic acid,
(S)-3-[4-(1-benzyl-1H-indol-5-ylmethoxy)-phenyl]-hex-4-ynoic acid,
(S)-3-[4-(1-benzyl-1H-benzotriazol-5-ylmethoxy)-phenyl]-hex-4-ynoic acid,
(S)-3-[4-(1-benzyl-1H-benzoimidazol-5-ylmethoxy)-phenyl]-hex-4-ynoic acid,
(S)-3-[4-(1-benzyl-7-methyl-1H-indazol-5-ylmethoxy)-phenyl]-hex-4-ynoic acid,
(S)-3-[4-(2-benzyl-7-methyl-2H-indazol-5-ylmethoxy)-phenyl]-hex-4-ynoic acid,
[6-(1-benzyl-7-methyl-1H-indazol-5-ylmethoxy)-2,3-dihydro-benzofuran-3-yl]-acetic acid,
[6-(1-benzyl-7-methyl-1H-indazol-5-ylmethoxy)-chroman-4-yl]-acetic acid,
(S)-3-[4-(1-isobutyl-7-methyl-1H-indazol-5-ylmethoxy)-phenyl]-hex-4-ynoic acid,
[7-(1-isobutyl-7-methyl-1H-indazol-5-ylmethoxy)-chroman-4-yl]-acetic acid,
(S)-3-[4-(1-isobutyl-1H-indazol-5-ylmethoxy)-phenyl]-hex-4-ynoic acid,
[7-(1-isobutyl-1H-indazol-5-ylmethoxy)-chroman-4-yl]-acetic acid,
(S)-3-[4-(1-phenethyl-1H-indazol-5-ylmethoxy)-phenyl]-hex-4-ynoic acid,
[7-(1-phenethyl-1H-indazol-5-ylmethoxy)-chroman-4-yl]-acetic acid,
(S)-3-{4-[1-(3-methyl-butyl)-1H-indazol-5-ylmethoxy]-phenyl}-hex-4-ynoic acid,
7-[1-(3-methyl-butyl)-1H-indazol-5-ylmethoxy]-chroman-4-yl}-acetic acid,
(S)-3-[4-(1-cyclohexyl methyl-1H-indazol-5-ylmethoxy)-phenyl]-hex-4-ynoic acid,
[7-(1-cyclohexyl methyl-1H-indazol-5-ylmethoxy)-chroman-4-yl]-acetic acid,
(S)-3-[4-(2-isobutyl-7-methyl-2H-indazol-5-ylmethoxy)-phenyl]-hex-4-ynoic acid,
(S)-3-[4-(1-pyridine-2-ylmethyl-1H-indazol-5-ylmethoxy)-phenyl]-hex-4-ynoic acid,
[7-(1-pyridine-2-ylmethyl-1H-indazol-5-ylmethoxy)-chroman-4-yl]-acetic acid,
(S)-3-[4-(1-benzyl-1H-pyrrolo[2,3-b]pyridin-5-ylmethoxy)-phenyl]-hex-4-ynoic acid,
(S)-3-[4-(1-isobutyl-1H-pyrrolo[2,3-b]pyridin-5-ylmethoxy)-phenyl]-hex-4-ynoic acid,
[7-(1-benzyl-7-methyl-1H-indol-6-ylmethoxy)-chroman-4-yl]-acetic acid,
[7-(2-benzyl-7-methyl-2H-indazol-5-ylmethoxy)-chroman-4-yl]-acetic acid,
(S)-3-[4-(1-pyridin-3-ylmethyl-1H-indazol-5-ylmethoxy)-phenyl]-hex-4-ynoic acid,
[7-(1-pyridin-3-ylmethyl-1H-indazol-5-ylmethoxy)-chroman-4-yl]-acetic acid,
7-[1-(2-ethoxy-ethyl)-1H-indazol-5-ylmethoxy]-chroman-4-yl}-acetic acid,
(S)-3-[4-(5-fluoro-1-isobutyl-1H-indazol-6-ylmethoxy)-phenyl]-hex-4-ynoic acid,
(S)-3-{4-[1-(tetrahydrofuran-2-ylmethyl)-1H-indazol-5-ylmethoxy]-phenyl}-hex-4-ynoic acid,
(S)-3-{4-[1-(3-methanesulfonyl-propyl)-1H-indazol-5-ylmethoxy]-phenyl}-hex-4-ynoic acid,
(S)-3-{4-[1-(tetrahydrofuran-3-ylmethyl)-1H-indazol-5-ylmethoxy]-phenyl}-hex-4-ynoic acid,
(S)-3-{4-[2-(tetrahydrofuran-3-ylmethyl)-2H-indazol-5-ylmethoxy]-phenyl}-hex-4-ynoic acid,
3-[4-(1-benzyl-1H-indazol-5-ylmethoxy)-phenyl]-3-methoxy-propanoic acid,
(S)-3-[4-(1-isobutyl-1H-pyrazolo[3,4-b]pyridin-5-ylmethoxy)-phenyl]-hex-4-ynoic acid, (S)-3-{4-[1-(2-ethoxy-ethyl)-1H-indazol-5-ylmethoxy]-phenyl}-hex-4-ynoic acid,
3-[4-(1-benzyl-1H-indazol-5-ylmethoxy)-phenyl]-butyric acid,
3-[4-(1-benzyl-1H-indazol-5-ylmethoxy)-phenyl]-pentanoic acid,
(S)-3-{4-[2-(2-ethoxy-ethyl)-2H-indazol-5-ylmethoxy]-phenyl}-hex-4-ynoic acid,
(S)-3-[4-(1-benzyl-3-methyl-2-oxo-2,3-dihydro-1H-benzoimidazol-5-ylmethoxy)-phenyl]-hex-4-ynoic acid,
3-[4-(1-benzyl-1H-indazol-5-ylmethoxy)-phenyl]-3-cyano-propanoic acid,
(S)-3-[4-(1-cyclopentylmethyl-1H-indazol-5-yl-methoxy)-phenyl]-hex-4-ynoic acid,
(S)-3-[4-(1-cyclopentyl-1H-indazol-5-ylmethoxy)-phenyl]-hex-4-ynoic acid,
(S)-3-[4-(1-cyclopropylmethyl-1H-indazol-5-yl-methoxy)-phenyl]-hex-4-ynoic acid,
(S)-3-[4-(3-isobutyl-3H-benzotriazol-5-ylmethoxy)-phenyl]-hex-4-ynoic acid,
2-[4-(1-benzyl-1H-indazol-6-ylmethoxy)-phenyl]-cyclopropanecarboxylic acid,
(S)-3-[4-(1-isobutyl-7-methyl-1H-indazol-5-ylmethoxy)-phenyl]-hex-4-ynoic acid,
(S)-3-[4-(1-cyclopentylmethyl-7-methyl-1H-indazol-5-ylmethoxy)-phenyl]-hex-4-ynoic acid,
(S)-3-[4-(1-isobutyl-3-methyl-1H-indazol-5-ylmethoxy)-phenyl]-hex-4-ynoic acid,
(S)-3-[4-(1-cyclopentyl-7-methyl-1H-indazol-5-yl-methoxy)-phenyl]-hex-4-ynoic acid,
(S)-3-[4-(1-cyclopentyl-1H-indazol-6-ylmethoxy)-phenyl]-hex-4-ynoic acid,
(S)-3-[4-(1-cyclopentylmethyl-1H-indazol-6-yl-methoxy)-phenyl]-hex-4-ynoic acid,
(S)-3-{4-[1-(2-methanesulfonyl-ethyl)-1H-indazol-5-yl-methoxy]-phenyl}-hex-4-ynoic acid,
(S)-3-{4-[1-(2-methoxy-ethyl)-1H-indazol-5-yl-methoxy]-phenyl}-hex-4-ynoic acid,
(S)-3-{4-[1-(3-methoxy-propyl)-1H-indazol-5-yl-methoxy]-phenyl}-hex-4-ynoic acid,
(S)-3-{4-[1-(3-methyl-oxetan-3-ylmethyl)-1H-indazol-6-ylmethoxy]-phenyl}-hex-4-ynoic acid,
(S)-3-[4-(1-isobutyl-3-methyl-1H-indazol-6-ylmethoxy)-phenyl]-hex-4-ynoic acid,
(S)-3-[4-(2-isobutyl-3-methyl-2H-indazol-6-ylmethoxy)-phenyl]-hex-4-ynoic acid,
(S)-3-[4-(1-isopropyl-1H-indazol-6-ylmethoxy)-phenyl]-hex-4-ynoic acid,
(S)-3-[4-(3-isobutyl-benzo[d]isoxazol-5-ylmethoxy)-phenyl]-hex-4-ynoic acid,
(S)-3-{4-[1-(2,2-dimethyl-propyl)-1H-indazol-6-yl-methoxy]-phenyl}-hex-4-ynoic acid,
(S)-3-[4-(1-isobutyl-6-methyl-1H-indazol-5-ylmethoxy)-phenyl]-hex-4-ynoic acid,
(S)-3-[4-(1-isobutyl-1H-indazol-4-ylmethoxy)-phenyl]-hex-4-ynoic acid,
(S)-3-[4-(1-isopropyl-3-methyl-1H-indazol-6-yl-methoxy)-phenyl]-hex-4-ynoic acid,
(S)-3-[4-(3-isobutyl-1-methyl-1H-indazol-5-ylmethoxy)-phenyl]-hex-4-ynoic acid,
(S)-3-[4-(1-isopropyl-3-methyl-1H-indazol-5-yl-methoxy)-phenyl]-hex-4-ynoic acid,
(S)-3-[4-(1-isobutyl-3-methoxymethyl-1H-indazol-6-yl-methoxy)-phenyl]-hex-4-ynoic acid,
(S)-3-[4-(3-fluoro-1-isobutyl-1H-indazol-4-ylmethoxy)-phenyl]-hex-4-ynoic acid,
(S)-3-[4-(1-isopropyl-1H-indazol-4-ylmethoxy)-phenyl]-hex-4-ynoic acid,
(S)-3-[4-(3-ethoxymethyl-1-isobutyl-1H-indazol-6-yl-methoxy)-phenyl]-hex-4-ynoic acid,
(S)-3-[4-(3-chloro-1-isobutyl-1H-indazol-4-ylmethoxy)-phenyl]-hex-4-ynoic acid,
(S)-3-[4-(1-isobutyl-3-isopropoxymethyl-1H-indazol-6-ylmethoxy)-phenyl]-hex-4-ynoic acid,
(S)-3-[4-(3-fluoro-1-isopropyl-1H-indazol-4-yl-methoxy)-phenyl]-hex-4-ynoic acid,
(S)-3-[4-(3-bromo-1-methyl-1H-indazol-7-ylmethoxy)-phenyl]-hex-4-ynoic acid,
(S)-3-[4-(1-isobutyl-3-methoxymethyl-7-methyl-1H-indazol-6-ylmethoxy)-phenyl]-hex-4-ynoic acid,
(S)-3-[4-(1-butyl-1H-indazol-4-ylmethoxy)-phenyl]-hex-4-ynoic acid,
(S)-3-[4-(1-butyl-3-fluoro-1H-indazol-4-ylmethoxy)-phenyl]-hex-4-ynoic acid,
(S)-3-[4-(1-cyclopropylmethyl-1H-indazol-4-yl-methoxy)-phenyl]-hex-4-ynoic acid,
(S)-3-[4-(1-cyclopropylmethyl-3-fluoro-1H-indazol-4-yl-methoxy)-phenyl]-hex-4-ynoic acid,
(S)-3-[4-(3-chloro-1-methyl-1H-indazol-7-ylmethoxy)-methyl]-hex-4-ynoic acid,
(S)-3-[4-(1-isopropyl-3-pyrazol-1-ylmethyl-1H-indazol-6-ylmethoxy)-phenyl]-hex-4-ynoic acid,
(S)-3-[4-(3-fluoro-1-methyl-1H-indazol-7-ylmethoxy)-phenyl]-hex-4-ynoic acid,
(S)-3-[4-(1-isobutyl-1H-pyrrolo[2,3-b]pyridin-4-yl-methoxy)-phenyl]-hex-4-ynoic acid,
(S)-3-[4-(1-butyl-3-methyl-1H-indazol-4-ylmethoxy)-phenyl]-hex-4-ynoic acid,
(S)-3-[4-(3-butyl-1-methyl-1H-indazol-7-ylmethoxy)-phenyl]-hex-4-ynoic acid,
(S)-3-[4-isobutyl-1-methyl-1H-indazol-7-ylmethoxy)-phenyl]-hex-4-ynoic acid,
(S)-3-[4-(1-isobutyl-7-methyl-1H-indazol-4-ylmethoxy)-phenyl]-hex-4-ynoic acid,
(S)-3-[4-(3-isopropyl-1-methyl-1H-indazol-7-yl-methoxy)-phenyl]-hex-4-ynoic acid,
(S)-3-[4-(1-methyl-3-propyl-1H-indazol-7-ylmethoxy)-phenyl]-hex-4-ynoic acid,
(S)-3-[4-(1-isobutyl-7-methyl-1H-indazol-6-ylmethoxy)-phenyl]-hex-4-ynoic acid,
(S)-3-[4-(1-isobutyl-3,7-dimethyl-1H-indazol-6-yl-methoxy)-phenyl]-hex-4-ynoic acid,
(S)-3-[4-(3-fluoro-1-isobutyl-7-methyl-1H-indazol-4-yl-methoxy)-phenyl]-hex-4-ynoic acid,
(S)-3-[4-(1-ethyl-3-fluoro-7-methyl-1H-indazol-6-yl-methoxy)-phenyl]-hex-4-ynoic acid,
(S)-3-[4-(1-isobutyl-7-methyl-3-morpholin-4-ylmethyl-1H-indazol-6-ylmethoxy)-phenyl]-hex-4-ynoic acid,
(S)-3-[4-(7-chloro-1-isobutyl-3-morpholin-4-ylmethyl-1H-indazol-6-ylmethoxy)-phenyl]-hex-4-ynoic acid,
(S)-3-[4-(1-isobutyl-7-methyl-3-pyrrolidin-1-ylmethyl-1H-indazol-6-ylmethoxy)-phenyl]-hex-4-ynoic acid,
(S)-3-[4-(1-isobutyl-7-methyl-3-piperidin-1-ylmethyl-1H-indazol-6-ylmethoxy)-phenyl]-hex-4-ynoic acid,
(S)-3-[4-(1-isobutyl-3-morpholin-4-ylmethyl-1H-indazol-6-ylmethoxy)-phenyl]-hex-4-ynoic acid,
(S)-3-[4-(1-isopropyl-7-methyl-1H-indazol-6-yl-methoxy)-phenyl]-hex-4-ynoic acid,
(S)-3-[4-(7-methyl-1-propyl-1H-indazol-6-ylmethoxy)-phenyl]-hex-4-ynoic acid,
(S)-3-[4-(3-fluoromethyl-1-isobutyl-7-methyl-1H-indazol-6-ylmethoxy)-phenyl]-hex-4-ynoic acid, (S)-3-[4-(1-isopropyl-7-methyl-1H-indazol-4-yl-methoxy)-phenyl]-hex-4-ynoic acid,
(S)-3-[4-(1-isopropyl-1H-pyrrolo[2,3-b]pyridin-4-yl-methoxy)-phenyl]-hex-4-ynoic acid,
(S)-3-[4-(3-fluoro-1-isobutyl-1H-pyrrolo[2,3-b]pyridin-4-ylmethoxy)-phenyl]-hex-4-ynoic acid,
(S)-3-[4-(7-methyl-1-pyridin-3-ylmethyl-1H-indazol-6-ylmethoxy)-phenyl]-hex-4-ynoic acid,
(S)-3-{4-[3-(3,3-difluoro-piperidin-1-ylmethyl)-1-isobutyl-7-methyl-1H-indazol-6-ylmethoxy]-phenyl}-hex-4-ynoic acid,
(S)-3-[4-(1-isobutyl-7-methyl-3-pyrazol-1-ylmethyl-1H-indazol-6-ylmethoxy)-phenyl]-hex-4-ynoic acid,
(S)-3-{4-[3-((S)-3-fluoro-pyrrolidin-1-ylmethyl)-1-isobutyl-7-methyl-1H-indazol-6-ylmethoxy]-phenyl}-hex-4-ynoic acid,
(S)-3-{4-[3-(3,3-difluoro-pyrrolidin-1-ylmethyl)-1-isobutyl-7-methyl-1H-indazol-6-ylmethoxy]-phenyl}-hex-4-ynoic acid,
(S)-3-{4-[3-(3,3-difluoro-pyrrolidin-1-ylmethyl)-1-isobutyl-1H-pyrrolo[2,3-b]pyridin-6-ylmethoxy]-phenyl}-hex-4-ynoic acid, and
(S)-3-{4-[3-(3,3-difluoro-piperidin-1-ylmethyl)-1-isobutyl-1H-pyrrolo[2,3-b]pyridin-6-ylmethoxy]-phenyl}-hex-4-ynoic acid.

3. The compound or the pharmaceutically acceptable salt or stereoisomer thereof according to claim 1, wherein the compound is for the treatment of diabetes.

4. A pharmaceutical composition, comprising the compound, or the pharmaceutically acceptable salt or stereoisomer thereof according to claim 1, and a pharmaceutically acceptable carrier.

5. An insulin secretagogue or hypoglycemic agent comprising as an active ingredient, the compound, or the pharmaceutically acceptable salt or stereoisomer thereof according to claim 1.

6. A GPR40 receptor agonist comprising the compound, or the pharmaceutically acceptable salt or stereoisomer thereof according to claim 1 as an active ingredient.

7. A pharmaceutical composition for treating diseases or disorders selected from the group consisting of diabetes, high blood sugar, glucose tolerance, impaired fasting blood glucose, and diabetes complications, comprising the compound, or the pharmaceutically acceptable salt or stereoisomer thereof according to claim 1 as an active ingredient, and a pharmaceutically acceptable carrier.

8. The pharmaceutical composition according to claim 7, wherein the diabetes complication is selected from hyperlipidemia, hypertension, retinopathy, renal failure, or obesity.

9. A method for treating a disease or disorder in a mammal, comprising administration of the compound, or the pharmaceutically acceptable salt or stereoisomer thereof according to claim 1 to the mammal,
wherein the disease or disorder is selected from the group consisting of diabetes, high blood sugar, glucose tolerance, impaired fasting blood glucose, and diabetes complications.

10. The method of claim 9, wherein the disease or disorder is diabetes.

11. The method of claim 9, wherein the disease or disorder is diabetes complication and the diabetes complication is selected from the group consisting of hyperlipidemia, hypertension, retinopathy, renal failure, and obesity.

* * * * *